(12) United States Patent
Beers et al.

(10) Patent No.: US 11,208,487 B2
(45) Date of Patent: Dec. 28, 2021

(54) ANTI-HLA-G ANTIBODIES, COMPOSITIONS COMPRISING ANTI-HLA-G ANTIBODIES AND METHODS OF USING ANTI-HLA-G ANTIBODIES

(71) Applicant: Tizona Therapeutics, South San Francisco, CA (US)

(72) Inventors: Courtney Beers, South San Francisco, CA (US); John Corbin, South San Francisco, CA (US); Doug Hodges, South San Francisco, CA (US); Achim Moesta, South San Francisco, CA (US); Vanessa Soros, South San Francisco, CA (US); Paul Fredrick Widboom, South San Francisco, CA (US); Joseph Robert Warfield, South San Francisco, CA (US)

(73) Assignee: Tizona Therapeutics, South San Francisco, CA (US)

( * ) Notice: Subject to any disclaimer, the term of this patent is extended or adjusted under 35 U.S.C. 154(b) by 116 days.

(21) Appl. No.: 16/584,421

(22) Filed: Sep. 26, 2019

(65) Prior Publication Data

US 2020/0102390 A1 Apr. 2, 2020

Related U.S. Application Data

(60) Provisional application No. 62/737,666, filed on Sep. 27, 2018.

(51) Int. Cl.
| | |
|---|---|
| *C07K 16/00* | (2006.01) |
| *C07K 16/28* | (2006.01) |
| *C07K 16/32* | (2006.01) |
| *G01N 33/569* | (2006.01) |
| *A61K 45/06* | (2006.01) |

(52) U.S. Cl.
CPC ...... *C07K 16/2833* (2013.01); *C07K 16/2818* (2013.01); *C07K 16/2827* (2013.01); *C07K 16/2896* (2013.01); *C07K 16/32* (2013.01); *G01N 33/56977* (2013.01); *A61K 45/06* (2013.01); *C07K 2317/24* (2013.01); *C07K 2317/31* (2013.01); *C07K 2317/54* (2013.01); *C07K 2317/55* (2013.01); *C07K 2317/565* (2013.01); *C07K 2317/626* (2013.01); *C07K 2317/732* (2013.01); *C07K 2317/76* (2013.01); *C07K 2317/92* (2013.01)

(58) Field of Classification Search
CPC ............ C07K 16/2833; C07K 16/2896; C07K 16/32; C07K 2317/54; C07K 2317/55; C07K 2317/565; C07K 2317/732; C07K 2317/76; G01N 33/56977
See application file for complete search history.

(56) References Cited

U.S. PATENT DOCUMENTS

| | | |
|---|---|---|
| 2007/0020703 A1 | 1/2007 | Menier et al. |
| 2007/0259403 A1 | 11/2007 | Miyagawa et al. |
| 2017/0226223 A1 | 8/2017 | Williams et al. |

FOREIGN PATENT DOCUMENTS

| | | |
|---|---|---|
| CN | 1718588 | 1/2006 |
| CN | 101967191 | 2/2011 |
| EP | 12306398 | 11/2012 |
| EP | 2730588 A1 | 5/2014 |
| WO | 9631604 A1 | 10/1996 |
| WO | 9942128 A1 | 8/1999 |
| WO | 200222784 A2 | 3/2002 |
| WO | 2010150233 A2 | 12/2010 |
| WO | 2010150235 A1 | 12/2010 |
| WO | 2013106586 A2 | 7/2013 |
| WO | 2014072534 A1 | 5/2014 |
| WO | 2016160622 A2 | 10/2016 |
| WO | 2017207775 A1 | 12/2017 |
| WO | 2018091580 A1 | 5/2018 |
| WO | 2019202040 A1 | 10/2019 |
| WO | 2020043899 A1 | 3/2020 |

OTHER PUBLICATIONS

Seitz, C et al., "The monoclonal antibody HCA2 recognises a broadly shared epitope on selected classical as well as several nn-classical HLA class I molecules" Molecular Immunology, vol. 35, 1998, pp. 819-827.
Donadi, E et al., "Implications of the polymorphism of HLA-G on its fuction, regulation, evolution and disease association" Cellular and Molecular Life Sciences, vol. 68, 2011, pp. 369-395.
Loke, Y et al., "Evaluation of trophoblast HLA-G antigen with a specific monoclonal antibody" Tissue Antigens, vol. 50, 1997, pp. 135-146.
Bensussan, A et al., "Detection of membrane-bound HLA-G translated products with a specific monoclonal antibdy" PNAS, vol. 92, 1995, p. 10292-10296.
Shiroishi, M et al., "Efficient Leukocyte Ig-like Receptor Signaling and Crystal Structure of Disulfide-linked HLA-G Dimer" The Journal of Biological Chemistry, vol. 281, 2006, p. 10439-10447.
Gonen-Gross, et al., "Complexes of HLA-G Protein on the Cell Surface Are Important for Leukocyte Ig-Like Receptor-1 Function" The Journal of Immunology, vol. 171, 2003, pp. 1343-1351.
Parish, D et al., "Immunogenicity of Low-Dose Intradermal Recombinant DNA Hepatitis B Vaccine" Southern Medical Journal, vol. 84, No. 4, 1991, pp. 426-430.
Contini et al., Soluble HLA-A, -B, -C and -G molecules induce apoptosis in T and NK CD8+ cells and inhibit cytotoxic T Cell activity through CD8 litigation; Eur J. Immunol. 33(2003), 125-134.
Liang et al., HLA-G inhibits the functions of murine dendritic cells via the PIR-B immune inhibitory receptor, Eur. J. Immunol. 32 (2002), 2418-2426 2002.

(Continued)

*Primary Examiner* — Lei Yao
(74) *Attorney, Agent, or Firm* — K&L Gates LLP

(57) ABSTRACT

Provided herein are antibodies that selectively bind to HLA-G and compositions comprising the antibodies. Also provided are methods of using the antibodies, such as therapeutic and diagnostic methods.

10 Claims, 15 Drawing Sheets

Specification includes a Sequence Listing.

(56) References Cited

OTHER PUBLICATIONS

Vergati et al., Strategies for Cancer Vaccine Development, J. Biomed. Biotechnol. 2010.

Loustau et al., HLA-G Neo-Expression on Tumors, Frontiers in Immunology 11(2020), Article 1685 Aug. 14, 2020.

Matsushita et al., Differential but Competitive Binding of Nogo Protein and class 1 Major Histocompatibility Complex (MHCI) to the PIR-B Ectodomain Provides an Inhibition of Cells, J. Biol. Chem. 286(29), 25739 25747 Feb. 6, 2011.

Molek and Bratkovic, Epitope Mapping of Mono- and Polyclonal Antibodies by Screening Phage-displayed Random Peptide Libraries, Acta Chim Slov.63 (2016), 914-919.

Zoller and Christ, Prophylactic Tumor Vaccination: Comparison of Effector Mechanisms Initiated by Protein Versus DNA Vaccination, J. Immunol. 166 (2001 ), 3440-3450 2001.

Paul et al., HLA-G, -E, -F Preworkshop: Tools and Protocols for Analysis of non-Classical Class I Genes Transxription and Protein Expression, (2000) Human Immunology 61 (11):1177-1195.

Lee N, et al., The membrane-bound and soluble forms of HLA-G bind identical sets of endogenous peptides but differ with respect to TAP association. Immunity. Nov. 1995;3(5):591-600.

Ye et al., Human Leukocyte antigen G expression: as a significant prognostic indicator for patients with colorectal cancer (2007) Modem Pathology 20 (3):375-383.

Tanabe et al. Structural and Functional Analysis of Monomorphic Determinants Recognized by Monoclonal Antibodies Reacting with the HLA Class I Domain (1992) Journal of Immunology 148 (10): 3202-3209.

Clements, C.S. et al., "Crystal structure of HLA-G: A nonclassical MHC class I molecule expressed at the fetal-maternal interface" PNAS, vol. 102, No. 9, Mar. 1, 2005 pp. 3360-3365.

Excerpt of p. 735 from Janeway's Immunobiology, p. 735, eds. Murphy et al., 7th ed., 2008.

Experimental data: 15E7 Blocking HLA-G6/ILT4 Interaction.

MEM-G/04 datasheets (GeneTex).

Ab7759 Data Sheet, ABcam, UK.

HC10 Data Sheet, Mouse anti Human HLA Class I Heavy Chain (Restricted expression), Nordic-MUbio, pp. 1-3.

Excerpt from "DNA Vaccines: Methods and Protocols" (2000) pp. 37-38.

Alignment of the amino acid sequence of the 3 domain of HLA-G with antigenic determinant C.

Annex 2—Characterization of 01G Antibody.

Annex 3—Alpha 3 Domain Immunization of Mice and Rabbits and Characterization of Obtained Sera and Monoclonal Antibodies.

Annex 4—1537 Specificity and Blocking Activity.

Annex 5—Hydrophobicity Profile of Alpha 3 Domain of HLA-G in Comparison to Other HLA-I.

Shiroishi, M, et al., Human Inhibitory receptors Ig-like transcript 2 (ILT2) and ILT4 compete with CDS for MHC class I binding and bind preferentially to HLA-G, PNAS, Jul. 22, 2003, vol. 100(15): 8856-8861.

Zhang, X. et al., "Methotrexate-Loaded PLGA Nanobubbles for Ultrasound Imaging and Synergistic Targeted Therapy of Residual Tumor During HIFU Ablation," Biomaterials (2014) vol. 35, pp. 5148-5161.

Aifen Lin et al: "Human Leukocyte Antigen-G (HLA-G) Expression in Cancers: Roles in Immune Evasion, Metastasis and Target for Therapy", Molecular Medicine, vol. 21, No. 1, Jan. 1, 2015 (Jan. 1, 2015), p. 1, XP055365402, Washington, DC; US ISSN: 1076-1551, DOI: 10.2119/molmed.2015.00083 the whole document, in particular p. 788, middle column-p. 789, left-hand column, first paragraph; figure 3.

Opposition of European Patent No. 2917229 (Application No. 13791794.4) filed by Regimbeau.

Opposition of European Patent No. 2917229 (Application No. 13791794.4) filed by Venner Shipley.

Opposition of European Patent No. 2917229 (Application No. 13791794.4) filed by F. Hoffman-La Roche AG.

Opposition of European Patent No. 2917229 (Application No. 13791794.4) filed by James Poole Limited.

Patentee (Invectys) Response to Opposition of European Patent No. 2917229 (Application No. 13791794.4).

Menier, Catherine et al., "Characterization of Monoclonal Antibodies Recognizing HLA-G or HLA-E: New Tools to Analyze the Expression of Nonclassical HLA Class I Molecules" Human Immunology, vol. 64, 2003, pp. 315-326.

Le Discorde, Magali et al., "HLA-G*0105N null allele encodes functional HLA-G isoforms." Biology of Reproduction, vol. 73(2), Aug. 2005, pp. 280-288.

Ishitani, Akiko et al., "Protein expression and peptide binding suggest unique and interacting functional roles for HLA-E, F, and G in maternal-placental immune recognition" The Journal of Immunology, Aug. 1, 2003; 171(3):1376-1384.

Gauster, M., et al.; Monoclonal antibody HC10 does not bind HLA-G; Rheumatology 46, 892-893 (2007).

Fournel S, et al., Comparative reactivity of different HLA-G monoclonal antibodies to soluble HLA-G molecules. Tissue Antigens. Jun. 2000;55(6):510-8.

Apps R, et al., A critical look at HLA-G. Trends Immunol. Jul. 2008;29(7):313-21.

McMaster M, et al., HLA-G isoforms produced by placental cytotrophoblasts and found in amniotic fluid are due to unusual glycosylation. J Immunol. Jun. 15, 1998;160(12) :5922-5928.

Van Lierop MJ, et al., Detection of HLA-G by a specific sandwich ELISA using monoclonal antibodies G233 and 56B. Mal Hum Reprod 2002 Aua;B(S):776-784.

Le Rond S, et al., Alloreactive CD4+ and CDS+ T cells express the immunotolerant HLA-G molecule in mixed ymphocyte reactions: in vivo implications in transplanted patients. Eur J Immunol. Mar. 2004;34(3) :649-660.

Desai, Smruti A. et al., "Chains-Microglobulin-Free HLA Class I Heavy-Microglobulin Associated and b2Antibody TP25.99 on b2 Determinants Recognized by Monoclonal Structural" The Journal of Immunology, 2000.

Chua et al. Chapter 40 Production of Monoclonal Antibody by DNA Immunization with Electroporation S. Li (ed.), Electroporation Protocols: Preclinical and Clinical Gene Medicine. Methods in Molecular Biology, vol. 423. 2008.

Nencioni et al., "Anticancer vaccination strategies" Annals of Oncology, 2004; 15 Suppl 4:iv153-60.

Kutzler, Michele A. et al., "DNA vaccines: ready for prime time?" Nature Reviews Genetics, Oct. 2008;9(10);174378.

Fioretti, Daniela et al., "DNA vaccines: developing new strategies against cancer" Journal of Biomedicine and Biotechnology, 2010;2010:174378.

Laddy, et al., "From Plasmids to Protection: A Review of DNA Vaccines Against Infectious Diseases" International Reviews of Immunology, 25:99-123, 2006.

Saade, Fadi et al., "Technologies for enhanced efficacy of DNA vaccines" Expert Rev. Vaccines, 11(2). 189-209 Feb. 2012.

Chaplin, David D., "Overview of the immune response" J Allergy Clin. Immunol, Feb. 2010; 125(2 Suppl 2): S3-23.

Xing Y, Hogquist KA. T-cell tolerance: central and peripheral. Cold Spring Harb Perspect Biol. Jun. 1, 2012 ;4(6): a006957.

Carosella et al. Beyond the increasing complexity of the immunomodulatory HLA-G molecule. Blood (2008) 111(10): 4862-4870 (a). HLA-G isoforms structures.

Pelanda et al., "Central B-cell tolerance: where selection begins" Cold Spring Harb Perspect Bio, Apr. 1, 2012:4(4):a007146.

Barnstable et al., "Production of monoclonal antibodies to group A erythrocytes, HLA and other human cell surface antigens-new tools for genetic analysis" Cell, May 1978; 14)1);9-20 (cited in Annex 1 and Annex 2).

Angal et al., "A single amino acid substitution abolishes the heterogeneity of chimeric mouse/human (IgG4) antibody" Molecular Immunology, Jan. 1993;30(1); 105-8 (cited in Annex 4).

Geraghty, D.E., et al., A human major histocompatibility complex class I gene that encodes a protein with shortened cytoplasmic segment. Proc. Natl. Acad. Sci. USA, 1987. 84(1): p. 9145-9149.

(56) References Cited

OTHER PUBLICATIONS

Agaugue, Sophie et al., "A human major histocompatibility complex class I gene that encodes a protein with shortened cytoplasmic segment." Immunobiology, 2011.
Carosella et al. HLA-G: from biology to clinical benefits Trends in Immunology vol. 29 No. 3 (126:132) 2008 (b).
Naji A, et al., Soluble HLA-G and HLA-G1 expressing antigen-presenting cells inhibit Tcell alloproliferation through IL T- 2/IL T-4/Faslmediated pathways. Hum Immunol. Apr. 2007;68(4):233-9.
Tran, Tri Minh, et al., The epitope recognized by pan-HLA class l-reactive monoclonal antibody W6/32 and its relationship to unusual stability of the HLA-B27 /~2-microglobulin complex.
Pule et al., "A chimeric T cell antigen receptor that augments cytokine release and supports clonal expansion of primary human T cells" Moleculalr Therapy: The Journal of the American Society of Gene Therapy, Academic Press; Nature Publishing Group, US, vol. 12, No. 5, Nov. 1, 2005 (Nov. 1, 2005).
Li Hua et al.: "Increasing the safety and efficacy of chimeric antigen receptor T Cell therapy", Protein & Cell, Springer Asia, Beijing, CN, vol. 8, No. 8, Apr. 22, 2017 (Apr. 22, 2017).
ANNEX 1—MEM-G/04 Specificity and Blocking Activity.
Riteau, B. et al., HLA-G2, -G3, and -G4 Isoforms Expressed as Nonmature Cell Surface Glycoproteins Inhibit NK and Antigen-Specific CTL Cytolysis Journal of Immunology, 2001; 166:5018-5026.
Le Gal, et al., HLA-G-mediated inhibition of antigen-specific cytotoxid T Lymphocytes, International Immunology, vol. 11, No. 8, pp. 1351-1356.
Paul, Pascale, et al., HLA-G expression in melanoma: A way for tumor cells to escape from immunosurveillance, Proc. Natl. Acad. Sci. USA vol. 95, pp. 4510-4515, Apr. 1998.
Paul, Pascale, et al., HLA-G, -E, -F Preworkshop: Tools and Protocols for Analysis of Non-Classical Class I Genes Transcription and Protein Expression, Human Immunology 61, 1177-1195 (2000).
Shiroishi, Mitsunori, et al.; Structural basis for recognition of the nonclassical MHC molecule HLA-G by the leukocyte lg-like receptor B2 (LILRB2/LIR2/ILT4/CD85d); 16412-16417, PNAS, Oct. 31, 2006, vol. 103, No. 44.
Loumagne, Laure, et al., "Alloreactive CD4+ and CDS+ T cells express the immunotolerant HLA-G molecule in mixed lymphocyte reactions: in vivo implications in transplanted patients.in vivo evidence that secretion of HLA-G by immunogenic tumor cells allows their evasion from immunosurveillance", International Journal of Cancer, 135, 2107-2117(2014).
Agaugue, S., et al., Role of HLA-G in tumor escape through expansion of myeloid-derived suppressor cells and cytokinic balance in favor of Th2 versus TM/TM1. Blood, 2011.117(26): p. 7021-7031.
Yari, F et al., "Production and Characterization of Monoclonal Antibodies with Specificity for Human HLA-G Isoforms" Hybridoma and Hybridomics, vol. 22, No. 5, 2003 particular relevance: pp. 301-306.
Rouas-Freiss, N et al., "Expression of tolerogenic HLA-G molecules in cancer prevents antitumor responses" Seminars in Cancer Biology, vol. 17, 2007, 413-421 (2007).
Desai, S, et al. Structural Relatedness of Distinct Determinants Recognized by Monoclonal Antibody TP25.99 on B2-Microglobulin-Associated and B2-Microglobulin-Free HLA Class I Heavy Chains, The Journal of Immunology, 2000, 165: 3275-3283.
Boyson, J et al., "Disulfide bond-mediated dimerization of HLA-G on the cell surface" PNAS, vol. 99, No. 25, 2002 16180-16185 (2002).
Kobayashi, Y et al., "Establishment of a Choriocarcinoma Model from Immortalized Normal Extravillous Trophoblast Dells Transduced with HRASV12" The Ameican Journal of Pathology, vol. 179, No. 3, Sep. 3, 2011, 1471-1482 (2011).
Mansfield, A et al., "Regional immunity in melanoma: immunosuppressive changes precede nodal metastasis" Modern Pathol, vol. 24, 2011 particular relevance: pp. 487-494 487-494 (2011).
Diaz-Lagares, A et al., "Nitric oxide produces HLA-G nitration and induces metalloprotease-dependent shedding creating a tolerogenic milieu" Immunology, vol. 126, No. 3, 2008, 436-445.
Paul, P et al., "HLA-G expression in Melanoma: A way for tumor cells to escape from immunosurveillance" PNAS, vol. 95, No. 8, 1998, pp. 4510-4515.
Markel, G et al., "Preclinical Evaluation of Adoptive Cell Therapy for Patients with Metastatic Renal Cell Carcinoma" Anticancer Research, vol. 29, 2009, pp. 145-154.
Lin, A et al., "HLA-G expression in Human ovarian carcinoma counteracts NK cell function" Annals of Oncology, vol. 18, 2007, pp. 1804-1809.
Pirrone et al., Applications of Hydrogen/Deuterium Exchange MS from 2012 to 2014, (2015) Analytical Chemistry 87: 99-118.
Morales et al., Placental Cell Expression of HLA-G2 Isoforms is Limited to the Invasive Trophoblast Phenotype, (2003) J. Immunol. 171 (11): 6215-6224.
Furukawa et al., Evaluation of the Reactivity and Receptor Competition of HLA-G Isoforms toward Available Antibodies: Implications of Structural Characteristics of HLA-G Isoforms (2019) Int. J. Mol. Sci. 20: 5947.

| Clone ID | Avid | | Monovalent | |
|---|---|---|---|---|
| | $K_D$ (M) | $k_{off}$ (S$^{-1}$) | $K_D$ (M) | $k_{off}$ (S$^{-1}$) |
| 38373 | 1.16E-11 | 1.18E-05 | 1.16E-09 | 4.23E-04 |
| 38375 | 2.14E-11 | 4.01E-05 | 2.83E-09 | 2.16E-03 |
| 38379 | 1.02E-11 | 1.61E-05 | 8.76E-10 | 4.05E-04 |
| 38381 | 7.17E-12 | 3.82E-05 | 1.31E-09 | 3.41E-04 |
| 38383 | 2.02E-11 | 3.82E-05 | 1.73E-09 | 1.38E-03 |
| 38410 | 1.53E-11 | 2.36E-05 | 1.36E-09 | 4.12E-04 |
| 38418 | 5.18E-11 | 3.55E-05 | 2.22E-09 | 1.45E-03 |
| 38422 | 5.75E-11 | 3.86E-05 | 1.97E-09 | 1.26E-03 |
| 38425 | 1.52E-11 | 3.32E-05 | 1.45E-09 | 6.74E-04 |
| 38426 | 1.68E-11 | 2.33E-05 | 1.01E-09 | 3.22E-04 |
| 37323 | 6.16E-12 | 1.57E-05 | 3.13E-09 | 1.08E-03 |
| 38389 | <1.0E-12 | <1.0E-07 | 5.58E-10 | 2.00E-04 |
| 38358 | 6.02E-12 | 1.73E-05 | 1.87E-10 | 8.35E-05 |
| 33351 | 2.32E-10 | 1.21E-04 | 2.08E-07 | 3.19E-02 |
| 33357 | 1.48E-10 | 1.50E-05 | 8.15E-09 | 2.45E-03 |
| 33303 | <1.0E-12 | <1.0E-07 | 1.73E-08 | 2.90E-03 |
| 33342 | 1.73E-09 | 2.56E-05 | ND | |
| 33343 | 1.54E-09 | 5.43E-03 | ND | |
| 33299 | 1.46E-09 | 7.00E-03 | ND | |
| 33361 | 1.17E-08 | 3.37E-03 | ND | |

FIG. 1

| Examples | Octet Bin | Alpha 3 Swap | R131A/S132A | F195S | D196A | Y197A | Y197H | E198A |
|---|---|---|---|---|---|---|---|---|
| MEMG/9 | | ++ | ++ | ++ | ++ | ++ | ++ | ++ |
| W6/32 | | ++ | ++ | ++ | ++ | ++ | ++ | ++ |
| 33303 | 3 | ++ | - | ++ | ++ | ++ | ++ | ++ |
| 37323 | 2 | ++ | ++ | ++ | ++ | ++ | + | ++ |
| 38358 | 1b | - | ++ | - | ++ | - | - | NA |
| 38373, 38375, 38379, 38381 | 1a | - | ++ | - | ++ | - | + | + |
| 38410, 38418, 38422, 38426 | 1a | - | ++ | - | ++ | + | + | - | ism. HLA-G expression is upregulated on a broad spectrum of tumors and is associated with poor prognosis and disease progression. Serum HLA-G levels are elevated in breast, lung, colorectal cancer (CRC), gastric, esophageal, neuroblastoma, cervical, and hematological cancers. HLA-G has also been found to be correlated with clinical parameters in advanced disease, such as, tumor metastasis, poor prognosis, immune escape, and tumor invasiveness.

HLA-G is an attractive target for diseases, such as, for example, cancer.

ANTI-HLA-G ANTIBODIES, COMPOSITIONS COMPRISING ANTI-HLA-G ANTIBODIES AND METHODS OF USING ANTI-HLA-G ANTIBODIES

RELATED APPLICATION

This application claims priority to U.S. provisional application No. 62/737,666, filed Sep. 27, 2018, which is incorporated by reference herein in its entirety.

FIELD

Provided herein are antibodies with binding specificity for HLA-G and compositions comprising the antibodies, including pharmaceutical compositions, diagnostic compositions, and kits. Also provided are methods of using anti-HLA-G antibodies for therapeutic and diagnostic purposes.

BACKGROUND

HLA-G histocompatibility antigen, class I, G, also known as human leukocyte antigen G (HLA-G), is a protein that in humans is encoded by the HLA-G gene. HLA-G belongs to the HLA nonclassical class I heavy chain paralogues. HLA-G is a heterodimer consisting of a heavy chain and a light chain (beta-2 microglobulin). There are membrane bound and soluble forms of HLA-G.

HLA-G is normally expressed at the maternal-fetal interface and other immune-privileged sites. HLA-G may play a role in immune tolerance in pregnancy, being expressed in the placenta by extravillous trophoblast cells, while the classical MHC class I genes (HLA-A and HLA-B) are not. As HLA-G was first identified in placenta samples, many studies have evaluated its role in pregnancy disorders, such as preeclampsia and recurrent pregnancy loss. See, Michita, Rafael Tomoyaet al., *Human Immunology.* 2016, 77 (10): 892-897, which is incorporated by reference herein in its entirety, including any drawings.

HLA-G has been shown to be immune-suppressive. By binding receptors expressed on various myeloid and lymphoid cells, HLA-G may directly inhibit the functions of NK cells, cytotoxic T-lymphocytes, B cells, neutrophils, monocytes, macrophages and dendritic cells. HLA-G also inhibits T and NK cell proliferation and cytolytic activities. HLA-G suppresses phagocytosis and induces the generation or expansion of regulatory T cells.

HLA-G mediates immune function through at least three ITIM-containing inhibitory receptors, ILT2, ILT4, and KIR2DL4. On lymphoid and myeloid cells, for example, HLA-G mediates function through ILT2. On myeloid cells, HLA-G mediates function through ILT4. On decidual NK cells, HLA-G mediates immune function through KIR2DL4 and ILT2.

HLA-G is an immune checkpoint target. HLA-G can directly inhibit immune cell function through receptor binding and/or trogocytosis and impairment of chemotaxis. HLA-G can lend tumor cells a higher invasive and metastatic potential. HLA-G promotes evasion of tumor immune surveillance, and enhances metastasis and the progression of malignancies. During tumor progression HLA-G has other effects, such as, inhibition of immune cell cytolysis, induction of immune cell apoptosis, and/or the generation of regulatory cells through receptor binding and/or trogocytosis.

SUMMARY

Provided herein are antibodies that selectively bind HLA-G. In some embodiments, the antibodies bind human HLA-G. In some embodiments, the antibodies comprise at least one CDR sequence defined by a consensus sequence provided in this disclosure. In some embodiments, the antibodies comprise one or more of an illustrative CDR, $V_H$, or $V_L$ sequence provided in this disclosure, or a variant thereof. In some aspects, the variant is a variant with one or more conservative amino acid substitutions.

Also provided are compositions and kits comprising the antibodies. In some embodiments, the compositions are pharmaceutical compositions. Any suitable pharmaceutical composition may be used. In some embodiments, the pharmaceutical composition is a composition for parenteral administration.

This disclosure also provides methods of using the anti-HLA-G antibodies provided herein. In some embodiments, the method is a method of treatment. In some embodiments, the method is an analytical method. In some embodiments, the method is a method of purifying and/or quantifying HLA-G.

In some embodiments, the method is a diagnostic method. In some embodiments, the diagnostic method comprises or consists of detecting tumor expressed HLA-G. In some embodiments, the diagnostic method comprises or consists of detecting soluble HLA-G. In some embodiments, the detection method comprises of consists of detecting HLA-G expression on immune cells.

In some embodiments, the antibodies are used to treat a disease or condition. In some aspects, the disease or condition is selected from a cancer, autoimmune disease, and infection. Some aspects provide for the use of any of the antibodies or pharmaceutical compositions provided herein to treat a disease or condition selected from a cancer, autoimmune disease, and infection.

BRIEF DESCRIPTION OF THE DRAWINGS

FIG. 1 provides a table showing avid and monomeric affinities of anti-HLA-G antibodies to recombinant HLA-G protein.

FIG. 6A and FIG. 6B provide evaluation of phagocytosis in a human macrophage assay. FIG. 6C provides evaluation of primary human NK cell cytotoxic activity. FIG. 6D provides evaluation of primary human CD8+ T cell function.

DETAILED DESCRIPTION

1. Definitions

Figure 2A:
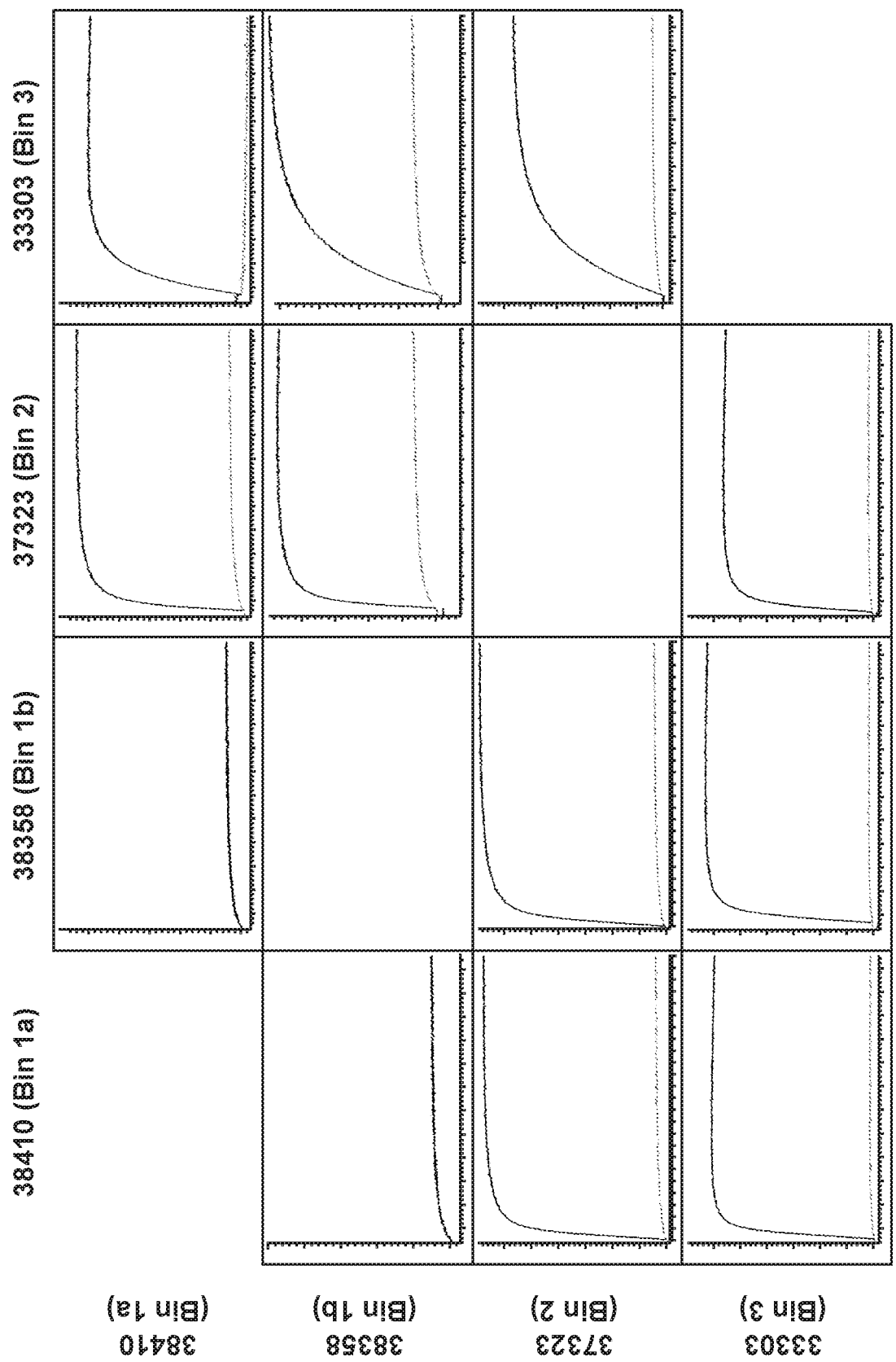
FIG. 2A and FIG. 2B provide biolayer interferometry sensorgrams showing anti-HLA-G antibodies that bind to HLA-G and can be separated into three biochemical bins based on their ability to cross-block each other when tested for binding in pairwise fashion.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value±10%, ±5%, or ±1%. In certain embodiments, the term "about" indicates the designated value±one standard deviation of that value.

The term "combinations thereof" includes every possible combination of elements to which the term refers.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region (CH). The heavy chain constant region typically comprises three domains, $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" describes a type of immunoglobulin molecule and is used herein in its broadest sense. An antibody specifically includes intact antibodies (e.g., intact immunoglobulins), and antibody fragments and antigen binding proteins. Antibodies comprise at least one antigen-binding domain. One example of an antigen-binding domain is an antigen binding domain formed by a $V_H$-$V_L$ dimer. An "HLA-G antibody," "anti-HLA-G antibody," "HLA-G Ab," "HLA-G-specific antibody," or "anti-HLA-G Ab" is an antibody, as described herein, which binds specifically to the antigen HLA-G.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and confer antigen specificity and binding affinity to the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

Unless otherwise specified, the numbering scheme used for identification of a particular CDR herein is the Kabat/Chothia numbering scheme. Where the residues encompassed by these two numbering schemes diverge, the numbering scheme is specified as either Kabat or Chothia.

TABLE 1

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain (Cm) of the heavy chain. Fab fragments may be generated, for example, by papain digestion of a full-length antibody.

"F(ab')$_2$" fragments contain two Fab' fragments joined, near the hinge region, by disulfide bonds. F(ab')$_2$ fragments may be generated, for example, by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety. "scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is provided as a solution comprising at least 85%, 90%, 95%, 98%, 99% to 100% by weight of an antibody, the remainder of the weight comprising the weight of other solutes dissolved in the solvent.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein.

Affinity can be determined, for example, using surface plasmon resonance (SPR) technology, such as a Biacore® instrument, or using bio-layer interferometry technology, such as an Octet® instrument.

With regard to the binding of an antibody to a target molecule, the terms "specific binding," "specifically binds to," "specific for," "selectively binds." and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that is similar to the target, such as an excess of non-labeled target. In that case, specific binding is indicated if the binding of the labeled target to a probe is competitively inhibited by the excess non-labeled target.

The term "$k_d$" (sec$^{-1}$), as used herein, refers to the dissociation rate constant of a particular antibody-antigen interaction. This value is also referred to as the $k_{off}$ value.

The term "$k_a$" (M$^{-1}$×sec$^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$.

The term "$K_A$" (M$^{-1}$), as used herein, refers to the association equilibrium constant of a particular antibody-antigen interaction. $K_A = k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example. Marks et al. (*Bio/Technology*, 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.*, 1994, 91:3809-3813); Schier et al., *Gene*, 1995, 169:147-155; Yelton et al., *J. Immunol.*, 1995, 155:1994-2004: Jackson et al., *J. Immunol.*, 1995, 154:3310-33199; and Hawkins et al, *J. Mol. Biol.*, 1992, 226:889-896, each of which is incorporated by reference in its entirety.

When used herein in the context of two or more antibodies, the term "competes with" or "cross-competes with" indicates that the two or more antibodies compete for binding to an antigen (e.g., HLA-G). In one exemplary assay, HLA-G is coated on a plate and allowed to bind a first antibody, after which a second, labeled antibody is added. If the presence of the first antibody reduces binding of the second antibody, then the antibodies compete. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 900%.

The term "epitope" means a portion of an antigen capable of specific binding to an antibody. Epitopes frequently consist of surface-accessible amino acid residues and/or sugar side chains and may have specific three-dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to HLA-G variants with different point-mutations.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, or CLUSTAL OMEGA software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of one or more amino acids with one or more chemically or functionally similar amino acids. Conservative substitution tables providing similar amino acids are well known in the art. Polypeptide sequences having such substitutions are known as "conservatively modified variants." By way of example, the following groups of amino acids are considered conservative substitutions for one another.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

| | |
|---|---|
| Alcohol Group-Containing Residues | S and T |
| Aliphatic Residues | I, L, V, and M |
| Cycloalkenyl-associated Residues | F, H, W, and Y |
| Hydrophobic Residues | A, C, F, G, H, I, L, M, V, W, and Y |
| Negatively Charged Residues | D and E |
| Polar Residues | C, D, E, H, K, N, Q, R, S, and T |
| Positively Charged Residues | H, K, and R |
| Small Residues | A, C, D, G, N, P, S, T, and V |
| Very Small Residues | A, G, and S |
| Residues Involved in Turn Formation | A, C, D, E, G, H, K, N, Q, R, S, P and T |
| Flexible Residues | Q, T, K, S, G, P, D, E, and R |

| | |
|---|---|
| Group 1 | A, S, and T |
| Group 2 | D and E |
| Group 3 | N and Q |
| Group 4 | R and K |

| | |
|---|---|
| Group 5 | I, L, and M |
| Group 6 | F, Y, and W |

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gin; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "therapeutically effective amount" or "effective amount" refers to an amount of an antibody or composition that when administered to a subject is effective to treat a disease or disorder.

As used herein, the term "subject" means a mammalian subject. Exemplary subjects include, but are not limited to humans, monkeys, dogs, cats, mice, rats, cows, horses, camels, avians, goats and sheep. In certain embodiments, the subject is a human. In some embodiments, the subject has cancer, an autoimmune disease or condition, and/or an infection that can be treated with an antibody provided herein. In some embodiments, the subject is a human that is suspected to have cancer, an autoimmune disease or condition, and/or an acute infection and chronic infection.

2. Antibodies

Provided herein are antibodies that selectively bind human HLA-G. In some aspects, the antibody selectively binds to the extracellular domain of human HLA-G.

In some embodiments, the antibody has one or more CDRs having particular lengths, in terms of the number of amino acid residues. In some embodiments, the Chothia CDR-H1 of the antibody is 6, 7, 8, or 9 residues in length. In some embodiments, the Kabat CDR-H1 of the antibody is 4, 5, 6, or 7 residues in length. In some embodiments, the Chothia CDR-H2 of the antibody is 5, 6, or 7 residues in length. In some embodiments, the Kabat CDR-H2 of the antibody is 15, 16, 17, or 18 residues in length. In some embodiments, the Kabat/Chothia CDR-H3 of the antibody is 5, 6, 7, 8, 9, 10, 11, 12, 13, 14 residues in length.

In some aspects, the Kabat/Chothia CDR-L1 of the antibody is 9, 10, 11, 12, 13, 14, 15, or 16 residues in length. In some aspects, the Kabat/Chothia CDR-L2 of the antibody is 6, 7, or 8 residues in length. In some aspects, the Kabat/Chothia CDR-L3 of the antibody is 8, 9, 10, 1, or 12 residues in length.

In some embodiments, the antibody comprises a light chain. In some aspects, the light chain is a kappa light chain. In some aspects, the light chain is a lambda light chain.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

In some embodiments, the antibody is an affinity matured antibody. In some aspects, the antibody is an affinity matured antibody derived from an illustrative sequence provided in this disclosure.

In some embodiments, the antibody blocks HLA-G interaction and/or binding to an ITIM inhibitory receptor. In some embodiments, the antibody blocks HLA-G interaction and/or binding to ILT2. In some embodiments, the antibody blocks HLA-G interaction and/or binding to ILT4. In some embodiments, the antibody blocks HLA-G interaction and/or binding to KIR2DL4. In embodiments, the antibody binds HLA-G but does not block the interaction between HLA-G and ILT2, ILT4, and/or KIRDL4. In some embodiments, the antibody disrupts HLA-G heterodimer and/or prevents dimerization of HLA-G.

In some embodiments, the antibody inhibits immune suppressive function. In some embodiments, the antibody inhibits HLA-G mediated suppression of NK cells. In some embodiments, the antibody inhibits HLA-G mediated suppression of cytotoxic T lymphocytes. In some embodiments, the antibody inhibits HLA-G mediated suppression of B cells. In some embodiments, the antibody inhibits HLA-G mediated suppression of neutrophils. In some embodiments, the antibody inhibits HLA-G mediated suppression of dendritic cells. In some embodiments, the antibody inhibits HLA-G mediated suppression of macrophages. In some embodiments, the antibody inhibits HLA-G mediated suppression of monocytes. In some embodiments, the antibody inhibits HLA-G mediated suppression of NK and/or T cell cytolysis and/or proliferation.

In some embodiments, the antibody prevents or inhibits HLA-G mediated suppression of phagocytosis. In some embodiments, the antibody mediates HLA-G mediated induction of T regulatory cells. In some embodiments, the antibody prevents or inhibits the generation or expansion of regulatory T cells.

The antibodies provided herein may be useful for the treatment of a variety of diseases and conditions, including cancers, autoimmune diseases, and infections. In some embodiments, the antibody inhibits HLA-G function on tumor cells. In some embodiments, the antibody inhibits HLA-G function on immune cells. In some embodiments, the antibody inhibits HLA-G function on myeloid cells. In some embodiments, the antibody inhibits HLA-G function on Tcell subsets. In some embodiments, the antibody inhibits metastasis. In some embodiments, the antibody inhibits angiogenesis.

In some embodiments, the antibody competes or is capable of competing for binding to human HLA-G with another antibody. In some embodiments, the antibody comprises or consists an antibody that is capable of competing for binding to human HLA-G with a reference antibody, wherein the reference antibody binds to an epitope comprising position 195, 197, and/or 198 of SEQ ID NO: 342 on a human HLA-G polypeptide. In some embodiments, the antibody and the reference antibody cross-compete or are capable of cross-competing for binding to human HLA-G with another antibody.

In some embodiments, the antibody binds to an epitope comprising position 195, 197, and/or 198 of SEQ ID NO: 342 on a human HLA-G polypeptide. In some aspects, the epitope comprises or consists of a contiguous or non-contiguous span of amino acids including residues 195, 197, and/or 198 of the sequence set forth in SEQ ID NO: 342. In some aspects, the epitope comprises a sequence that is identical or corresponds to residues 195, 197, and/or 198 of a sequence that is within the sequence set forth in SEQ ID NO: 342. In some aspects, the epitope has a sequence that has a 60%, 65%, 70%, 75%, 80%, 85%, 90%, or 95% identity to a sequence that is within the sequence set forth in SEQ ID NO: 342. In some aspects, the epitope has 1, 2, 3, 4, 5, 6, 7, 8, or 9 substitutions from a sequence that is within the sequence set forth in forth in SEQ ID NO: 342. In some aspects, the epitope has 1, 2, or 3 substitutions from residues a sequence that is within the sequence set forth in SEQ ID NO: 342. In some aspects, the antibody makes contact with any of the residues set forth in FIG. 9.

2.1. CDR-H3 Sequences

In some embodiments, the antibody comprises a CDR-H3 sequence comprising, consisting of, or consisting essentially of a sequence selected from SEQ ID NOS: 76-101. In some aspects, the antibody comprises a CDR-H3 sequence comprising, consisting of, or consisting essentially of SEQ ID NO: 76. In some aspects, the antibody comprises a CDR-H3 sequence comprising, consisting of, or consisting essentially of SEQ ID NO: 77. In some aspects, the antibody comprises a CDR-H3 sequence comprising, consisting of, or consisting essentially of SEQ ID NO: 78. In some aspects, the antibody comprises a CDR-H3 sequence comprising, consisting of, or consisting essentially of SEQ ID NO: 79. In some aspects, the antibody comprises a CDR-H3 sequence comprising, consisting of, or consisting essentially of SEQ ID NO: 80. In some aspects, the antibody comprises a CDR-H3 sequence comprising, consisting of, or consisting essentially of SEQ ID NO: 81. In some aspects, the antibody comprises a CDR-H3 sequence comprising, consisting of, or consisting essentially of SEQ ID NO: 82. In some aspects, the antibody comprises a CDR-H3 sequence comprising, consisting of, or consisting essentially of SEQ ID NO: 83. In some aspects, the antibody comprises a CDR-H3 sequence comprising, consisting of, or consisting essentially of SEQ ID NO: 84. In some aspects, the antibody comprises a CDR-H3 sequence comprising, consisting of, or consisting essentially of SEQ ID NO: 85. In some aspects, the antibody comprises a CDR-H3 sequence comprising, consisting of, or consisting essentially of SEQ ID NO: 86. In some aspects, the antibody comprises a CDR-H3 sequence comprising, consisting of, or consisting essentially of SEQ ID NO: 87. In some aspects, the antibody comprises a CDR-H3 sequence comprising, consisting of, or consisting essentially of SEQ ID NO: 88. In some aspects, the antibody comprises a CDR-H3 sequence comprising, consisting of, or consisting essentially of SEQ ID NO: 89. In some aspects, the antibody comprises a CDR-H3 sequence comprising, consisting of, or consisting essentially of SEQ ID NO: 90. In some aspects, the antibody comprises a CDR-H3 sequence comprising, consisting of, or consisting essentially of SEQ ID NO: 91. In some aspects, the antibody comprises a CDR-H3 sequence comprising, consisting of, or consisting essentially of SEQ ID NO: 92. In some aspects, the antibody comprises a CDR-H3 sequence comprising, consisting of, or consisting essentially of SEQ ID NO: 93. In some aspects, the antibody comprises a CDR-H3 sequence comprising, consisting of, or consisting essentially of SEQ ID NO: 94. In some aspects, the antibody comprises a CDR-H3 sequence comprising, consisting of, or consisting essentially of SEQ ID NO: 95. In some aspects, the antibody comprises a CDR-H3 sequence comprising, consisting of, or consisting essentially of SEQ ID NO: 96. In some aspects, the antibody comprises a CDR-H3 sequence comprising, consisting of, or consisting essentially of SEQ ID NO: 97. In some aspects, the antibody comprises a CDR-H3 sequence comprising, consisting of, or consisting essentially of SEQ ID NO: 98. In some aspects, the antibody comprises a CDR-H3 sequence comprising, consisting of, or consisting essentially of SEQ ID NO: 99. In some aspects, the antibody comprises a CDR-H3 sequence comprising, consisting of, or consisting essentially of SEQ ID NO: 100. In some aspects, the antibody comprises a CDR-H3 sequence comprising, consisting of, or consisting essentially of SEQ ID NO: 101.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

2.2. $V_H$ Sequences Comprising Illustrative CDRs

In some embodiments, the antibody comprises a $V_H$ sequence comprising one or more CDR-H sequences comprising, consisting of, or consisting essentially of one or more illustrative CDR-H sequences provided in this disclosure, and variants thereof.

2.2.1. V$_H$ Sequences Comprising Illustrative Kabat CDRs

In some embodiments, the antibody comprises a V$_H$ sequence comprising one or more Kabat CDR-H sequences comprising, consisting of, or consisting essentially of one or more illustrative Kabat CDR-H sequences provided in this disclosure, and variants thereof.

2.2.1.1. Kabat CDR-H3

In some embodiments, the antibody comprises a V$_H$ sequence comprising a Kabat CDR-H3 sequence comprising, consisting of, or consisting essentially of a sequence selected from SEQ ID NOS: 76-101. In some aspects, the antibody comprises a V$_H$ sequence comprising a Kabat CDR-H3 sequence comprising, consisting of, or consisting essentially of SEQ ID NO: 76. In some aspects, the antibody comprises a V$_H$ sequence comprising a Kabat CDR-H3 sequence comprising, consisting of, or consisting essentially of SEQ ID NO: 77. In some aspects, the antibody comprises a V$_H$ sequence comprising a Kabat CDR-H3 sequence comprising, consisting of, or consisting essentially of SEQ ID NO: 78. In some aspects, the antibody comprises a V$_H$ sequence comprising a Kabat CDR-H3 sequence comprising, consisting of, or consisting essentially of SEQ ID NO: 79. In some aspects, the antibody comprises a V$_H$ sequence comprising a Kabat CDR-H3 sequence comprising, consisting of, or consisting essentially of SEQ ID NO: 80. In some aspects, the antibody comprises a V$_H$ sequence comprising a Kabat CDR-H3 sequence comprising, consisting of, or consisting essentially of SEQ ID NO: 81. In some aspects, the antibody comprises a V$_H$ sequence comprising a Kabat CDR-H3 sequence comprising, consisting of, or consisting essentially of SEQ ID NO: 82. In some aspects, the antibody comprises a V$_H$ sequence comprising a Kabat CDR-H3 sequence comprising, consisting of, or consisting essentially of SEQ ID NO: 83. In some aspects, the antibody comprises a V$_H$ sequence comprising a Kabat CDR-H3 sequence comprising, consisting of, or consisting essentially of SEQ ID NO: 84. In some aspects, the antibody comprises a V$_H$ sequence comprising a Kabat CDR-H3 sequence comprising, consisting of, or consisting essentially of SEQ ID NO: 85. In some aspects, the antibody comprises a V$_H$ sequence comprising a Kabat CDR-H3 sequence comprising, consisting of, or consisting essentially of SEQ ID NO: 86. In some aspects, the antibody comprises a V$_H$ sequence comprising a Kabat CDR-H3 sequence comprising, consisting of, or consisting essentially of SEQ ID NO: 87. In some aspects, the antibody comprises a V$_H$ sequence comprising a Kabat CDR-H3 sequence comprising, consisting of, or consisting essentially of SEQ ID NO: 88. In some aspects, the antibody comprises a V$_H$ sequence comprising a Kabat CDR-H3 sequence comprising, consisting of, or consisting essentially of SEQ ID NO: 89. In some aspects, the antibody comprises a V$_H$ sequence comprising a Kabat CDR-H3 sequence comprising, consisting of, or consisting essentially of SEQ ID NO: 90. In some aspects, the antibody comprises a V$_H$ sequence comprising a Kabat CDR-H3 sequence comprising, consisting of, or consisting essentially of SEQ ID NO: 91. In some aspects, the antibody comprises a V$_H$ sequence comprising a Kabat CDR-H3 sequence comprising, consisting of, or consisting essentially of SEQ ID NO: 92. In some aspects, the antibody comprises a V$_H$ sequence comprising a Kabat CDR-H3 sequence comprising, consisting of, or consisting essentially of SEQ ID NO: 94. In some aspects, the antibody comprises a VF sequence comprising a Kabat CDR-H3 sequence comprising, consisting of, or consisting essentially of SEQ ID NO: 95. In some aspects, the antibody comprises a V$_H$ sequence comprising a Kabat CDR-H3 sequence comprising consisting of, or consisting essentially of SEQ ID NO: 96. In some aspects, the antibody comprises a V$_H$ sequence comprising a Kabat CDR-H3 sequence comprising, consisting of, or consisting essentially of SEQ ID NO: 97. In some aspects, the antibody comprises a V$_H$ sequence comprising a Kabat CDR-H3 sequence comprising, consisting of, or consisting essentially of SEQ ID NO: 98. In some aspects, the antibody comprises a V$_H$ sequence comprising a Kabat CDR-H3 sequence comprising, consisting of, or consisting essentially of SEQ ID NO: 99. In some aspects, the antibody comprises a V$_H$ sequence comprising a Kabat CDR-H3 sequence comprising, consisting of, or consisting essentially of SEQ ID NO: 100. In some aspects, the antibody comprises a V$_H$ sequence comprising a Kabat CDR-H3 sequence comprising, consisting of, or consisting essentially of SEQ ID NO: 101.

2.2.1.2. Kabat CDR-H2

In some embodiments, the antibody comprises a V$_H$ sequence comprising a Kabat CDR-H2 sequence comprising, consisting of, or consisting essentially of a sequence selected from SEQ ID NOS: 54-71. In some aspects, the antibody comprises a V$_H$ sequence comprising a Kabat CDR-H2 sequence comprising, consisting of, or consisting essentially of SEQ ID NO: 54. In some aspects, the antibody comprises a V$_H$ sequence comprising a Kabat CDR-H2 sequence comprising, consisting of, or consisting essentially of SEQ ID NO: 55. In some aspects, the antibody comprises a V$_H$ sequence comprising a Kabat CDR-H2 sequence comprising, consisting of, or consisting essentially of SEQ ID NO: 56. In some aspects, the antibody comprises a V$_H$ sequence comprising a Kabat CDR-H2 sequence comprising, consisting of, or consisting essentially of SEQ ID NO: 57. In some aspects, the antibody comprises a V$_H$ sequence comprising a Kabat CDR-H2 sequence comprising, consisting of, or consisting essentially of SEQ ID NO: 58. In some aspects, the antibody comprises a V$_H$ sequence comprising a Kabat CDR-H2 sequence comprising, consisting of, or consisting essentially of SEQ ID NO: 59. In some aspects, the antibody comprises a V$_H$ sequence comprising a Kabat CDR-H2 sequence comprising, consisting of, or consisting essentially of SEQ ID NO: 60. In some aspects, the antibody comprises a V$_H$ sequence comprising a Kabat CDR-H2 sequence comprising, consisting of, or consisting essentially of SEQ ID NO: 61. In some aspects, the antibody comprises a V$_H$ sequence comprising a Kabat CDR-H2 sequence comprising, consisting of, or consisting essentially of SEQ ID NO: 62. In some aspects, the antibody comprises a V$_H$ sequence comprising a Kabat CDR-H2 sequence comprising, consisting of, or consisting essentially of SEQ ID NO: 63. In some aspects, the antibody comprises a V$_H$ sequence comprising a Kabat CDR-H2 sequence comprising, consisting of, or consisting essentially of SEQ ID NO: 64. In some aspects, the antibody comprises a V$_H$ sequence comprising a Kabat CDR-H2 sequence comprising, consisting of, or consisting essentially of SEQ ID NO: 65. In some aspects, the antibody comprises a V$_H$ sequence comprising a Kabat CDR-H2 sequence comprising, consisting of, or consisting essentially of SEQ ID NO: 66. In some aspects, the antibody comprises a V$_H$ sequence comprising a Kabat CDR-H2 sequence comprising, consisting of, or consisting essentially of SEQ ID NO: 67. In some aspects, the antibody comprises a V$_H$ sequence comprising a Kabat CDR-H2 sequence comprising, consisting of, or consisting essentially of SEQ ID NO: 68. In some aspects, the antibody comprises a V$_H$ sequence comprising a Kabat CDR-H2 sequence comprising, consisting of, or consisting essentially of SEQ ID NO: 69. In some aspects, the antibody comprises a V$_H$ sequence comprising a Kabat CDR-H2 sequence comprising, consisting of, or consisting essentially of SEQ ID NO: 70. In some aspects, the antibody comprises a $V_H$ sequence comprising a Kabat CDR-H2 sequence comprising, consisting of, or consisting essentially of SEQ ID NO: 71.

2.2.1.3. Kabat CDR-H1

In some embodiments, the antibody comprises a $V_H$ sequence comprising a Kabat CDR-H1 sequence comprising, consisting of, or consisting essentially of a sequence selected from SEQ ID NOS: 18-34. In some aspects, the antibody comprises a $V_H$ sequence comprising a Kabat CDR-H1 sequence comprising, consisting of, or consisting essentially of SEQ ID NO: 18. In some aspects, the antibody comprises a $V_H$ sequence comprising a Kabat CDR-H1 sequence comprising, consisting of, or consisting essentially of SEQ ID NO: 19. In some aspects, the antibody comprises a $V_H$ sequence comprising a Kabat CDR-H1 sequence comprising, consisting of, or consisting essentially of SEQ ID NO: 20. In some aspects, the antibody comprises a $V_H$ sequence comprising a Kabat CDR-H1 sequence comprising, consisting of, or consisting essentially of SEQ ID NO: 21. In some aspects, the antibody comprises a $V_H$ sequence comprising a Kabat CDR-H1 sequence comprising, consisting of, or consisting essentially of SEQ ID NO: 22. In some aspects, the antibody comprises a $V_H$ sequence comprising a Kabat CDR-H1 sequence comprising, consisting of, or consisting essentially of SEQ ID NO: 23. In some aspects, the antibody comprises a $V_H$ sequence comprising a Kabat CDR-H1 sequence comprising, consisting of, or consisting essentially of SEQ ID NO: 24. In some aspects, the antibody comprises a $V_H$ sequence comprising a Kabat CDR-H1 sequence comprising, consisting of, or consisting essentially of SEQ ID NO: 25. In some aspects, the antibody comprises a $V_H$ sequence comprising a Kabat CDR-H1 sequence comprising, consisting of, or consisting essentially of SEQ ID NO: 26. In some aspects, the antibody comprises a $V_H$ sequence comprising a Kabat CDR-H1 sequence comprising, consisting of, or consisting essentially of SEQ ID NO: 27. In some aspects, the antibody comprises a $V_H$ sequence comprising a Kabat CDR-H1 sequence comprising, consisting of, or consisting essentially of SEQ ID NO: 28. In some aspects, the antibody comprises a $V_H$ sequence comprising a Kabat CDR-H1 sequence comprising, consisting of, or consisting essentially of SEQ ID NO: 29. In some aspects, the antibody comprises a $V_H$ sequence comprising a Kabat CDR-H1 sequence comprising, consisting of, or consisting essentially of SEQ ID NO: 30. In some aspects, the antibody comprises a $V_H$ sequence comprising a Kabat CDR-H1 sequence comprising, consisting of, or consisting essentially of SEQ ID NO: 31. In some aspects, the antibody comprises a $V_H$ sequence comprising a Kabat CDR-H1 sequence comprising, consisting of, or consisting essentially of SEQ ID NO: 32. In some aspects, the antibody comprises a $V_H$ sequence comprising a Kabat CDR-H1 sequence comprising, consisting of, or consisting essentially of SEQ ID NO: 33. In some aspects, the antibody comprises a $V_H$ sequence comprising a Kabat CDR-H1 sequence comprising, consisting of, or consisting essentially of SEQ ID NO: 34.

2.2.1.4. Kabat CDR-H3+Kabat CDR-H2

In some embodiments, the antibody comprises a $V_H$ sequence comprising a Kabat CDR-H3 sequence comprising, consisting of, or consisting essentially of a sequence selected from SEQ ID NOS: 76-101, and a Kabat CDR-H2 sequence comprising, consisting of, or consisting essentially of a sequence selected from SEQ ID NOS: 54-71. In some aspects, the Kabat CDR-H3 sequence and the Kabat CDR-H2 sequence are both from a single illustrative $V_H$ sequence provided in this disclosure. For example, in some aspects, the Kabat CDR-H3 and Kabat CDR-H2 are both from a single illustrative $V_H$ sequence selected from SEQ ID NOS: 170-200.

2.2.1.5. Kabat CDR-H3+Kabat CDR-H1

In some embodiments, the antibody comprises a $V_H$ sequence comprising a Kabat CDR-H3 sequence comprising, consisting of, or consisting essentially of a sequence selected from SEQ ID NOS: 76-101, and a Kabat CDR-H1 sequence comprising, consisting of, or consisting essentially of a sequence selected from SEQ ID NOS: 18-34. In some aspects, the Kabat CDR-H3 sequence and the Kabat CDR-H1 sequence are both from a single illustrative $V_H$ sequence provided in this disclosure. For example, in some aspects, the Kabat CDR-H3 and Kabat CDR-H1 are both from a single illustrative $V_H$ sequence selected from SEQ ID NOS: 170-200.

2.2.1.6. Kabat CDR-H1+Kabat CDR-H2

In some embodiments, the antibody comprises a $V_H$ sequence comprising a Kabat CDR-H1 sequence comprising, consisting of, or consisting essentially of a sequence selected from SEQ ID NOS: 18-34 and a Kabat CDR-H2 sequence comprising, consisting of, or consisting essentially of a sequence selected from SEQ ID NOS: 54-71. In some aspects, the Kabat CDR-H1 sequence and the Kabat CDR-H2 sequence are both from a single illustrative $V_H$ sequence provided in this disclosure. For example, in some aspects, the Kabat CDR-H1 and Kabat CDR-H2 are both from a single illustrative $V_H$ sequence selected from SEQ ID NOS: 170-200.

2.2.1.7. Kabat CDR-H1+Kabat CDR-H2+Kabat CDR-H3

In some embodiments, the antibody comprises a $V_H$ sequence comprising a Kabat CDR-H1 sequence comprising, consisting of, or consisting essentially of a sequence selected from SEQ ID NOS: 18-34, a Kabat CDR-H2 sequence comprising, consisting of, or consisting essentially of a sequence selected from SEQ ID NOS: 54-71, and a Kabat CDR-H3 sequence comprising, consisting of, or consisting essentially of a sequence selected from SEQ ID NOS: 76-101. In some aspects, the Kabat CDR-H1 sequence, Kabat CDR-H2 sequence, and Kabat CDR-H3 sequence are all from a single illustrative $V_H$ sequence provided in this disclosure. For example, in some aspects, the Kabat CDR-H1, Kabat CDR-H2, and Kabat CDR-H3 are all from a single illustrative $V_H$ sequence selected from SEQ ID NOS: 170-200.

In some aspects, the antibody comprises a $V_H$ sequence comprising a Kabat CDR-H1 sequence comprising SEQ ID NO: 18, a Kabat CDR-H2 sequence comprising SEQ ID NO: 54, and a Kabat CDR-H3 sequence comprising SEQ ID NO: 76. In some aspects, the antibody comprises a $V_H$ sequence comprising a Kabat CDR-H1 sequence comprising SEQ ID NO: 19, a Kabat CDR-H2 sequence comprising SEQ ID NO: 55, and a Kabat CDR-H3 sequence comprising SEQ ID NO: 77. In some aspects, the antibody comprises a $V_H$ sequence comprising a Kabat CDR-H1 sequence comprising SEQ ID NO: 20, a Kabat CDR-H2 sequence comprising SEQ ID NO: 56, and a Kabat CDR-H3 sequence comprising SEQ ID NO: 78. In some aspects, the antibody comprises a $V_H$ sequence comprising a Kabat CDR-H1 sequence comprising SEQ ID NO: 21, a Kabat CDR-H2 sequence comprising SEQ ID NO: 57, and a Kabat CDR-H3 sequence comprising SEQ ID NO: 79. In some aspects, the antibody comprises a $V_H$ sequence comprising a Kabat CDR-H1 sequence comprising SEQ ID NO: 22, a Kabat CDR-H2 sequence comprising SEQ ID NO: 58, and a Kabat CDR-H3 sequence comprising SEQ ID NO: 80. In some aspects, the antibody comprises a $V_H$ sequence comprising a Kabat CDR-H1 sequence comprising SEQ ID NO: 21, a Kabat CDR-H2 sequence comprising SEQ ID NO: 57, and a Kabat CDR-H3 sequence comprising SEQ ID NO: 76. In some aspects, the antibody comprises a $V_H$ sequence comprising a Kabat CDR-H1 sequence comprising SEQ ID NO: 23, a Kabat CDR-H2 sequence comprising SEQ ID NO: 59, and a Kabat CDR-H3 sequence comprising SEQ ID NO: 76. In some aspects, the antibody comprises a $V_H$ sequence comprising a Kabat CDR-H1 sequence comprising SEQ ID NO: 23, a Kabat CDR-H2 sequence comprising SEQ ID NO: 60, and a Kabat CDR-H3 sequence comprising SEQ ID NO: 81. In some aspects, the antibody comprises a $V_H$ sequence comprising a Kabat CDR-H1 sequence comprising SEQ ID NO: 23, a Kabat CDR-H2 sequence comprising SEQ ID NO: 59, and a Kabat CDR-H3 sequence comprising SEQ ID NO: 82. In some aspects, the antibody comprises a $V_H$ sequence comprising a Kabat CDR-H1 sequence comprising SEQ ID NO: 23, a Kabat CDR-H2 sequence comprising SEQ ID NO: 59, and a Kabat CDR-H3 sequence comprising SEQ ID NO: 76. In some aspects, the antibody comprises a $V_H$ sequence comprising a Kabat CDR-H1 sequence comprising SEQ ID NO: 23, a Kabat CDR-H2 sequence comprising SEQ ID NO: 59, and a Kabat CDR-H3 sequence comprising SEQ ID NO: 81. In some aspects, the antibody comprises a $V_H$ sequence comprising a Kabat CDR-H1 sequence comprising SEQ ID NO: 21, a Kabat CDR-H2 sequence comprising SEQ ID NO: 57, and a Kabat CDR-H3 sequence comprising SEQ ID NO: 83. In some aspects, the antibody comprises a $V_H$ sequence comprising a Kabat CDR-H1 sequence comprising SEQ ID NO: 21, a Kabat CDR-H2 sequence comprising SEQ ID NO: 57, and a Kabat CDR-H3 sequence comprising SEQ ID NO: 84. In some aspects, the antibody comprises a $V_H$ sequence comprising a Kabat CDR-H1 sequence comprising SEQ ID NO: 24, a Kabat CDR-H2 sequence comprising SEQ ID NO: 61, and a Kabat CDR-H3 sequence comprising SEQ ID NO: 85. In some aspects, the antibody comprises a $V_H$ sequence comprising a Kabat CDR-H1 sequence comprising SEQ ID NO: 24, a Kabat CDR-H2 sequence comprising SEQ ID NO: 61, and a Kabat CDR-H3 sequence comprising SEQ ID NO: 86. In some aspects, the antibody comprises a $V_H$ sequence comprising a Kabat CDR-H1 sequence comprising SEQ ID NO: 25, a Kabat CDR-H2 sequence comprising SEQ ID NO: 62, and a Kabat CDR-H3 sequence comprising SEQ ID NO: 87. In some aspects, the antibody comprises a $V_H$ sequence comprising a Kabat CDR-H1 sequence comprising SEQ ID NO: 26, a Kabat CDR-H2 sequence comprising SEQ ID NO: 63, and a Kabat CDR-H3 sequence comprising SEQ ID NO: 88. In some aspects, the antibody comprises a $V_H$ sequence comprising a Kabat CDR-H1 sequence comprising SEQ ID NO: 26, a Kabat CDR-H2 sequence comprising SEQ ID NO: 63, and a Kabat CDR-H3 sequence comprising SEQ ID NO: 89. In some aspects, the antibody comprises a $V_H$ sequence comprising a Kabat CDR-H1 sequence comprising SEQ ID NO: 25, a Kabat CDR-H2 sequence comprising SEQ ID NO: 63, and a Kabat CDR-H3 sequence comprising SEQ ID NO: 90. In some aspects, the antibody comprises a $V_H$ sequence comprising a Kabat CDR-H1 sequence comprising SEQ ID NO: 27, a Kabat CDR-H2 sequence comprising SEQ ID NO: 64, and a Kabat CDR-H3 sequence comprising SEQ ID NO: 90. In some aspects, the antibody comprises a $V_H$ sequence comprising a Kabat CDR-H1 sequence comprising SEQ ID NO: 28, a Kabat CDR-H2 sequence comprising SEQ ID NO: 62, and a Kabat CDR-H3 sequence comprising SEQ ID NO: 91. In some aspects, the antibody comprises a $V_H$ sequence comprising a Kabat CDR-H1 sequence comprising SEQ ID NO: 29, a Kabat CDR-H2 sequence comprising SEQ ID NO: 64, and a Kabat CDR-H3 sequence comprising SEQ ID NO: 92. In some aspects, the antibody comprises a $V_H$ sequence comprising a Kabat CDR-H1 sequence comprising SEQ ID NO: 25, a Kabat CDR-H2 sequence comprising SEQ ID NO: 65, and a Kabat CDR-H3 sequence comprising SEQ ID NO: 93. In some aspects, the antibody comprises a $V_H$ sequence comprising a Kabat CDR-H1 sequence comprising SEQ ID NO: 30, a Kabat CDR-H2 sequence comprising SEQ ID NO: 66, and a Kabat CDR-H3 sequence comprising SEQ ID NO: 94. In some aspects, the antibody comprises a $V_H$ sequence comprising a Kabat CDR-H1 sequence comprising SEQ ID NO: 31, a Kabat CDR-H2 sequence comprising SEQ ID NO: 67, and a Kabat CDR-H3 sequence comprising SEQ ID NO: 95. In some aspects, the antibody comprises a $V_H$ sequence comprising a Kabat CDR-H1 sequence comprising SEQ ID NO: 32, a Kabat CDR-H2 sequence comprising SEQ ID NO: 68, and a Kabat CDR-H3 sequence comprising SEQ ID NO: 96. In some aspects, the antibody comprises a $V_H$ sequence comprising a Kabat CDR-H1 sequence comprising SEQ ID NO: 33, a Kabat CDR-H2 sequence comprising SEQ ID NO: 69, and a Kabat CDR-H3 sequence comprising SEQ ID NO: 97. In some aspects, the antibody comprises a $V_H$ sequence comprising a Kabat CDR-H1 sequence comprising SEQ ID NO: 34, a Kabat CDR-H2 sequence comprising SEQ ID NO: 70, and a Kabat CDR-H3 sequence comprising SEQ ID NO: 98. In some aspects, the antibody comprises a $V_H$ sequence comprising a Kabat CDR-H1 sequence comprising SEQ ID NO: 18, a Kabat CDR-H2 sequence comprising SEQ ID NO: 54, and a Kabat CDR-H3 sequence comprising SEQ ID NO: 99. In some aspects, the antibody comprises a $V_H$ sequence comprising a Kabat CDR-H1 sequence comprising SEQ ID NO: 31, a Kabat CDR-H2 sequence comprising SEQ ID NO: 71, and a Kabat CDR-H3 sequence comprising SEQ ID NO: 100. In some aspects, the antibody comprises a $V_H$ sequence comprising a Kabat CDR-H1 sequence comprising SEQ ID NO: 24, a Kabat CDR-H2 sequence comprising SEQ ID NO: 61, and a Kabat CDR-H3 sequence comprising SEQ ID NO: 101.

2.2.1.8. Variants of $V_H$ Sequences Comprising Illustrative Kabat CDRs

In some embodiments, the $V_H$ sequences provided herein comprise a variant of an illustrative Kabat CDR-H3, CDR-H2, and/or CDR-H1 sequence provided in this disclosure.

In some aspects, the Kabat CDR-H3 sequence comprises, consists of, or consists essentially of a variant of an illustrative Kabat CDR-H3 sequence provided in this disclosure. In some aspects, the Kabat CDR-H3 sequence comprises, consists of, or consists essentially of a sequence having at least 70%, 75%, 80%, 85%, 90%, or 95% identity with any of the illustrative Kabat CDR-H3 sequences provided in this disclosure. In some aspects, the Kabat CDR-H3 sequence comprises, consists of, or consists essentially of any of the illustrative Kabat CDR-H3 sequences provided in this disclosure, with 1, 2, or 3 amino acid substitutions. In some aspects, the amino acid substitutions are conservative amino acid substitutions.

In some aspects, the Kabat CDR-H2 sequence comprises, consists of, or consists essentially of a variant of an illustrative Kabat CDR-H2 sequence provided in this disclosure. In some aspects, the Kabat CDR-H2 sequence comprises, consists of, or consists essentially of a sequence having at least 70%, 75%, 80%, 85%, 90%, or 95% identity with any of the illustrative Kabat CDR-H2 sequences provided in this disclosure. In some aspects, the Kabat CDR-H2 sequence comprises, consists of, or consists essentially of any of the illustrative Kabat CDR-H2 sequences provided in this disclosure, with 1, 2, or 3 amino acid substitutions. In some aspects, the amino acid substitutions are conservative amino acid substitutions.

In some aspects, the Kabat CDR-H1 sequence comprises, consists of, or consists essentially of a variant of an illustrative Kabat CDR-H1 sequence provided in this disclosure. In some aspects, the Kabat CDR-H1 sequence comprises, consists of, or consists essentially of a sequence having at least 70%, 75%, 80%, 85%, 90%, or 95% identity with any of the illustrative Kabat CDR-H1 sequences provided in this disclosure. In some aspects, the Kabat CDR-H1 sequence comprises, consists of, or consists essentially of any of the illustrative Kabat CDR-H1 sequences provided in this disclosure, with 1, 2, or 3 amino acid substitutions. In some aspects, the amino acid substitutions are conservative amino acid substitutions.

2.2.2. $V_H$ Sequences Comprising Illustrative Chothia CDRs

In some embodiments, the antibody comprises a $V_H$ sequence comprising one or more Chothia CDR-H sequences comprising, consisting of, or consisting essentially of one or more illustrative Chothia CDR-H sequences provided in this disclosure, and variants thereof.

2.2.2.1. Chothia CDR-H3

In some embodiments, the antibody comprises a $V_H$ sequence comprising a Chothia CDR-H3 sequence comprising, consisting of, or consisting essentially of a sequence selected from SEQ ID NOS: 76-101. In some aspects, the antibody comprises a $V_H$ sequence comprising a Chothia CDR-H3 sequence comprising, consisting of, or consisting essentially of SEQ ID NO: 76. In some aspects, the antibody comprises a $V_H$ sequence comprising a Chothia CDR-H3 sequence comprising, consisting of, or consisting essentially of SEQ ID NO: 77. In some aspects, the antibody comprises a $V_H$ sequence comprising a Chothia CDR-H3 sequence comprising, consisting of, or consisting essentially of SEQ ID NO: 78. In some aspects, the antibody comprises a $V_H$ sequence comprising a Chothia CDR-H3 sequence comprising, consisting of, or consisting essentially of SEQ ID NO: 79. In some aspects, the antibody comprises a $V_H$ sequence comprising a Chothia CDR-H3 sequence comprising, consisting of, or consisting essentially of SEQ ID NO: 80. In some aspects, the antibody comprises a $V_H$ sequence comprising a Chothia CDR-H3 sequence comprising, consisting of, or consisting essentially of SEQ ID NO: 81. In some aspects, the antibody comprises a $V_H$ sequence comprising a Chothia CDR-H3 sequence comprising, consisting of, or consisting essentially of SEQ ID NO: 82. In some aspects, the antibody comprises a $V_H$ sequence comprising a Chothia CDR-H3 sequence comprising, consisting of, or consisting essentially of SEQ ID NO: 83. In some aspects, the antibody comprises a $V_H$ sequence comprising a Chothia CDR-H3 sequence comprising, consisting of, or consisting essentially of SEQ ID NO: 84. In some aspects, the antibody comprises a $V_H$ sequence comprising a Chothia CDR-H3 sequence comprising, consisting of, or consisting essentially of SEQ ID NO: 85. In some aspects, the antibody comprises a $V_H$ sequence comprising a Chothia CDR-H3 sequence comprising, consisting of, or consisting essentially of SEQ ID NO: 86. In some aspects, the antibody comprises a $V_H$ sequence comprising a Chothia CDR-H3 sequence comprising, consisting of, or consisting essentially of SEQ ID NO: 87. In some aspects, the antibody comprises a $V_H$ sequence comprising a Chothia CDR-H3 sequence comprising, consisting of, or consisting essentially of SEQ ID NO: 88. In some aspects, the antibody comprises a Vii sequence comprising a Chothia CDR-H3 sequence comprising, consisting of, or consisting essentially of SEQ ID NO: 89. In some aspects, the antibody comprises a $V_H$ sequence comprising a Chothia CDR-H3 sequence comprising, consisting of, or consisting essentially of SEQ ID NO: 90. In some aspects, the antibody comprises a $V_H$ sequence comprising a Chothia CDR-H3 sequence comprising, consisting of, or consisting essentially of SEQ ID NO: 91. In some aspects, the antibody comprises a $V_H$ sequence comprising a Chothia CDR-H3 sequence comprising, consisting of, or consisting essentially of SEQ ID NO: 92. In some aspects, the antibody comprises a $V_H$ sequence comprising a Chothia CDR-H3 sequence comprising, consisting of, or consisting essentially of SEQ ID NO: 93. In some aspects, the antibody comprises a $V_H$ sequence comprising a Chothia CDR-H3 sequence comprising, consisting of, or consisting essentially of SEQ ID NO: 94. In some aspects, the antibody comprises a $V_H$ sequence comprising a Chothia CDR-H3 sequence comprising, consisting of, or consisting essentially of SEQ ID NO: 95. In some aspects, the antibody comprises a $V_H$ sequence comprising a Chothia CDR-H3 sequence comprising, consisting of, or consisting essentially of SEQ ID NO: 96. In some aspects, the antibody comprises a $V_H$ sequence comprising a Chothia CDR-H3 sequence comprising, consisting of, or consisting essentially of SEQ ID NO: 97. In some aspects, the antibody comprises a $V_H$ sequence comprising a Chothia CDR-H3 sequence comprising, consisting of, or consisting essentially of SEQ ID NO: 98. In some aspects, the antibody comprises a $V_H$ sequence comprising a Chothia CDR-H3 sequence comprising, consisting of, or consisting essentially of SEQ ID NO: 99. In some aspects, the antibody comprises a $V_H$ sequence comprising a Chothia CDR-H3 sequence comprising, consisting of, or consisting essentially of SEQ ID NO: 100. In some aspects, the antibody comprises a $V_H$ sequence comprising a Chothia CDR-H3 sequence comprising, consisting of, or consisting essentially of SEQ ID NO: 101.

2.2.2.2. Chothia CDR-H2

In some embodiments, the antibody comprises a $V_H$ sequence comprising a Chothia CDR-H2 sequence comprising, consisting of, or consisting essentially of a sequence selected from SEQ ID NOS: 38-50. In some aspects, the antibody comprises a $V_H$ sequence comprising a Chothia CDR-H2 sequence comprising, consisting of, or consisting essentially of SEQ ID NO: 38. In some aspects, the antibody comprises a $V_H$ sequence comprising a Chothia CDR-H2 sequence comprising, consisting of, or consisting essentially of SEQ ID NO: 39. In some aspects, the antibody comprises a $V_H$ sequence comprising a Chothia CDR-H2 sequence comprising, consisting of, or consisting essentially of SEQ ID NO: 40. In some aspects, the antibody comprises a $V_H$ sequence comprising a Chothia CDR-H2 sequence comprising, consisting of, or consisting essentially of SEQ ID NO: 41. In some aspects, the antibody comprises a $V_H$ sequence comprising a Chothia CDR-H2 sequence comprising, consisting of, or consisting essentially of SEQ ID NO: 42. In some aspects, the antibody comprises a $V_H$ sequence comprising a Chothia CDR-H2 sequence comprising, consisting of, or consisting essentially of SEQ ID NO: 43. In some aspects, the antibody comprises a $V_H$ sequence comprising a Chothia CDR-H2 sequence comprising, consisting of, or consisting essentially of SEQ ID NO: 44. In some aspects, the antibody comprises a $V_H$ sequence comprising a Chothia CDR-H2 sequence comprising, consisting of, or consisting essentially of SEQ ID NO: 45. In some aspects, the antibody comprises a $V_H$ sequence comprising a Chothia CDR-H2 sequence comprising, consisting of, or consisting essentially of SEQ ID NO: 46. In some aspects, the antibody comprises a $V_H$ sequence comprising a Chothia CDR-H2 sequence comprising, consisting of, or consisting essentially of SEQ ID NO: 47. In some aspects, the antibody comprises a $V_H$ sequence comprising a Chothia CDR-H2 sequence comprising, consisting of, or consisting essentially of SEQ ID NO: 48. In some aspects, the antibody comprises a $V_H$ sequence comprising a Chothia CDR-H2 sequence comprising, consisting of, or consisting essentially of SEQ ID NO: 49. In some aspects, the antibody comprises a $V_H$ sequence comprising a Chothia CDR-H2 sequence comprising, consisting of, or consisting essentially of SEQ ID NO: 50.

2.2.2.3. Chothia CDR-H1

In some embodiments, the antibody comprises a $V_H$ sequence comprising a Chothia CDR-H1 sequence comprising, consisting of, or consisting essentially of a sequence selected from SEQ ID NOS: 1-14. In some aspects, the antibody comprises a $V_H$ sequence comprising a Chothia CDR-H1 sequence comprising, consisting of, or consisting essentially of SEQ ID NO: 1. In some aspects, the antibody comprises a $V_H$ sequence comprising a Chothia CDR-H1 sequence comprising, consisting of, or consisting essentially of SEQ ID NO: 2. In some aspects, the antibody comprises a $V_H$ sequence comprising a Chothia CDR-H1 sequence comprising, consisting of, or consisting essentially of SEQ ID NO: 3. In some aspects, the antibody comprises a $V_H$ sequence comprising a Chothia CDR-H1 sequence comprising, consisting of, or consisting essentially of SEQ ID NO: 4. In some aspects, the antibody comprises a $V_H$ sequence comprising a Chothia CDR-H1 sequence comprising, consisting of, or consisting essentially of SEQ ID NO: 5. In some aspects, the antibody comprises a $V_H$ sequence comprising a Chothia CDR-H1 sequence comprising, consisting of, or consisting essentially of SEQ ID NO: 6. In some aspects, the antibody comprises a $V_H$ sequence comprising a Chothia CDR-H1 sequence comprising, consisting of, or consisting essentially of SEQ ID NO: 7. In some aspects, the antibody comprises a $V_H$ sequence comprising a Chothia CDR-H1 sequence comprising, consisting of, or consisting essentially of SEQ ID NO: 8. In some aspects, the antibody comprises a $V_H$ sequence comprising a Chothia CDR-H1 sequence comprising, consisting of, or consisting essentially of SEQ ID NO: 9. In some aspects, the antibody comprises a $V_H$ sequence comprising a Chothia CDR-H1 sequence comprising, consisting of, or consisting essentially of SEQ ID NO: 10. In some aspects, the antibody comprises a $V_H$ sequence comprising a Chothia CDR-H1 sequence comprising, consisting of, or consisting essentially of SEQ ID NO: 11. In some aspects, the antibody comprises a $V_H$ sequence comprising a Chothia CDR-H1 sequence comprising, consisting of, or consisting essentially of SEQ ID NO: 12. In some aspects, the antibody comprises a VF sequence comprising a Chothia CDR-H1 sequence comprising, consisting of, or consisting essentially of SEQ ID NO: 13. In some aspects, the antibody comprises a $V_H$ sequence comprising a Chothia CDR-H1 sequence comprising, consisting of, or consisting essentially of SEQ ID NO: 14.

2.2.2.4. Chothia CDR-H3+Chothia CDR-H2

In some embodiments, the antibody comprises a $V_H$ sequence comprising a Chothia CDR-H3 sequence comprising, consisting of, or consisting essentially of a sequence selected from SEQ ID NOS: 76-101, and a Chothia CDR-H2 sequence comprising, consisting of, or consisting essentially of a sequence selected from SEQ ID NOS: 38-50. In some aspects, the Chothia CDR-H3 sequence and the Chothia CDR-H2 sequence are both from a single illustrative $V_H$ sequence provided in this disclosure. For example, in some aspects, the Chothia CDR-H3 and Chothia CDR-H2 are both from a single illustrative $V_H$ sequence selected from SEQ ID NOS: 170-200.

2.2.2.5. Chothia CDR-H3+Chothia CDR-H1

In some embodiments, the antibody comprises a $V_H$ sequence comprising a Chothia CDR-H3 sequence comprising, consisting of, or consisting essentially of a sequence selected from SEQ ID NOS: 76-101, and a Chothia CDR-H1 sequence comprising, consisting of, or consisting essentially of a sequence selected from SEQ ID NOS: 1-14. In some aspects, the Chothia CDR-H3 sequence and the Chothia CDR-H1 sequence are both from a single illustrative $V_H$ sequence provided in this disclosure. For example, in some aspects, the Chothia CDR-H3 and Chothia CDR-H1 are both from a single illustrative $V_H$ sequence selected from SEQ ID NOS: 170-200.

2.2.2.6. Chothia CDR-H1+Chothia CDR-H2

In some embodiments, the antibody comprises a $V_H$ sequence comprising a Chothia CDR-H1 sequence comprising, consisting of, or consisting essentially of a sequence selected from SEQ ID NOS: 1-14 and a Chothia CDR-H2 sequence comprising, consisting of, or consisting essentially of a sequence selected from SEQ ID NOS: 38-50. In some aspects, the Chothia CDR-H1 sequence and the Chothia CDR-H2 sequence are both from a single illustrative $V_H$ sequence provided in this disclosure. For example, in some aspects, the Chothia CDR-H1 and Chothia CDR-H2 are both from a single illustrative $V_H$ sequence selected from SEQ ID NOS: 170-200.

2.2.2.7. Chothia CDR-H1+Chothia CDR-H2+Chothia CDR-H3

In some embodiments, the antibody comprises a $V_H$ sequence comprising a Chothia CDR-H1 sequence comprising, consisting of, or consisting essentially of a sequence selected from SEQ ID NOS: 1-14, a Chothia CDR-H2 sequence comprising, consisting of, or consisting essentially of a sequence selected from SEQ ID NOS: 38-50, and a Chothia CDR-H3 sequence comprising, consisting of, or consisting essentially of a sequence selected from SEQ ID NOS: 76-101. In some aspects, the Chothia CDR-H1 sequence, Chothia CDR-H2 sequence, and Chothia CDR-H3 sequence are all from a single illustrative $V_H$ sequence provided in this disclosure. For example, in some aspects, the Chothia CDR-H1, Chothia CDR-H2, and Chothia CDR-H3 are all from a single illustrative $V_H$ sequence selected from SEQ ID NOS: 170-200.

In some embodiments, the antibody comprises a $V_H$ sequence comprising a Chothia CDR-H1 sequence comprising SEQ ID NO: 1, a Chothia CDR-H2 sequence comprising SEQ ID NO: 38, and a Chothia CDR-H3 sequence comprising SEQ ID NO: 76. In some embodiments, the antibody comprises a $V_H$ sequence comprising a Chothia CDR-H1 sequence comprising SEQ ID NO: 2, a Chothia CDR-H2 sequence comprising SEQ ID NO: 39, and a Chothia CDR-H3 sequence comprising SEQ ID NO: 77. In some embodiments, the antibody comprises a $V_H$ sequence comprising a Chothia CDR-H1 sequence comprising SEQ ID NO: 2, a Chothia CDR-H2 sequence comprising SEQ ID NO: 40, and a Chothia CDR-H3 sequence comprising SEQ ID NO: 78. In some embodiments, the antibody comprises a $V_H$ sequence comprising a Chothia CDR-H1 sequence comprising SEQ ID NO: 3, a Chothia CDR-H2 sequence comprising SEQ ID NO: 41, and a Chothia CDR-H3 sequence comprising SEQ ID NO: 79. In some embodiments, the antibody comprises a $V_H$ sequence comprising a Chothia CDR-H1 sequence comprising SEQ ID NO: 4, a Chothia CDR-H2 sequence comprising SEQ ID NO: 41, and a Chothia CDR-H3 sequence comprising SEQ ID NO: 80. In some embodiments, the antibody comprises a $V_H$ sequence comprising a Chothia CDR-H1 sequence comprising SEQ ID NO: 3, a Chothia CDR-H2 sequence comprising SEQ ID NO: 41, and a Chothia CDR-H3 sequence comprising SEQ ID NO: 76. In some embodiments, the antibody comprises a $V_H$ sequence comprising a Chothia CDR-H1 sequence comprising SEQ ID NO: 2, a Chothia CDR-H2 sequence comprising SEQ ID NO: 42, and a Chothia CDR-H3 sequence comprising SEQ ID NO: 76. In some embodiments, the antibody comprises a $V_H$ sequence comprising a Chothia CDR-H1 sequence comprising SEQ ID NO: 2, a Chothia CDR-H2 sequence comprising SEQ ID NO: 43, and a Chothia CDR-H3 sequence comprising SEQ ID NO: 81. In some embodiments, the antibody comprises a $V_H$ sequence comprising a Chothia CDR-H1 sequence comprising SEQ ID NO: 2, a Chothia CDR-H2 sequence comprising SEQ ID NO: 42, and a Chothia CDR-H3 sequence comprising SEQ ID NO: 82. In some embodiments, the antibody comprises a $V_H$ sequence comprising a Chothia CDR-H1 sequence comprising SEQ ID NO: 5, a Chothia CDR-H2 sequence comprising SEQ ID NO: 42, and a Chothia CDR-H3 sequence comprising SEQ ID NO: 76. In some embodiments, the antibody comprises a $V_H$ sequence comprising a Chothia CDR-H1 sequence comprising SEQ ID NO: 2, a Chothia CDR-H2 sequence comprising SEQ ID NO: 42, and a Chothia CDR-H3 sequence comprising SEQ ID NO: 81. In some embodiments, the antibody comprises a $V_H$ sequence comprising a Chothia CDR-H1 sequence comprising SEQ ID NO: 3, a Chothia CDR-H2 sequence comprising SEQ ID NO: 41, and a Chothia CDR-H3 sequence comprising SEQ ID NO: 83. In some embodiments, the antibody comprises a $V_H$ sequence comprising a Chothia CDR-H1 sequence comprising SEQ ID NO: 3, a Chothia CDR-H2 sequence comprising SEQ ID NO: 41, and a Chothia CDR-H3 sequence comprising SEQ ID NO: 84. In some embodiments, the antibody comprises a $V_H$ sequence comprising a Chothia CDR-H1 sequence comprising SEQ ID NO: 6, a Chothia CDR-H2 sequence comprising SEQ ID NO: 44, and a Chothia CDR-H3 sequence comprising SEQ ID NO: 85. In some embodiments, the antibody comprises a $V_H$ sequence comprising a Chothia CDR-H1 sequence comprising SEQ ID NO: 6, a Chothia CDR-H2 sequence comprising SEQ ID NO: 44, and a Chothia CDR-H3 sequence comprising SEQ ID NO: 86. In some embodiments, the antibody comprises a $V_H$ sequence comprising a Chothia CDR-H1 sequence comprising SEQ ID NO: 7, a Chothia CDR-H2 sequence comprising SEQ ID NO: 45, and a Chothia CDR-H3 sequence comprising SEQ ID NO: 87. In some embodiments, the antibody comprises a $V_H$ sequence comprising a Chothia CDR-H1 sequence comprising SEQ ID NO: 8, a Chothia CDR-H2 sequence comprising SEQ ID NO: 44, and a Chothia CDR-H3 sequence comprising SEQ ID NO: 88. In some embodiments, the antibody comprises a $V_H$ sequence comprising a Chothia CDR-H1 sequence comprising SEQ ID NO: 8, a Chothia CDR-H2 sequence comprising SEQ ID NO: 44, and a Chothia CDR-H3 sequence comprising SEQ ID NO: 89. In some embodiments, the antibody comprises a $V_H$ sequence comprising a Chothia CDR-H1 sequence comprising SEQ ID NO: 7, a Chothia CDR-H2 sequence comprising SEQ ID NO: 44, and a Chothia CDR-H3 sequence comprising SEQ ID NO: 90. In some embodiments, the antibody comprises a $V_H$ sequence comprising a Chothia CDR-H1 sequence comprising SEQ ID NO: 9, a Chothia CDR-H2 sequence comprising SEQ ID NO: 44, and a Chothia CDR-H3 sequence comprising SEQ ID NO: 90. In some embodiments, the antibody comprises a $V_H$ sequence comprising a Chothia CDR-H1 sequence comprising SEQ ID NO: 6, a Chothia CDR-H2 sequence comprising SEQ ID NO: 45, and a Chothia CDR-H3 sequence comprising SEQ ID NO: 91. In some embodiments, the antibody comprises a $V_H$ sequence comprising a Chothia CDR-H1 sequence comprising SEQ ID NO: 8, a Chothia CDR-H2 sequence comprising SEQ ID NO: 44, and a Chothia CDR-H3 sequence comprising SEQ ID NO: 92. In some embodiments, the antibody comprises a $V_H$ sequence comprising a Chothia CDR-H1 sequence comprising SEQ ID NO: 7, a Chothia CDR-H2 sequence comprising SEQ ID NO: 44, and a Chothia CDR-H3 sequence comprising SEQ ID NO: 93. In some embodiments, the antibody comprises a $V_H$ sequence comprising a Chothia CDR-H1 sequence comprising SEQ ID NO: 10, a Chothia CDR-H2 sequence comprising SEQ ID NO: 46, and a Chothia CDR-H3 sequence comprising SEQ ID NO: 94. In some embodiments, the antibody comprises a $V_H$ sequence comprising a Chothia CDR-H1 sequence comprising SEQ ID NO: 11, a Chothia CDR-H2 sequence comprising SEQ ID NO: 47, and a Chothia CDR-H3 sequence comprising SEQ ID NO: 95. In some embodiments, the antibody comprises a $V_H$ sequence comprising a Chothia CDR-H1 sequence comprising SEQ ID NO: 12, a Chothia CDR-H2 sequence comprising SEQ ID NO: 48, and a Chothia CDR-H3 sequence comprising SEQ ID NO: 96. In some embodiments, the antibody comprises a $V_H$ sequence comprising a Chothia CDR-H1 sequence comprising SEQ ID NO: 13, a Chothia CDR-H2 sequence comprising SEQ ID NO: 44, and a Chothia CDR-H3 sequence comprising SEQ ID NO: 97. In some embodiments, the antibody comprises a $V_H$ sequence comprising a Chothia CDR-H1 sequence comprising SEQ ID NO: 14, a Chothia CDR-H2 sequence comprising SEQ ID NO: 49, and a Chothia CDR-H3 sequence comprising SEQ ID NO: 98. In some embodiments, the antibody comprises a $V_H$ sequence comprising a Chothia CDR-H1 sequence comprising SEQ ID NO: 1, a Chothia CDR-H2 sequence comprising SEQ ID NO: 38, and a Chothia CDR-H3 sequence comprising SEQ ID NO: 99. In some embodiments, the antibody comprises a $V_H$ sequence comprising a Chothia CDR-H1 sequence comprising SEQ ID NO: 11, a Chothia CDR-H2 sequence comprising SEQ ID NO: 50, and a Chothia CDR-H3 sequence comprising SEQ ID NO: 100. In some embodiments, the antibody comprises a $V_H$ sequence comprising a Chothia CDR-H1 sequence comprising SEQ ID NO: 6, a Chothia CDR-H2 sequence comprising SEQ ID NO: 44, and a Chothia CDR-H3 sequence comprising SEQ ID NO: 101.

2.2.2.8. Variants of $V_H$ Sequences Comprising Illustrative Chothia CDRs

In some embodiments, the $V_H$ sequences provided herein comprise a variant of an illustrative Chothia CDR-H3, CDR-H2, and/or CDR-H1 sequence provided in this disclosure.

In some aspects, the Chothia CDR-H3 sequence comprises, consists of, or consists essentially of a variant of an illustrative Chothia CDR-H3 sequence provided in this disclosure. In some aspects, the Chothia CDR-H3 sequence comprises, consists of, or consists essentially of a sequence having at least 70%, 75%, 80%, 85%, 90%, or 95% identity with any of the illustrative Chothia CDR-H3 sequences provided in this disclosure. In some aspects, the Chothia CDR-H3 sequence comprises, consists of, or consists essentially of any of the illustrative Chothia CDR-H3 sequences provided in this disclosure, with 1, 2, or 3 amino acid substitutions. In some aspects, the amino acid substitutions are conservative amino acid substitutions.

In some aspects, the Chothia CDR-H2 sequence comprises, consists of, or consists essentially of a variant of an illustrative Chothia CDR-H2 sequence provided in this disclosure. In some aspects, the Chothia CDR-H2 sequence comprises, consists of, or consists essentially of a sequence having at least 70%, 75%, 80%, 85%, 90%, or 95% identity with any of the illustrative Chothia CDR-H2 sequences provided in this disclosure. In some aspects, the Chothia CDR-H2 sequence comprises, consists of, or consists essentially of any of the illustrative Chothia CDR-H2 sequences provided in this disclosure, with 1, 2, or 3 amino acid substitutions. In some aspects, the amino acid substitutions are conservative amino acid substitutions.

In some aspects, the Chothia CDR-H1 sequence comprises, consists of, or consists essentially of a variant of an illustrative Chothia CDR-H1 sequence provided in this disclosure. In some aspects, the Chothia CDR-H1 sequence comprises, consists of, or consists essentially of a sequence having at least 70%, 75%, 80%, 85%, 90%, or 95% identity with any of the illustrative Chothia CDR-H1 sequences provided in this disclosure. In some aspects, the Chothia CDR-H1 sequence comprises, consists of, or consists essentially of any of the illustrative Chothia CDR-H1 sequences provided in this disclosure, with 1, 2, or 3 amino acid substitutions. In some aspects, the amino acid substitutions are conservative amino acid substitutions.

2.3. $V_H$ Sequences

In some embodiments, the antibody comprises a $V_H$ sequence comprising, consisting of, or consisting essentially of a sequence selected from SEQ ID NOS: 170-200. In some aspects, the antibody comprises a $V_H$ sequence comprising, consisting of, or consisting essentially of SEQ ID NO: 170. In some aspects, the antibody comprises a $V_H$ sequence comprising, consisting of, or consisting essentially of SEQ ID NO: 171. In some aspects, the antibody comprises a $V_H$ sequence comprising, consisting of, or consisting essentially of SEQ ID NO: 172. In some aspects, the antibody comprises a $V_H$ sequence comprising, consisting of, or consisting essentially of SEQ ID NO: 173. In some aspects, the antibody comprises a $V_H$ sequence comprising, consisting of, or consisting essentially of SEQ ID NO: 174. In some aspects, the antibody comprises a $V_H$ sequence comprising, consisting of, or consisting essentially of SEQ ID NO: 175. In some aspects, the antibody comprises a $V_H$ sequence comprising, consisting of, or consisting essentially of SEQ ID NO: 176. In some aspects, the antibody comprises a $V_H$ sequence comprising, consisting of, or consisting essentially of SEQ ID NO: 177. In some aspects, the antibody comprises a $V_H$ sequence comprising, consisting of, or consisting essentially of SEQ ID NO: 178. In some aspects, the antibody comprises a $V_H$ sequence comprising, consisting of, or consisting essentially of SEQ ID NO: 179. In some aspects, the antibody comprises a $V_H$ sequence comprising, consisting of, or consisting essentially of SEQ ID NO: 180. In some aspects, the antibody comprises a $V_H$ sequence comprising, consisting of, or consisting essentially of SEQ ID NO: 181. In some aspects, the antibody comprises a $V_H$ sequence comprising, consisting of, or consisting essentially of SEQ ID NO: 182. In some aspects, the antibody comprises a $V_H$ sequence comprising, consisting of, or consisting essentially of SEQ ID NO: 183. In some aspects, the antibody comprises a $V_H$ sequence comprising, consisting of, or consisting essentially of SEQ ID NO: 184. In some aspects, the antibody comprises a $V_H$ sequence comprising, consisting of, or consisting essentially of SEQ ID NO: 185. In some aspects, the antibody comprises a $V_H$ sequence comprising, consisting of, or consisting essentially of SEQ ID NO: 186. In some aspects, the antibody comprises a $V_H$ sequence comprising, consisting of, or consisting essentially of SEQ ID NO: 187. In some aspects, the antibody comprises a $V_H$ sequence comprising, consisting of, or consisting essentially of SEQ ID NO: 188. In some aspects, the antibody comprises a $V_H$ sequence comprising, consisting of or consisting essentially of SEQ ID NO: 189. In some aspects, the antibody comprises a $V_H$ sequence comprising, consisting of, or consisting essentially of SEQ ID NO: 190. In some aspects, the antibody comprises a $V_H$ sequence comprising, consisting of, or consisting essentially of SEQ ID NO: 191. In some aspects, the antibody comprises a $V_H$ sequence comprising, consisting of, or consisting essentially of SEQ ID NO: 192. In some aspects, the antibody comprises a $V_H$ sequence comprising, consisting of, or consisting essentially of SEQ ID NO: 193. In some aspects, the antibody comprises a $V_H$ sequence comprising, consisting of or consisting essentially of SEQ ID NO: 194. In some aspects, the antibody comprises a $V_H$ sequence comprising, consisting of, or consisting essentially of SEQ ID NO: 195. In some aspects, the antibody comprises a Vii sequence comprising, consisting of, or consisting essentially of SEQ ID NO: 196. In some aspects, the antibody comprises a $V_H$ sequence comprising, consisting of, or consisting essentially of SEQ ID NO: 197. In some aspects, the antibody comprises a $V_H$ sequence comprising, consisting of, or consisting essentially of SEQ ID NO: 198. In some aspects, the antibody comprises a $V_H$ sequence comprising, consisting of or consisting essentially of SEQ ID NO: 199. In some aspects, the antibody comprises a $V_H$ sequence comprising, consisting of, or consisting essentially of SEQ ID NO: 200.

23.1. Variants of $V_H$ Sequences

In some embodiments, the $V_H$ sequences provided herein comprise, consist of, or consist essentially of a variant of an illustrative $V_H$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.5% identity with any of the illustrative $V_H$ sequences provided in this disclosure.

In some embodiments, the $V_H$ sequence comprises, consists of, or consists essentially of any of the illustrative $V_H$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.4. CDR-L3 Sequences

In some embodiments, the antibody comprises a CDR-L3 sequence comprising, consisting of, or consisting essentially of a sequence selected from SEQ ID NOS: 149-166. In some aspects, the antibody comprises a CDR-L3 sequence comprising, consisting of, or consisting essentially of SEQ ID NO: 149. In some aspects, the antibody comprises a CDR-L3 sequence comprising, consisting of, or consisting essentially of SEQ ID NO: 150. In some aspects, the antibody comprises a CDR-L3 sequence comprising, consisting of, or consisting essentially of SEQ ID NO: 151. In some aspects, the antibody comprises a CDR-L3 sequence comprising, consisting of, or consisting essentially of SEQ ID NO: 152. In some aspects, the antibody comprises a CDR-L3 sequence comprising, consisting of, or consisting essentially of SEQ ID NO: 153. In some aspects, the antibody comprises a CDR-L3 sequence comprising, consisting of, or consisting essentially of SEQ ID NO: 154. In some aspects, the antibody comprises a CDR-L3 sequence comprising, consisting of, or consisting essentially of SEQ ID NO: 155. In some aspects, the antibody comprises a CDR-L3 sequence comprising, consisting of, or consisting essentially of SEQ ID NO: 156. In some aspects, the antibody comprises a CDR-L3 sequence comprising, consisting of, or consisting essentially of SEQ ID NO: 157. In some aspects, the antibody comprises a CDR-L3 sequence comprising, consisting of, or consisting essentially of SEQ ID NO: 158. In some aspects, the antibody comprises a CDR-L3 sequence comprising, consisting of, or consisting essentially of SEQ ID NO: 159. In some aspects, the antibody comprises a CDR-L3 sequence comprising, consisting of, or consisting essentially of SEQ ID NO: 160. In some aspects, the antibody comprises a CDR-L3 sequence comprising, consisting of, or consisting essentially of SEQ ID NO: 161. In some aspects, the antibody comprises a CDR-L3 sequence comprising, consisting of, or consisting essentially of SEQ ID NO: 162. In some aspects, the antibody comprises a CDR-L3 sequence comprising, consisting of, or consisting essentially of SEQ ID NO: 163. In some aspects, the antibody comprises a CDR-L3 sequence comprising, consisting of, or consisting essentially of SEQ ID NO: 164. In some aspects, the antibody comprises a CDR-L3 sequence comprising, consisting of, or consisting essentially of SEQ ID NO: 165. In some aspects, the antibody comprises a CDR-L3 sequence comprising, consisting of, or consisting essentially of SEQ ID NO: 166.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.5. $V_L$ Sequences Comprising Illustrative CDRs

In some embodiments, the antibody comprises a $V_L$ sequence comprising one or more CDR-L sequences comprising, consisting of, or consisting essentially of one or more illustrative CDR-L sequences provided in this disclosure, and variants thereof.

2.5.1. CDR-L3

In some embodiments, the antibody comprises a $V_L$ sequence comprising a CDR-L3 sequence comprising, consisting of, or consisting essentially of a sequence selected from SEQ ID NOS: 149-166. In some aspects, the antibody comprises a $V_L$ sequence comprising a CDR-L3 sequence comprising, consisting of, or consisting essentially of SEQ ID NO: 149. In some aspects, the antibody comprises a $V_L$ sequence comprising a CDR-L3 sequence comprising, consisting of, or consisting essentially of SEQ ID NO: 150. In some aspects, the antibody comprises a $V_L$ sequence comprising a CDR-L3 sequence comprising, consisting of, or consisting essentially of SEQ ID NO: 151. In some aspects, the antibody comprises a $V_L$ sequence comprising a CDR-L3 sequence comprising, consisting of, or consisting essentially of SEQ ID NO: 152. In some aspects, the antibody comprises a $V_L$ sequence comprising a CDR-L3 sequence comprising, consisting of, or consisting essentially of SEQ ID NO: 153. In some aspects, the antibody comprises a $V_L$ sequence comprising a CDR-L3 sequence comprising, consisting of, or consisting essentially of SEQ ID NO: 154. In some aspects, the antibody comprises a $V_L$ sequence comprising a CDR-L3 sequence comprising, consisting of, or consisting essentially of SEQ ID NO: 155. In some aspects, the antibody comprises a $V_L$ sequence comprising a CDR-L3 sequence comprising, consisting of, or consisting essentially of SEQ ID NO: 156. In some aspects, the antibody comprises a $V_L$ sequence comprising a CDR-L3 sequence comprising, consisting of, or consisting essentially of SEQ ID NO: 157. In some aspects, the antibody comprises a $V_L$ sequence comprising a CDR-L3 sequence comprising, consisting of, or consisting essentially of SEQ ID NO: 158. In some aspects, the antibody comprises a $V_L$ sequence comprising a CDR-L3 sequence comprising, consisting of, or consisting essentially of SEQ ID NO: 159. In some aspects, the antibody comprises a $V_L$ sequence comprising a CDR-L3 sequence comprising, consisting of, or consisting essentially of SEQ ID NO: 160. In some aspects, the antibody comprises a $V_L$ sequence comprising a CDR-L3 sequence comprising, consisting of, or consisting essentially of SEQ ID NO: 161. In some aspects, the antibody comprises a $V_L$ sequence comprising a CDR-L3 sequence comprising, consisting of, or consisting essentially of SEQ ID NO: 162. In some aspects, the antibody comprises a $V_L$ sequence comprising a CDR-L3 sequence comprising, consisting of, or consisting essentially of SEQ ID NO: 163. In some aspects, the antibody comprises a $V_L$ sequence comprising a CDR-L3 sequence comprising, consisting of, or consisting essentially of SEQ ID NO: 164. In some aspects, the antibody comprises a $V_L$ sequence comprising a CDR-L3 sequence comprising, consisting of, or consisting essentially of SEQ ID NO: 165. In some aspects, the antibody comprises a $V_L$ sequence comprising a CDR-L3 sequence comprising, consisting of, or consisting essentially of SEQ ID NO: 166.

2.5.2. CDR-L2

In some embodiments, the antibody comprises a $V_L$ sequence comprising a CDR-L2 sequence comprising, consisting of, or consisting essentially of a sequence selected from SEQ ID NOS: 128-145. In some aspects, the antibody comprises a $V_L$ sequence comprising a CDR-L2 sequence comprising, consisting of, or consisting essentially of SEQ ID NO: 128. In some aspects, the antibody comprises a $V_L$ sequence comprising a CDR-L2 sequence comprising, consisting of, or consisting essentially of SEQ ID NO: 129. In some aspects, the antibody comprises a $V_L$ sequence comprising a CDR-L2 sequence comprising, consisting of, or consisting essentially of SEQ ID NO: 130. In some aspects, the antibody comprises a $V_L$ sequence comprising a CDR-L2 sequence comprising, consisting of, or consisting essentially of SEQ ID NO: 131. In some aspects, the antibody comprises a $V_L$ sequence comprising a CDR-L2 sequence comprising, consisting of, or consisting essentially of SEQ ID NO: 132. In some aspects, the antibody comprises a $V_L$ sequence comprising a CDR-L2 sequence comprising, consisting of, or consisting essentially of SEQ ID NO: 133. In some aspects, the antibody comprises a $V_L$ sequence comprising a CDR-L2 sequence comprising, consisting of, or consisting essentially of SEQ ID NO: 134. In some aspects, the antibody comprises a $V_L$ sequence comprising a CDR-L2 sequence comprising, consisting of, or consisting essentially of SEQ ID NO: 135. In some aspects, the antibody comprises a $V_L$ sequence comprising a CDR-L2 sequence comprising, consisting of, or consisting essentially of SEQ ID NO: 136. In some aspects, the antibody comprises a $V_L$ sequence comprising a CDR-L2 sequence comprising, consisting of, or consisting essentially of SEQ ID NO: 137. In some aspects, the antibody comprises a $V_L$ sequence comprising a CDR-L2 sequence comprising, consisting of, or consisting essentially of SEQ ID NO: 138. In some aspects, the antibody comprises a $V_L$ sequence comprising a CDR-L2 sequence comprising, consisting of, or consisting essentially of SEQ ID NO: 139. In some aspects, the antibody comprises a $V_L$ sequence comprising a CDR-L2 sequence comprising, consisting of, or consisting essentially of SEQ ID NO: 140. In some aspects, the antibody comprises a $V_L$ sequence comprising a CDR-L2 sequence comprising, consisting of, or consisting essentially of SEQ ID NO: 141. In some aspects, the antibody comprises a $V_L$ sequence comprising a CDR-L2 sequence comprising, consisting of, or consisting essentially of SEQ ID NO: 142. In some aspects, the antibody comprises a $V_L$ sequence comprising a CDR-L2 sequence comprising, consisting of, or consisting essentially of SEQ ID NO: 143. In some aspects, the antibody comprises a $V_L$ sequence comprising a CDR-L2 sequence comprising, consisting of, or consisting essentially of SEQ ID NO: 144. In some aspects, the antibody comprises a $V_L$ sequence comprising a CDR-L2 sequence comprising, consisting of, or consisting essentially of SEQ ID NO: 145.

2.5.3. CDR-L1

In some embodiments, the antibody comprises a $V_L$ sequence comprising a CDR-L1 sequence comprising, consisting of, or consisting essentially of a sequence selected from SEQ ID NOS: 105-124. In some aspects, the antibody comprises a $V_L$ sequence comprising a CDR-L1 sequence comprising, consisting of, or consisting essentially of SEQ ID NO: 105. In some aspects, the antibody comprises a $V_L$ sequence comprising a CDR-L1 sequence comprising, consisting of, or consisting essentially of SEQ ID NO: 106. In some aspects, the antibody comprises a $V_L$ sequence comprising a CDR-L1 sequence comprising, consisting of, or consisting essentially of SEQ ID NO: 107. In some aspects, the antibody comprises a $V_L$ sequence comprising a CDR-L1 sequence comprising, consisting of, or consisting essentially of SEQ ID NO: 108. In some aspects, the antibody comprises a $V_L$ sequence comprising a CDR-L1 sequence comprising, consisting of, or consisting essentially of SEQ ID NO: 109. In some aspects, the antibody comprises a $V_L$ sequence comprising a CDR-L1 sequence comprising, consisting of, or consisting essentially of SEQ ID NO: 110. In some aspects, the antibody comprises a $V_L$ sequence comprising a CDR-L1 sequence comprising, consisting of, or consisting essentially of SEQ ID NO: 111. In some aspects, the antibody comprises a $V_L$ sequence comprising a CDR-L1 sequence comprising, consisting of, or consisting essentially of SEQ ID NO: 112. In some aspects, the antibody comprises a $V_L$ sequence comprising a CDR-L1 sequence comprising, consisting of, or consisting essentially of SEQ ID NO: 113. In some aspects, the antibody comprises a $V_L$ sequence comprising a CDR-L1 sequence comprising, consisting of, or consisting essentially of SEQ ID NO: 114. In some aspects, the antibody comprises a $V_L$ sequence comprising a CDR-L1 sequence comprising, consisting of, or consisting essentially of SEQ ID NO: 115. In some aspects, the antibody comprises a $V_L$ sequence comprising a CDR-L1 sequence comprising, consisting of, or consisting essentially of SEQ ID NO: 116. In some aspects, the antibody comprises a $V_L$ sequence comprising a CDR-L1 sequence comprising, consisting of, or consisting essentially of SEQ ID NO: 117. In some aspects, the antibody comprises a $V_L$ sequence comprising a CDR-L1 sequence comprising, consisting of, or consisting essentially of SEQ ID NO: 18. In some aspects, the antibody comprises a $V_L$ sequence comprising a CDR-L1 sequence comprising, consisting of, or consisting essentially of SEQ ID NO: 119. In some aspects, the antibody comprises a $V_L$ sequence comprising a CDR-L1 sequence comprising, consisting of, or consisting essentially of SEQ ID NO: 120. In some aspects, the antibody comprises a $V_L$ sequence comprising a CDR-L1 sequence comprising, consisting of, or consisting essentially of SEQ ID NO: 121. In some aspects, the antibody comprises a $V_L$ sequence comprising a CDR-L1 sequence comprising, consisting of, or consisting essentially of SEQ ID NO: 122. In some aspects, the antibody comprises a $V_L$ sequence comprising a CDR-L1 sequence comprising, consisting of, or consisting essentially of SEQ ID NO: 123. In some aspects, the antibody comprises a $V_L$ sequence comprising a CDR-L1 sequence comprising, consisting of, or consisting essentially of SEQ ID NO: 124.

2.5.4. CDR-L3+CDR-L2

In some embodiments, the antibody comprises a $V_L$ sequence comprising a CDR-L3 sequence comprising, consisting of, or consisting essentially of a sequence selected from SEQ ID NOS: 149-166 and a CDR-L2 sequence comprising, consisting of, or consisting essentially of a sequence selected from SEQ ID NOS: 128-145. In some aspects, the CDR-L3 sequence and the CDR-L2 sequence are both from a single illustrative $V_L$ sequence provided in this disclosure. For example, in some aspects, the CDR-L3 and CDR-L2 are both from a single illustrative $V_L$ sequence selected from SEQ ID NOS: 204-228.

2.5.5. CDR-L3+CDR-L1

In some embodiments, the antibody comprises a $V_L$ sequence comprising a CDR-L3 sequence comprising, consisting of, or consisting essentially of a sequence selected from SEQ ID NOS: 149-166 and a CDR-L1 sequence comprising, consisting of, or consisting essentially of a sequence selected from SEQ ID NOS: 105-124. In some aspects, the CDR-L3 sequence and the CDR-L1 sequence are both from a single illustrative $V_L$ sequence provided in this disclosure. For example, in some aspects, the CDR-L3 and CDR-L1 are both from a single illustrative $V_L$ sequence selected from SEQ ID NOS: 204-228.

2.5.6. CDR-L1+CDR-L2

In some embodiments, the antibody comprises a $V_L$ sequence comprising a CDR-L1 sequence comprising, consisting of, or consisting essentially of a sequence selected from SEQ ID NOS: 105-124 and a CDR-L2 sequence comprising, consisting of, or consisting essentially of a sequence selected from SEQ ID NOS: 128-145. In some aspects, the CDR-L1 sequence and the CDR-L2 sequence are both from a single illustrative $V_L$ sequence provided in this disclosure. For example, in some aspects, the CDR-L1 and CDR-L2 are both from a single illustrative $V_L$ sequence selected from SEQ ID NOS: 204-228.

2.5.7. CDR-L1+CDR-L2+CDR-L3

In some embodiments, the antibody comprises a $V_L$ sequence comprising a CDR-L1 sequence comprising, consisting of, or consisting essentially of a sequence selected from SEQ ID NOS: 105-124, a CDR-L2 sequence comprising, consisting of, or consisting essentially of a sequence selected from SEQ ID NOS: 128-145, and a CDR-L3 sequence comprising, consisting of, or consisting essentially of a sequence selected from SEQ ID NOS: 149-166. In some aspects, the CDR-L1 sequence, CDR-L2 sequence, and CDR-L3 sequence are all from a single illustrative $V_L$ sequence provided in this disclosure. For example, in some aspects, the CDR-L1, CDR-L2, and CDR-L3 are all from a single illustrative $V_L$ sequence selected from SEQ ID NOS: 204-228.

In some aspects, the antibody comprises a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a VL sequence comprising a CDR-L1 sequence comprising SEQ ID NO: 106, a CDR-L2 sequence comprising SEQ ID NO: 129, and a CDR-L3 sequence SEQ ID NO: 150. In some aspects, the antibody comprises a VL sequence comprising a CDR-L1 sequence comprising SEQ ID NO: 107, a CDR-L2 sequence comprising SEQ ID NO: 128, and a CDR-L3 sequence SEQ ID NO: 151. In some aspects, the antibody comprises a VL sequence comprising a CDR-L1 sequence comprising SEQ ID NO: 108, a CDR-L2 sequence comprising SEQ ID NO: 130, and a CDR-L3 sequence SEQ ID NO: 151. In some aspects, the antibody comprises a VL sequence comprising a CDR-L1 sequence comprising SEQ ID NO: 109, a CDR-L2 sequence comprising SEQ ID NO: 131, and a CDR-L3 sequence SEQ ID NO: 152. In some aspects, the antibody comprises a VL sequence comprising a CDR-L1 sequence comprising SEQ ID NO: 107, a CDR-L2 sequence comprising SEQ ID NO: 132, and a CDR-L3 sequence SEQ ID NO: 153. In some aspects, the antibody comprises a VL sequence comprising a CDR-L1 sequence comprising SEQ ID NO: 110, a CDR-L2 sequence comprising SEQ ID NO: 132, and a CDR-L3 sequence SEQ ID NO: 151. In some aspects, the antibody comprises a VL sequence comprising a CDR-L1 sequence comprising SEQ ID NO: 111, a CDR-L2 sequence comprising SEQ ID NO: 133, and a CDR-L3 sequence SEQ ID NO: 151. In some aspects, the antibody comprises a VL sequence comprising a CDR-L1 sequence comprising SEQ ID NO: 105, a CDR-L2 sequence comprising SEQ ID NO: 128, and a CDR-L3 sequence SEQ ID NO: 154. In some aspects, the antibody comprises a VL sequence comprising a CDR-L1 sequence comprising SEQ ID NO: 112, a CDR-L2 sequence comprising SEQ ID NO: 134, and a CDR-L3 sequence SEQ ID NO: 155. In some aspects, the antibody comprises a VL sequence comprising a CDR-L1 sequence comprising SEQ ID NO: 113, a CDR-L2 sequence comprising SEQ ID NO: 135, and a CDR-L3 sequence SEQ ID NO: 156. In some aspects, the antibody comprises a VL sequence comprising a CDR-L1 sequence comprising SEQ ID NO: 114, a CDR-L2 sequence comprising SEQ ID NO: 136, and a CDR-L3 sequence SEQ ID NO: 157. In some aspects, the antibody comprises a VL sequence comprising a CDR-L1 sequence comprising SEQ ID NO: 115, a CDR-L2 sequence comprising SEQ ID NO: 135, and a CDR-L3 sequence SEQ ID NO: 157. In some aspects, the antibody comprises a VL sequence comprising a CDR-L1 sequence comprising SEQ ID NO: 116, a CDR-L2 sequence comprising SEQ ID NO: 128, and a CDR-L3 sequence SEQ ID NO: 155. In some aspects, the antibody comprises a VL sequence comprising a CDR-L1 sequence comprising SEQ ID NO: 117, a CDR-L2 sequence comprising SEQ ID NO: 137, and a CDR-L3 sequence SEQ ID NO: 155. In some aspects, the antibody comprises a VL sequence comprising a CDR-L1 sequence comprising SEQ ID NO: 118, a CDR-L2 sequence comprising SEQ ID NO: 137, and a CDR-L3 sequence SEQ ID NO: 158. In some aspects, the antibody comprises a VL sequence comprising a CDR-L1 sequence comprising SEQ ID NO: 118, a CDR-L2 sequence comprising SEQ ID NO: 138, and a CDR-L3 sequence SEQ ID NO: 155. In some aspects, the antibody comprises a VL sequence comprising a CDR-L1 sequence comprising SEQ ID NO: 119, a CDR-L2 sequence comprising SEQ ID NO: 139, and a CDR-L3 sequence SEQ ID NO: 159. In some aspects, the antibody comprises a VL sequence comprising a CDR-L1 sequence comprising SEQ ID NO: 120, a CDR-L2 sequence comprising SEQ ID NO: 140, and a CDR-L3 sequence SEQ ID NO: 160. In some aspects, the antibody comprises a VL sequence comprising a CDR-L1 sequence comprising SEQ ID NO: 121, a CDR-L2 sequence comprising SEQ ID NO: 141, and a CDR-L3 sequence SEQ ID NO: 161. In some aspects, the antibody comprises a VL sequence comprising a CDR-L1 sequence comprising SEQ ID NO: 122, a CDR-L2 sequence comprising SEQ ID NO: 142, and a CDR-L3 sequence SEQ ID NO: 162. In some aspects, the antibody comprises a VL sequence comprising a CDR-L1 sequence comprising SEQ ID NO: 105, a CDR-L2 sequence comprising SEQ ID NO: 143, and a CDR-L3 sequence SEQ ID NO: 163. In some aspects, the antibody comprises a VL sequence comprising a CDR-L1 sequence comprising SEQ ID NO: 105, a CDR-L2 sequence comprising SEQ ID NO: 143, and a CDR-L3 sequence SEQ ID NO: 164. In some aspects, the antibody comprises a VL sequence comprising a CDR-L1 sequence comprising SEQ ID NO: 123, a CDR-L2 sequence comprising SEQ ID NO: 144, and a CDR-L3 sequence SEQ ID NO: 165. In some aspects, the antibody comprises a VL sequence comprising a CDR-L1 sequence comprising SEQ ID NO: 124, a CDR-L2 sequence comprising SEQ ID NO: 145, and a CDR-L3 sequence SEQ ID NO: 166.

2.5.8. Variants of $V_L$ Sequences Comprising Illustrative CDR-Ls

In some embodiments, the $V_L$ sequences provided herein comprise a variant of an illustrative CDR-L3, CDR-L2, and/or CDR-L1 sequence provided in this disclosure.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L sequence comprises, consists of, or consists essentially of a sequence having at least 70%, 75%, 80%, 85%, 90%, or 95% identity with any of the illustrative CDR-L sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

2.6. $V_L$ Sequences

In some embodiments, the antibody comprises a $V_L$ sequence comprising, consisting of, or consisting essentially of a sequence selected from SEQ ID NOS: 204-228. In some aspects, the antibody comprises a $V_L$ sequence comprising, consisting of, or consisting essentially of SEQ ID NO: 204. In some aspects, the antibody comprises a $V_L$ sequence comprising, consisting of, or consisting essentially of SEQ ID NO: 205. In some aspects, the antibody comprises a $V_L$ sequence comprising, consisting of, or consisting essentially of SEQ ID NO: 206. In some aspects, the antibody comprises a $V_L$ sequence comprising, consisting of, or consisting essentially of SEQ ID NO: 207. In some aspects, the antibody comprises a $V_L$ sequence comprising, consisting of, or consisting essentially of SEQ ID NO: 208. In some aspects, the antibody comprises a $V_L$ sequence comprising, consisting of, or consisting essentially of SEQ ID NO: 209. In some aspects, the antibody comprises a $V_L$ sequence comprising, consisting of, or consisting essentially of SEQ ID NO: 210. In some aspects, the antibody comprises a $V_L$ sequence comprising, consisting of, or consisting essentially of SEQ ID NO: 211. In some aspects, the antibody comprises a $V_L$ sequence comprising, consisting of, or consisting essentially of SEQ ID NO: 212. In some aspects, the antibody comprises a $V_L$ sequence comprising, consisting of, or consisting essentially of SEQ ID NO: 213. In some aspects, the antibody comprises a $V_L$ sequence comprising, consisting of, or consisting essentially of SEQ ID NO: 214. In some aspects, the antibody comprises a $V_L$ sequence comprising, consisting of, or consisting essentially of SEQ ID NO: 215. In some aspects, the antibody comprises a $V_L$ sequence comprising, consisting of, or consisting essentially of SEQ ID NO: 216. In some aspects, the antibody comprises a $V_L$ sequence comprising, consisting of, or consisting essentially of SEQ ID NO: 217. In some aspects, the antibody comprises a $V_L$ sequence comprising, consisting of, or consisting essentially of SEQ ID NO: 218. In some aspects, the antibody comprises a $V_L$ sequence comprising, consisting of, or consisting essentially of SEQ ID NO: 219. In some aspects, the antibody comprises a $V_L$ sequence comprising, consisting of, or consisting essentially of SEQ ID NO: 220. In some aspects, the antibody comprises a $V_L$ sequence comprising, consisting of, or consisting essentially of SEQ ID NO: 221. In some aspects, the antibody comprises a $V_L$ sequence comprising, consisting of, or consisting essentially of SEQ ID NO: 222. In some aspects, the antibody comprises a $V_L$ sequence comprising, consisting of, or consisting essentially of SEQ ID NO: 223. In some aspects, the antibody comprises a $V_L$ sequence comprising, consisting of, or consisting essentially of SEQ ID NO: 224. In some aspects, the antibody comprises a $V_L$ sequence comprising, consisting of, or consisting essentially of SEQ ID NO: 225. In some aspects, the antibody comprises a $V_L$ sequence comprising, consisting of, or consisting essentially of SEQ ID NO: 226. In some aspects, the antibody comprises a $V_L$ sequence comprising, consisting of, or consisting essentially of SEQ ID NO: 227. In some aspects, the antibody comprises a $V_L$ sequence comprising, consisting of, or consisting essentially of SEQ ID NO: 228.

2.6.1. Variants of $V_L$ Sequences

In some embodiments, the $V_L$ sequences provided herein comprise, consist of, or consist essentially of a variant of an illustrative $V_L$ sequence provided in this disclosure.

In some aspects, the $V_L$ sequence comprises, consists of, or consists essentially of a variant of an illustrative $V_L$ sequence provided in this disclosure. In some aspects, the $V_L$ sequence comprises, consists, or consists essentially of a sequence having at least 85%, 90%, 95%, 96%, 97%, 98%, 99%, or 99.05% identity with any of the illustrative $V_L$ sequences provided in this disclosure.

In some embodiments, the $V_L$ sequence comprises, consists of, or consists essentially of any of the illustrative $V_L$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.7. Pairs

2.7.1. CDR-H3-CDR-L3 Pairs

In some embodiments, the antibody comprises a CDR-H3 sequence and a CDR-L3 sequence. In some aspects, the CDR-H3 sequence is part of a $V_H$ and the CDR-L3 sequence is part of a $V_L$.

In some aspects, the CDR-H3 sequence is a CDR-H3 sequence comprising, consisting of, or consisting essentially of SEQ ID NOS: 76-101, and the CDR-L3 sequence is a CDR-L3 sequence comprising, consisting of, or consisting essentially of SEQ ID NOS: 149-166.

In some aspects, the CDR-H3 sequence is SEQ ID NO: 76 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 77 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 78 and the CDR-L3 sequence is selected from SEQ ID NOS:

149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 79 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 80 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 81 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 82 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 83 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 84 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 85 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 86 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 87 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 88 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 89 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 90 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 91 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 92 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 93 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 94 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 95 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 96 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 97 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 98 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 99 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 100 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 101 and the CDR-L3 sequence is selected from SEQ ID NOS: 149-166. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

2.7.1.1. Variants of CDR-H3-CDR-L3 Pairs

In some embodiments, the CDR-H3-CDR-L3 pairs provided herein comprise a variant of an illustrative CDR-H3 and/or CDR-L1 sequence provided in this disclosure.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.7.2. $V_H$-$V_L$ Pairs

In some embodiments, the antibody comprises a $V_H$ sequence and a $V_L$ sequence.

In some aspects, the $V_H$ sequence is a $V_H$ sequence comprising, consisting of, or consisting essentially of SEQ ID NOS: 170-200 and the $V_L$ sequence is a $V_L$ sequence comprising, consisting of, or consisting essentially of SEQ ID NOS: 204-228.

In some aspects, the $V_H$ sequence is SEQ ID NO: 170 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_H$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 171 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 172 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_H$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 173 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 174 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 175 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 176 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 177 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 178 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 179 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 180 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 181 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 182 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_H$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 183 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the VF sequence is SEQ ID NO: 184 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 185 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 186 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 187 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 188 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 189 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_H$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 190 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 191 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 192 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the VF sequence is SEQ ID NO: 193 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 194 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 195 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_H$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 196 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 197 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_L$ sequence is SEQ ID NO: 198 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 199 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

In some aspects, the $V_H$ sequence is SEQ ID NO: 200 and the $V_L$ sequence is selected from SEQ ID NOS: 204-228. In some aspects, the $V_L$ sequence is SEQ ID NO: 204. In some aspects, the $V_L$ sequence is SEQ ID NO: 205. In some aspects, the $V_L$ sequence is SEQ ID NO: 206. In some aspects, the $V_L$ sequence is SEQ ID NO: 207. In some aspects, the $V_L$ sequence is SEQ ID NO: 208. In some aspects, the $V_L$ sequence is SEQ ID NO: 209. In some aspects, the $V_L$ sequence is SEQ ID NO: 210. In some aspects, the $V_L$ sequence is SEQ ID NO: 211. In some aspects, the $V_L$ sequence is SEQ ID NO: 212. In some aspects, the $V_L$ sequence is SEQ ID NO: 213. In some aspects, the $V_L$ sequence is SEQ ID NO: 214. In some aspects, the $V_L$ sequence is SEQ ID NO: 215. In some aspects, the $V_L$ sequence is SEQ ID NO: 216. In some aspects, the $V_L$ sequence is SEQ ID NO: 217. In some aspects, the $V_L$ sequence is SEQ ID NO: 218. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_H$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228.

2.7.3. CDR-H1+CDR-H2+CDR-H3+CDR-L11+CDR-L2+CDR-L3

In some aspects, the antibody comprises a $V_H$ sequence comprising a Kabat CDR-H1 sequence comprising SEQ ID NO: 18, a Kabat CDR-H2 sequence comprising SEQ ID NO: 54, and a Kabat CDR-H3 sequence comprising SEQ ID NO: 76 and a $V_L$ sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Kabat CDR-H1 sequence comprising SEQ ID NO: 19, a Kabat CDR-H2 sequence comprising SEQ ID NO: 55, and a Kabat CDR-H3 sequence comprising SEQ ID NO: 77 and a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Kabat CDR-H1 sequence comprising SEQ ID NO: 20, a Kabat CDR-H2 sequence comprising SEQ ID NO: 56, and a Kabat CDR-H3 sequence comprising SEQ ID NO: 78 and a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Kabat CDR-H1 sequence comprising SEQ ID NO: 21, a Kabat CDR-H2 sequence comprising SEQ ID NO: 57, and a Kabat CDR-H3 sequence comprising SEQ ID NO: 79 and a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Kabat CDR-H1 sequence comprising SEQ ID NO: 22, a Kabat CDR-H2 sequence comprising SEQ ID NO: 58, and a Kabat CDR-H3 sequence comprising SEQ ID NO: 80 and a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Kabat CDR-H1 sequence comprising SEQ ID NO: 21, a Kabat CDR-H2 sequence comprising SEQ ID NO: 57, and a Kabat CDR-H3 sequence comprising SEQ ID NO: 76 and a VL sequence comprising a CDR-L1 sequence comprising SEQ ID NO: 106, a CDR-L2 sequence comprising SEQ ID NO: 129, and a CDR-L3 sequence SEQ ID NO: 150. In some aspects, the antibody comprises a $V_H$ sequence comprising a Kabat CDR-H1 sequence comprising SEQ ID NO: 23, a Kabat CDR-H2 sequence comprising SEQ ID NO: 59, and a Kabat CDR-H3 sequence comprising SEQ ID NO: 76 and a VL sequence comprising a CDR-L1 sequence comprising SEQ ID NO: 107, a CDR-L2 sequence comprising SEQ ID NO: 128, and a CDR-L3 sequence SEQ ID NO: 151. In some aspects, the antibody comprises a $V_H$ sequence comprising a Kabat CDR-H1 sequence comprising SEQ ID NO: 23, a Kabat CDR-H2 sequence comprising SEQ ID NO: 60, and a Kabat CDR-H3 sequence comprising SEQ ID NO: 81 and a VL sequence comprising a CDR-L1 sequence comprising SEQ ID NO: 108, a CDR-L2 sequence comprising SEQ ID NO: 130, and a CDR-L3 sequence SEQ ID NO: 151. In some aspects, the antibody comprises a $V_H$ sequence comprising a Kabat CDR-H1 sequence comprising SEQ ID NO: 23, a Kabat CDR-H2 sequence comprising SEQ ID NO: 59, and a Kabat CDR-H3 sequence comprising SEQ ID NO: 82 and a VL sequence comprising a CDR-L1 sequence comprising SEQ ID NO: 109, a CDR-L2 sequence comprising SEQ ID NO: 131, and a CDR-L3 sequence SEQ ID NO: 152. In some aspects, the antibody comprises a $V_H$ sequence comprising a Kabat CDR-H1 sequence comprising SEQ ID NO: 23, a Kabat CDR-H2 sequence comprising SEQ ID NO: 59, and a Kabat CDR-H3 sequence comprising SEQ ID NO: 76 and a VL sequence comprising a CDR-L1 sequence comprising SEQ ID NO: 107, a CDR-L2 sequence comprising SEQ ID NO: 132, and a CDR-L3 sequence SEQ ID NO:153. In some aspects, the antibody comprises a $V_H$ sequence comprising a Kabat CDR-H1 sequence comprising SEQ ID NO: 23, a Kabat CDR-H2 sequence comprising SEQ ID NO: 59, and a Kabat CDR-H3 sequence comprising SEQ ID NO: 81 and a VL sequence comprising a CDR-L1 sequence comprising SEQ ID NO: 110, a CDR-L2 sequence comprising SEQ ID NO: 132, and a CDR-L3 sequence SEQ ID NO: 151. In some aspects, the antibody comprises a $V_H$ sequence comprising a Kabat CDR-H1 sequence comprising SEQ ID NO: 21, a Kabat CDR-H2 sequence comprising SEQ ID NO: 57, and a Kabat CDR-H3 sequence comprising SEQ ID NO: 83 and a VL sequence comprising a CDR-L1 sequence comprising SEQ ID NO: 111, a CDR-L2 sequence comprising SEQ ID NO: 133, and a CDR-L3 sequence SEQ ID NO: 151. In some aspects, the antibody comprises a $V_H$ sequence comprising a Kabat CDR-H1 sequence comprising SEQ ID NO: 21, a Kabat CDR-H2 sequence comprising SEQ ID NO: 57, and a Kabat CDR-H3 sequence comprising SEQ ID NO: 84 and a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Kabat CDR-H1 sequence comprising SEQ ID NO: 24, a Kabat CDR-H2 sequence comprising SEQ ID NO: 61, and a Kabat CDR-H3 sequence comprising SEQ ID NO: 85 and a VL sequence comprising a CDR-L1 sequence comprising SEQ ID NO: 105, a CDR-L2 sequence comprising SEQ ID NO: 128, and a CDR-L3 sequence SEQ ID NO: 154. In some aspects, the antibody comprises a $V_H$ sequence comprising a Kabat CDR-H1 sequence comprising SEQ ID NO: 24, a Kabat CDR-H2 sequence comprising SEQ ID NO: 61, and a Kabat CDR-H3 sequence comprising SEQ ID NO: 86 and a VL sequence comprising a CDR-L1 sequence comprising SEQ ID NO: 105, a CDR-L2 sequence comprising SEQ ID NO: 128, and a CDR-L3 sequence SEQ ID NO: 154. In some aspects, the antibody comprises a $V_H$ sequence comprising a Kabat CDR-H1 sequence comprising SEQ ID NO: 25, a Kabat CDR-H2 sequence comprising SEQ ID NO: 62, and a Kabat CDR-H3 sequence comprising SEQ ID NO: 87 and a VL sequence comprising a CDR-L1 sequence comprising SEQ ID NO: 112, a CDR-L2 sequence comprising SEQ ID NO: 134, and a CDR-L3 sequence SEQ ID NO: 155. In some aspects, the antibody comprises a $V_H$ sequence comprising a Kabat CDR-H sequence comprising SEQ ID NO: 26, a Kabat CDR-H2 sequence comprising SEQ ID NO: 63, and a Kabat CDR-H3 sequence comprising SEQ ID NO: 88 and a VL sequence comprising a CDR-L1 sequence comprising SEQ ID NO: 113, a CDR-L2 sequence comprising SEQ ID NO: 135, and a CDR-L3 sequence SEQ ID NO: 156. In some aspects, the antibody comprises a $V_H$ sequence comprising a Kabat CDR-H1 sequence comprising SEQ ID NO: 26, a Kabat CDR-H2 sequence comprising SEQ ID NO: 63, and a Kabat CDR-H3 sequence comprising SEQ ID NO: 89 and a VL sequence comprising a CDR-L1 sequence comprising SEQ ID NO: 114, a CDR-L2 sequence comprising SEQ ID NO: 136, and a CDR-L3 sequence SEQ ID NO: 157. In some aspects, the antibody comprises a $V_H$ sequence comprising a Kabat CDR-H1 sequence comprising SEQ ID NO: 25, a Kabat CDR-H2 sequence comprising SEQ ID NO: 63, and a Kabat CDR-H3 sequence comprising SEQ ID NO: 90 and a VL sequence comprising a CDR-L1 sequence comprising SEQ ID NO: 115, a CDR-L2 sequence comprising SEQ ID NO: 135, and a CDR-L3 sequence SEQ ID NO: 157. In some aspects, the antibody comprises a $V_H$ sequence comprising a Kabat CDR-H sequence comprising SEQ ID NO: 27, a Kabat CDR-H2 sequence comprising SEQ ID NO: 64, and a Kabat CDR-H3 sequence comprising SEQ ID NO: 90 and a VL sequence comprising a CDR-L1 sequence comprising SEQ ID NO: 116, a CDR-L2 sequence comprising SEQ ID NO: 128, and a CDR-L3 sequence SEQ ID NO: 155. In some aspects, the antibody comprises a $V_H$ sequence comprising a Kabat CDR-H1 sequence comprising SEQ ID NO: 28, a Kabat CDR-H2 sequence comprising SEQ ID NO: 62, and a Kabat CDR-H3 sequence comprising SEQ ID NO: 91 and a VL sequence comprising a CDR-L1 sequence comprising SEQ ID NO: 117, a CDR-L2 sequence comprising SEQ ID NO: 137, and a CDR-L3 sequence SEQ ID NO: 155. In some aspects, the antibody comprises a $V_H$ sequence comprising a Kabat CDR-H1 sequence comprising SEQ ID NO: 29, a Kabat CDR-H2 sequence comprising SEQ ID NO: 64, and a Kabat CDR-H3 sequence comprising SEQ ID NO: 92 and a VL sequence comprising a CDR-L1 sequence comprising SEQ ID NO: 118, a CDR-L2 sequence comprising SEQ ID NO: 137, and a CDR-L3 sequence SEQ ID NO: 158. In some aspects, the antibody comprises a $V_H$ sequence comprising a Kabat CDR-H1 sequence comprising SEQ ID NO: 25, a Kabat CDR-H2 sequence comprising SEQ ID NO: 65, and a Kabat CDR-H3 sequence comprising SEQ ID NO: 93 and a VL sequence comprising a CDR-L1 sequence comprising SEQ ID NO: 118, a CDR-L2 sequence comprising SEQ ID NO: 138, and a CDR-L3 sequence SEQ ID NO: 155. In some aspects, the antibody comprises a $V_H$ sequence comprising a Kabat CDR-H1 sequence comprising SEQ ID NO: 30, a Kabat CDR-H2 sequence comprising SEQ ID NO: 66, and a Kabat CDR-H3 sequence comprising SEQ ID NO: 94 and a VL sequence comprising a CDR-L1 sequence comprising SEQ ID NO: 119, a CDR-L2 sequence comprising SEQ ID NO: 139, and a CDR-L3 sequence SEQ ID NO: 159. In some aspects, the antibody comprises a $V_H$ sequence comprising a Kabat CDR-H1 sequence comprising SEQ ID NO: 31, a Kabat CDR-H2 sequence comprising SEQ ID NO: 67, and a Kabat CDR-H3 sequence comprising SEQ ID NO: 95 and a VL sequence comprising a CDR-L1 sequence comprising SEQ ID NO: 120, a CDR-L2 sequence comprising SEQ ID NO: 140, and a CDR-L3 sequence SEQ ID NO: 160. In some aspects, the antibody comprises a $V_H$ sequence comprising a Kabat CDR-H1 sequence comprising SEQ ID NO: 32, a Kabat CDR-H2 sequence comprising SEQ ID NO: 68, and a Kabat CDR-H3 sequence comprising SEQ ID NO: 96 and a VL sequence comprising a CDR-L1 sequence comprising SEQ ID NO: 121, a CDR-L2 sequence comprising SEQ ID NO: 141, and a CDR-L3 sequence SEQ ID NO: 161. In some aspects, the antibody comprises a $V_H$ sequence comprising a Kabat CDR-H1 sequence comprising SEQ ID NO: 33, a Kabat CDR-H2 sequence comprising SEQ ID NO: 69, and a Kabat CDR-H3 sequence comprising SEQ ID NO: 97 and a VL sequence comprising a CDR-L1 sequence comprising SEQ ID NO: 122, a CDR-L2 sequence comprising SEQ ID NO: 142, and a CDR-L3 sequence SEQ ID NO: 162. In some aspects, the antibody comprises a $V_H$ sequence comprising a Kabat CDR-H1 sequence comprising SEQ ID NO: 34, a Kabat CDR-H2 sequence comprising SEQ ID NO: 70, and a Kabat CDR-H3 sequence comprising SEQ ID NO: 98 and a VL sequence comprising a CDR-L1 sequence comprising SEQ ID NO: 105, a CDR-L2 sequence comprising SEQ ID NO: 143, and a CDR-L3 sequence SEQ ID NO: 163. In some aspects, the antibody comprises a $V_H$ sequence comprising a Kabat CDR-H1 sequence comprising SEQ ID NO: 18, a Kabat CDR-H2 sequence comprising SEQ ID NO: 54, and a Kabat CDR-H3 sequence comprising SEQ ID NO: 99 and a VL sequence comprising a CDR-L1 sequence comprising SEQ ID NO: 105, a CDR-L2 sequence comprising SEQ ID NO: 143, and a CDR-L3 sequence SEQ ID NO: 164. In some aspects, the antibody comprises a $V_H$ sequence comprising a Kabat CDR-H1 sequence comprising SEQ ID NO: 31, a Kabat CDR-H2 sequence comprising SEQ ID NO: 71, and a Kabat CDR-H3 sequence comprising SEQ ID NO: 100 and a VL sequence comprising a CDR-L1 sequence comprising SEQ ID NO: 123, a CDR-L2 sequence comprising SEQ ID NO: 144, and a CDR-L3 sequence SEQ ID NO: 165. In some aspects, the antibody comprises a $V_H$ sequence comprising a Kabat CDR-H1 sequence comprising SEQ ID NO: 24, a Kabat CDR-H2 sequence comprising SEQ ID NO: 61, and a Kabat CDR-H3 sequence comprising SEQ ID NO: 101 and a VL sequence comprising a CDR-L1 sequence comprising SEQ ID NO: 124, a CDR-L2 sequence comprising SEQ ID NO: 145, and a CDR-L3 sequence SEQ ID NO: 166.

In some aspects, the antibody comprises a $V_H$ sequence comprising a Chothia CDR-H1 sequence comprising SEQ ID NO: 1, a Chothia CDR-H2 sequence comprising SEQ ID NO: 38, and a Chothia CDR-H3 sequence comprising SEQ ID NO: 76 and a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Chothia CDR-H1 sequence comprising SEQ ID NO: 2, a Chothia CDR-H2 sequence comprising SEQ ID NO: 39, and a Chothia CDR-H3 sequence comprising SEQ ID NO: 77 and a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Chothia CDR-H1 sequence comprising SEQ ID NO: 2, a Chothia CDR-H2 sequence comprising SEQ ID NO: 40, and a Chothia CDR-H3 sequence comprising SEQ ID NO: 78 and a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Chothia CDR-H1 sequence comprising SEQ ID NO: 3, a Chothia CDR-H2 sequence comprising SEQ ID NO: 41, and a Chothia CDR-H3 sequence comprising SEQ ID NO: 79 and a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Chothia CDR-H1 sequence comprising SEQ ID NO: 4, a Chothia CDR-H2 sequence comprising SEQ ID NO: 41, and a Chothia CDR-H3 sequence comprising SEQ ID NO: 80 and a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Chothia CDR-H1 sequence comprising SEQ ID NO: 3, a Chothia CDR-H2 sequence comprising SEQ ID NO: 41, and a Chothia CDR-H3 sequence comprising SEQ ID NO: 76 and a VL sequence comprising a CDR-L1 sequence comprising SEQ ID NO: 106, a CDR-L2 sequence comprising SEQ ID NO: 129, and a CDR-L3 sequence SEQ ID NO: 150. In some aspects, the antibody comprises a $V_H$ sequence comprising a Chothia CDR-H1 sequence comprising SEQ ID NO: 2, a Chothia CDR-H2 sequence comprising SEQ ID NO: 42, and a Chothia CDR-H3 sequence comprising SEQ ID NO: 76 and a VL sequence comprising a CDR-L1 sequence comprising SEQ ID NO: 107, a CDR-L2 sequence comprising SEQ ID NO: 128, and a CDR-L3 sequence SEQ ID NO: 151. In some aspects, the antibody comprises a $V_H$ sequence comprising a Chothia CDR-H1 sequence comprising SEQ ID NO: 2, a Chothia CDR-H2 sequence comprising SEQ ID NO: 43, and a Chothia CDR-H3 sequence comprising SEQ ID NO: 81 and a VL sequence comprising a CDR-L1 sequence comprising SEQ ID NO: 108, a CDR-L2 sequence comprising SEQ ID NO: 130, and a CDR-L3 sequence SEQ ID NO: 151. In some aspects, the antibody comprises a $V_H$ sequence comprising a Chothia CDR-H1 sequence comprising SEQ ID NO: 2, a Chothia CDR-H2 sequence comprising SEQ ID NO: 42, and a Chothia CDR-H3 sequence comprising SEQ ID NO: 82 and a VL sequence comprising a CDR-L1 sequence comprising SEQ ID NO: 109, a CDR-L2 sequence comprising SEQ ID NO: 131, and a CDR-L3 sequence SEQ ID NO: 152. In some aspects, the antibody comprises a $V_H$ sequence comprising a Chothia CDR-H1 sequence comprising SEQ ID NO: 5, a Chothia CDR-H2 sequence comprising SEQ ID NO: 42, and a Chothia CDR-H3 sequence comprising SEQ ID NO: 76 and a VL sequence comprising a CDR-L1 sequence comprising SEQ ID NO: 107, a CDR-L2 sequence comprising SEQ ID NO: 132, and a CDR-L3 sequence SEQ ID NO: 153. In some aspects, the antibody comprises a $V_H$ sequence comprising a Chothia CDR-H1 sequence comprising SEQ ID NO: 2, a Chothia CDR-H2 sequence comprising SEQ ID NO: 42, and a Chothia CDR-H3 sequence comprising SEQ ID NO: 81 and a VL sequence comprising a CDR-L1 sequence comprising SEQ ID NO: 110, a CDR-L2 sequence comprising SEQ ID NO: 132, and a CDR-L3 sequence SEQ ID NO: 151. In some aspects, the antibody comprises a $V_H$ sequence comprising a Chothia CDR-H1 sequence comprising SEQ ID NO: 3, a Chothia CDR-H2 sequence comprising SEQ ID NO: 41, and a Chothia CDR-H3 sequence comprising SEQ ID NO: 83 and a VL sequence comprising a CDR-L1 sequence comprising SEQ ID NO: 111, a CDR-L2 sequence comprising SEQ ID NO: 133, and a CDR-L3 sequence SEQ ID NO: 151. In some aspects, the antibody comprises a $V_H$ sequence comprising a Chothia CDR-H1 sequence comprising SEQ ID NO: 3, a Chothia CDR-H2 sequence comprising SEQ ID NO: 41, and a Chothia CDR-H3 sequence comprising SEQ ID NO: 84 and a VL sequence comprising a CDR-L1 sequence comprising SEQ ID NO: 105, a CDR-L2 sequence comprising SEQ ID NO: 128, and a CDR-L3 sequence SEQ ID NO: 149. In some aspects, the antibody comprises a $V_H$ sequence comprising a Chothia CDR-H1 sequence comprising SEQ ID NO: 6, a Chothia CDR-H2 sequence comprising SEQ ID NO: 44, and a Chothia CDR-H3 sequence comprising SEQ ID NO: 85 and a VL sequence comprising a CDR-L1 sequence comprising SEQ ID NO: 105, a CDR-L2 sequence comprising SEQ ID NO: 128, and a CDR-L3 sequence SEQ ID NO: 154. In some aspects, the antibody comprises a $V_H$ sequence comprising a Chothia CDR-H1 sequence comprising SEQ ID NO: 6, a Chothia CDR-H2 sequence comprising SEQ ID NO: 44, and a Chothia CDR-H3 sequence comprising SEQ ID NO: 86 and a VL sequence comprising a CDR-L1 sequence comprising SEQ ID NO: 105, a CDR-L2 sequence comprising SEQ ID NO: 128, and a CDR-L3 sequence SEQ ID NO: 154. In some aspects, the antibody comprises a $V_H$ sequence comprising a Chothia CDR-H1 sequence comprising SEQ ID NO: 7, a Chothia CDR-H2 sequence comprising SEQ ID NO: 45, and a Chothia CDR-H3 sequence comprising SEQ ID NO: 87 and a VL sequence comprising a CDR-L1 sequence comprising SEQ ID NO: 112, a CDR-L2 sequence comprising SEQ ID NO: 134, and a CDR-L3 sequence SEQ ID NO: 155. In some aspects, the antibody comprises a $V_H$ sequence comprising a Chothia CDR-H1 sequence comprising SEQ ID NO: 8, a Chothia CDR-H2 sequence comprising SEQ ID NO: 44, and a Chothia CDR-H3 sequence comprising SEQ ID NO: 88 and a VL sequence comprising a CDR-L1 sequence comprising SEQ ID NO: 113, a CDR-L2 sequence comprising SEQ ID NO: 135, and a CDR-L3 sequence SEQ ID NO: 156. In some aspects, the antibody comprises a $V_H$ sequence comprising a Chothia CDR-H1 sequence comprising SEQ ID NO: 8, a Chothia CDR-H2 sequence comprising SEQ ID NO: 44, and a Chothia CDR-H3 sequence comprising SEQ ID NO: 89 and a VL sequence comprising a CDR-L1 sequence comprising SEQ ID NO: 114, a CDR-L2 sequence comprising SEQ ID NO: 136, and a CDR-L3 sequence SEQ ID NO: 157. In some aspects, the antibody comprises a $V_H$ sequence comprising a Chothia CDR-H1 sequence comprising SEQ ID NO: 7, a Chothia CDR-H2 sequence comprising SEQ ID NO: 44, and a Chothia CDR-H3 sequence comprising SEQ ID NO: 90 and a VL sequence comprising a CDR-L1 sequence comprising SEQ ID NO: 115, a CDR-L2 sequence comprising SEQ ID NO: 135, and a CDR-L3 sequence SEQ ID NO: 157. In some aspects, the antibody comprises a $V_H$ sequence comprising a Chothia CDR-H1 sequence comprising SEQ ID NO: 9, a Chothia CDR-H2 sequence comprising SEQ ID NO: 44, and a Chothia CDR-H3 sequence comprising SEQ ID NO: 90 and a VL sequence comprising a CDR-L1 sequence comprising SEQ ID NO: 116, a CDR-L2 sequence comprising SEQ ID NO: 128, and a CDR-L3 sequence SEQ ID NO: 155. In some aspects, the antibody comprises a $V_H$ sequence comprising a Chothia CDR-H1 sequence comprising SEQ ID NO: 6, a Chothia CDR-H2 sequence comprising SEQ ID NO: 45, and a Chothia CDR-H3 sequence comprising SEQ ID NO: 91 and a VL sequence comprising a CDR-L1 sequence comprising SEQ ID NO: 117, a CDR-L2 sequence comprising SEQ ID NO: 137, and a CDR-L3 sequence SEQ ID NO: 155. In some aspects, the antibody comprises a $V_H$ sequence comprising a Chothia CDR-H1 sequence comprising SEQ ID NO: 8, a Chothia CDR-H2 sequence comprising SEQ ID NO: 44, and a Chothia CDR-H3 sequence comprising SEQ ID NO: 92 and a VL sequence comprising a CDR-L1 sequence comprising SEQ ID NO: 118, a CDR-L2 sequence comprising SEQ ID NO: 137, and a CDR-L3 sequence SEQ ID NO: 158. In some aspects, the antibody comprises a $V_H$ sequence comprising a Chothia CDR-H1 sequence comprising SEQ ID NO: 7, a Chothia CDR-H2 sequence comprising SEQ ID NO: 44, and a Chothia CDR-H3 sequence comprising SEQ ID NO: 93 and a VL sequence comprising a CDR-L1 sequence comprising SEQ ID NO: 118, a CDR-L2 sequence comprising SEQ ID NO: 138, and a CDR-L3 sequence SEQ ID NO: 155. In some aspects, the antibody comprises a $V_H$ sequence comprising a Chothia CDR-H1 sequence comprising SEQ ID NO: 10, a Chothia CDR-H2 sequence comprising SEQ ID NO: 46, and a Chothia CDR-H3 sequence comprising SEQ ID NO: 94 and a VL sequence comprising a CDR-L1 sequence comprising SEQ ID NO: 119, a CDR-L2 sequence comprising SEQ ID NO: 139, and a CDR-L3 sequence SEQ ID NO: 159. In some aspects, the antibody comprises a $V_H$ sequence comprising a Chothia CDR-H1 sequence comprising SEQ ID NO: 11, a Chothia CDR-H2 sequence comprising SEQ ID NO: 47, and a Chothia CDR-H3 sequence comprising SEQ ID NO: 95 and a VL sequence comprising a CDR-L sequence comprising SEQ ID NO: 120, a CDR-L2 sequence comprising SEQ ID NO: 140, and a CDR-L3 sequence SEQ ID NO: 160. In some aspects, the antibody comprises a $V_H$ sequence comprising a Chothia CDR-H1 sequence comprising SEQ ID NO: 12, a Chothia CDR-H2 sequence comprising SEQ ID NO: 48, and a Chothia CDR-H3 sequence comprising SEQ ID NO: 96 and a VL sequence comprising a CDR-L1 sequence comprising SEQ ID NO: 121, a CDR-L2 sequence comprising SEQ ID NO: 141, and a CDR-L3 sequence SEQ ID NO: 161. In some aspects, the antibody comprises a $V_H$ sequence comprising a Chothia CDR-H1 sequence comprising SEQ ID NO: 13, a Chothia CDR-H2 sequence comprising SEQ ID NO: 44, and a Chothia CDR-H3 sequence comprising SEQ ID NO: 97 and a VL sequence comprising a CDR-L1 sequence comprising SEQ ID NO: 122, a CDR-L2 sequence comprising SEQ ID NO: 142, and a CDR-L3 sequence SEQ ID NO: 162. In some aspects, the antibody comprises a $V_H$ sequence comprising a Chothia CDR-H1 sequence comprising SEQ ID NO: 14, a Chothia CDR-H2 sequence comprising SEQ ID NO: 49, and a Chothia CDR-H3 sequence comprising SEQ ID NO: 98 and a VL sequence comprising a CDR-L1 sequence comprising SEQ ID NO: 105, a CDR-L2 sequence comprising SEQ ID NO: 143, and a CDR-L3 sequence SEQ ID NO: 163. In some aspects, the antibody comprises a $V_H$ sequence comprising a Chothia CDR-H1 sequence comprising SEQ ID NO: 1, a Chothia CDR-H2 sequence comprising SEQ ID NO: 38, and a Chothia CDR-H3 sequence comprising SEQ ID NO: 99 and a VL sequence comprising a CDR-L1 sequence comprising SEQ ID NO: 105, a CDR-L2 sequence comprising SEQ ID NO: 143, and a CDR-L3 sequence SEQ ID NO: 164. In some aspects, the antibody comprises a $V_H$ sequence comprising a Chothia CDR-H1 sequence comprising SEQ ID NO: 11, a Chothia CDR-H2 sequence compris-ing SEQ ID NO: 50, and a Chothia CDR-H3 sequence comprising SEQ ID NO: 100 and a VL sequence comprising a CDR-L1 sequence comprising SEQ ID NO: 123, a CDR-L2 sequence comprising SEQ ID NO: 144, and a CDR-L3 sequence SEQ ID NO: 165. In some aspects, the antibody comprises a $V_H$ sequence comprising a Chothia CDR-H1 sequence comprising SEQ ID NO: 6, a Chothia CDR-H2 sequence comprising SEQ ID NO: 44, and a Chothia CDR-H3 sequence comprising SEQ ID NO: 101 and a VL sequence comprising a CDR-L1 sequence comprising SEQ ID NO: 124, a CDR-L2 sequence comprising SEQ ID NO: 145, and a CDR-L3 sequence SEQ ID NO: 166.

2.7.3.1. Variants of $V_H$-$V_L$ Pairs

In some embodiments, the $V_H$-$V_L$ pairs provided herein comprise a variant of an illustrative $V_H$ and/or $V_L$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.1% identity with any of the illustrative $V_H$ sequences provided in this disclosure.

In some embodiments, the $V_H$ sequence comprises, consists of, or consists essentially of any of the illustrative $V_H$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.05% identity with any of the illustrative $V_L$ sequences provided in this disclosure.

In some embodiments, the $V_L$ sequence comprises, consists of, or consists essentially of any of the illustrative $V_L$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.7.4 HC+LC

In some aspects, the antibody comprises or consists of one or more heavy chains consisting of an HC sequence and one or more light chains consisting of an LC sequence. In some aspects, the antibody comprises or consists of two identical heavy chains consisting of an HC sequence and two identical light chains consisting of an LC sequence.

In some aspects, the HC sequence is an HC sequence comprising, consisting of, or consisting essentially of a sequence selected from SEQ ID NOS: 232-262 and the LC sequence is an LC sequence comprising, consisting of, or consisting essentially of SEQ ID NOS: 300-330. In some embodiments, the HC sequence is an HC sequence consisting of a sequence selected from SEQ ID NOS: 232-262 and the LC sequence is an LC sequence consisting of a sequence selected from SEQ ID NOS: 300-330. In some embodiments, the HC sequence is an HC sequence comprising, consisting of, or consisting essentially of a sequence selected from SEQ ID NOS: 266-296 and the LC sequence is an LC sequence comprising, consisting of, or consisting essentially of SEQ ID NOS: 300-330. In some embodiments, the HC sequence is an HC sequence consisting of a sequence selected from SEQ ID NOS: 266-296 and the LC sequence is an LC sequence consisting of a sequence selected from SEQ ID NOS: 300-330.

In some aspects, the HC sequence is an HC sequence consisting of SEQ ID NO: 232 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 233 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 234 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 235 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 236 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 237 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 238 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 239 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 240 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 241 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 242 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 243 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 244 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 245 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 246 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 247 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 248 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 249 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 250 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 251 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 252 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 253 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 254 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 255 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 256 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 257 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 258 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 259 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 260 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 261 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 262 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 266 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 267 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 268 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 269 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 270 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 271 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 272 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 273 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 274 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 275 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 276 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 277 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 278 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302.

In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 279 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 280 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 281 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 282 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 283 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 284 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 285 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 286 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 287 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 288 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 289 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 290 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 291 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 292 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 293 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 294 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 295 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 296 and the LC sequence is an LC sequence consisting of a sequence selected from SEQ ID NOS: 300-330. In some aspects, the LC sequence is SEQ ID NO: 300. In some aspects, the LC sequence is SEQ ID NO: 301. In some aspects, the LC sequence is SEQ ID NO: 302. In some aspects, the LC sequence is SEQ ID NO: 303. In some aspects, the LC sequence is SEQ ID NO: 304. In some aspects, the LC sequence is SEQ ID NO: 305. In some aspects, the LC sequence is SEQ ID NO: 306. In some aspects, the LC sequence is SEQ ID NO: 307. In some aspects, the LC sequence is SEQ ID NO: 308. In some aspects, the LC sequence is SEQ ID NO: 309. In some aspects, the LC sequence is SEQ ID NO: 310. In some aspects, the LC sequence is SEQ ID NO: 311. In some aspects, the LC sequence is SEQ ID NO: 312. In some aspects, the LC sequence is SEQ ID NO: 313. In some aspects, the LC sequence is SEQ ID NO: 314. In some aspects, the LC sequence is SEQ ID NO: 315. In some aspects, the LC sequence is SEQ ID NO: 316. In some aspects, the LC sequence is SEQ ID NO: 317. In some aspects, the LC sequence is SEQ ID NO: 318. In some aspects, the LC sequence is SEQ ID NO: 319. In some aspects, the LC sequence is SEQ ID NO: 320. In some aspects, the LC sequence is SEQ ID NO: 321. In some aspects, the LC sequence is SEQ ID NO: 322. In some aspects, the LC sequence is SEQ ID NO: 323. In some aspects, the LC sequence is SEQ ID NO: 324. In some aspects, the LC sequence is SEQ ID NO: 325. In some aspects, the LC sequence is SEQ ID NO: 326. In some aspects, the LC sequence is SEQ ID NO: 327. In some aspects, the LC sequence is SEQ ID NO: 328. In some aspects, the LC sequence is SEQ ID NO: 329. In some aspects, the LC sequence is SEQ ID NO: 330.

In some aspects, the HC sequence is an HC sequence consisting of SEQ ID NO: 232 and the LC sequence is an LC sequence consisting of sequence SEQ ID NO: 300. In some aspects, the HC sequence is an HC sequence consisting of SEQ ID NO: 233 and the LC sequence is an LC sequence consisting of sequence SEQ ID NO: 301. In some aspects, the HC sequence is an HC sequence consisting of SEQ ID NO: 234 and the LC sequence is an LC sequence consisting of sequence SEQ ID NO: 302. In some aspects, the HC sequence is an HC sequence consisting of SEQ ID NO: 235 and the LC sequence is an LC sequence consisting of sequence SEQ ID NO: 303. In some aspects, the HC sequence is an HC sequence consisting of SEQ ID NO: 236 and the LC sequence is an LC sequence consisting of sequence SEQ ID NO: 304. In some aspects, the HC sequence is an HC sequence consisting of SEQ ID NO: 237 and the LC sequence is an LC sequence consisting of sequence SEQ ID NO: 305. In some aspects, the HC sequence is an HC sequence consisting of SEQ ID NO: 238 and the LC sequence is an LC sequence consisting of sequence SEQ ID NO: 306. In some aspects, the HC sequence is an HC sequence consisting of SEQ ID NO: 239 and the LC sequence is an LC sequence consisting of sequence SEQ ID NO: 307. In some aspects, the HC sequence is an HC sequence consisting of SEQ ID NO: 240 and the LC sequence is an LC sequence consisting of sequence SEQ ID NO: 308. In some aspects, the HC sequence is an HC sequence consisting of SEQ ID NO: 241 and the LC sequence is an LC sequence consisting of sequence SEQ ID NO: 309. In some aspects, the HC sequence is an HC sequence consisting of SEQ ID NO: 242 and the LC sequence is an LC sequence consisting of sequence SEQ ID NO: 310. In some aspects, the HC sequence is an HC sequence consisting of SEQ ID NO: 243 and the LC sequence is an LC sequence consisting of sequence SEQ ID NO: 311. In some aspects, the HC sequence is an HC sequence consisting of SEQ ID NO: 244 and the LC sequence is an LC sequence consisting of sequence SEQ ID NO: 312. In some aspects, the HC sequence is an HC sequence consisting of SEQ ID NO: 245 and the LC sequence is an LC sequence consisting of sequence SEQ ID NO: 313. In some aspects, the HC sequence is an HC sequence consisting of SEQ ID NO: 246 and the LC sequence is an LC sequence consisting of sequence SEQ ID NO: 314. In some aspects, the HC sequence is an HC sequence consisting of SEQ ID NO: 247 and the LC sequence is an LC sequence consisting of sequence SEQ ID NO: 315. In some aspects, the HC sequence is an HC sequence consisting of SEQ ID NO: 248 and the LC sequence is an LC sequence consisting of sequence SEQ ID NO: 316. In some aspects, the HC sequence is an HC sequence consisting of SEQ ID NO: 249 and the LC sequence is an LC sequence consisting of sequence SEQ ID NO: 317. In some aspects, the HC sequence is an HC sequence consisting of SEQ ID NO: 250 and the LC sequence is an LC sequence consisting of sequence SEQ ID NO: 318. In some aspects, the HC sequence is an HC sequence consisting of SEQ ID NO: 251 and the LC sequence is an LC sequence consisting of sequence SEQ ID NO: 319. In some aspects, the HC sequence is an HC sequence consisting of SEQ ID NO: 252 and the LC sequence is an LC sequence consisting of sequence SEQ ID NO: 320. In some aspects, the HC sequence is an HC sequence consisting of SEQ ID NO: 253 and the LC sequence is an LC sequence consisting of sequence SEQ ID NO: 321. In some aspects, the HC sequence is an HC sequence consisting of SEQ ID NO: 254 and the LC sequence is an LC sequence consisting of sequence SEQ ID NO: 322. In some aspects, the HC sequence is an HC sequence consisting of SEQ ID NO: 255 and the LC sequence is an LC sequence consisting of sequence SEQ ID NO: 323. In some aspects, the HC sequence is an HC sequence consisting of SEQ ID NO: 256 and the LC sequence is an LC sequence consisting of sequence SEQ ID NO: 324. In some aspects, the HC sequence is an HC sequence consisting of SEQ ID NO: 257 and the LC sequence is an LC sequence consisting of sequence SEQ ID NO: 325. In some aspects, the HC sequence is an HC sequence consisting of SEQ ID NO: 258 and the LC sequence is an LC sequence consisting of sequence SEQ ID NO: 326. In some aspects, the HC sequence is an HC sequence consisting of SEQ ID NO: 259 and the LC sequence is an LC sequence consisting of sequence SEQ ID NO: 327. In some aspects, the HC sequence is an HC sequence consisting of SEQ ID NO: 260 and the LC sequence is an LC sequence consisting of sequence SEQ ID NO: 328. In some aspects, the HC sequence is an HC sequence consisting of SEQ ID NO: 261 and the LC sequence is an LC sequence consisting of sequence SEQ ID NO: 329. In some aspects, the HC sequence is an HC sequence consisting of SEQ ID NO: 262 and the LC sequence is an LC sequence consisting of sequence SEQ ID NO: 330.

In some aspects, the HC sequence is an HC sequence consisting of SEQ ID NO: 266 and the LC sequence is an LC sequence consisting of a sequence SEQ ID NO: 300. In some aspects, the HC sequence is an HC sequence consisting of SEQ ID NO: 267 and the LC sequence is an LC sequence consisting of sequence SEQ ID NO: 301. In some aspects, the HC sequence is an HC sequence consisting of SEQ ID NO: 268 and the LC sequence is an LC sequence consisting of sequence SEQ ID NO: 302. In some aspects, the HC sequence is an HC sequence consisting of SEQ ID NO: 269 and the LC sequence is an LC sequence consisting of sequence SEQ ID NO: 303. In some aspects, the HC sequence is an HC sequence consisting of SEQ ID NO: 270 and the LC sequence is an LC sequence consisting of sequence SEQ ID NO: 304. In some aspects, the HC sequence is an HC sequence consisting of SEQ ID NO: 271 and the LC sequence is an LC sequence consisting of sequence SEQ ID NO: 305. In some aspects, the HC sequence is an HC sequence consisting of SEQ ID NO: 272 and the LC sequence is an LC sequence consisting of sequence SEQ ID NO: 306. In some aspects, the HC sequence is an HC sequence consisting of SEQ ID NO: 273 and the LC sequence is an LC sequence consisting of sequence SEQ ID NO: 307. In some aspects, the HC sequence is an HC sequence consisting of SEQ ID NO: 274 and the LC sequence is an LC sequence consisting of sequence SEQ ID NO: 308. In some aspects, the HC sequence is an HC sequence consisting of SEQ ID NO: 275 and the LC sequence is an LC sequence consisting of sequence SEQ ID NO: 309. In some aspects, the HC sequence is an HC sequence consisting of SEQ ID NO: 276 and the LC sequence is an LC sequence consisting of sequence SEQ ID NO: 310. In some aspects, the HC sequence is an HC sequence consisting of SEQ ID NO: 277 and the LC sequence is an LC sequence consisting of sequence SEQ ID NO: 311. In some aspects, the HC sequence is an HC sequence consisting of SEQ ID NO: 278 and the LC sequence is an LC sequence consisting of sequence SEQ ID NO: 312. In some aspects, the HC sequence is an HC sequence consisting of SEQ ID NO: 279 and the LC sequence is an LC sequence consisting of sequence SEQ ID NO: 313. In some aspects, the HC sequence is an HC sequence consisting of SEQ ID NO: 280 and the LC sequence is an LC sequence consisting of sequence SEQ ID NO: 314. In some aspects, the HC sequence is an HC sequence consisting of SEQ ID NO: 281 and the LC sequence is an LC sequence consisting of sequence SEQ ID NO: 315. In some aspects, the HC sequence is an HC sequence consisting of SEQ ID NO: 282 and the LC sequence is an LC sequence consisting of sequence SEQ ID NO: 316. In some aspects, the HC sequence is an HC sequence consisting of SEQ ID NO: 283 and the LC sequence is an LC sequence consisting of sequence SEQ ID NO: 317. In some aspects, the HC sequence is an HC sequence consisting of SEQ ID NO: 284 and the LC sequence is an LC sequence consisting of sequence SEQ ID NO: 318. In some aspects, the HC sequence is an HC sequence consisting of SEQ ID NO: 285 and the LC sequence is an LC sequence consisting of sequence SEQ ID NO: 319. In some aspects, the HC sequence is an HC sequence consisting of SEQ ID NO: 286 and the LC sequence is an LC sequence consisting of sequence SEQ ID NO: 320. In some aspects, the HC sequence is an HC sequence consisting of SEQ ID NO: 287 and the LC sequence is an LC sequence consisting of sequence SEQ ID NO: 321. In some aspects, the HC sequence is an HC sequence consisting of SEQ ID NO: 288 and the LC sequence is an LC sequence consisting of sequence SEQ ID NO: 322. In some aspects, the HC sequence is an HC sequence consisting of SEQ ID NO: 289 and the LC sequence is an LC sequence consisting of sequence SEQ ID NO: 323. In some aspects, the HC sequence is an HC sequence consisting of SEQ ID NO: 290 and the LC sequence is an LC sequence consisting of sequence SEQ ID NO: 324. In some aspects, the HC sequence is an HC sequence consisting of SEQ ID NO: 291 and the LC sequence is an LC sequence consisting of sequence SEQ ID NO: 325. In some aspects, the HC sequence is an HC sequence consisting of SEQ ID NO: 292 and the LC sequence is an LC sequence consisting of sequence SEQ ID NO: 326. In some aspects, the HC sequence is an HC sequence consisting of SEQ ID NO: 293 and the LC sequence is an LC sequence consisting of sequence SEQ ID NO: 327. In some aspects, the HC sequence is an HC sequence consisting of SEQ ID NO: 294 and the LC sequence is an LC sequence consisting of sequence SEQ ID NO: 328. In some aspects, the HC sequence is an HC sequence consisting of SEQ ID NO: 295 and the LC sequence is an LC sequence consisting of sequence SEQ ID NO: 329. In some aspects, the HC sequence is an HC sequence consisting of SEQ ID NO: 296 and the LC sequence is an LC sequence consisting of sequence SEQ ID NO: 330.

2.8. Consensus Sequences

In some embodiments, provided herein are anti-HLA-G antibodies comprising one or more sequences defined by consensus sequences. Each consensus sequence is based, at least in part, on one or more alignments of two or more useful anti-HLA-G CDR sequences provided in this disclosure. Based on such alignments, a person of skill in the art would recognize that different amino acid residues may useful in certain positions of the CDRs. Accordingly, each consensus sequence encompasses two or more useful anti-HLA-G CDR sequences.

2.8.1. CDR-H3 Consensus Sequences

In some embodiments, the antibody comprises a CDR-H3 sequence defined by the consensus sequence G-$y_2$-$y_3$-R-A-V-P-F-$y_9$-$y_{10}$ (SEQ ID NOS: 76-84), where $y_2$ is I, P, Q, T, or V; $y_3$ is A, F, K, or R; $y_9$ is A, D, Q, or V; $y_{10}$ is D, R, or Y.

In some aspects, when $y_2$ is I; $y_3$ is A or R; $y_9$ is F; and $y_{10}$ is Y. In some aspects, when $y_2$ is V; $y_3$ is R; $y_9$ is A, D, Q, or V; and $y_{10}$ is D, R, or Y. In some aspects, when $y_3$ is R; $y_2$ is 1, T, or V; $y_9$ is A, D, or Q; and $y_{10}$ is D, R, or Y. In some aspects, when $y_9$ is D; $y_2$ is I, P, Q, or V; $y_3$ is A, F, K, or R; and $y_{10}$ is Y. In some aspects, when $y_{10}$ is Y; $y_2$ is I, P, R, or V; $y_3$ is A, F, K, or R; and $y_9$ is D. In some aspects, when Yon is D; $y_2$ is V; $y_3$ is R; and $y_9$ is A or V.

In some aspects, when $y_2$ is V; $y_3$ is R: $y_9$ is D; and $y_{10}$ is Y. In some aspects, when $y_2$ is I; $y_3$ is A; Y is D; and $y_{10}$ is Y. In some aspects, when $y_2$ is P; $y_3$ is K; $y_9$ is D; and Yon is Y. In some aspects, when $y_2$ is V; $y_3$ is R; $y_9$ is V; and $y_{10}$ is D. In some aspects, when $y_2$ is V; $y_3$ is R; Y is Q; and $y_{10}$ is R. In some aspects, when $y_2$ is T; $y_3$ is R; $y_9$ is D; and $y_{10}$ is Y. In some aspects, when $y_2$ is V; $y_3$ is R; $y_9$ is A; and $y_{10}$ is D. In some aspects, when $y_2$ is I; $y_3$ is R; $y_9$ is D; and $y_{10}$ is Y. In some aspects, when $y_2$ is Q; $y_3$ is F; $y_9$ is D; and $y_{10}$ is Y.

In some embodiments, the antibody comprises a CDR-H3 sequence defined by the consensus sequence G-G-$\Phi_3$-$\Phi_4$-$\Phi_5$-Y-S-R-G-P-$\Phi_{11}$-D-V (SEQ ID NOS: 85-93), where $\Phi_3$ is E, G, Q, or T; $\Phi_4$ is A, H, P, Q. or V; $\Phi_5$ is K or T; and $\Phi_{11}$ is F, L, or M.

In some aspects, $\Phi_3$ is G; when $\Phi_4$ is A or Q; $\Phi_5$ is T; and $\Phi_{11}$ is V. In some aspects, $\Phi_3$ is T; when $\Phi_4$ is H, P, or V; $\Phi_5$ is I, T, or Y; and $\Phi_{11}$ is V. In some aspects, $\Phi_4$ is H; when $\Phi_3$ is T; $\Phi_5$ is T; and $\Phi_{11}$ is F, L, or M. In some aspects, $\Phi_4$ is V; when $\Phi_3$ is E, T, or Q; $\Phi_5$ is K or T; and $\Phi_{11}$ is L. In some aspects, $\Phi_5$ is T; when $\Phi_3$ is E, G. T, or Q; $\Phi_4$ is A, H, Q, or V; and $\Phi_{11}$ is F, L, or M. In some aspects, $\Phi_{11}$ is L; when $\Phi_3$ is E, G, T, or Q; $\Phi_4$ is A, H, P, Q, or V; and $\Phi_5$ is I, K, or T.

In some aspects, when $\Phi_3$ is T; when $\Phi_4$ is H; $\Phi_5$ is T; and $\Phi_{11}$ is M. In some aspects, when $\Phi_3$ is T; when $\Phi_4$ is H; $\Phi_5$ is T; and $\Phi_{11}$ is F. In some aspects, when $\Phi_3$ is T; when $\Phi_4$ is P; $\Phi_5$ is I; and $\Phi_{11}$ is L. In some aspects, when $\Phi_3$ is G; when $\Phi_4$ is Q; $\Phi_5$ is T; and $\Phi_{11}$ is L. In some aspects, when $\Phi_3$ is G; when $\Phi_4$ is A; $\Phi_5$ is T; and $\Phi_{11}$ is L. In some aspects, when $\Phi_3$ is T; when $\Phi_4$ is H; $\Phi_5$ is T; and $\Phi_{11}$ is L. In some aspects, when $\Phi_3$ is T; when $\Phi_4$ is H; $\Phi_5$ is T; and $\Phi_{11}$ is L. In some aspects, when $\Phi_3$ is T: when $\Phi_4$ is V; $\Phi_5$ is K; and $\Phi_{11}$ is L. In some aspects, when $\Phi_3$ is Q; when $\Phi_4$ is V; $\Phi_5$ is T; and $\Phi_{11}$ is L. In some aspects, when $\Phi_3$ is E; when $\Phi_4$ is V; $\Phi_5$ is T; and $\Phi_{11}$ is L.

2.8.2. Chothia CDR-H2 Consensus Sequences

In some embodiments, the antibody comprises a Chothia CDR-H2 sequence defined by the consensus sequence Y-$\varepsilon_2$-S-$\varepsilon_4$-S(SEQ ID NOS: 38 and 44-45), where $\varepsilon_2$ is H or Y and $\varepsilon_4$ is A or G.

In some aspects, when $\varepsilon_2$ is H; $\varepsilon_4$ is A or G. In some aspects, when $\varepsilon_4$ is G, $\varepsilon_2$ is H or Y.

In some aspects, when $\varepsilon_2$ is Y; $\varepsilon_4$ is G. In some aspects, when $\varepsilon_2$ is H; $\varepsilon_4$ is G. In some aspects, when $\varepsilon_2$ is H; $\varepsilon_4$ is A.

In some embodiments, the antibody comprises a Chothia CDR-H2 sequence defined by the consensus sequence $\alpha_1$-$\alpha_2$-S-G-S(SEQ ID NOS: 39, 41-42, and 49), where $\alpha_1$ is A, H, or S; and $\alpha_2$ is S or Y.

In some aspects, when $\alpha_1$, is S; $\alpha_2$ is S or Y.

In some aspects, when $\alpha_1$ is S; $\alpha_2$ is S. In some aspects, when $\alpha_1$ is S; $\alpha_2$ is Y. In some aspects, when $\alpha_1$ is H; $\alpha_2$ is Y. In some aspects, when $\alpha_1$ is A; $\alpha_2$ is Y.

In some embodiments, the antibody comprises a Chothia CDR-H2 sequence defined by the consensus sequence $\beta_1$-$\beta_2$-S-G-$\beta_5$-$\beta_6$ (SEQ ID NOS: 56-60), where $\beta_1$ is A or S; $\beta_2$ is G or S; $\beta_5$ is 1 or S; and $\beta_6$ is T or V.

In some aspects, when $\beta_1$ is S, $\beta_2$ is G or S; $\beta_5$ is I or S; and $\beta_6$ is T or V. In some aspects, when $\beta_2$ is S, $\beta_1$ is A or S; $\beta_5$ is S; and $\beta_6$ is T or V. In some aspects, when $\beta_5$ is S, $\beta_1$ is A or S; $\beta_2$ is S; and $\beta_6$ is T or V. In some aspects, when $\beta_6$ is T, $\beta_1$ is S; $\beta_2$ is G or S; and $\beta_5$ is I or T.

In some aspects, when $\beta_1$ is A; $\beta_2$ is S; $\beta_5$ is S; and $\beta_6$ is V. In some aspects, when $\beta_1$ is S; $\beta_2$ is G; $\beta_5$ is I; and $\beta_6$ is T. In some aspects, when $\beta_1$ is S; $\beta_2$ is S; $\beta_5$ is S; and $\beta_6$ is T.

2.83. Chothia CDR-H1 Consensus Sequences

In some embodiments, the antibody comprises a Chothia CDR-H1 sequence defined by the consensus sequence G-G-S-I-S-S-$\Omega_7$-$\Omega_8$-$\Omega_9$ (SEQ ID NOS: 1-4 and 13-14), where $\Omega_7$ is S or A; Us is D, S, or N; and $\Omega_9$ is T, N, Y, or is absent.

In some aspects, when $\omega_7$ is S; $\Omega_8$ is D, N. or S; and $\Omega_9$ is T. Y, or is absent.

In some aspects, when $\Omega_8$ is D; $\omega_7$ is S or A; and $\Omega_9$ is N, T, or Y.

In some aspects, when $\Omega_8$ is T; $\Omega_7$ is S; and $\Omega_8$ is D or S. In some aspects, when $\Omega_9$ is Y; $\Omega_7$ is S; and $\Omega_8$ is D or S.

In some aspects, when $\Omega_7$ is S; $\Omega_8$ is D; and $\Omega_9$ is Y. In some aspects, when $\Omega_7$ is S; $\Omega_8$ is S; and $\Omega_9$ is T. In some aspects, when $\Omega_7$ is S; $\Omega_8$ is D; and $\Omega_9$ is T. In some aspects, when $\omega_7$ is A; $\Omega_8$ is D; and $\Omega_9$ is N. In some aspects, when $\Omega_7$ is S; $\Omega_8$ is N; and $\Omega_9$ is absent. In some aspects, when $\Omega_7$ is S; $\Omega_8$ is S; and $\Omega_9$ is Y.

In some embodiments, the antibody comprises a Chothia CDR-H1 sequence defined by the consensus sequence G-Y-S-I-$v_5$-S-G-$v_8$ (SEQ ID NOS: 6-9), where $v_5$ is S or L and $v_8$ is F, H, or Y.

In some aspects, when $v_5$ is S, $v_5$ is F, H, or Y.

In some aspects, when $v_5$ is S, $v_8$ is F. In some aspects, when $v_5$ is S, $v_8$ is H. In some aspects, when $v_5$ is S. $v_8$ is Y. In some aspects, when $v_5$ is L. $v_8$ is Y.

In some embodiments, the antibody comprises a Chothia CDR-H1 sequence defined by the consensus sequence G-F-T-F-$\kappa_5$-$\kappa_6$-$\kappa_7$ (SEQ ID NOS: 10-12), where $\kappa_5$ is D or s; $\kappa_6$ is D, N, or S; and $\kappa_7$ is S or Y.

In some aspects, when $\kappa_5$ is S; $\kappa_6$ is D or S; and $\kappa_7$ is S or Y. In some aspects, when $\kappa_7$ is Y; $\kappa_5$ is D or S; and $\kappa_6$ is N or D.

In some aspects, when $\kappa_5$ is D; $\kappa_6$ is N; and $\kappa_7$ is Y. In some aspects, when $\kappa_5$ is S; $\kappa_6$ is D; and $\kappa_7$ is Y. In some aspects, when $\kappa_5$ is S; $\kappa_6$ is S; and $\kappa_7$ is S.

2.8.4. Kabat CDR-H2 Consensus Sequences

In some embodiments, the antibody comprises a Kabat CDR-H2 sequence defined by the consensus sequence $\beta_1$-I-$\beta_3$-$\beta_4$-$\beta_5$-$\beta_6$-$\beta_7$-T-$\beta_9$-Y-N-P-S-L-K-S(SEQ ID NOS: 54-65 and 69-70) where $\beta_1$ is A, E, G, or S; $\beta_3$ is A, H, S, or Y; $\beta_4$, is H, S, or Y; $\beta_5$ is N or S; $\beta_2$ is A or G; $\beta_7$ is A, L, or S; and $\beta_9$ is A, N, L, V, or Y.

In some aspects, when $\beta_1$ is S; $\beta_3$ is A, H, S, or Y; $\beta_4$ is H, S, or Y; $\beta_5$ is N or S; $\beta_6$ is A or G; $\beta_7$ is A, L, or S; and $\beta_9$ is A, N, L, V, or Y. In some aspects, when $\beta_1$ is G; $\beta_3$ is A or Y; $\beta_4$ is H or Y; $\beta_5$ is G or S; $\beta_6$ is A or G; $\beta_7$ is S; and $\beta_9$ is A or Y. In some aspects, when $\beta_3$ is Y; $\beta_1$ is A, E, G, or S; $\beta_4$ is H or Y; $\beta_5$ is S; $\beta_6$ is A or G; $\beta_7$ is S; and $\beta_9$ is A, N, V, or Y. In some aspects, when $\beta_3$ is S. $\beta_1$ is S; is S or Y; $\beta_5$ is N or S; $\beta_6$ is A or G; $\beta_7$ is L or S; and $\beta_9$ is Y. In some aspects, when $\beta_3$ is H; $\beta_1$ is S; $\beta_4$ is H or Y; $\beta_5$ is S; $\beta_6$ is G; $\beta_7$ is A or S; and $\beta_9$ is L or Y. In some aspects, when $\beta_4$ is Y; $\beta_1$ is S or G; $\beta_3$ is A, H, S, or Y; s is N or S; $\beta_6$ is A or G; $\beta_7$ is L or S; and $\beta_9$ is L or Y. In some aspects, when $\beta_4$ s H; $\beta_1$ is A, E, G, S; $\beta_3$ is H or Y; $\beta_5$ is S; $\beta_6$ is A or G; $\beta_7$ is A or S; and $\beta_9$ is A, N, Y or V. In some aspects, when $\beta_5$ is S; $\beta_1$ is A, E, G, or S; $\beta_3$ is A, H, S, or Y; $\beta_4$ is H, S, or Y; $\beta_6$ is A or G; $\beta_7$ is A or S; and $\beta_9$ is A, L, N, Y, or V. In some aspects, when $\beta_6$ is G; $\beta_1$ is A, E, G, or S; $\beta_3$ is A, H, S, or Y; $\beta_4$ is H, S, or Y; $\beta_5$ is S; $\beta_7$ is S; and $\beta_9$ is A, N, L, V, or Y. In some aspects, when $\beta_6$ is A; $\beta_1$ is G or S; $\beta_3$ is S or Y; $\beta_4$ is H or Y; $\beta_5$ is N or S; $\beta_7$ is L or S; and $\beta_9$ is A or Y. In some aspects, when $\beta_7$ is S; $\beta_1$ is A, E, G, or S; $\beta_3$ is A, H, S, or Y; $\beta_4$ is H, S, or Y; $\beta_5$ is S; $\beta_6$ is A or G; and $\beta_9$ is A, L, N, V, or Y. In some aspects, when $\beta_9$ is Y; $\beta_1$ is G or S; $\beta_3$ is A, H, S, or Y; $\beta_4$ is H, S or Y; $\beta_5$ is N or S; $\beta_6$ is A or G; and $\beta_7$ is A, L, or S. In some aspects, when $\beta_9$ is A; $\beta_1$ is G; $\beta_3$ is Y; $\beta_4$ is H; $\beta_5$ is S; $\beta_6$ is A or G; and $\beta_7$ is S.

In some aspects, when $\beta_1$ is S; $\beta_3$ is Y; $\beta_4$ is Y; $\beta_5$ is S; $\beta_6$ is G; and $\beta_7$ is S; and $\beta_9$ is Y. In some aspects, when $\beta_1$ is S; $\beta_3$ is S; $\beta_4$ is S; $\beta_5$ is S; $\beta_6$ is G; and $\beta_7$ is S; and $\beta_9$ is Y. In some aspects, when $\beta_1$ is S; $\beta_3$ is H; $\beta_4$ is H; $\beta_5$ is S; $\beta_6$ is G; and $\beta_7$ is A; and $\beta_9$ is Y. In some aspects, when $\beta_1$ is S; $\beta_3$ is H; $\beta_4$ is Y; $\beta_5$ is S; $\beta_6$ is G; and $\beta_7$ is S; and $\beta_9$ is L. In some aspects, when $\beta_1$ is S; $\beta_3$ is H; $\beta_4$ is Y; $\beta_5$ is S; $\beta_6$ is G; and $\beta_7$ is S; and $\beta_9$ is Y. In some aspects, when $\beta_1$ is G; $\beta_3$ is A; $\beta_5$ is Y; $\beta_5$ is S; $\beta_6$ is G; and $\beta_7$ is S; and $\beta_9$ is Y. In some aspects, when $\beta_1$ is S; $\beta_3$ is S; $\beta_4$ is Y; $\beta_5$ is N; $\beta_6$ is A; and $\beta_7$ is L; and $\beta_9$ is Y. In some aspects, when $\beta_1$ is S; $\beta_3$ is Y; $\beta_4$ is H; $\beta_5$ is S; $\beta_6$ is G; and $\beta_7$ is S; and $\beta_9$ is Y. In some aspects, when $\beta_1$ is G; $\beta_3$ is Y; $\beta_4$ is H; $\beta_5$ is S; $\beta_6$ is A; and $\beta_7$ is S; and $\beta_9$ is A. In some aspects, when $\beta_1$ is G; $\beta_3$ is Y; $\beta_4$ is H; $\beta_5$ is G; and $\beta_7$ is Y; and $\beta_9$ is Y. In some aspects, when $\beta_1$ is A; $\beta_3$ is Y; $\beta_4$ is H; $\beta_5$ is S; $\beta_6$ is G; and $\beta_7$ is S; and $\beta_9$ is V. In some aspects, when $\beta_1$ is G; $\beta_3$ is Y; $\beta_4$ is H; $\beta_5$ is S; $\beta_6$ is G; and $\beta_7$ is S: and $\beta_9$ is A. In some aspects, when $\beta_1$ is E; $\beta_3$ is Y; $\beta_4$ is H; $\beta_5$ is S; $\beta_6$ is G; and $\beta_7$ is S; and $\beta_9$ is N. In some aspects, when $\beta_1$ is S; $\beta_3$ is S; $\beta_4$ is Y; $\beta_5$ is S; $\beta_6$ is G; and $\beta_7$ is S; and p is Y.

2.8.5. Kabat CDR-H1 Consensus Sequences

In some embodiments, the antibody comprises a Kabat CDR-H1 sequence defined by the consensus sequence S-S-$\Delta_3$-$\Delta_4$-Y-W-$\Delta_7$ (SEQ ID NOS: 18-21, 23, and 34), where $\Delta_3$ is D or S; $\Delta_4$ is T or Y; and $\Delta_7$ is A, G, or S.

In some aspects, when $\Delta_3$ is D; $\Delta_4$ is T or Y; and $\Delta_7$ is G. In some aspects, when $\Delta_3$ is S; $\Delta_4$ is T or Y; and $\Delta_7$ is A, G, or S. In some aspects, when $\Delta_4$ is T; $\Delta_3$ is D or S; and $\Delta_7$ is A, G, or S. In some aspects, when $\Delta_4$ is Y; $\Delta_3$ is D or S; and $\Delta_7$ is G. In some aspects, when $\Delta_7$ is G; $\Delta_3$ is D or S; and $\Delta_4$ is T or Y.

In some aspects, when $\Delta_3$ is D; $\Delta_4$ is Y; and $\Delta_7$ is G. In some aspects, when $\Delta_3$ is S; $\Delta_4$ is T; and $\Delta_7$ is A. In some aspects, when $\Delta_3$ is S; $\Delta_4$ is T; and $\Delta_7$ is G. In some aspects, when $\Delta_3$ is D; $\Delta_4$ is T; and $\Delta_7$ is G. In some aspects, when $\Delta_3$ is S; $\Delta_4$ is T; and $\Delta_7$ is S. In some aspects, when $\Delta_3$ is S; $\Delta_4$ is Y; and $\Delta_7$ is G.

In some embodiments, the antibody comprises a Kabat CDR-H1 sequence defined by the consensus sequence S-G-$\theta_3$-Y-W-$\theta_6$ (SEQ ID NOS: 24-29), where $\theta_3$ is F, H, or Y; and $\theta_6$ is F, G, I, L, or T.

In some aspects, when $\theta_3$ is H, $\theta_6$ is I or T. In some aspects, when $\theta_3$ is Y, $\theta_6$ is F, G, or L. In some aspects, when $\theta_6$ is T, $\theta_3$ is F or H.

In some aspects, when $\theta_3$ is Y, $\theta_6$ is G. In some aspects, when $\theta_3$ is Y, $\theta_6$ is F. In some aspects, when $\theta_3$ is H, $\theta_6$ is I. In some aspects, when $\theta_3$ is F, $\theta_6$ is T. In some aspects, when $\theta_3$ is Y, $\theta_6$ is L. In some aspects, when $\theta_3$ is H, $\theta_6$ is T.

2.8.6. CDR-L3 Consensus Sequences

In some embodiments, the antibody comprises a CDR-L3 sequence defined by the consensus sequence Q-$\pi_2$-$\pi_3$-$\pi_4$-H-S-P-Y-T (SEQ ID NOS: 149-153), where $\pi_2$ is Q or W; $\pi_3$ is A, T, or V; and $\pi_4$ is I or V.

In some aspects, when $\pi_2$ is Q; $\pi_3$ is A, T, or V; and $\pi_4$ is I or V. In some aspects, when $\pi_3$ is A; $\pi_2$ is Q or W; and $\pi_4$ is I or V. In some aspects, when $\pi_4$ is V; $\pi_2$ is Q or W; and $\pi_3$ is A, T, or V.

In some aspects, when $\pi_2$ is Q; $\pi_3$ is A; and $\pi_4$ is V. In some aspects, when $\pi_2$ is W; A; is A; and $\pi_4$ is V. In some aspects, when $\pi_2$ is Q; $\pi_3$ is V; and $\pi_4$ is V. In some aspects, when $\pi_2$ is Q; $\pi_3$ is T; and $\pi_4$ is V. In some aspects, when $\pi_2$ is Q; $\pi_3$ is A; and $\pi_4$ is I.

In some embodiments, the antibody comprises a CDR-L3 sequence defined by the consensus sequence Q-Q-$\lambda_3$-S-$\lambda_5$-Y-P-P-T (SEQ ID NOS: 154-158), where $\lambda_3$ is F, H, or V; and $\lambda_5$ is I, L, or S.

In some aspects, when $\lambda_3$ is H; $\lambda_5$ is I, L, or S. In some aspects, when $\lambda_5$ is H; $\lambda_3$ is F, H, or V.

In some aspects, when $\lambda_3$ is H, $\lambda_5$ is S. In some aspects, when $\lambda_3$ is H, $\lambda_5$ is L. In some aspects, when $\lambda_3$ is F, $\lambda_5$ is S. In some aspects, when $\lambda_3$ is V, $\lambda_5$ is S. In some aspects, when $\lambda_3$ is H, $\lambda_5$ is I.

In some embodiments, the antibody comprises a CDR-L3 sequence defined by the consensus sequence Q-Q-$\omega_3$-$\omega_4$-$\omega_5$-$\omega_6$-P-I-T (SEQ ID NOS: 160-161 and 163-164), where $\omega_3$ is A, L, V, or Y; $\omega_4$ is G, P, V, or Y; $\omega_5$ is S, L, or F; and $\omega_6$ is D, L, S, or Y.

In some aspects, when $\omega_5$ is S; $\omega_3$ is V or Y; $\omega_4$ is G or V; and $\omega_6$ is D or S.

In some aspects, when $\omega_3$ is A; $\omega_4$ is Y; $\omega_5$ is L; and $\omega_6$ is Y. In some aspects, when $\omega_3$ is L; $\omega_4$ is P; $\omega_5$ is F; and $\omega_6$ is L. In some aspects, when $\omega_3$ is Y; $\omega_4$ is V; $\omega_5$ is S; and $\omega_6$ is D. In some aspects, when $\omega_3$ is V; $\omega_4$ is G; $\omega_5$ is S; and $\omega_6$ is S.

2.8.7. CDR-L2 Consensus Sequences

In some embodiments, the antibody comprises a CDR-L2 sequence defined by the consensus sequence $\psi_1$-A-S-$\psi_4$-R-A-$\psi_7$ (SEQ ID NOS: 128, 130, 132, 134-138, 143, and 145), where $\psi_1$ is D or G; $\psi_4$ is A, D, N, R, S, T, or Y; and $\psi_7$ is A, N, S, or T.

In some aspects, when $\psi_1$ is G; $\psi_4$ is A, D, N, R, S, T, or Y; and $\psi_7$ is A, N, or T. In some aspects, when $\psi_1$ is D; $\psi_4$ is S or T; and $\psi_7$ is S or T. In some aspects, when $\psi_4$ is S; $\psi_1$ is G or D; and $\psi_7$ is S or T. In some aspects, when $\psi_4$ is N; $\psi_1$ is G or D; and $\psi_7$ is A or T. In some aspects, when $\psi_4$ is T; $\psi_1$ is G or D; and $\psi_7$ is T. In some aspects, when $\psi_7$ is T; $\psi_1$ is G or D; and $\psi_4$ is A, N, R, S, T, or Y.

In some aspects, when $\psi_1$ is G; $\psi_4$ is S; and $\psi_7$ is T. In some aspects, when $\psi_1$ is G; $\psi_4$ is A; and $\psi_7$ is T. In some aspects, when $\psi_1$ is N; $\psi_4$ is S; and $\psi_7$ is A. In some aspects, when $\psi_1$ is G; $\psi_4$ is N; and $\psi_7$ is T. In some aspects, when $\psi_1$ is D; $\psi_4$ is S; and $\psi_7$ is S. In some aspects, when $\psi_1$ is D; $\psi_4$ is S; and $\psi_7$ is T. In some aspects, when $\psi_1$ is G; $\psi_4$ is D; and $\psi_7$ is N. In some aspects, when $\psi_1$ is G; $\psi_4$ is Y; and $\psi_7$ is T. In some aspects, when $\psi_1$ is G; $\psi_4$ is R; and $\psi_7$ is T. In some aspects, when $\psi_1$ is G; $\psi_4$ is T; and $\psi_7$ is T.

2.8.8. CDR-L1 Consensus Sequences

In some embodiments, the antibody comprises a CDR-L1 sequence defined by the consensus sequence $\phi_1$-A-S-Q-$\phi_5$-V-S-S-$\phi_9$-$\phi_{10}$-L-A (SEQ ID NOS: 105-112 and 117), where $\phi_1$ is E, G, K, Q, or R; $\phi_5$ is A or S; $\phi_9$ is A, D, N, S, or T; and $\phi_{10}$ is F or Y.

In some aspects, when $\phi_1$ is R; $\phi_5$ is Q or S; $\phi_9$ is A, S, or T; and $\phi_{10}$ is S or Y. In some aspects, when $\phi_1$ is G; $\phi_5$ is Q or S; $\phi_9$ is A or D; and $\phi_{10}$ is F or Y. In some aspects, when $\phi_1$ is Q; $\phi_5$ is A or S; $\phi_9$ is N or S; and $\phi_{10}$ is Y. In some aspects, when $\phi_5$ is S; $\phi_1$ is E, G, Q, or R; $\phi_9$ is A, D, S, or T; and $\phi_{10}$ is F or Y. In some aspects, when $\phi_5$ is A; $\phi_1$ is K or Q; $\phi_9$ is N or S; and $\phi_{10}$ is Y. In some aspects, when $\phi_9$ is S; $\phi_1$ is E, K, Q, or R; $\phi_5$ is A or S; and $\phi_{10}$ is Y. In some aspects, when $\phi_9$ is A; $\phi_1$ is G or R; $\phi_5$ is S; and $\phi_{10}$ is F or Y. In some aspects, when $\phi_{10}$ is Y; $\phi_1$ is E, G, K, Q, or R; $\phi_5$ is A or S; and $\phi_9$ is A, D, N, S, or T.

In some aspects, when $\phi_1$ is R; $\phi_5$ is S; $\phi_9$ is S; and $\phi_{10}$ is Y. In some aspects, when $\phi_1$ is G; $\phi_5$ is S; $\phi_9$ is D; and $\phi_{10}$ is Y. In some aspects, when $\phi_1$ is Q; $\phi_5$ is A; $\phi_9$ is N; and $\phi_{10}$ is Y. In some aspects, when $\phi_1$ is G; $\phi_5$ is S; $\phi_9$ is A; and $\phi_{10}$ is F. In some aspects, when $\phi_1$ is R; $\phi_5$ is S; $\phi_9$ is T; and $\phi_{10}$ is Y. In some aspects, when $\phi_1$ is Q; $\phi_5$ is S; $\phi_9$ is S; and $\phi_{10}$ is Y. In some aspects, when $\phi_1$ is K; $\phi_5$ is A; $\phi_9$ is S; and $\phi_{10}$ is Y. In some aspects, when $\phi_1$ is E; $\phi_5$ is S; $\phi_9$ is S; and $\phi_{10}$ is Y. In some aspects, when $\phi_1$ is R; $\phi_5$ is S; $\phi_9$ is A; and $\phi_{10}$ is Y.

In some embodiments, the antibody comprises a CDR-L1 sequence defined by the consensus sequence R-A-S-Q-S-$\sigma_6$-$\sigma_7$-S-$\sigma_9$-L-$\sigma_{11}$ (SEQ ID NOS: 119 and 123-124), where $\sigma_6$ is I or V; $\sigma_7$ is N or S; $\sigma_9$ is N, W, or Y; $\sigma_{11}$ is A or N.

In some aspects, when $\sigma_6$ is I, $\sigma_7$ is N or S; $\sigma_9$ is W or Y; and $\sigma_{11}$ is A or N. In some aspects, when $\sigma_7$ is S, $\sigma_6$ is I or V; $\sigma_9$ is N or Y: and $\sigma_{11}$ is A or N. In some aspects, when $\sigma_{11}$ is A, $\sigma_6$ is I or V; $\sigma_7$ is N or S; and $\sigma_9$ is N or W.

In some aspects, when $\sigma_6$ is I; $\sigma_7$ is N; $\sigma_9$ is W; and $\sigma_{11}$ is A. In some aspects, when $\sigma_6$ is I; $\sigma_7$ is S; $\sigma_9$ is Y; and $\sigma_{11}$ is N. In some aspects, when $\sigma_6$ is V; $\sigma_7$ is S; $\sigma_9$ is N; and $\sigma_{11}$ is A.

In some embodiments, the antibody comprises a CDR-L1 sequence defined by the consensus sequence $\Gamma_1$-$\Gamma_2$-S-Q-S-V-S-$\Gamma_8$-$\Gamma_9$-Y-L-A (SEQ ID NOS: 113-116), where $\Gamma_1$ is E or R; $\Gamma_2$ is A or V; F is A or V; $\Gamma_8$ is A, D, or S; and $\Gamma_{10}$ is A or S.

In some aspects, when $\Gamma_1$ is E; $\Gamma_2$ is A or V; $\Gamma_8$ is A or S; and $\Gamma_9$ is A or S. In some aspects, when $\Gamma_2$ is A; $\Gamma_1$ is E; $\Gamma_8$ is A or S; and $\Gamma_9$ is A or S. In some aspects, when $\Gamma_2$ is V; $\Gamma_1$ is E or R; $\Gamma_8$ A or S; and $\Gamma_9$ is A or S. In some aspects, when $\Gamma_8$ is A; $\Gamma_1$ is E; $\Gamma_2$ is A or V; and $\Gamma_9$ is A or S. In some aspects, when $\Gamma_9$ is S; $\Gamma_1$ is E; $\Gamma_2$ is A or V; and $\Gamma_8$ is A. In some aspects, when $\Gamma_9$ is A; $\Gamma_1$ is E or R; $\Gamma_2$ is A or V; and $\Gamma_8$ D or S.

In some aspects, when $\Gamma_1$ is E; $\Gamma_2$ is A; $\Gamma_8$ is A; and $\Gamma_9$ is S. In some aspects, when $\Gamma_1$ is E; $\Gamma_2$ is A; $\Gamma_8$ is S; and $\Gamma_9$ is A. In some aspects, when $\Gamma_1$ is R; $\Gamma_2$ is V; $\Gamma_8$ is A; and $\Gamma_9$ is A. In some aspects, when $\Gamma_1$ is E; $\Gamma_2$ is V; $\Gamma_8$ is A; and $\Gamma_9$ is S.

3. Germine

In some embodiments, the antibody that specifically binds HLA-G is an antibody comprising a variable region that is encoded by a particular germline, gene, or a variant thereof. The illustrative antibodies provided herein comprise variable regions that are encoded by the heavy chain variable region germline genes $V_H$3-23, $V_H$4-39, $V_H$3-11, and $V_H$4-0B or variants thereof; and the light chain variable region germline genes VK1-33, VK3-20, VK1-12, and VK1-05 or variants thereof. One of skill in the art would recognize that the CDR sequences provided herein may also be useful when combined with variable regions encoded by other variable region germline genes or variants thereof. In particular, the CDR sequences provided herein may be useful when combined with variable regions encoded by variable region germline genes, or variants thereof, that are structurally similar to the variable region germline genes recited above. For example, in some embodiments, a CDR-H sequence provided herein may be combined with a variable region encoded by a variable region germline gene selected from the $V_H$1 or $V_H$3 family, or a variant thereof. In some embodiments, a CDR-L sequence provided herein may be combined with a variable region encoded by a variable region germline gene selected from the Vλ3, Vκ1, Vκ3, and Vκ4 families, or a variant thereof.

4. Affinity

In some embodiments, the affinity of the antibody for HLA-G, as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the antibody is between about $10^{-7}$ M and $10^{-11}$ M. In some embodiments, the affinity of the antibody is between about $10^{-7}$ M and $10^{-11}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody is between about $10^{-8}$ M and $10^{-11}$ M. In some embodiments, the affinity of the antibody is between about $10^{-9}$ M and $10^{-11}$ M. In some embodiments, the affinity of the antibody is between about $10^{-10}$ M and $10^{-11}$ M.

In some embodiments, the affinity of the antibody for human HLA-G is between about $1.00 \times 10^{-8}$ M and $9.43 \times 10^{-10}$ M. In some embodiment, the affinity of the antibody for human HLA-G is about $1.00 \times 10^{-8}$ M, about $1.08 \times 10^{-8}$ M, about $1.10 \times 10^{-8}$ M, about $1.13 \times 10^{-8}$ M, about $1.14 \times 10^{-8}$ M, about $1.16 \times 10^{-8}$ M, about $1.29 \times 10^{-8}$ M, about $1.40 \times 10^{-8}$ M, about $1.41 \times 10^{-8}$ M, about $1.46 \times 10^{-8}$ M, about $1.67 \times 10^{-8}$ M, about $1.79 \times 10^{-8}$ M, about $1.81 \times 10^{-8}$ M, about $2.04 \times 10^{-8}$ M, about $2.30 \times 10^{-8}$ M, about $2.49 \times 10^{-8}$ M, about $2.59 \times 10^{-8}$ M, about $2.94 \times 10^{-8}$ M, about $2.95 \times 10^{-8}$ M, about $3.11 \times 10^{-8}$ M, about $3.98 \times 10^{-9}$ M, about $4.1 \times 10^{-9}$ M, about $4.20 \times 10^{-9}$ M, about $4.33 \times 10^{-9}$ M, about $4.39 \times 10^{-9}$ M, about $4.42 \times 10^{-9}$ M, about $4.72 \times 10^{-9}$ M, about $5.24 \times 10^{-9}$ M, about $5.30 \times 10^{-9}$ M, about $5.35 \times 10^{-9}$ M, about $5.40 \times 10^{-9}$ M, about $5.55, 10^{-9}$ M, about $5.56 \times 10^{-9}$ M, about $5.80 \times 10^{-9}$ M, about $5.89 \times 10^{-9}$ M, about $5.92 \times 10^{-9}$ M, about $5.98 \times 10^{-9}$ M, about $5.99 \times 10^{-9}$ M, about $6.10 \times 10^{-9}$ M, about $6.34 \times 10^{-9}$ M, about $6.66 \times 10^{-9}$ M, about $6.75 \times 10^{-9}$ M, about $7.19 \times 10^{-9}$ M, about $7.69 \times 10^{-9}$ M, about $7.93 \times 10^{-9}$ M, about $8.23 \times 10^{-9}$ M, about $8.34 \times 10^{-9}$ M, about $8.37 \times 10^{-9}$ M, about $8.62 \times 10^{-9}$ M, about $8.82 \times 10^{-9}$ M, about $9.21 \times 10^{-9}$ M, about $9.51 \times 10^{-9}$ M, about $1.62 \times 10^{-10}$ M, about $1.63 \times 10^{-10}$ M, $1.64 \times 10^{-10}$ M, about $1.65 \times 10^{-10}$ M, about $1.66 \times 10^{-10}$ M, about $1.71 \times 10^{-10}$ M, about $1.72 \times 10^{-10}$ M, about $1.86 \times 10^{-10}$ M, about $1.78 \times 10^{-10}$ M, about $1.97 \times 10^{-10}$ M, about $1.98 \times 10^{-10}$ M, about $1.99 \times 10^{-10}$ M, about $2.29 \times 10^{-10}$ M, about $3.24 \times 10^{-10}$ M, about $6.47 \times 10^{-10}$ M, about $6.96 \times 10^{-10}$ M, about $7.84 \times 10^{-10}$ M, about $9.41 \times 10^{-10}$ M, or about $9.43 \times 10^{-10}$ M.

In some embodiments the antibody has a k when associating with human HLA-G of between about $1.41 \times 10^5$ M$^{-1} \times$ sec$^{-1}$ and about $1.07 \times 10^6$ M$^{-1} \times$sec$^{-1}$. In some embodiments the antibody has a $k_{on}$ when associating with human HLA-G of about $1.41 \times 10^5$ M$^{-1} \times$sec$^{-1}$, about $1.49 \times 10^5$ M$^{-1} \times$sec$^{-1}$, about $1.66 \times 10^5$ M$^{-1} \times$sec$^{-1}$, about $2.90 \times 10^5$ M$^{-1} \times$sec$^{-1}$, about $3.60 \times 10^5$ M$^{-1} \times$sec$^{-1}$, about $3.74 \times 10^5$ M$^{-1} \times$sec$^{-1}$, about $3.78 \times 10^5$ M$^{-1} \times$sec$^{-1}$, about $4.03 \times 10^5$ M$^{-1} \times$sec$^{-1}$, about $4.30 \times 10^5$ M$^{-1} \times$sec$^{-1}$, about $4.32 \times 10^5$ M$^{-1} \times$sec$^{-1}$, about $4.34 \times 10^5$ M$^{-1} \times$sec$^{-1}$, about $4.60 \times 10^5$ M$^{-1} \times$sec$^{-1}$, about $4.64 \times 10^5$ M$^{-1} \times$sec$^{-1}$, about $4.80 \times 10^5$ M$^{-1} \times$sec$^{-1}$, about $4.84 \times 10^5$ M$^{-1} \times$sec$^{-1}$, about $4.87 \times 10^5$ M$^{-1} \times$sec$^{-1}$, about $4.91 \times 10^5$ M$^{-1} \times$sec$^{-1}$, about $4.96 \times 10^5$ M$^{-1} \times$sec$^{-1}$, about $4.97 \times 10^5$ M$^{-1} \times$sec$^{-1}$, about $4.98 \times 10^5$ M$^{-1} \times$sec$^{-1}$, about $5.01 \times 10^5$ M$^{-1} \times$sec$^{-1}$, about $5.14 \times 10^5$ M$^{-1} \times$sec$^{-1}$, about $5.19 \times 10^5$ M$^{-1} \times$sec$^{-1}$, about $5.20 \times 10^5$ M$^{-1} \times$sec$^{-1}$, about $5.26 \times 10^5$ M$^{-1} \times$sec$^{-1}$, about $5.27 \times 10^5$ M$^{-1} \times$sec$^{-1}$, about $5.30 \times 10^5$ M$^{-1} \times$sec$^{-1}$, about $5.61 \times 10^5$ M$^{-1} \times$sec$^{-1}$, about $5.90 \times 10^5$ M$^{-1} \times$sec$^{-1}$, about $6.31 \times 10^5$ M$^{-1} \times$sec$^{-1}$, about $6.32 \times 10^5$ M$^{-1} \times$sec$^{-1}$, about $6.36 \times 10^5$ M$^{-1} \times$sec$^{-1}$, about $6.46 \times 10^5$ M$^{-1} \times$sec$^{-1}$, about $6.53 \times 10^5$ M$^{-1} \times$sec$^{-1}$, about $6.66 \times 10^5$ M$^{-1} \times$sec$^{-1}$, about $6.84 \times 10^5$ M$^{-1} \times$sec$^{-1}$, about $7.20 \times 10^5$ M$^{-1} \times$sec$^{-1}$, about $7.24 \times 10^5$ M$^{-1} \times$sec$^{-1}$, about $7.48 \times 10^5$ M$^{-1} \times$sec$^{-1}$, about $7.36 \times 10^5$ M$^{-1} \times$sec$^{-1}$, about $7.58 \times 10^5$ M$^{-1} \times$sec$^{-1}$, about $7.77 \times 10^5$ M$^{-1} \times$sec$^{-1}$, about $7.92'10^5$ M$^{-1} \times$sec$^{-1}$, about $7.94 \times 10^5$ M$^{-1} \times$sec$^{-1}$, about $7.96 \times 10^5$ M$^{-1} \times$sec$^{-1}$, about $8.03 \times 10^5$ M$^{-1} \times$sec$^{-1}$, about $8.24 \times 10$ M$^{-1} \times$sec$^{-1}$, about $8.26 \times 10^5$ M$^{-1} \times$sec$^{-1}$, about $8.55 \times 10^5$ M$^{-1} \times$sec$^{-1}$, about $8.63 \times 10^5$ M$^{-1} \times$sec$^{-1}$, about $8.66 \times 10^5$ M$^{-1} \times$sec$^{-1}$, about $8.74 \times 10^5$ M$^{-1} \times$sec$^{-1}$, about $8.79 \times 10^5$ M$^{-1} \times$sec$^{-1}$, about $8.92 \times 10^5$ M$^{-1} \times$sec$^{-1}$, about $8.96 \times 10^5$ M$^{-1} \times$sec$^{-1}$, about $9.09 \times 10^5$ M$^{-1} \times$sec$^{-1}$, about $9.31 \times 10^5$ M$^{-1} \times$sec$^{-1}$, about $9.35 \times 10^5$ M$^{-1} \times$sec$^{-1}$, about $9.38 \times 10^5$ M$^{-1} \times$sec$^{-1}$, about $9.46 \times 10^5$ M$^{-1} \times$sec$^{-1}$, about $9.54 \times 10^5$ s M$^{-1} \times$sec$^{-1}$, about $9.73 \times 10^5$ M$^{-1} \times$sec$^{-1}$, about $9.83 \times 10^5$ M$^{-1} \times$sec$^{-1}$, about $9.84 \times 10^5$ M$^{-1} \times$sec$^{-1}$, about $9.91 \times 10^5$ M$^{-1} \times$sec$^{-1}$, about $1.05 \times 10^5$ M$^{-1} \times$sec$^{-1}$, or about $1.07 \times 10^6$ M$^{-1} \times$sec$^{-1}$.

In some embodiments the antibody has a $k_{off}$ when associating with human HLA-G of between about $1.06 \times 10^2$ sec$^{-1}$ and about $8.55 \times 10^5$ sec$^{-1}$. In some embodiments the antibody has a $k_{off}$ of about $1.06 \times 10^{-2}$ sec$^{-1}$, about $1.13 \times 10^{-2}$ sec$^{-1}$, about $1.87 \times 10^{-2}$ sec$^{-1}$, about $2.13 \times 10^{-2}$ sec$^{-1}$, about $3.62 \times 10^{-3}$ sec$^{-1}$, about $3.66 \times 10^{-3}$ sec$^{-1}$, about $3.75 \times 10^{-3}$ sec$^{-1}$, about $3.78 \times 10^{-3}$ sec$^{-1}$, about $3.83 \times 10^{-3}$ sec$^{-1}$, about $3.96 \times 10^{-3}$ sec$^{-1}$, about $4.17 \times 10^{-3}$ sec$^{-1}$, about $4.27 \times 10^{-3}$ sec$^{-1}$, about $4.29 \times 10^{-3}$ sec$^{-1}$, about $4.41 \times 10^{-3}$ sec$^{-1}$, about $4.42 \times 10^{-3}$ sec$^{-1}$, about $4.46 \times 10^{-3}$ sec$^{-1}$, about $4.54 \times 10^{-3}$ sec$^{-1}$, about $4.65 \times 10^{-3}$ sec$^{-1}$, about $4.85 \times 10^{-3}$ sec$^{-1}$, about $4.88 \times 10^{-3}$ sec$^{-1}$, about $4.89 \times 10^{-3}$ sec$^{-1}$, about $4.98 \times 10^{-3}$ sec$^{-1}$, about $5.26 \times 10^{-3}$ sec$^{-1}$, about $5.44 \times 10^{-3}$ sec$^{-1}$, about $5.47 \times 10^{-3}$ sec$^{-1}$, about $5.71 \times 10^{-3}$ sec$^{-1}$, about $5.72 \times 10^{-3}$ sec$^{-1}$, about $5.84 \times 10^{-3}$ sec$^{-1}$, about $5.90 \times 10^{-3}$ sec$^{-1}$, about $5.92 \times 10^{-3}$ sec$^{-1}$, about $5.93 \times 10^{-3}$ sec$^{-1}$, about $6.24 \times 10^{-3}$ sec$^{-1}$, about $6.25 \times 10^{-3}$ sec$^{-1}$, about $6.28 \times 10^{-1}$ sec$^{-1}$, about $6.49 \times 10^{-3}$ sec$^{-1}$, about $6.50 \times 10^{-3}$ sec$^{-1}$, about $6.71 \times 10^{-3}$ sec$^{-1}$, about $6.78 \times 10^{-3}$ sec$^{-1}$, about $6.83 \times 10^{-3}$ sec$^{-1}$, about $6.98 \times 10^{-3}$ sec$^{-1}$, about $7.17 \times 10^{-3}$ sec$^{-1}$, about $7.42 \times 10^{-3}$ sec$^{-1}$, about $8.12 \times 10^{-3}$ sec$^{-1}$, about $8.16 \times 10^{-3}$ sec$^{-1}$, about $8.26 \times 10^{-3}$ sec$^{-1}$, about $8.64 \times 10^{-3}$ sec$^{-1}$, about $8.76 \times 10^{-3}$ sec$^{-1}$, about $8.91 \times 10^{-3}$ sec$^{-1}$, about $9.31 \times 10^{-3}$ sec$^{-1}$, about $9.32 \times 10^{-3}$ sec$^{-1}$, about $9.87 \times 10^{-3}$ sec$^{-1}$, about $1.82 \times 10^{-4}$ sec$^{-1}$, about $4.38 \times 10^{-4}$ sec$^{-1}$, about $4.59 \times 10^{-4}$ sec$^{-1}$, about $4.99 \times 10^{-4}$ sec$^{-1}$, about $5.73 \times 10^{-4}$ sec$^{-1}$, about $6.03 \times 10^{-4}$ sec$^{-1}$, or about $8.55 \times 10^{-5}$ sec$^{-1}$.

In some aspects, the $K_D$, $k_a$, and $k_d$ are determined at 25° C. In some embodiments, the $K_D$, $k_a$, and $k_d$ are determined by surface plasmon resonance. In some embodiments, the $K_D$, $k_a$, and $k_d$ are determined according to the methods described in the examples.

5. Inhibition of HLA-G

In some aspects, the antibody decreases the affinity of HLA-G for its ligand(s). In some aspects, the antibody disrupts the association of HLA-G with beta-2-microglobulin and/or its cognate peptide. In some aspects the antibody prevents HLA-G dimerization or oligomerization.

In some aspects, the antibody inhibits HLA-G function on tumor cells. In some aspects, the antibody inhibits HLA-G function on immune cells. In some embodiments, the antibody blocks HLA-G interaction and/or binding to an ITIM inhibitory receptor. In some embodiments, the antibody blocks HLA-G interaction and/or binding to ILT2. In some embodiments, the antibody blocks HLA-G interaction and/or binding to ILT4. In some embodiments, the antibody blocks HLA-G interaction and/or binding to KIR2DL4.

In some embodiments, the antibody inhibits immune suppressive function. In some embodiments, the antibody inhibits HLA-G mediated suppression of NK cells. In some embodiments, the antibody inhibits HLA-G mediated suppression of cytotoxic T lymphocytes. In some embodiments, the antibody inhibits HLA-G mediated suppression of B cells. In some embodiments, the antibody inhibits HLA-G mediated suppression of neutrophils. In some embodiments, the antibody inhibits HLA-G mediated suppression of dendritic cells. In some embodiments, the antibody inhibits HLA-G mediated suppression of macrophages. In some embodiments, the antibody inhibits HLA-G mediated suppression of monocytes. In some embodiments, the antibody inhibits HLA-G mediated suppression of NK and/or T cell cytolysis and/or proliferation.

In some embodiments, the antibody prevents or inhibits HLA-G mediated suppression of phagocytosis. In some embodiments, the antibody mediates HLA-G mediated induction of T regulatory cells. In some embodiments, the antibody prevents or inhibits the generation or expansion of regulatory T cells. In some embodiments, the antibody inhibits tumor growth by antibody-dependent cellular cytotoxicity (ADCC) or phagocytosis (ADCP).

In some aspects, the decrease is about or less than a 10% decrease, about or less than a 20% decrease, about or less than a 30% decrease, about or less than a 40% decrease, about or less than a 50% decrease, about or less than a 60% decrease, about or less than a 70% decrease, about or less than an 80% decrease, about or less than a 90% decrease, or about a complete decrease. In some aspects, the increase is about or greater than a 10% increase, about or greater than a 20% increase, about or greater than a 30% increase, about or greater than a 40% increase, about or greater than a 50% increase, about or greater than a 60% increase, about or greater than a 70% increase, about or greater than an 80% increase, about or greater than a 90% increase, or a complete increase.

6. HLA-G Assays

In some embodiments, the antibody binds to an epitope of HLA-G. An epitope often consists of a number of contiguous amino acids such as, for example, without limitation, 5-6 amino acids. In some embodiments, the epitope comprises or consists of contiguous or non-contiguous amino acids. In some embodiments, the contiguous or non-contiguous amino acids are within a domain of HLA-G. In some embodiments, the domain comprises or consists of an alpha three domain.

In some aspects, HLA-G has a sequence identical to the amino acid sequence set forth in SEQ ID NO: 342. In some aspects, the epitope has an amino acid sequence that is within the amino acid sequence set forth in SEQ ID NO: 342. In some aspects, the epitope has an amino acid sequence that is 60%, 65%, 70%, 75%, 80%, 85%, 90%, or 95% identical to a sequence that is within the sequence set forth in SEQ ID NO: SEQ ID NO: 342.

In some aspects, the epitope comprises or consists of a contiguous or non-contiguous span of amino acids including residues 195, 197, and/or 198 of the sequence set forth in SEQ ID NO: 342. In some aspects, the epitope comprises a sequence that is identical or corresponds to residues 195, 197, and/or 198 of a sequence that is within the sequence set forth in SEQ ID NO: 342. In some aspects, the epitope has a sequence that has a 60%, 65%, 70%, 75%, 80%, 85%, 90%, or 95% identity to a sequence that is within the sequence set forth in SEQ ID NO: 342. In some aspects, the epitope has 1, 2, 3, 4, 5, 6, 7, 8, or 9 substitutions from a sequence that is within the sequence set forth in forth in SEQ ID NO: 342. In some aspects, the epitope has 1, 2 or 3 substitutions from residues a sequence that is within the sequence set forth in SEQ ID NO: 342. In some aspects, the antibody makes contact with any of the residues set forth in FIG. 9.

In some aspects, the antibody competes with any of the antibodies set forth herein. Competition could be, for example, without limitation, binding competition, inhibition competition, or any other form of competition. In some aspects, the antibody competes with 1, 2, 3, 4, 5, 6, 7, 8, 9, 10, 11, 12, or 13 of antibodies 38410, 38418, 38422, 38426, 38381, 38358, 37323, 38373, 38375, 38379, 38389, 33303, or 33357. In some aspects, the antibody competes with any of the antibodies set forth in FIG. 2 or FIG. 3. In some aspects, the antibody competes with 1, 2, 3, 4, 5, 6, 7, or 8 of 38373, 38375, 38379, 38418, 38422, 38426, 38410 or 38381. In some aspects, the antibody competes with 38358. In some aspects, the antibody competes with 1, 2, 3, 4, 5, 6, 7, 8, or 9 of 38373, 38375, 38379, 38418, 38422, 38426, 38410 or 38381, or 38358. In some aspects, the antibody competes with one or both of 37323 and/or 38389. In some aspects, the antibody competes with one or both of 33303 and/or 33357.

7. Glycosylation Variants

In some embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

In certain embodiments, the antibody is glycosylated. In certain embodiments, the antibody is deglycosylated. Carbohydrates may be removed by standard techniques. In certain embodiments, the antibody is aglycosylated, for instance by expression in a system that does not glycosylate.

8. Fc Variants

In some embodiments, amino acid modifications may be introduced into the Fc region of an antibody provided herein to generate an Fc region variant. In some embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

In some embodiments, the Fc is modified. In some embodiments, a hinge of an IgG1 or IgG4 antibody is modified. Modification of a hinge region stabilizes an antibody and prevents formation of unwanted bispecific antibodies. In some embodiments, the modification comprises an L234A, L235A, and/or G237A according to a Kabat numbering scheme or residues number 117, 118, and 120, respectively, wherein residues are numbered according to any of SEQ ID NO: 334. In some embodiments, the modification comprises an EU S228P or an S241P according to a Kabat numbering scheme or number 108 according to SEQ ID NO: 335. In some embodiments, an IgG Fc is engineered to modulate antibody effector function (See Wang et al., Protein Cell, 2018, January; 9(1): 63-73), which is incorporated by reference herein in its entirety, including any drawings).

Non-limiting examples of in vitro assays to assess ADCC activity of a molecule of interest are provided in U.S. Pat. Nos. 5,500,362 and 5,821,337; Hellstrom et al., *Proc. Natl. Acad. Sci. U.S.A.,* 1986, 83:7059-7063; Hellstrom et al., *Proc. Natl. Acad. Sci. U.S.A.,* 1985, 82:1499-1502; and Bruggemann et al., *J. Exp. Med.,* 1987, 166:1351-1361. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. *Proc. Natl. Acad. Sci. U.S.A.,* 1998, 95:652-656.

C1q binding assays may also be carried out to confirm that the antibody is unable to bind C1q and hence lacks CDC activity. Examples of C1q binding assays include those described in WO 2006/029879 and WO 2005/100402.

Complement activation assays include those described, for example, in Gazzano-Santoro et al., *J. Immunol. Methods,* 1996, 202:163-171; Cragg et al., *Blood,* 2003, 101: 1045-1052; and Cragg and Glennie, *Blood,* 2004, 103:2738-2743.

FcRn binding and in vivo clearance (half-life determination) can also be measured, for example, using the methods described in Petkova et al., *Intl. Immunol.,* 2006, 18:1759-1769.

9. Preparation of Antibodies 9.1. Antigen Preparation

The HLA-G antigen to be used for production of antibodies may be intact HLA-G or a fragment of HLA-G. The intact HLA-G, or fragment of HLA-G, may be in the form of an isolated protein or expressed by a cell. Other forms of HLA-G useful for generating antibodies will be apparent to those skilled in the art.

9.2. Monoclonal Antibodies

Monoclonal antibodies may be obtained, for example, using the hybridoma method first described by Kohler et al., *Nature,* 1975, 256:495-497, and/or by recombinant DNA methods (see e.g., U.S. Pat. No. 4,816,567). Monoclonal antibodies may also be obtained, for example, using phage or yeast-based libraries. See e.g., U.S. Pat. Nos. 8,258,082 and 8,691,730.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* $3^{rd}$ ed. (1986) Academic Press, San Diego, Calif.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.* 1984, 133:3001.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

9.3. Humanized Antibodies

Humanized antibodies may be generated by replacing most, or all, of the structural portions of a monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature,* 1991, 349:293-299; Rader et al., *Proc. Nat. Acad. Sci. U.S.A.,* 1998, 95:8910-8915; Steinberger et al., *J. Biol. Chem.,* 2000. 275:36073-36078; Queen et al., *Proc. Natl. Acad. Sci. U.S.A.,* 1989, 86:10029-10033; and U.S. Pat. Nos. 5,585,089, 5,693,761, 5,693,762, and 6,180,370.

9.4. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.,* 1993, 90:2551; Jakobovits et al., *Nature,* 1993, 362:255-258; Bruggermann et al., *Year in Immuno.,* 1993, 7:33; and U.S. Pat. Nos. 5,591,669, 5,589, 369 and 5,545,807. Human antibodies can also be derived from phage-display libraries (see e.g., Hoogenboom et al., *J. Mol. Biol.,* 1991, 227:381-388; Marks et al., *J. Mol. Biol.,* 1991, 222:581-597; and U.S. Pat. Nos. 5,565,332 and 5,573, 905). Human antibodies may also be generated by in vitro activated B cells (see e.g., U.S. Pat. Nos. 5,567,610 and 5,229,275). Human antibodies may also be derived from yeast-based libraries (see e.g., U.S. Pat. No. 8,691,730).

10. Vectors, Host Cells, and Recombinant Methods

The invention also provides isolated nucleic acids encoding anti-HLA-G antibodies, vectors and host cells comprising the nucleic acids and recombinant techniques for the production of the antibodies.

For recombinant production of the antibody, the nucleic acid encoding it may be isolated and inserted into a replicable vector for further cloning (i.e., amplification of the DNA) or expression. In some aspects, the nucleic acid may be produced by homologous recombination, for example as described in U.S. Pat. No. 5,204,244.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615.

Suitable host cells include any prokaryotic (e.g., bacterial), lower eukaryotic (e.g., yeast), or higher eukaryotic (e.g., mammalian) cells. Suitable prokaryotes include cubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella, Bacilli* (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for anti-HLA-G antibody-encoding vectors. *Saccharomyces cerevisiae*, or common baker's yeast, is a commonly used lower eukaryotic host microorganism. However, a number of other genera, species, and strains are available and useful, such as *Schizosaccharomyces pombe, Kluyveromyces* (*K. lactis, K. fragilis, K. bulgaricus, K. wickeramii, K. waltii, K. drasophilarum, K. thermotolerans,* and *K. marxianus*), *Yarrowia, Pichia pastoris, Candida* (*C. albicans*), *Trichoderma reesia, Neuraspora crassa, Schwanniomyces* (*S. occidentalis*), and filamentous fungi such as, for example *Penicillium, Tolypocladium,* and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-HLA-G antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469, or WO 90/03430 and WO 87/00195 may be used.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology*, 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation.

In some embodiments, the antibody is produced in a cell-free system. In some aspects, the cell-free system is an in vitro transcription and translation system as described in Yin et al., *mAbs*, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.*, 1983, 62:1-13). Protein G is useful for all mouse isotypes and for human γ3 (Guss et al., *EMBO J.*, 1986, 5:1567-1575).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation. Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

11. Pharmaceutical Compositions and Methods of Administration

Any of the antibodies provided herein can be provided in any appropriate pharmaceutical composition and be administered by any suitable route of administration. Suitable routes of administration include, but are not limited to, the inhalation, intra-arterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes. In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

Further encompassed herein are anhydrous pharmaceutical compositions and dosage forms comprising an antibody, since water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

In some embodiments, the pharmaceutical composition further comprises one or both of an antibody to an immune inhibitory receptor or ligand and/or an antibody to an immune stimulatory receptor and/or ligand. In some embodiments, the pharmaceutical composition further comprises an effective amount of at least one of the following: an anti-ILT2 antibody; an anti-ILT-4 antibody; an anti-ILT4 antibody; an anti-KIR2DL4 antibody; an anti-HLA-E antibody; an anti-NKG2A antibody; an anti-HLA-F antibody; an anti-PD-L1 antibody; an anti-PD-1 antibody; an anti-CTLA4 antibody; an anti-CD38 antibody; an anti-CD73 antibody; an anti-A2A receptor antibody; an anti-A2B receptor antibody; an anti-A2A/A2B dual receptor antibody or a combination thereof; an anti-CD39 antibody; an anti-CD73 antibody; an anti-CD47 antibody; and/or a small molecule inhibitor. In some embodiments, the pharmaceutical composition further comprises an anti-Tim-3 antibody: an anti-TIGIT antibody; an anti-Vista antibody; an anti-CD94 antibody; an anti-ILT2 antibody, an anti-ILT4 antibody, an anti-PD-L1 antibody, and/or an anti-CD47 antibody; a small molecule inhibitor; a bi-specific T cell engager, CAR-T therapy, CAR-NK therapy, CAR-Macrophage therapy, engineered cell therapy, and/or adaptive T cell therapy; an oncolytic virus; a chemotherapy; and/or an ADCC capable therapy using effector competent antibodies such as anti-CD19, anti-CD20, anti-EGFR, anti-Her2, anti-SLAMF7, anti-CD52, anti-BCMA, anti-GD2, anti-CD38, and/or anti-CCR4. In some embodiments, ADCC capable therapy is enhanced ADCC capable therapy. In some embodiments, the effector is enhanced through afucosylation, point mutations, or another method.

11.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intra-arterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

11.2. Dosage and Unit Dosage Forms

In human therapeutics, the doctor will determine the posology which he considers most appropriate according to a preventive or curative treatment and according to the age, weight, condition and other factors specific to the subject to be treated.

The amount of the antibody or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or for times weekly. It may be necessary to use dosages of the antibody outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

12. Therapeutic Applications

For therapeutic applications, the antibodies of the invention are administered to a mammal, generally a human, in a pharmaceutically acceptable dosage form such as those known in the art and those discussed above. For example, the antibodies of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibodies also are suitably administered by peritumoral, intralesional, or perilesional routes, to exert local as well as systemic therapeutic effects. The intraperitoneal route may be particularly useful, for example, in the treatment of ovarian tumors.

The antibodies provided herein may be useful for the treatment of any disease or condition involving HLA-G, such as cancer, autoimmune disease, and infection.

Any suitable cancer may be treated with the antibodies provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, Burkitt Lymphoma, carcinoma of unknown primary origin, cardiac tumor, cervical cancer, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hairy cell leukemia, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, leukemia, lip and oral cavity cancer, liver cancer, lobular carcinoma in situ, lung cancer, lymphoma, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-Hodgkin lymphoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor. In some embodiments, the cancer is selected from breast, lung, CRC, gastric, esophageal, neuroblastoma, cervical, and hematological cancers.

Any suitable autoimmune disease may be treated with the antibodies provided herein. Illustrative suitable autoimmune diseases, or diseases with an autoimmune component, include, for example, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies, Balo disease, Behcet's disease, bullous pemphigoid, cardiomyopathy, Castleman disease, Celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, colitis, congenital heart block, coxsackie myocarditis, CREST disease, essential mixed cryoglobulincmia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibromyalgia, fibrosing alveolitis, giant cell arteritis (temporal arteritis), giant cell myocarditis, glomerulonephritis, Goodpasture's syndrome, granulomatosis with polyangiitis (GPA) (formerly called Wegener's Granulomatosis), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, inflammatory bowel disease, interstitial cystitis, juvenile arthritis, juvenile diabetes (Type I diabetes), juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (SLE), Lyme disease (chronic), Meníere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with Streptococcus), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, rimary sclerosing cholangitis, psoriasis, psoriatic arthritis, idiopathic pulmonary fibrosis, pyoderma gangrenosum, pure red cell aplasia, Raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombotic disease, thrombocytopenic purpura (TTP), Tolosa-Hunt syndrome, transverse myelitis, type I diabetes, ulcerative colitis, undifferentiated connective tissue disease (UCTD), uveitis, vasculitis, vesiculobullous dermatosis, vitiligo, and Wegener's granulomatosis (now termed Granulomatosis with Polyangiitis (GPA).

Any suitable infection may be treated with the antibodies provided herein. Illustrative suitable infections include, for example, hepatitis A virus, hepatitis B virus, hepatitis C virus (HCV), human immunodeficiency virus (HIV), and other viral infections.

Some embodiments provide for treatment of a subject suffering from cancer, a chronic infection, or from an inflammatory disease, comprising the step of administering to the subject a pharmaceutical composition comprising an effective amount of any of the antibodies set forth herein. Some embodiments provide for treatment of a subject suffering from cancer, a chronic infection, or from an inflammatory disease, comprising the step of administering to the subject a pharmaceutical composition comprising an effective amount of any of the antibodies set forth herein in combination with an effective amount of another antibody set forth herein. In some embodiments, the cancer is a hematological cancer.

Some embodiments provide a method for modulating immune system function in a subject in need thereof, comprising the step of contacting a population of immune cells of the subject with a pharmaceutical composition comprising an effective amount of the antibody as set forth herein, under conditions such that the immune system is modulated. Some embodiments provide a method for modulating immune system function in a subject in need thereof, comprising the step of contacting a population of immune cells of the subject with an effective amount of any of the antibodies set forth herein in combination with an effective amount of another antibody set forth herein. In some embodiments, the antibody comprises a bispecific antibody or a complexing antibody.

In some embodiments, the bispecific antibody or the complexing antibody is administered in an amount sufficient to achieve 1, 2, 3, 4, 5, 6, 7, or 8 of the following in the subject:
  a) inhibition of immune suppression;
  b) reduction of levels of regulatory T cells;
  c) increase an activity of myeloid cells;
  d) increase in activity of cytotoxic T lymphocytes, NK cells, B cells, neutrophils, monocytes, macrophages, and/or dendritic cells;
  e) increase in phagocytic activity;
  f) inhibition of metastasis;
  g) inhibition of tumor growth; and/or
  h) induction of tumor regression.

In some embodiments, the bispecific antibody binds HLA-G and HLA-E.

In some embodiments, the method for modulating immune system function in a subject in need thereof further comprises administering chemotherapy, administering radiation therapy, and/or administering one or more additional therapeutic agents. In some embodiments, the one or more additional therapeutic agents comprise one or more immunostimulatory agents. In some embodiments, the one or more immunostimulatory agents comprise an antagonist to an inhibitory receptor of an immune cell. In some embodiments, the inhibitory receptor is at least one of ILT2, ILT3, ILT4, KIR2DL4, CTLA-4, PD-1, CD39, CD73, PD-L1, PD-L2, LAG-3, TIGIT, B7-H3, B7-H4, Tim3, neuritin, BTLA, CECAM-1, CECAM-5, VISTA, LAIR1, CD160, 2B4, TGF-B, NKG2A, and/or a Killer-cell immunoglobulin-like receptor (KIR).

In some embodiments, the one or more immunostimulatory agents comprise an agonist of a co-stimulatory receptor of an immune cell. In some embodiments, the co-stimulatory receptor comprises one or more of OX40, CD2, CD27, ICAM-1, LFA-1, ICOS (CD278), 4-1BB (CD137), GITR, CD28, CD30, CD40, BAFFR, HVEM, CD7, LIGHT, NKG2C, SLAMF7, NKp30, NKp46, NKp80, CD160, and/or a CD83 ligand.

In some embodiments, the one or more immunostimulatory agents comprise a cytokine. In some embodiments, the cytokine is at least one of IL-1, IL-2, IL-5, IL-7, IL-10, IL-12, IL-15, IL-21, and/or IL-27. In some embodiments, the one or more immunostimulatory agents comprise an oncolytic virus. In some embodiments, the oncolytic virus comprises one or more of the oncolytic virus is a Herpes simplex virus, a Vesicular stomatitis virus, an adenovirus, a Newcastle disease virus, a vaccinia virus, or a maraba virus. In some embodiments, the one or more immunostimulatory agents comprise a chimeric antigen engineered T cell. In some embodiments, immunostimulatory agents comprise a bi- or multi-specific T cell directed antibody. In some embodiments, the one or more immunostimulatory agents comprises or consists of an ADCC competent antibody that may target CD19, CD20, EGFR, Her2, SLAMF7, CD52, BCMA, GD2, CD38, or CCR4. In some embodiments, the ADCC competent antibody is effector enhanced through afucosylation, point mutations, or otherwise.

In some embodiments, the one or more immunostimulatory agents comprise a bi-specific T cell engager and/or CAR-T therapy, CAR-NK therapy, CAR-macrophage therapy, adoptive T cell therapy.

13. Diagnostic Applications and Diagnostic Methods

In some embodiments, the antibodies provided herein are used in diagnostic applications and/or diagnostic methods. For example, an anti-HLA-G antibody may be useful in assays for HLA-G protein. In some aspects, the antibody can be used to detect the expression of HLA-G in various cells and tissues. In some embodiments, the antibody can be used to detect the soluble HLA-G in fluids. In some embodiments, the fluids comprise or consist of blood, serum, ascites, and/or other fluids. The assays may be useful, for example, evaluating cancer and autoimmune disease.

In some embodiments, the diagnostic method comprises or consists of detecting tumor expressed HLA-G. In some embodiments, the diagnostic method comprises or consists of detecting soluble HLA-G. In some embodiments the detection method comprises or consists of detecting HLA-G expression on immune cells.

In some diagnostic applications, the antibody may be labeled with a detectable moiety. Suitable detectable moieties include, but are not limited to radioisotopes, fluorescent labels, and enzyme-substrate labels. In another embodiment of the invention, the anti-HLA-G antibody need not be labeled, and the presence thereof can be detected using a labeled antibody which specifically binds to the anti-HLA-G antibody.

14. Affinity Purification Reagents

The antibodies of the invention may be used as affinity purification agents. In this process, the antibodies may be immobilized on a solid phase such a resin or filter paper, using methods well known in the art. The immobilized antibody is contacted with a sample containing the HLA-G protein (or fragment thereof) to be purified, and thereafter the support is washed with a suitable solvent that will remove substantially all the material in the sample except the HLA-G protein, which is bound to the immobilized antibody. Finally, the support is washed with another suitable solvent, such as glycine buffer, pH 5.0, that will release the HLA-G protein from the antibody.

15. Kits

In some embodiments, an anti-HLA-G antibody provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the anti-HLA-G antibody. In some embodiments, the anti-HLA-G antibody is provided in the form of a pharmaceutical composition.

EXAMPLES

Example 1: Selection of HLA-G Antibodies

HLA-G antibodies were selected from a synthetic library of human antibodies presented on the surface of yeast cells in IgG format, as generally described, e.g., in WO2009036379; WO2010105256; WO2012009568; and Xu et al., Protein Eng. Des. Sel., 2013, 26:663-670 (each incorporated by reference in its entirety), and more specifically as provided below. The sequences and characteristics of the antibodies isolated from the recombinant library are provided in Table S.

Eight naïve human synthetic yeast libraries each of ~10E+09 diversity were propagated as described in WO2009036379; WO2010105256; WO2012009568; and Xu et al., Protein Eng. Des. Sel., 2013, 26:663-670; each incorporated by reference in its entirety. For the first two rounds of selection, a magnetic bead sorting technique utilizing the Miltenyi MACS® system was performed, as described in Siegel et al., J. Immunol. Meth., 2004, 286: 141-153. The following rounds of selection were performed using flow cytometry-based sorting. For all rounds of selection, the antigen was biotinylated human HLA-G, decreasing concentrations of antigen were used in each subsequent round of selection. In addition to selection on antigen, some rounds of selection were employed to reduce the number of non-specific binders utilizing soluble membrane proteins from CHO cells (see WO2014179363 and Xu et al., Protein Eng. Des. Sel., 2013, 26:663-670, each incorporated by reference in its entirety). In addition to the CHO cell proteins, deselections against recombinant HLA-A/B/C proteins were performed to maintain specific binding to HLA-G. After the final round of sorting, yeast were plated and individual colonies were picked for characterization and for nomination of clones for affinity maturation.

Antibody variable domains of interest were synthesized, with codon optimization to maximize transient expression in host cells. The variable regions were cloned into expression vectors containing human immunoglobulin constant domains and their sequence confirmed. Antibody heavy and light chain vector pairings were transfected into Expi293 cells using the Expifectamine system (Invitrogen). Transient cultures were harvested on day 4 and clarified cell culture supernatant IgG titer was estimated using Bio-Layer Interferometry (BLI) using Octet (ForteBio) alongside standards. Antibodies were subsequently purified on a Protein A column and eluted using low pH glycine. Purified antibody samples were then buffer-exchanged or dialyzed into downstream assay-compatible buffers.

Antibody purity was assessed by running samples on SDS-PAGE and on an analytical size exclusion chromatography column.

Light Chain Shuffling: Heavy chain plasmids were extracted from naïve outputs (described herein) and transformed into a pre-made naïve light chain library with a diversity of 10E+06. Selections were performed as described above with one round of MACS sorting and three rounds of FACS sorting using decreasing amounts of biotinylated HLA-G antigen for respective rounds.

Example 2: Affinity Maturation

Optimization of nave clones was carried out utilizing four maturation strategies; diversification of CDR-H1 and CDR-H2; diversification of CDR-H3; diversification of CDR-L1, L2 and L3; shuffling of diversified heavy and light chains.

CDR-H1 and CDR-H2 Selection: The CDR-H3s from clones selected from light chain batch diversification, light chain diversification, and naive discovery efforts were independently recombined into premade libraries with CDR-H1 and CDR-H2 variants of a diversity of >10E+8. Selections were performed using HLA-G antigen. Affinity pressures were applied by using decreasing concentrations of antigen and HLA-G specificity was maintained with deselections against HLA-A/B/C antigens.

CDR-H3 Selection: After characterization of CDR-H1 and CDR-H2 variants, clones with binding to HLA antigens outside of HLA-G were removed. Chemical liabilities were also removed from the variable regions when applicable. The remaining clones obtained from the CDR-H1 and CDR-H2 selection procedure were subject to additional rounds of affinity maturation via walking dimer mutagenesis of the CDR-H3. Selections were performed using HLA-G as antigen generally as described above, except for employing FACS sorting for all selection rounds.

CDR-L1, L2, L3 Selection: Clones obtained from the CDR-H1 and CDR-H2 selection procedure were subject to additional rounds of affinity maturation via mutagenesis of the light chain. The CDR-L1 and CDR-L2 diversity was derived from a pre-made library while CDR-L3 diversity was derived from walking monomer mutagenesis. Selections were performed using HLA-G as antigen, starting with one round of MACS followed by three rounds of FACS in the CDR-L1, L2, L3 process described here.

Diversified Heavy Chain and Light Chain Shuffling: Outputs from CDR-H3 diversification and CDR-L1, L2, L3 diversification described above were recombined and selections were performed using HLA-G as antigen generally as described above, except for employing FACS sorting for all selection rounds.

Example 3: Binding Affinity of Anti-HLA-G Antibodies to Recombinant HLA-G

Binding kinetics were measured using the Octet Red96 system (Pall ForteBio) at 30° C. in running buffer (1× Pall ForteBio Kinetics Buffer diluted into 1×PBS pH 7.4). In brief, 0.16 μg % ml of biotinylated recombinant HLA-G/β2m/peptide heterotrimer was loaded onto streptavidin (SA) biosensors to a binding response of approximately 0.25 nm. After a short baseline step in running buffer, the biosensors were exposed to varying concentrations (1.5, 3.0, or 30 nM) of full-length anti-HLA-G mAbs for the association step. Dissociation of the complex was monitored upon dipping the sensors to running buffer once again for up to 30 min. Data was processed using ForteBio Octet DataAnalysis software (version 10) with background subtraction of biosensors without HLA-G. A 1:1 Langmuir binding model was fit to each sensorgram to obtain association and dissociation rates via local-full or local-partial fitting. $K_D$ was calculated from the ratio of $k_d$ to $k_a$. Monovalent affinities were obtain using identical methods but Fabs were used instead of IgGs.

FIG. 1 provides a table showing avid and monovalent affinities of anti-HLA-G antibodies to recombinant HLA-G protein. Data shown in FIG. 1 had $R^2 > 0.98$. ND=not determined using Fabs. The avid $K_D$ values ranged from 11.7 nanomolar to sub picomolar with off-rates ($k_{off}$) ranging from $0.007$ sec$^{-1}$ to the Octet off-rate limit ($1.0 \times 10^{-7}$ sec$^{-1}$). Monovalent $K_D$ values ranged from 0.187 nM to 208 nM, but monovalent affinities for clones that had weaker avid affinities were not determined.

Example 4: Antibodies that Bind to HLA-G and Bin Separately from Other Antibodies Epitope binning assays to recombinant HLA-G heterotrimer were determined using the Octet Red96 system (Pall ForteBio) at 30'C in running buffer (1× Pall ForteBio Kinetics Buffer diluted into 1×PBS pH 7.4). Briefly, 0.16 µg/ml of biotinylated recombinant HLA-G/β2m/peptide heterotrimer was loaded onto streptavidin (SA) biosensors to a binding response of approximately 0.25 nm. After a short baseline step in running buffer, the biosensor was dipped into 20 µg/ml of each mAb and continued until the binding response to HLA-G reached saturation. For the competing association step, equimolar concentrations of each mAb to the saturating mAb was used.

Epitope binning was performed in each direction (every mAb was used as both the saturating mAb (association step 1) as well as the competing mAb (association step 2)). Self-blocking sensorgrams are shown in gray. Non-self sensograms are shown in black; black sensorgrams represent the pairwise binning mAb. Sensorgrams from only the second association step were shown in FIG. 2.

FIG. 2A provides biolayer interferometry sensorgrams showing tested antibodies that bind HLA-G can be divided into three distinct chemical bins, with one chemical bin being further divided. Gray sensorgrams indicate self-blocking; black sensorgrams indicate pairwise binning. The y-axis show saturating antibody; the x-axis shows competing antibody.

Figure 2B:
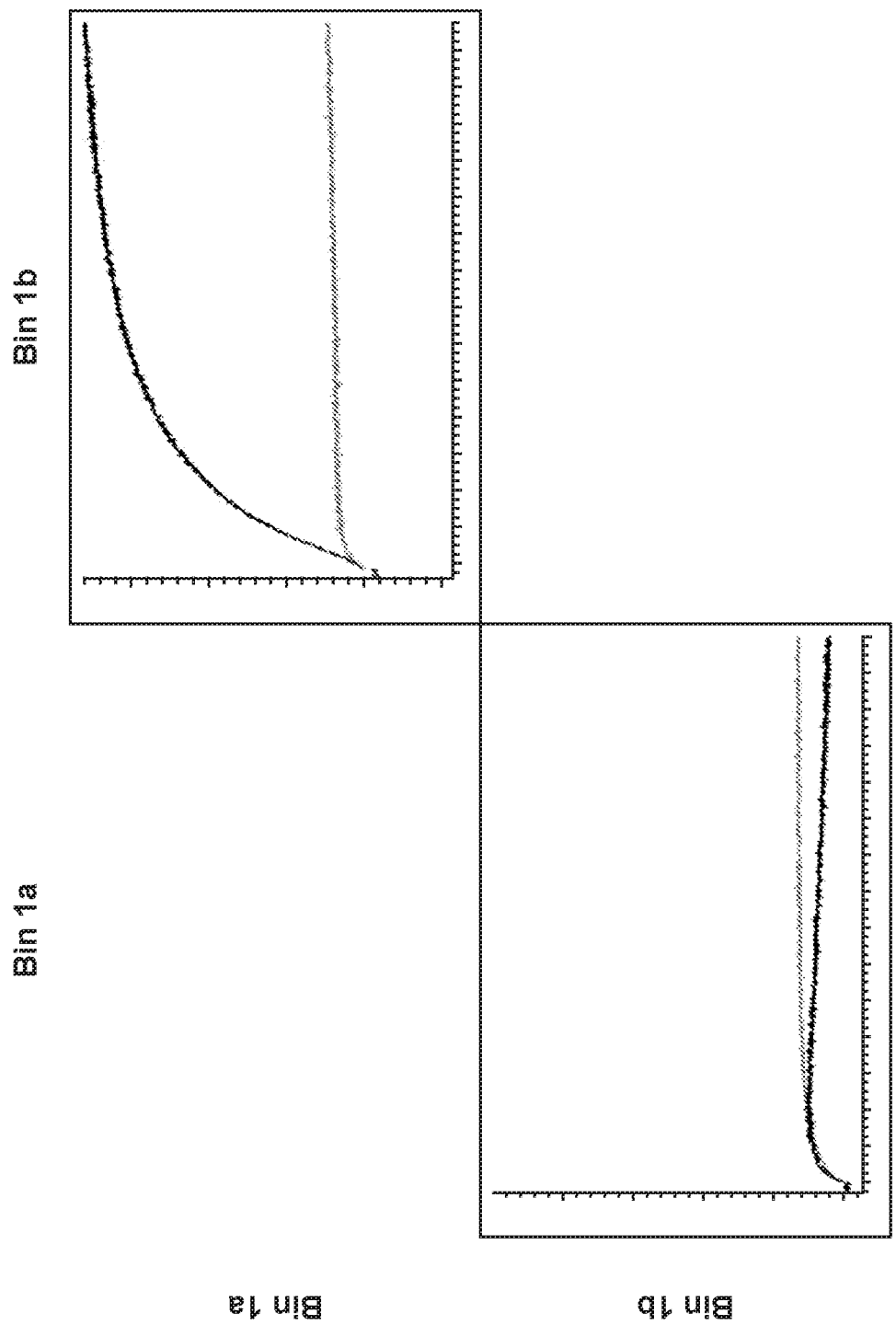

FIG. 2B provides biolayer sensorgrams showing antibodies (Fabs) that bind HLA-G and can be separated into two sub-bins from a broader bin 1. Bin 1a Fabs do not block competing bin 1b Fabs. However, bin 1b Fabs block bin 1a Fabs. As described above, gray sensorograms indicated self-blocking and black sensorograms represent pairwise binning. The y-axis represents the saturating Fab and the x-axis represents the competing Fab.

Example 5: Anti-HLA-G Antibodies that Block HLA-G Interaction/Binding to Recombinant ILT2 and ILT4

Blocking assays between recombinant HLA-G heterotrimer and recombinant extracellular domain of ILT2 or ILT4 proteins was determined using the Octet Red96 system (Pall ForteBio) at 30° C. in running buffer (1× Pall ForteBio Kinetics Buffer diluted into 1× PBS pH 7.4). Briefly, 0.16 µg/ml of biotinylated recombinant HLA-G/2m/peptide heterotrimer was loaded onto streptavidin (SA) biosensors to a binding response of approximately 0.25 nm. After a short baseline step in running buffer, the biosensor was dipped into at least 200 nM of each mAb (up to 0.5 µM for weakly binding mAbs) and continued until the binding response to HLA-G reached saturation. A second association step immediately followed by dipping into wells containing dimerized ILT2 or ILT4. Dimers were obtained via pre-incubation of the His-tagged ILT2 or ILT4 with anti-His mAb (MAB050, R&D Systems). ILT2/ILT4 binding response to mAb-saturated HLA-G (black sensorgrams) was compared to HLA-G in the absence of anti-HLA-G mAb (gray sensorgrams).

Figure 3:
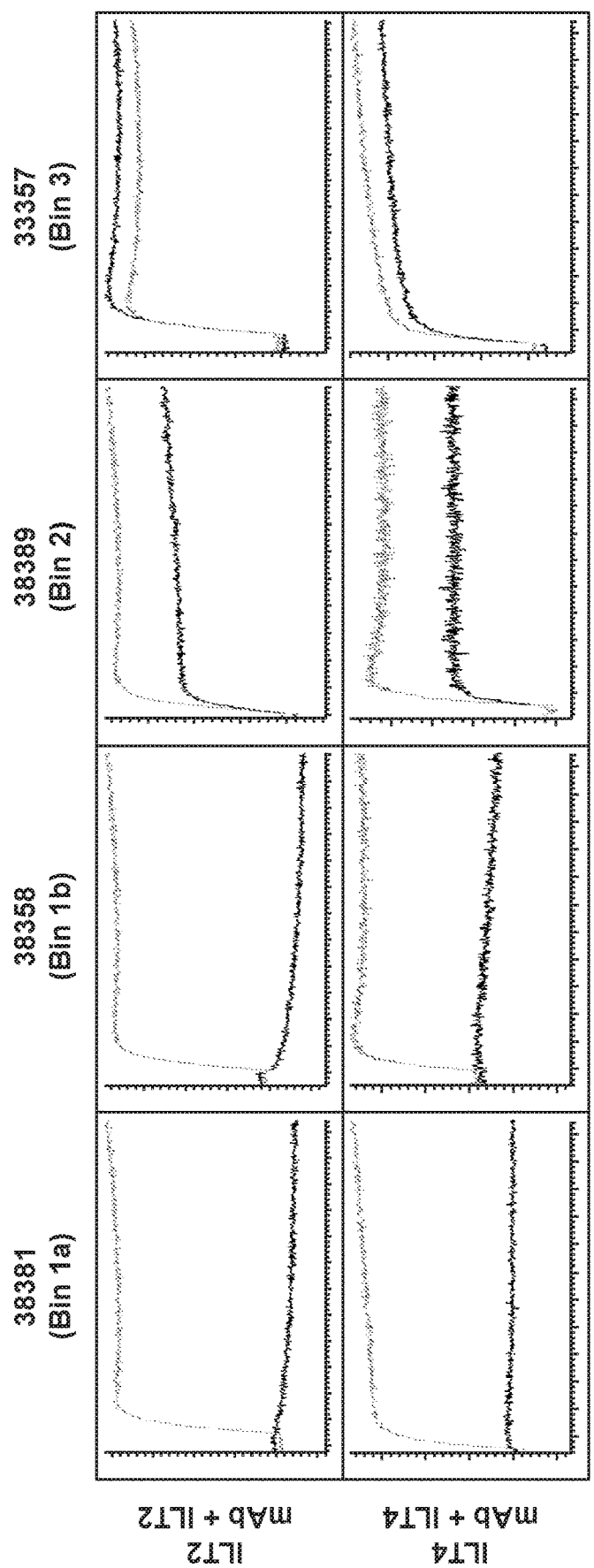
FIG. 3 provide biolayer interferometry sensorgrams showing antibodies that bind and block HLA-G interaction with ILT2 and ILT4 at varying levels of effectiveness.

Sensorgrams from the second association step are shown in FIG. 3. The provided sensorgrams show antibodies that bind and fully block HLA-G interaction with ILT2 and ILT4, for example, the bin1a and bin1b antibodies 38381 and 38358, respectively. As indicated, gray sensorgrams indicate ILT2 or ILT4 binding in the absence of antibody; black sensorgrams represent ILT2 or ILT4 binding in the presence of antibody.

FIG. 3 also provides biolayer interferometry sensorgrams showing antibodies that bind but do not block HLA-G interaction with ILT2 or ILT4, for example, the bin 3 antibodies such as 33357. Gray sensorgrams indicate ILT2 or ILT4 binding response in the absence of antibody; black sensorgrams indicate ILT2 or ILT4 binding in the presence of antibody.

The provided sensorgrams also show antibodies that bind and block HLA-G interaction with ILT2 or ILT4 to an intermediate effect, such as the bin 2 antibody 38389.

Example 6: Anti-HLA-G Antibodies Bind to HLA-G Naturally Expressed on JEG-3 Cells JEG-3 parentals or HLA-G-knock out (JEG-3 KO) cells were incubated with 100 nM of anti-HLA-G antibodies for 2 hours at 4° C. in wash buffer (Phosphate Buffered Saline (PBS), 2% Fetal bovine serum (FBS) and 2 mM EDTA). Cells were then washed in wash buffer and incubated with an APC conjugated secondary antibody (goat anti-human IgG Kappa) at a 1:500 dilution in wash buffer for 30 minutes at 4° C. Cells were subsequently washed and resuspended in 1% paraformaldehyde/wash buffer followed by sample acquisition using a BD Fortessa X-20 flow cytometer (Becton Dickinson). Sample data was exported as FCS files and analyzed using FlowJo software v10 (Tree Star, Inc.).

Figure 4:
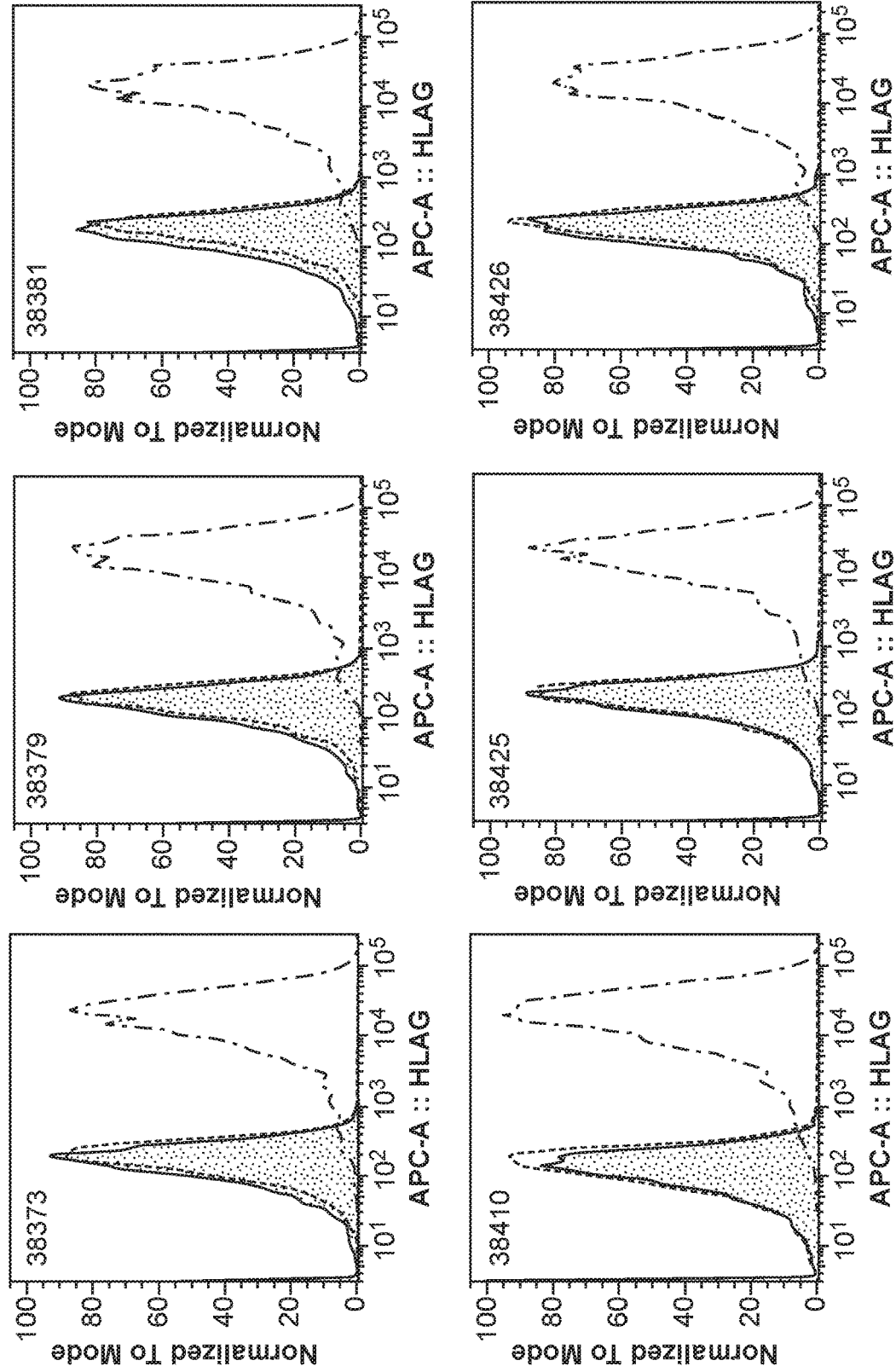
FIG. 4 shows evaluation of anti-HLA-G antibodies binding to naturally expressed HLA-G found on JEG-3 tumor cells.

The results are shown in FIG. 4. The shaded histogram represents binding of an isotype control to JEG-3 cells at the same concentration.

Example 7: Anti-HLA-G Antibodies Abrogate Suppression Mediated Through HLA-G-ILT2 or ILT4 Interaction in NKL Killing Assay Inhibition of NKL cytotoxicity via the ILT2-HLA-G interaction or ILT4-HLA-G interaction is abrogated by anti-HLA-G antibodies. NKL (Effector) cells were co-incubated with 721.221 (Target) cells+/–HLA-G expression at an E:T ratio of 4:1 overnight at 37° C. 721.221s were pre-incubated with 200 nanomolar (nM) Fab fragments or full-length intact anti-HLA-G antibodies for 60 minutes at 37° C. Prior to antibody pre-treatment, 721.221 cells were labelled with 1:1000 CellTrace Violet (CTV) (Invitrogen) in 37° C. PBS.

After overnight co-incubation, cells were washed once in 4° C. wash buffer (Phosphate Buffeed Saline, 2% FBS, 2 mM EDTA) and then stained with 1:2000 Fixable Viability Dye eFluor™ 780 (Invitrogen) 30 minutes at 4° C. Cells were washed again in 4° C. wash buffer resuspended in wash buffer and analyzed for percent dead 721.221 cells by flow cytometry analysis on a BD Celesta flow cytometer. Percent of dead 721.221 cells was determined by gating on CTV positive cells, then dividing the Fixable Viability Dye positive portion of these cells by the total CTV count.

Antibody MEM-G/9 is a commercially available antibody (See, Fournel et al., Tissue Antigens 200: 55: 510-518 (1999), which is incorporated by reference in its entirety herein, including any drawings).

Figure 5A:
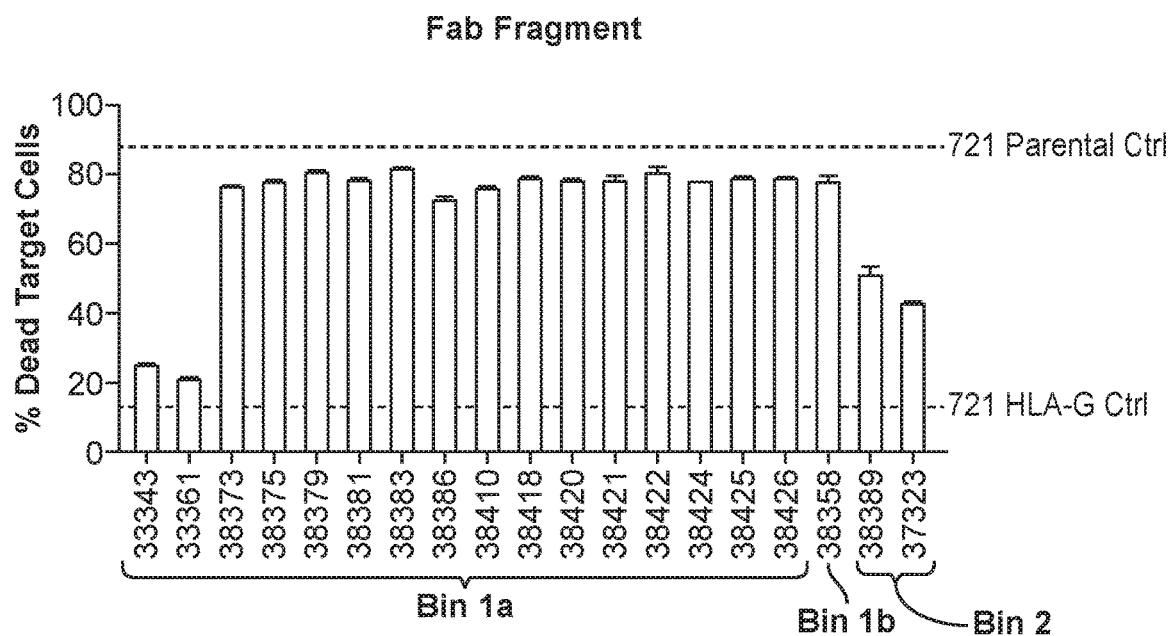
FIG. 5A, FIG. 5B, FIG. 5C, and FIG. 5D provide data showing anti-HLA-G Fabs and antibodies that restore NKL killing activity by blocking suppression mediated through interaction of HLA-G with ILT2 or ILT4.
Figure 5B:
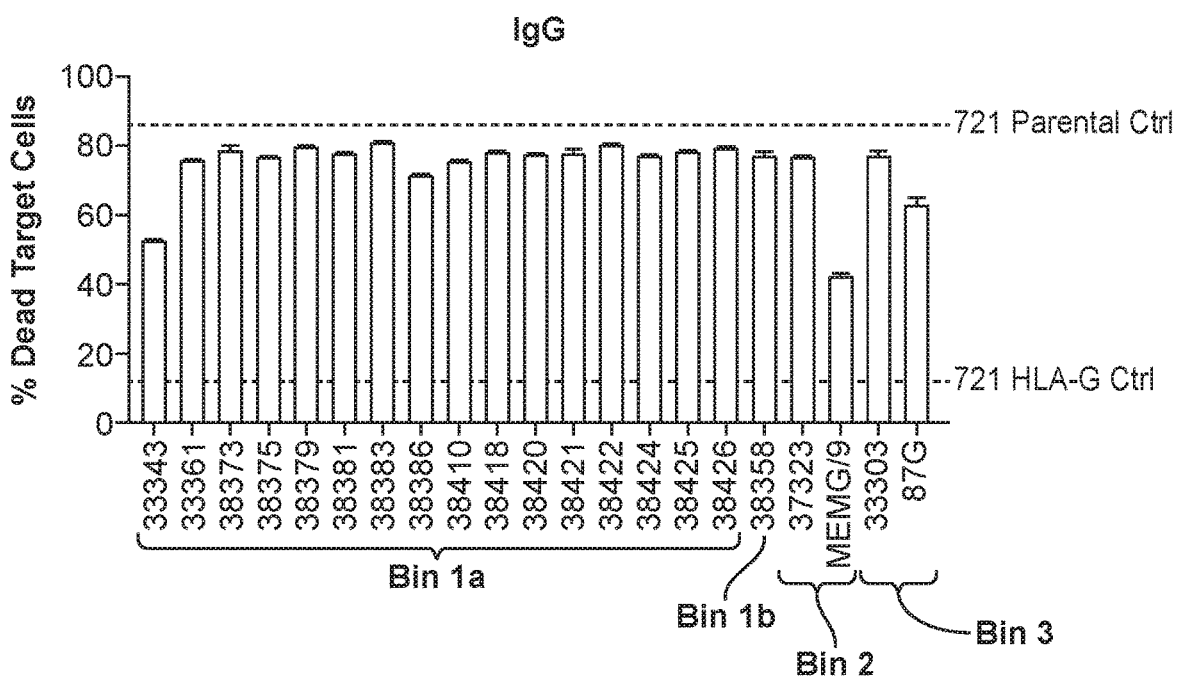

FIG. 5A (Fab fragments) and FIG. 5B (intact IgG) show the effect on NKL cells that endogenously express ILT2. The percent of dead target cells is shown for each antibody (indicated as a unique clone number in the figure) in addition to control values representing minimum and maximum killing in the presence and absence of HLA-G, respectively. As can be seen from FIG. 5, Bin 1 antibodies show the best blockade of all the antibodies tested.

Figure 5C:
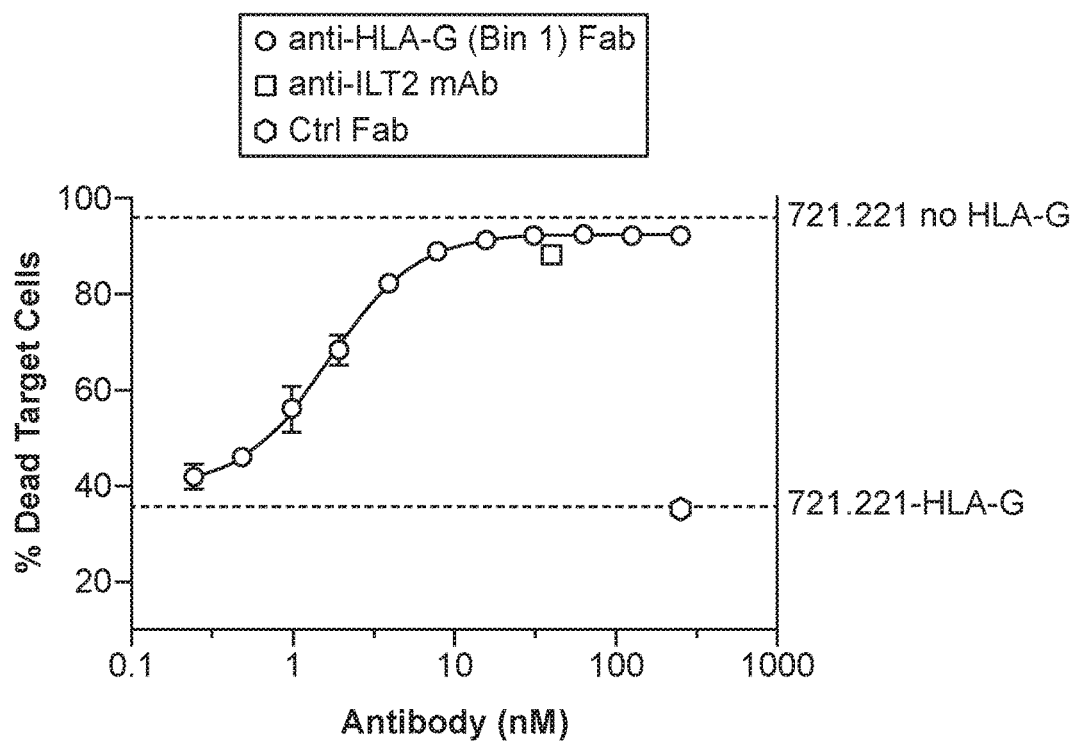

FIG. 5C demonstrates the dose response of a specific Bin 1 anti-HLA-G Fab fragment for blockade of HLA-G-mediated suppression of NKL killing through endogenously expressed ILT2.

Figure 5D:
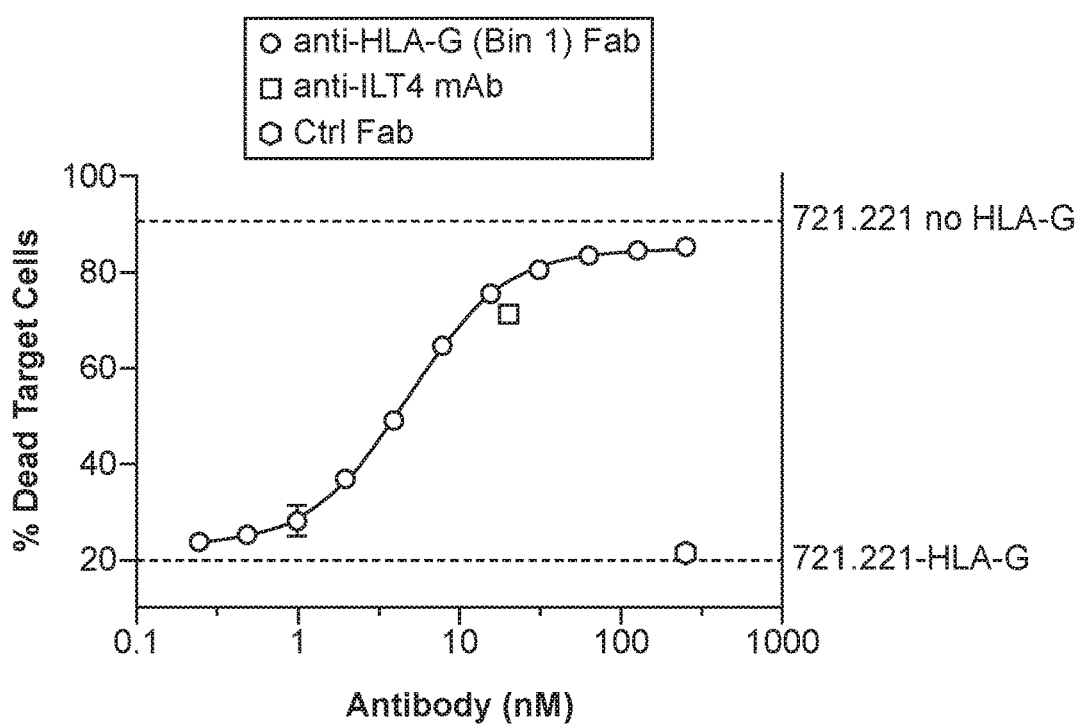

FIG. 5D demonstrates the dose response of a specific Bin 1 anti-HLA-G Fab fragment for blockade of HLA-G-mediated suppression of NKL killing through engineered expression of ILT4 (engineered cell line modified by knocking down ILT2 and retrovirally transduced to express ILT4).

Example 8: Fab Fragments of Anti-HLA-G Antibodies Reverse HLA-G Mediated Suppression of Macrophage Phagocytosis, NK Cell Cytotoxicity, and CD8+ T Cell Activity $CD14^+$ enriched cells were differentiated into adherent macrophages by incubating at 37° C., 5% $CO_2$ for 7 days in complete RPMI (cRPMI) with recombinant human M-CSF. Cells were harvested after 7 days, washed, and resuspended in cRPMI. Cells were plated in a 96-well round bottom plate at 50,000 cells/well in 50 μl cRPMI and incubated at 37° C., 5% $CO_2$, before being combined with the target cells.

The target cells, consisting of either 721.221 parental cells or 721.221-HLA-G, were stained with CTV (1:1000) at 37° C. in PBS, washed and plated in cRPMI at 25,000 cells per well. Cells were subsequently incubated with anti-CD47 antibody with or without anti-HLA-G Fabs for 1 hour at 37° C., 5% $CO_2$. The mixture of 721.221 and antibody was then combined with macrophages and incubated for either 2 hours or overnight at 37° C., 5% $CO_2$. The final ratio of macrophage to 721.221 target cell was 2:1. After either the 2 hour or overnight incubation, cells were blocked with wash buffer/BD Fc Block™/2% mouse serum for 20 minutes and then stained with anti-CD11b and live/dead discrimination dye for 20 minutes. Cells were then washed, resuspended in wash buffer and analyzed on the BD Fortessa flow cytometer. Sample data was exported as FCS files and analyzed using FlowJo software v10.

In the 2-hour format assay, macrophages were assayed for the presence of CTV as a readout of phagocytic uptake of $CTV^+$ target cells. Live cells were gated on $CD11b^+/CTV^+$ and reported as a percent of total live macrophages. For the overnight assay, macrophage killing activity was assessed by measuring absolute counts of remaining live $CTV^+$ cells per well.

Figure 6A:
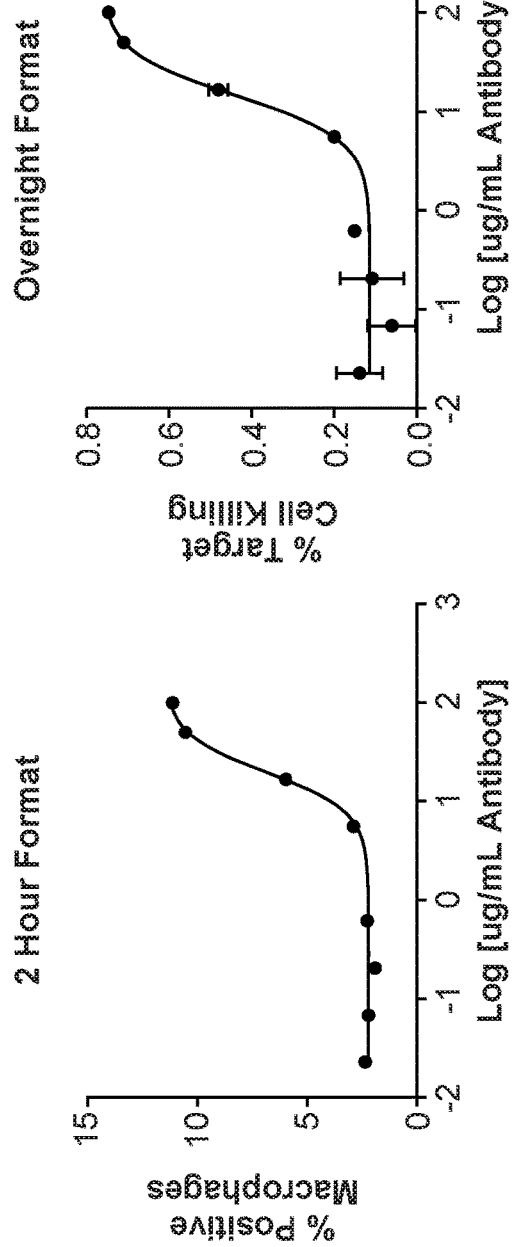
FIG. 6A.
Figure 6B:
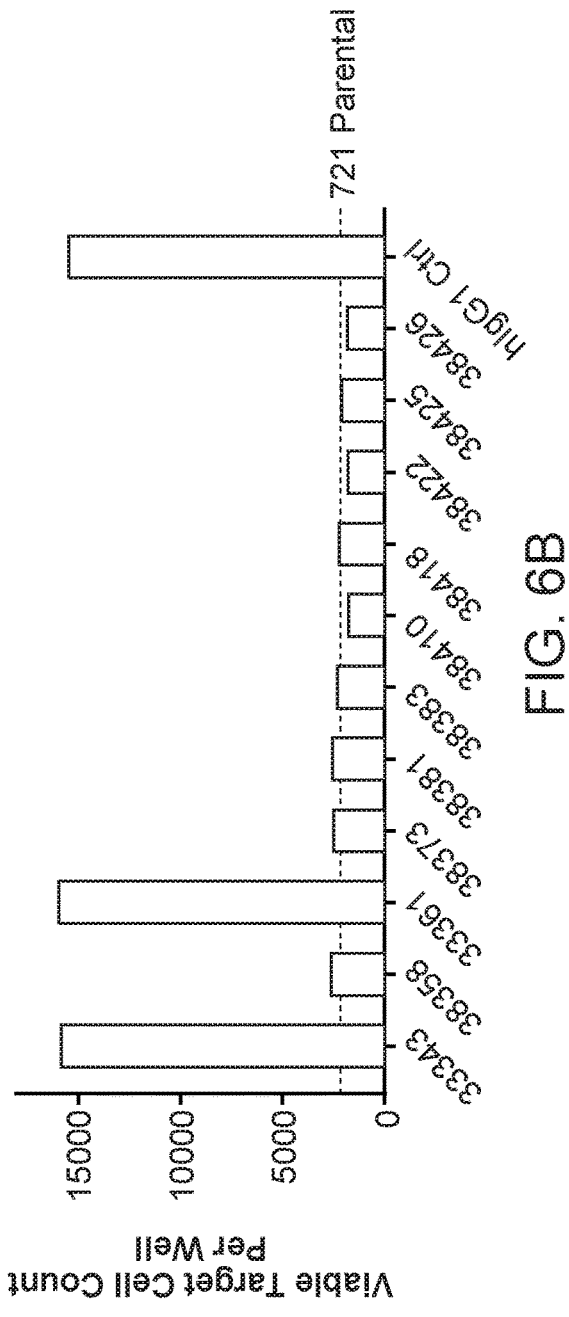
FIG. 6B, FIG. 6C, and FIG. 6D provides evaluation of anti-HLA-G antibodies to reverse HLA-G mediated suppression of primary human cells.

FIG. 6A compares results between the two hour and overnight assay formats using an anti-HLA-G antibody (Fab fragment). The overnight assay achieves similar results as the two hour assay that directly measures phagocytosis of target cells. FIG. 6B shows the results of Fab fragments of each anti-HLA-G antibody that were tested in the overnight assay to determine the level of restored phagocytic activity.

To demonstrate inhibition of primary human NK cell cytotoxicity is abrogated by an anti-HLA-G antibody, HLA-G expressing target cells (721.221-HLA-G) were pre-incubated with a representative Bin 1 antibody (Fab fragment) and then co-cultured with human primary NK (Effector) cells from 3 separate donors at an E:T ratio of 4:1 overnight at 37° C. Prior to antibody pre-treatment, 721.221 cells were labelled with 1:1000 CellTrace Violet (CTV) (Invitrogen) in 37° C. PBS.

After overnight co-incubation, cells were washed once in 4° C. wash buffer (Phosphate Buffered Saline, 2% FBS, 2 mM EDTA) and then stained with 1:2000 Fixable Viability Dye eFluor 780 (Invitrogen) for 30 minutes at 4° C. Cells were washed, resuspended in wash buffer, and analyzed for percent dead 721.221 cells by flow cytometry analysis on a BD Celesta flow cytometer. Percent of dead 721.221 cells was determined by gating on CTV positive cells, then dividing the Fixable Viability Dye positive portion of these cells by the total CTV count.

Figure 6C:
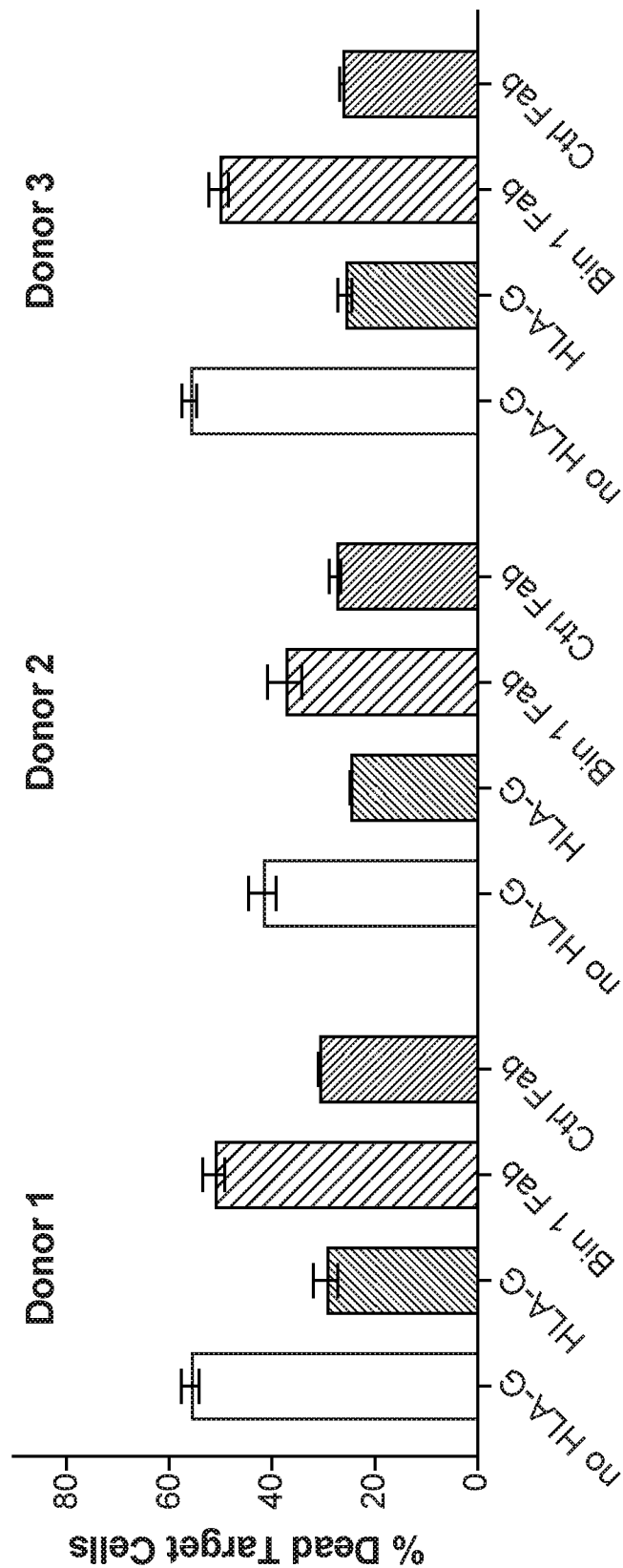

The results are shown in FIG. 6C. The percent of dead target cells is shown for the Bin 1 antibody (Fab) in addition to control values representing co-cultures with 721.221 target cells with and without HLA-G expression (noted as HLA-G and no HLA-G in figure, respectively). An isotype control Fab (Ctrl Fab) was used as a negative control.

To demonstrate an anti-HLA-G antibody reverses HLA-G mediated suppression of cytotoxic primary $CD8^+$ T cell function, human $CD8^+$ T cells treated with CD3/CD28 activator (ImmunoCult™, Stem Cell Technologies) for 1 hour were mixed with antibody pre-treated 721.221 cells (with and without expression of HLA-G) and co-cultured overnight at 37° C. After overnight co-incubation, Monensin Solution (ThermoFisher) and eFluor 450-CD107a (ThermoFisher) were added; the final amount of each reagent was 0.5 μg/mL antibody and 2 μM Monensin. The assay was incubated for 4 hours.

After the incubation, cells were washed and stained over several steps which included the following: (1) live/dead cell staining using Fixable Viability Dye eFluor 780 (ThermoFisher); (2) Fc blocking with staining buffer (Phosphate Buffered Saline, 2% FBS, 2 mM EDTA) containing 6% normal mouse serum and 5 μL Human TruStain FcX™ per sample (Biolegend) for 15 minutes at 4° C.; (3) CD8 and ILT2 staining with Alexa Fluor 700-CD8 (Biolegend, Clone SKI) and PE-CD85j/ILT2 (Biolegend, Clone HP-F1, ThermoFisher); Fixation and permeabilization using fix/perm reagent (ThermoFisher); (5) Intracellular staining with Brilliant Violet 711-IFN-γ (Biolegend, Clone 4S.B3) and APC-TNF-α (Biolegend, Clone MAb11) diluted in Permeabilization Buffer (ThermoFisher) for 20 minutes at 4° C. After the staining steps, cells were washed, centrifuged, and resuspended in staining buffer followed by sample acquisition on a BD Fortessa X-20 flow cytometer using the high throughput sampler.

FCS data was analyzed using FlowJo version 10 analysis software (FlowJo, LLC). Gates were made to select single cells, live cells, and the cell type of interest. $CD8^+$ T cell populations were defined based on $CD8^+ILT2^+$ or $CD8^+ILT2^-$. To determine the percent of cells positive for CD107a, IFN-γ, or TNF-α, gating was performed on each $CD8^+$ T cell population and determined using fluorescence minus one cells and unstimulated cells.

Figure 6D:
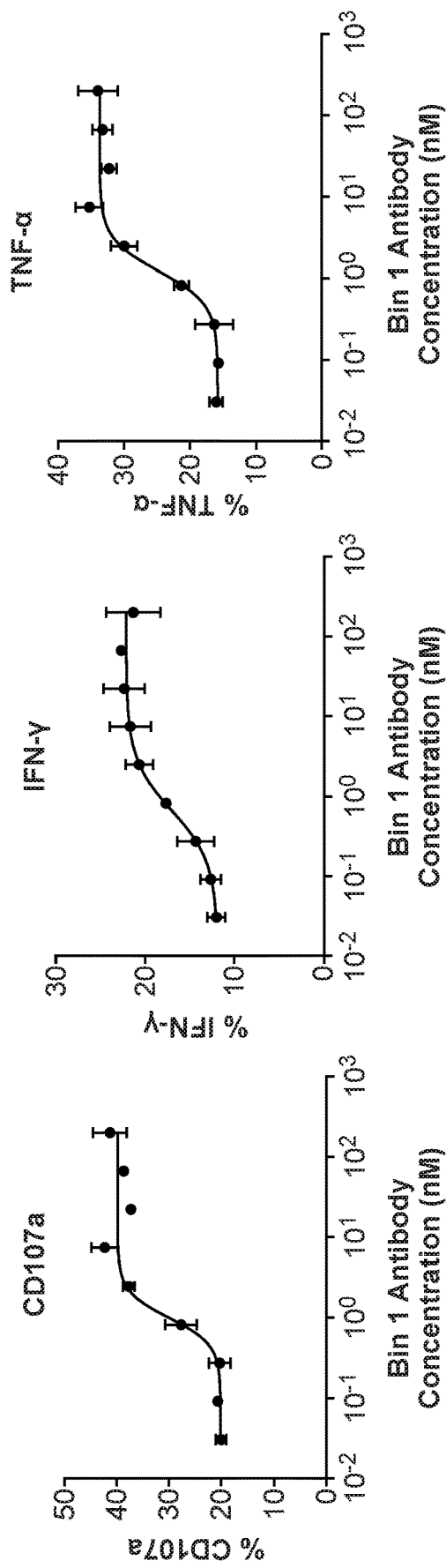

Results depicted in FIG. 6D demonstrate that blockade of HLA-G with an anti-HLA-G antibody (representative Bin 1 clone) restored CD107a, IFN-γ, and TNF-α expression in $CD8^+$ $ILT2^+$ T cells in a dose-dependent manner. There was no effect from HLA-G target cell expression or anti-HLA-G antibody treatment on $CD8^+ILT2^-$ cells (data not shown).

Example 9: Anti-HLA-G Antibodies that are Selective Binders to HLA-G and do not Bind to Classical HLA Class I Antigens Binding of antibodies to HLA antigens (97 different antigens spanning HLA-A, -B, and -C haplotypes) was determined using the LABScreen single antigen class I-combi assay (One Lambda). Antibodies at concentrations greater than 300 nM were incubated with single antigen LABScreen beads in binding buffer (Phosphate Buffered Saline, 10% FBS, 2 mM EDTA) for 45 minutes in the dark at room temperature with gentle shaking. Beads were washed twice with 200 µL of IX LABScreen wash buffer in a 96-well V-bottom plate by centrifugation at 1500 g and removal of buffer by aspiration. Beads were then incubated with a PE-conjugated secondary antibody (polyclonal goat anti-human or anti-mouse in 1× wash buffer) for 30 minutes at room temperature in dark with gentle shaking. After incubation, beads were washed twice, resuspended in 90 µL of wash buffer, and then transferred to a 96-well flat bottom plate. Acquisition was performed on a Luminex 100 instrument and data output as a CSV file. Results for each single HLA antigen bead group were tabulated from median fluorescent intensity values.

Antibody 87G is a commercially available antibody and represents a blocking antibody (See, Odum et al., Eur. J. Immunol. 22: 2121-2131 (1991) and Lee et al., Immunity, 591-600 Volume 3, Issue 5 (1995), each of which is incorporated by reference in its entirety herein, including any drawings).

collection of twenty-eight B-LCL cell lines (shown in Table X). Cells were obtained from the International Histocompatibility Working Group cell line collection that holds a repository of B-LCL cell lines which have been HLA-typed. The cells were maintained in supplemented RPMI-1640 media containing 15% fetal bovine serum.

For antibody binding, anti-HLA antibodies were first conjugated to DyLight 650 (Thermo Fisher) by primary amine labeling via the NHS-ester moiety. Unconjugated dye was removed by flowing the antibody preparation through dye removal resin. Conjugation efficiency was between 1 to 3 moles of DyLight 650 per mole of antibody. B-LCL cell lines (ranging from 10,000 to 100,000 cells per well) were incubated with 300 nM of labeled antibodies in cold PBS containing 10% FBS and human Fc block (BD Biosciences). After 2 hours at 4° C., cells were washed twice in cold wash buffer (Phosphate Buffered Saline, 2% FBS, 2 mM EDTA) followed by sample acquisition on a BD FACS Celesta instrument. To assess overall HLA class I expression, a pan HLA class I antibody, clone W6/32, conjugated to FITC was incubated separately with each individual cell line. All cell lines were strongly positive for class I expression (data not shown). Data was exported as FCS files and analyzed using FlowJo software v10. Gating was performed on live singlet cells using DAPI for live-dead discrimination. Geometric MFI is shown for each B-LCL cell line.

TABLE X

| IHW ID | Alternate ID | Sex | Ethnic/Population Group | Workshop Involvement | HLA A* | | HLA B* | | HLA Cw* | |
|---|---|---|---|---|---|---|---|---|---|---|
| IHW09367 | LCK |   | Asian | 13 | 0203 | 1102 | 4601 | 380201 | 0702 | 1202 |
| IHW09458 | FH70EY | M |   | 13 | 3002 | 6802 | 0801 | 5301 | 0401 | 07 |
| IHW09383 | FH9 | M | Other | 13 | 2402 | 3303 | 4801 | 44032 | 0801 | 0701 |
| IHW09397 | DUG150 |   | Unknown | 13 | 02 | 680101 | 5802 | 4501 | 0602 | 1601 |
| IHW09057 | TEM | M | Jewish | 10, 12 | 6601 |   | 3801 |   | 1203 |   |
| IHW09010 | AMAI | M | Algerian | 10, 12 | 6802 |   | 5301 |   | 0401 |   |
| IHW09436 | FH48 | M | Caucasian | 13 | 2402 | 0201 | 4427 | 070201 | 070201 | 0704 |
| IHW01167 | 1413-1090 | M | Caucasian | CEPH | 680102 | 0201 | 0801 | 4402 | 0701 | 0501 |
| IHW01075 | 1344-8354 | F | Caucasian | CEPH | 2402 | 0301 | 4001 | 5101 | 030401 | 0102 |
| IHW01185 | 1416-1337 | M | Caucasian | CEPH | 0205 | 2501 | 4901 | 4402 | 0701 | 0501 |
| IHW09431 | FH43 | M | American Black | 13 | 3001 | 3301 | 5301 | 8101 | 04 | 08 |
| IHW01124 | 1362-8563 | M | Caucasian | CEPH | 0201 | 2902 | 3501 | 4403 | 0401 | 1601 |
| IHW01133 | 1362-8572 | F | Caucasian | CEPH | 2902 | 2601 | 4403 | 4402 | 1601 | 0501 |
| IHW01092 | 1346-8603 | M | Caucasian | CEPH | 0201 | 1101 | 0702 | 3501 | 0702 | 0401 |
| IHW09371 | ISH4 |   | Asian | 13 | 0218 | 1101 | 1501 | 4601 | 0102 | 040101 |
| IHW09433 | FH45 | M | Asian | 13 | 1101 | 02 | 3802 | 4101 | 0702 | 17 |
| IHW09380 | FH6 | M | Hispanic | 13 | 2402 | 2901 | 2702 | 0705 | 1505 | 020202 |
| IHW09411 | FH29 | F | Hispanic | 13 | 0201 | 2902 | 1516 | 440301 | 1402 | 1601 |
| IHW09401 | TER-259 |   | USA White/ American Indian | 13 | 3201 | 6802 | 0801 | 44020101 | 0102 | 07 |
| IHW09398 | FH18 | F | American Black | 13 | 3601 | 7401 | 5301 | 5703 | 0401 | 0701 |
| IHW09382 | FH8 | F | Am. Black | 13 | 110101 | 3402 | 8201 | 270502 | 0302 | 0102 |
| IHW01026 | 1332-8257 | F | Caucasian | CEPH | 0301 | 3001 | 3501 | 0702 | 0401 | 0702 |
| IHW09409 | FH27 | M | Native American | 13 | 310102 | 3401 | 350101 | 380201 | 0401 | 0702 |
| IHW09452 | FH64 |   | Unknown | 13 | 02 | 3201 | 44 | 1801 | 05 | 07 |
| IHW01028 | 1332-8259 | F | Caucasian | CEPH | 0301 | 0301 | 3501 | 2705 | 0401 | 020202 |
| IHW01061 | 1341-8465 | F | Caucasian | CEPH | 0201 | 680102 | 0702 | 0702 | 0702 | 0702 |
| IHW01099 | 1347-8434 | M | Caucasian | CEPH | 2501 | 0101 | 0801 | 1501 | 0701 | 0602 |
| IHW01136 | 1362-8575 | M | Caucasian | CEPH | 0101 | 1101 | 0702 | 5101 | 0702 | 1502 |

Figure 7A:
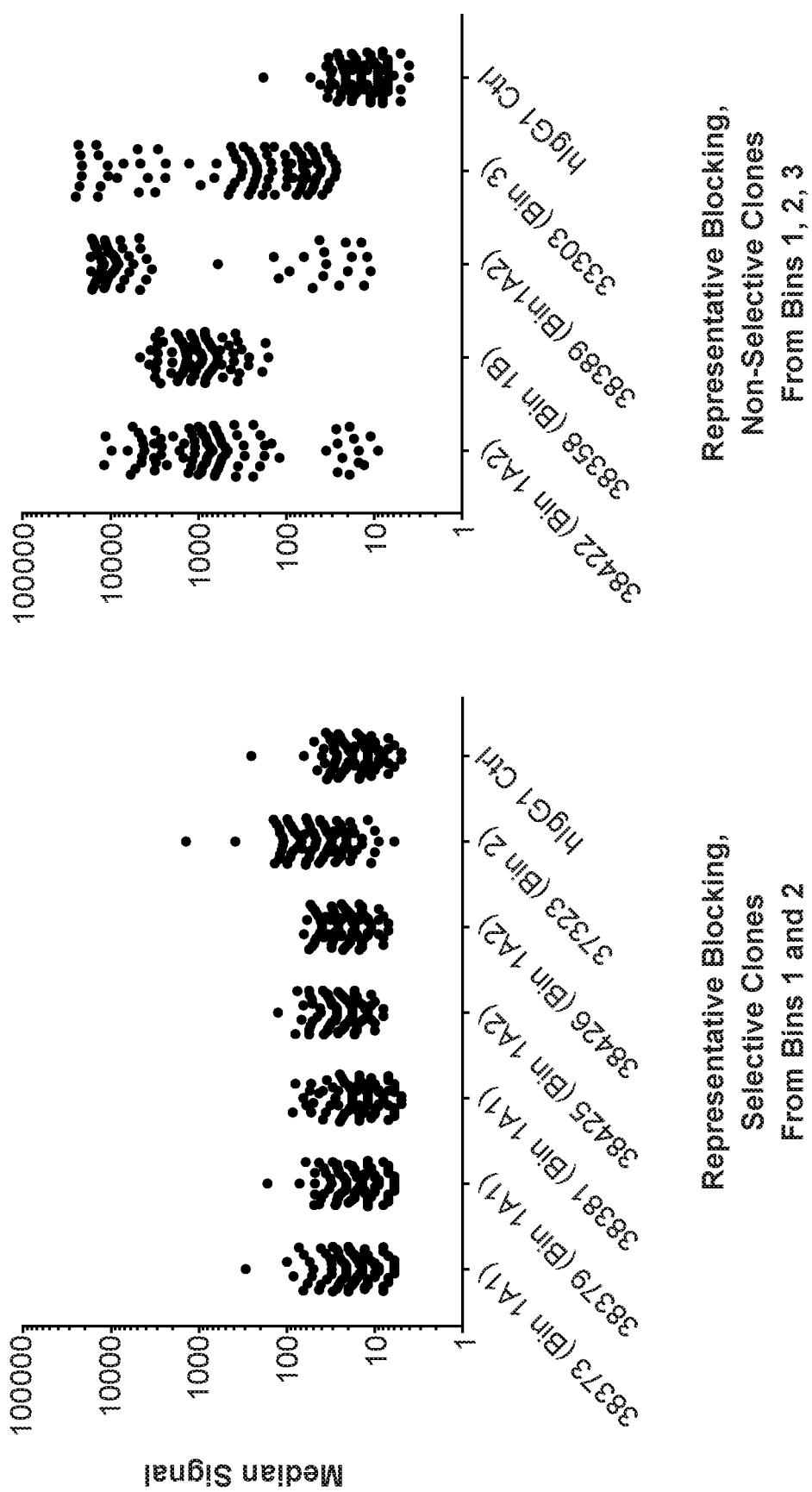
FIG. 7A and FIG. 7B shows results representing values for binding of anti-HLA-G antibodies to individual recombinant HLA class Ia antigens immobilized on beads.
Figure 7B:
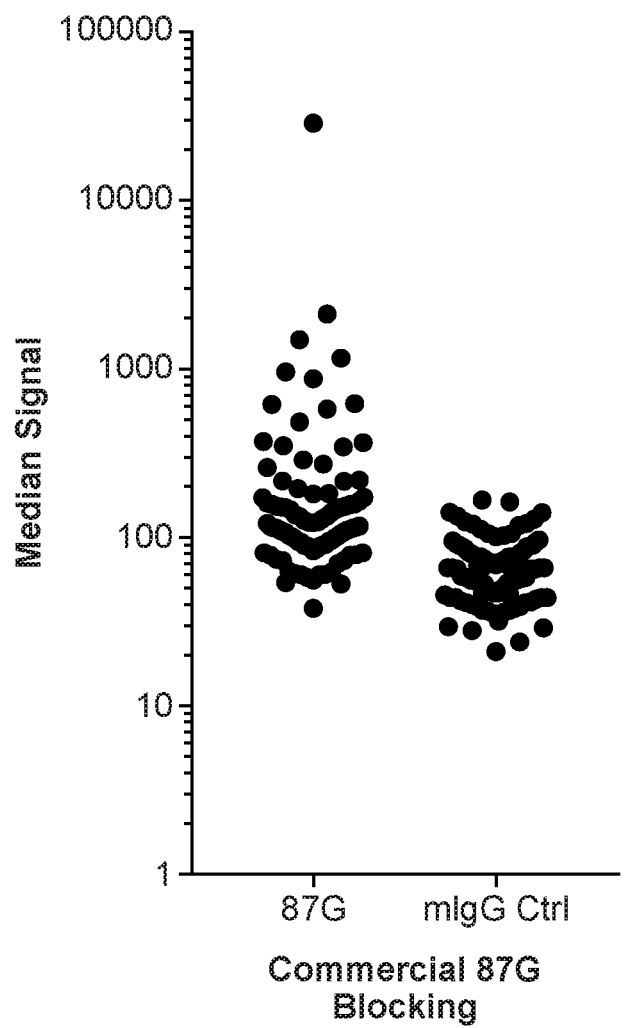

The results are shown in FIG. 7. Binding values (median fluorescent signal) to each single HLA antigen are shown for each anti-HLA-G antibody.

Figure 8:
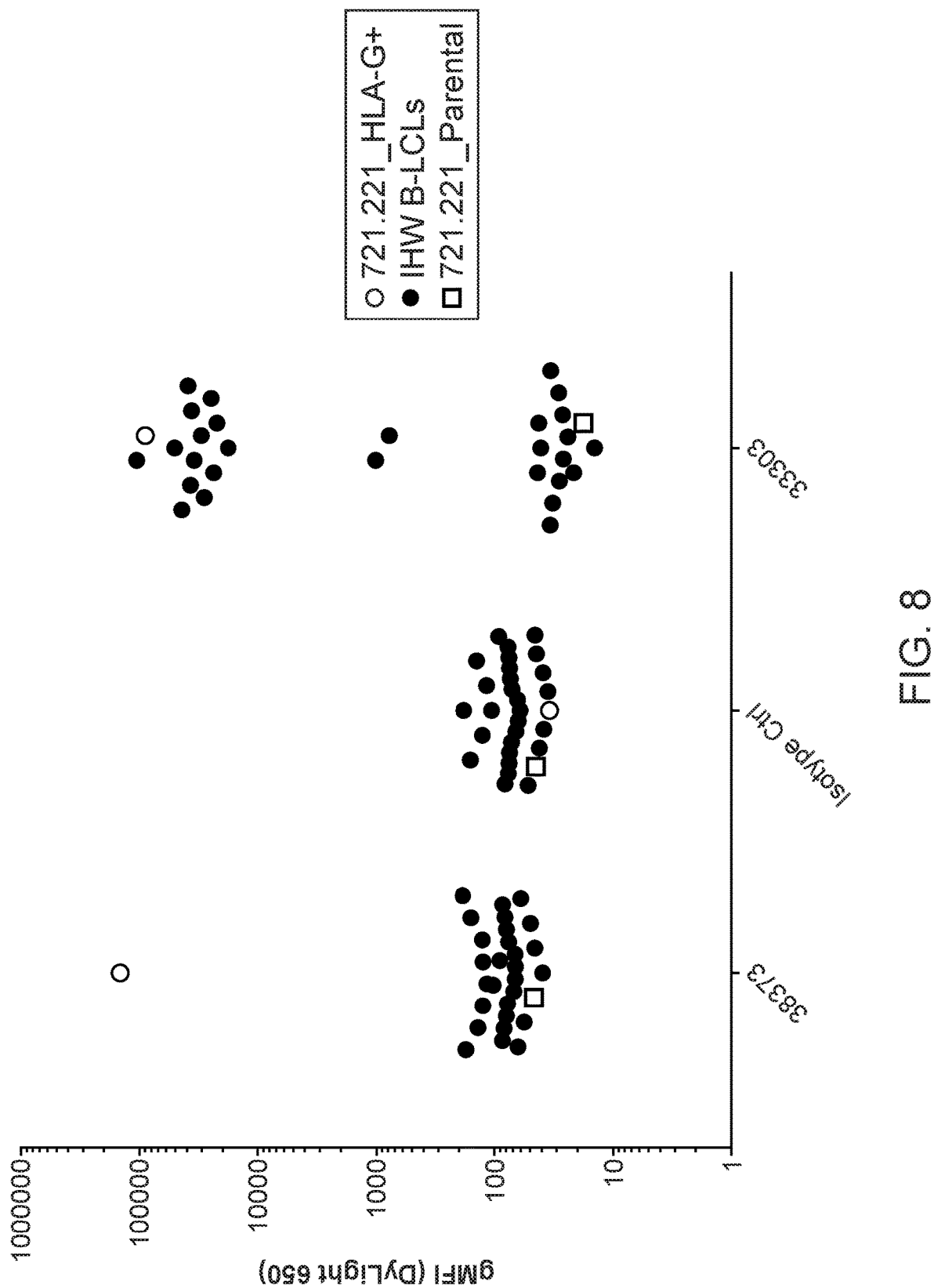
FIG. 8 shows the evaluation of anti-HLA-G antibodies binding to a panel of 28 HLA-typed B-LCL lines.

Example 10: Anti-HLA-G Antibodies that do not Bind to Classical HLA Class Antigens Expressed at Physiological Levels on B-LCL Cells Binding of antibodies to physiological levels of native HLA class Ia proteins was assessed by flow cytometry on a The results are shown in FIG. 8. Binding levels are provided as geometric MFI. Class I-negative 721.221 cell lines with and without expression of HLA-G were used as controls.

Example 11: Critical HLA-G Amino Acid Determinants Required for HLA-G Antibody Binding 721.221 LCL cells transiently expressing various point mutants of HLA-G were established using the Neon® Transfection System (ThermoFisher Scientific). Cells were transfected with 1 µg of plasmid per point mutantin the 10 µL reaction format. Cells were cultured for 72 hours prior to staining with anti-HLA-G antibodies.

721.221 LCL cells (expressing various point mutants or a domain swap where the primary amino acid sequence encoding the alpha 3 domain was substituted with the analogous sequence from HLA-A*101) were incubated with each antibody (100 nM) in wash buffer (Phosphate Buffered Saline, 2% FBS, 2 mM EDTA) for 60 minutes at 4° C. Cells were then washed with cold wash buffer and incubated with fluorescently labelled secondary antibody at 4° C. for 30 minutes. Numbered antibodies were incubated with 1:500 R-Phycoerythrin labelled goat-anti-human IgG (Jackson ImmunoResearch). W6/32 was incubated with 1:500 Alexa Fluor 488 goat-anti-mouse IgG (Jackson ImmunoResearch). MEMG/9 (Invitrogen) was pre-conjugated with Allophycocyanin. After incubation with secondary antibody, cells were washed and resuspended in cold wash buffer prior to analysis by flow cytometry on a BD Celesta instrument. Sample data was exported as FCS files and analyzed using FlowJo software v10. As shown in FIG. 9, mutation of residues 195, 197, and/or 198 results in loss of binding by bin 1 anti-HLA-G antibodies, revealing those residues are critical, though unlikely to be the only determinants for bin 1 antibody binding. Intriguingly, the biochemical bin defined by Octet as bin 1a (FIG. 2B) can be further distinguished based on either sensitivity to mutation at residue 197 (for example, 38379) or mutation at residue 198 (for example, 38410)

Figures 9A, 9B:
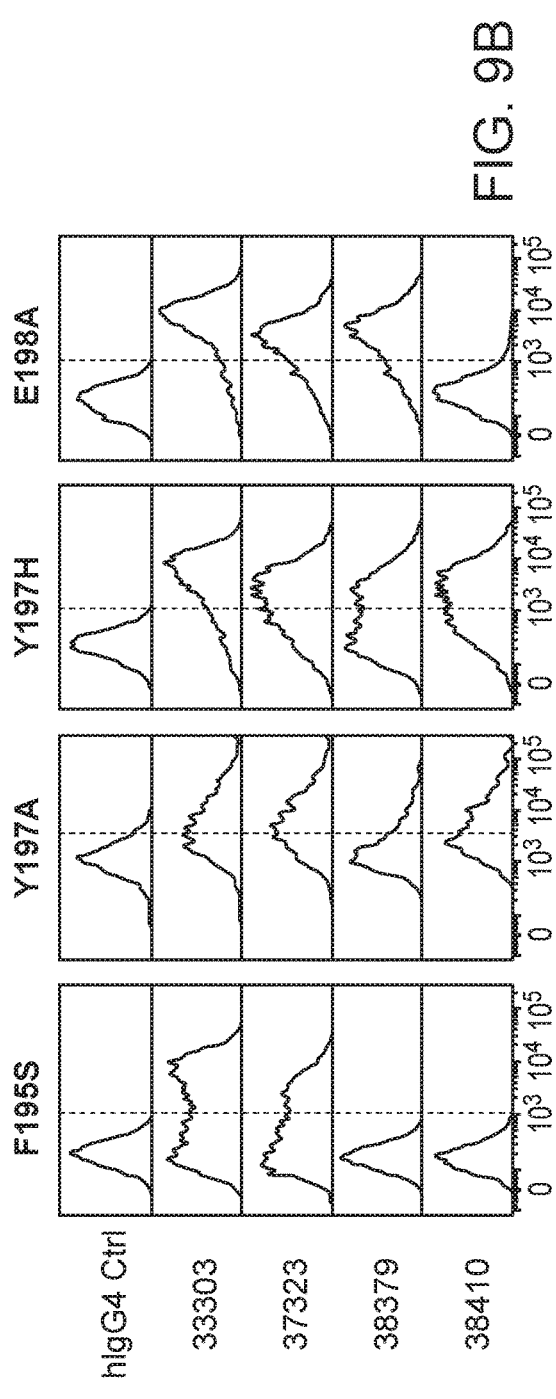
FIG. 9A and FIG. 9B show the evaluation of anti-HLA-G antibodies binding to various forms of HLA-G after site-directed mutagenesis.

FIG. 9A shows the evaluation of HLA-G antibodies binding to various forms of HLA-G after site directed mutagenesis. FIG. 9B provides representative antibody binding histograms for each of the three point mutants (F195S, Y197A, Y197H, E198A).

Figure 10:
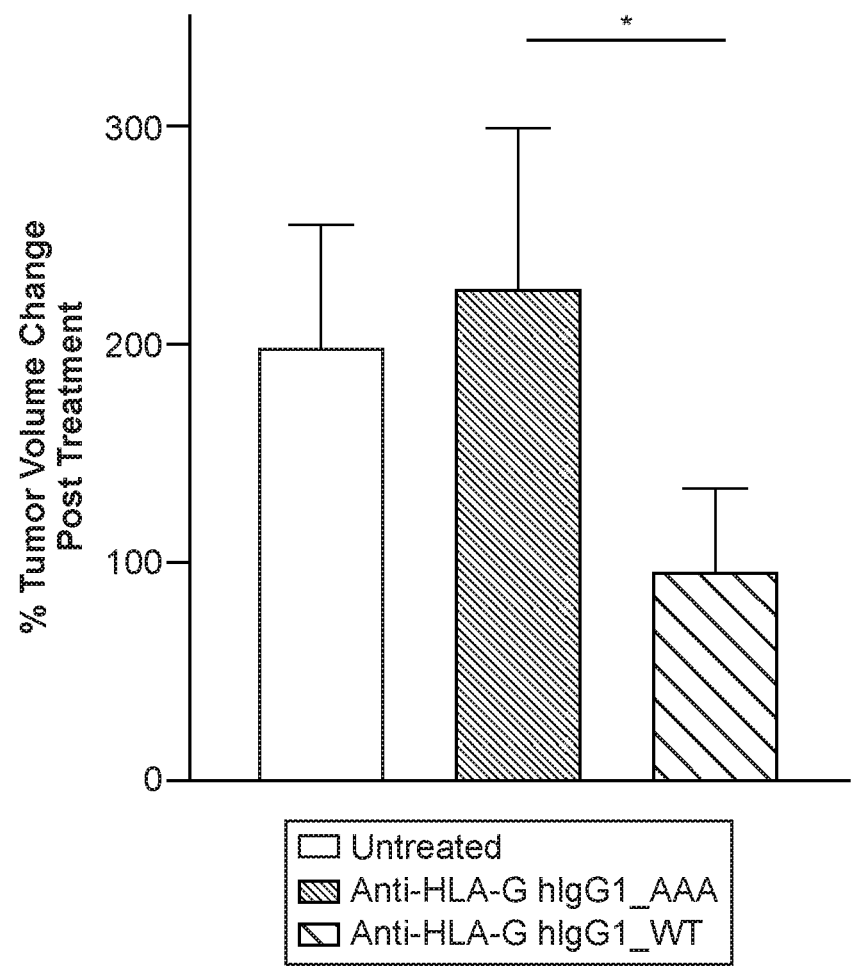
FIG. 10 provides evidence for tumor growth inhibition by an anti-HLA-G antibody with and Fe effector function in a mouse tumor xenograft tumor model using 721.221 cells expressing HLA-G.

Example 12: Tumor Growth Inhibition for an Ant-HLA-G Antibody with and without Effector Function in a Mouse Xenograft Model Using 721.221 Cells Expressing HLA-G NOD/SCID mice were implanted subcutaneously with 10 million HLA-G expressing 721.221 cells in Matrigel on the right flank. On day 29 post-implantation, mice were randomized into groups based on tumor volume and dosed intraperitoneally with 300 µg of either an effector competent anti-HLA-G human IgG1 antibody (hIgG1 WT), the same anti-HLA-G antibody with mutations in the Fc domain to abrogate Fc receptor interactions (hIgG1_AAA), or left untreated. A second dose of antibody was given three days later. Data provided in FIG. 10 represents the percent change in tumor volume six days after initial treatment. These results demonstrate that an anti-HLA-G antibody can inhibit the growth of tumors expressing HLA-G by engaging Fc receptor dependent effector mechanisms, which may include antibody-dependent cellular cytotoxicity (ADCC) or phagocytosis (ADCP).

Example S: Sequences

Table S provides sequences referred to herein.

TABLE S

Sequences.

| SEQ ID NO: | Region | Scheme/ Clone | Sequence |
|---|---|---|---|
| 1 | CDR-H1 | Chothia | GGSISSSDY |
| 2 | CDR-H1 | Chothia | GGSISSSST |
| 3 | CDR-H1 | Chothia | GGSISSSDT |
| 4 | CDR-H1 | Chothia | GGSISSADN |
| 5 | CDR-H1 | Chothia | GGSVSSSST |
| 6 | CDR-H1 | Chothia | GYSTSSGY |
| 7 | CDR-H1 | Chothia | GYSILSGY |
| 8 | CDR-H1 | Chothia | GYSISSGH |
| 9 | CDR-H1 | Chothia | GYSISSGF |
| 10 | CDR-H1 | Chothia | GFTFDNY |
| 11 | CDR-H1 | Chothia | GFTFSDY |
| 12 | CDR-H1 | Chothia | GFTFSSS |
| 13 | CDR-H1 | Chothia | GGSISSSN |
| 14 | CDR-H1 | Chothia | GGSISSSSY |
| 15 | | | |
| 16 | | | |
| 17 | | | |
| 18 | CDR-H1 | Kabat | SSDYYWG |
| 19 | CDR-H1 | Kabat | SSSTYWA |
| 20 | CDR-H1 | Kabat | SSSTYWG |
| 21 | CDR-H1 | Kabat | SSDTYWG |
| 22 | CDR-H1 | Kabat | SADNYWG |
| 23 | CDR-H1 | Kabat | SSSTYWS |
| 24 | CDR-H1 | Kabat | SGYYWG |

TABLE S-continued

Sequences.

| SEQ ID NO: | Region | Scheme/Clone | Sequence |
|---|---|---|---|
| 25 | CDR-H1 | Kabat | SGYYWF |
| 26 | CDR-H1 | Kabat | SGHYWI |
| 27 | CDR-H1 | Kabat | SGFYWT |
| 28 | CDR-H1 | Kabat | SGYYWL |
| 29 | CDR-H1 | Kabat | SGHYWT |
| 30 | CDR-H1 | Kabat | NYAMH |
| 31 | CDR-H1 | Kabat | DYYMS |
| 32 | CDR-H1 | Kabat | SSAMA |
| 33 | CDR-H1 | Kabat | SSNWWS |
| 34 | CDR-H1 | Kabat | SSSYYWG |
| 35 | | | |
| 36 | | | |
| 37 | | | |
| 38 | CDR-H2 | Chothia | YYSGS |
| 39 | CDR-H2 | Chothia | SSSGS |
| 40 | CDR-H2 | Chothia | HHSGA |
| 41 | CDR-H2 | Chothia | HYSGS |
| 42 | CDR-H2 | Chothia | AYSGS |
| 43 | CDR-H2 | Chothia | SYNAL |
| 44 | CDR-H2 | Chothia | YHSGS |
| 45 | CDR-H2 | Chothia | YHSAS |
| 46 | CDR-H2 | Chothia | SARAGI |
| 47 | CDR-H2 | Chothia | ASSGSV |
| 48 | CDR-H2 | Chothia | SGSGIT |
| 49 | CDR-H2 | Chothia | SYSGS |
| 50 | CDR-H2 | Chothia | SSSGST |
| 51 | | | |
| 52 | | | |
| 53 | | | |
| 54 | CDR-H2 | Kabat | SIYYSGSTYYNPSLKS |
| 55 | CDR-H2 | Kabat | SISSSGSTYYNPSLKS |
| 56 | CDR-H2 | Kabat | SIHHSGATYYNPSLKS |
| 57 | CDR-H2 | Kabat | SIHYSGSTLYNPSLKS |
| 58 | CDR-H2 | Kabat | SIHYSGSTYYNPSLKS |
| 59 | CDR-H2 | Kabat | GIAYSGSTYYNPSLKS |
| 60 | CDR-H2 | Kabat | SISYNALTYYNPSLKS |
| 61 | CDR-H2 | Kabat | SIYHSGSTYYNPSLKS |
| 62 | CDR-H2 | Kabat | GIYHSASTAYMPSLKS |
| 63 | CDR-H2 | Kabat | GIYHSGSTYYNPSLKS |
| 64 | CDR-H2 | Kabat | AIYHSGSTVYNPSLKS |
| 65 | CDR-H2 | Kabat | GIYHSGSTAYNPSLKS |
| 66 | CDR-H2 | Kabat | AISARAGITYYADSVKG |
| 67 | CDR-H2 | Kabat | YIASSGSVIYYADSVKG |
| 68 | CDR-H2 | Kabat | TISGSGITTWYADSVKG |
| 69 | CDR-H2 | Kabat | EIYHSGSTNYNPSLKS |
| 70 | CDR-H2 | Kabat | SISYSGSTYYNPSLKS |
| 71 | CDR-H2 | Kabat | YISSSGSTIYYADSVKG |
| 72 | | | |
| 73 | | | |
| 74 | | | |
| 75 | | | |
| 76 | CDR-H3 | | GVRRAVPFDY |
| 77 | CDR-H3 | | GIARAVPFDY |

TABLE S-continued

Sequences.

| SEQ ID NO: | Region | Scheme/Clone | Sequence |
|---|---|---|---|
| 78 | CDR-H3 | | GPKRAVPFDY |
| 79 | CDR-H3 | | GVRRAVPFVD |
| 80 | CDR-H3 | | GVRRAVPFQR |
| 81 | CDR-H3 | | GTRRAVPFDY |
| 82 | CDR-H3 | | GVRRAVPFAD |
| 83 | CDR-H3 | | GIRRAMPFDY |
| 84 | CDR-H3 | | GQFRAVPFDY |
| 85 | CDR-H3 | | GGTHTYSRGPMDV |
| 86 | CDR-H3 | | GGTHTYSRGPFDV |
| 87 | CDR-H3 | | GGTPIYSRGPLDV |
| 88 | CDR-H3 | | GGGQTYSRGPLDV |
| 89 | CDR-H3 | | GGGATYSRGPLDV |
| 90 | CDR-H3 | | GGTHTYSRGPLDV |
| 91 | CDR-H3 | | GGTVKYSRGPLDV |
| 92 | CDR-H3 | | GGQVTYSRGPLDV |
| 93 | CDR-H3 | | GGEVTYSRGPLDV |
| 94 | CDR-H3 | | RIGYSYGTAPPFDV |
| 95 | CDR-H3 | | HGTPRAFDI |
| 96 | CDR-H3 | | GSRHLNAFNR |
| 97 | CDR-H3 | | GVYHDPYGMDV |
| 98 | CDR-H3 | | TELGKMHFDY |
| 99 | CDR-H3 | | GSPRYMQD |
| 100 | CDR-H3 | | HSSLGTHNWFDP |
| 101 | CDR-H3 | | EGALSYSWLAAFDI |
| 102 | | | |
| 103 | | | |
| 104 | | | |
| 105 | CDR-L1 | | RASQSVSSSYLA |
| 106 | CDR-L1 | | GASQSVSSDYLA |
| 107 | CDR-L1 | | QASQAVSSNYLA |
| 108 | CDR-L1 | | GASQSVSSAFLA |
| 109 | CDR-L1 | | RASQSVSSTYLA |
| 110 | CDR-L1 | | QASQSVSSSYLA |
| 111 | CDR-L1 | | KASQAVSSSYLA |
| 112 | CDR-L1 | | EASQSVSSSYLA |
| 113 | CDR-L1 | | EASQSVSASYLA |
| 114 | CDR-L1 | | EASQSVSSAYLA |
| 115 | CDR-L1 | | RVSQSVSDAYLA |
| 116 | CDR-L1 | | EVSQSVSASYLA |
| 117 | CDR-L1 | | RASQSVSSAYLA |
| 118 | CDR-L1 | | RASNAVSSSYLA |
| 119 | CDR-L1 | | RASQSINSWLA |
| 120 | CDR-L1 | | AASQGISSDLA |
| 121 | CDR-L1 | | RASQDISTYLN |
| 122 | CDR-L1 | | RSSQSLLHSNGYNYLD |
| 123 | CDR-L1 | | RASQSISSYLN |
| 124 | CDR-L1 | | RASQSVSSNLA |
| 125 | | | |
| 126 | | | |
| 127 | | | |
| 128 | CDR-L2 | | GASSRT |

TABLE S-continued

Sequences.

| SEQ ID NO: | Region | Scheme/Clone | Sequence |
|---|---|---|---|
| 129 | CDR-L2 | | GAYSLAT |
| 130 | CDR-L2 | | GASARAT |
| 131 | CDR-L2 | | GASSREA |
| 132 | CDR-L2 | | GASNRAA |
| 133 | CDR-L2 | | GASSRQD |
| 134 | CDR-L2 | | GASNRAT |
| 135 | CDR-L2 | | DASSRAS |
| 136 | CDR-L2 | | DASTRAT |
| 137 | CDR-L2 | | GASDRAN |
| 138 | CDR-L2 | | GASYRAT |
| 139 | CDR-L2 | | DASSLES |
| 140 | CDR-L2 | | SASSTQS |
| 141 | CDR-L2 | | DAFNLET |
| 142 | CDR-L2 | | LGSNRAS |
| 143 | CDR-L2 | | GASRRAT |
| 144 | CDR-L2 | | AASSLQS |
| 145 | CDR-L2 | | GASTRAT |
| 146 | | | |
| 147 | | | |
| 148 | | | |
| 149 | CDR-L3 | | QQAVHSPYT |
| 150 | CDR-L3 | | QWAVHSPYT |
| 151 | CDR-L3 | | QQVVHSPYT |
| 152 | CDR-L3 | | QQTVHSPYT |
| 153 | CDR-L3 | | QQAIHSPYT |
| 154 | CDR-L3 | | QQHSSYPPT |
| 155 | CDR-L3 | | QQHSLYPPT |
| 156 | CDR-L3 | | QQFSSYPPT |
| 157 | CDR-L3 | | QQVSSYPPT |
| 158 | CDR-L3 | | QQHSIYPPT |
| 159 | CDR-L3 | | QQYDSHIT |
| 160 | CDR-L3 | | QQAYLYPIT |
| 161 | CDR-L3 | | QQLPFLPIT |
| 162 | CDR-L3 | | MQALGGPWT |
| 163 | CDR-L3 | | QQYVSDPIT |
| 164 | CDR-L3 | | QQVGSSPIT |
| 165 | CDR-L3 | | QQSHLVPRT |
| 166 | CDR-L3 | | QQANHHPPFT |
| 167 | | | |
| 168 | | | |
| 169 | | | |
| 170 | VH | | QLQLQESGPGLVKPSETLSLTCTVSGGSISSSD YYWGWIRQPPGKGLEWIGSIYYSGSTYYNPSLK SRVTISVDTSKNQFSLKLSSVTAADTAVYYCAR GVRRAVPFDYWGQGTLVTVSS |
| 171 | VH | | QLQLQESGPGLVKPSETLSLTCTVSGGSISSSS TYWAWIRQPPGKGLEWIGSISSSGSTYYNPSLK SRVTISVDTSKNQFSLKLSSVTAADTAVYYCAR GIARAVPFDYWGQGTLVTVSS |
| 172 | VH | | QLQLQESGPGLVKPSETLSLTCTVSGGSISSSS TYWGWIRQSPGKGLEWIGSIHHSGATYYNPSLK SRVTISVDTSKNQFSLKTSSVTAADTAVYYCAR GPKRAVPFDYWGQGTLVTVSS |
| 173 | VH | | QLQLQESGPGLVKPSETLSLTCTVSGGSISSSD TYWGWIRQPPGKGLEWIGSIHYSGSTLYNPSLK SRVTISVDTSKNQFSLKLSSVTAADTAVYYCAR GVRRAVPFVDWGQGTLVTVSS |
| 174 | VH | | QLQLQESGPGLVKPSETLSLTCTVSGGSISSAD NYWGWIRQPPGKGLEWIGSIHYSGSTYYNPSLK SRVTISVDTSKNQFSLKLSSVTAADTAVYYCAR GVRRAVPFQRWGQGTLVTVSS |
| 175 | VH | | QLQLQESGPGLVKPSETLSLTCTVSGGSISSSD TYWGWIRQPPGKGPEWIGSIHYSGSTLYNPSLK SRVTISVDTSKNQFSLKLSSVTAADTAVYYCAR GVRRAVPFDYWGQGTLVTVSS |

TABLE S-continued

Sequences.

| SEQ ID NO: | Region | Scheme/Clone | Sequence |
|---|---|---|---|
| 176 | VH | | QLQLQESGPGLVKPSETLSLTCTVSGGSISSSSTYWSWIRQPPGKGLEWIGGIAYSGSTYYNPSLKSRVTISVDTSKNQFSLKLSSVTAADTAVYYCARGVRRAVPFDYWGQGTLVTVSS |
| 177 | VH | | QLQLQESGPGLVKPSETLSLTCTVSGGSISSSSTYWSWIRQPPGKGLEWIGSISYNALTYYNPSLKSRVTISVDTSKNQFSLKLSSVTAADTAVYYCARGTRRAVPFDTWGQGTLVTVSS |
| 178 | VH | | QLQLQESGPGLVKPSETLSLTCTVSGGSISSSSTYWSWIRQPPGKGLEWIGGIAYSGSTYYNPSLKSRVTISVDTSKNQFSLKLSSVTAADTAVYYCARGVRRAVPFADWGQGTLVTVSS |
| 179 | VH | | QLQLQESGPGLVKPSETLSLTCTVSGGSVSSSSTYWSWIRQPPGKGLEWIGGIAYSGSTYYNPSLKSRVTISVDTSKNQFSLKLSSVTAADTAVYYCARGVRRAVPFDYWGQGTLVTVSS |
| 180 | VH | | QLQLQESGPGLVKPSETLSLTCTVSGGSISSSSTYWSWIRQPPGKGLEWIGGIAYSGSTYYNPSLKSRVTISVDTSKNQFSLKLSSVTAADTAVYYCARGTRRAVPFDYWGQGTLVTVSS |
| 181 | VH | | QLQLQESGPGLVKPSETLSLTCTVSGGSISSSDTYWGWIRQPPGKGLEWIGSIHYGSTLYNPSLKSRVTISVDTSKNQFSLKLSSVTAADTAVYYCARGIRRAVPFDYWGQGTLVTVSS |
| 182 | VH | | QLQLQESGPGLVKPSETLSLTCTVSGGSISSSDTYWGWIRQPPGKGLEWIGSIHYSGSTLYNPSLKSRVTISVDTSKNQFSLKLSSVTAADTAVYYCARGQFRAVPFDYWGQGTLVTVSS |
| 183 | VH | | QVQLQESGPGLVKPSETLSLTCAVSGYSISSGYYWGWIRQPPGKGLEWIGSIYHSGSTYYNPSLKSRVTISVDTSKNQFSLKLSSVTAADTAVYYCARGGTHTYSRGPMDVWGQGTTVTVSS |
| 184 | VH | | QLQLQESGPRLVKPSETLSLTCAVSGYSISSGYYWGWIRQPPGKGLEWIGSIYHSGSTYYNPSLKSRVTISVDTSKNQFSLKLSSVTAADTAVYYCARGGTHTYSRGPFDVWGQGTTVTVSS |
| 185 | VH | | LVQLQESGPGLVKPSETLSLTCAVSGYSILSGYYWFWIRQPPGKGLEWIGGIYHSASTAYNPSLKSRVTISVDTSKNQFSLKLSSVTAADTAVYYCARGGTPIYSRGPLDVWGQGTTVTVSS |
| 186 | VH | | QVQLQESGPGLVKPSETLSLTCAVSGYSISSGHYWIWIRQPPGKGLEWIGGIYHSGSTYYNPSLKSRVTISVDTSKDQFSLKLSSVTAADTAVYYCARGGGQTYSRGPLDVWGQGTTVTVSS |
| 187 | VH | | QVQLQESGPGLVKPPETLSLTCAVSGYSISSGHYWIWIRQPPGKGLEWIGGIYHSGSTYYNPSLKSRVTISVDTSKNQFSLKLSSVTAADTAVYYCARGGGATYSRGPLDVWGQGTTVTVSS |
| 188 | VH | | QVQLQESGPGLVKPSETLSLTCAVSGYSILSGYYWFWIRQPPGKGLEWIGGIYHSGSTYYNPSLKSRVTISVDTSKNQFSLKLSSVTAADTAVYYCARGGTHTYSRGPLDVWGQGTTVTVSS |
| 189 | VH | | QVQLQESGPGLVKPSETLSLTCAVSGYSISSGFYWTWIRQPPGKGLEWIGAIYHSGSTVYNPSLKSRVTISVDTSKNQFSLKLSSVTAADTAVYYCARGGTHTYSRGPLDVWGQGTTVTVSS |
| 190 | VH | | QVQLQESGPGLVKPSETLSLTCAVSGYSISSGYYWLWIRQPPGKGLEWIGGIYHSASTAYNPSLKSRVTISVDTSKNQFSLKLSSVTAADTAVYYCARGGTVKYSRGPLDVWGQGTTVTVSS |
| 191 | VH | | QVQLQESGPGLVKPSETLSLTCAVSGYSISSGHYWTWIRQPPGKGLEWIGAIYHSGSTVYNPSLKSRVTISVDTSKNQFSLKLSSVTAADTAVYYCARGGQVTYSRGPLDVWGQGTTVTVSS |
| 192 | VH | | QVQLQESGPGLVKPSETLSLTCAVSGYSILSGYYWFWIRQPPGKGLEWIGGIYHSGSTAYNPSLKSRVTISVDTSKNQFSLKLSSVTAADTAVYYCARGGEVTYSRGPLDVWGQGTTVTVSS |
| 193 | VH | | EVQLLESGGGLVQPGGSLRLSCAASGFTFDNYAMHWVRQAPGKGLEWVSAISARAGITYYADSVKGRFTISRDNSKNTLYLQMNSLRAEDTAVYYCARRIGYSYGTAPPFDVWGQGTTVTVSS |
| 194 | VH | | QVQLVESGGGLVQPGGSLRLSCAASGFTFSDYYMSWIRQAPGKGLEWVSYIASSGSVIYYADSVKGRFTISRDNAKNSLYLQMNSLRAEDTAVYYCARHGTPRAFDIWGQGTTVTVSS |
| 195 | VH | | EVQLLESGGGLVQPGGSLRLSCAASGFTFSSSAMAWVRQAPGKGLEWVSTISGSGITTWYADSVKGRFTISRDNSKNTLYLQMNSLRAEDTAVYYCAKGSRHLNAFNRWGQGTTVTVSS |
| 196 | VH | | QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCARGVYHYDPYGMDVWGQGTTVTVSS |
| 197 | VH | | QLQLQESGPGLVKPSETLSLTCTVSGGSISSSSYYWGWIRQPPGKGLEWIGSISYSGSTYYNPSLKSRVTISVDTSRNQFSLKLSSVTAADTAVYYCARTELGKMHFDYWGQGTLVTVSS |
| 198 | VH | | QLQLQESGPGLVKPSETLSLTCTVSGGSISSSDYYWGWIRQPPGKGLEWIGSIYYSGSTYYNPSLKSRVTISVDTSKNQFSLKLSSVTAADTAVYYCARGSPRYMQDWGQGTLVTVSS |
| 199 | VH | | QVQLVESGSGLVKPGGSLRLSCAASGFTFSDYYMSWIRQAPGKGLEWVSYISSSGSTIYYADSVKGRFTISRDNAKNSLYLQMNSLRAEDTAVYYCARHSSLGTHNWFDPWGQGTLVTVSS |
| 200 | VH | | QVQLQESGPGLVKPSETLSLTCAVSGYSISSGYYWGWIRQPPGKGLEWIGSIYHSGSTYYNPSLKSRVTISVDTSKNQFSLKLSSVTAADTAVYYCAREGALSYSWLAAFDIWGQGTMVTVSS |
| 201 | | | |
| 202 | | | |
| 203 | | | |
| 204 | VL | | EIVLTQSPGTLSLSPGERATLSCRASQSVSSSYLAWYQQKPGQAPRLLIYGASSRATGIPDRFSGSGSGTDFTLTISRLEPEDFAVYYCQQAVHSPYTFGGGTKVEIK |
| 205 | VL | | EIVLTQSPGTLSLSPGERATLSCGASQSVSSDYLAWYQQKPGQAPRLLIYGAYSLATGIPDRFSGSGSGTDFTLTISRLRPEDFAVYYCQWAVHSPYTFGGGTKVEIK |
| 206 | VL | | EIVLTQSPGTLSLSPGERATLSCQASQAVSSNYLAWYQQKPGQAPRLLIYGASSRATGIPDRFSGSGSGTDFTLTISRLEPEDFAVYYCQQVVHSPYTFGGGTKVEIK |

TABLE S-continued

Sequences

| SEQ ID NO: | Region | Scheme/Clone | Sequence |
|---|---|---|---|
| 207 | VL | | EIVLTQSPGTLSLSPGERATLSCGASQSVSSAF LAWYQQKPGQAPRLLIYGASARATGIPDRFSGS GSGTDFTLTISRLEPEDFAVYYCQQVHSPYTF GGGTKVEIK |
| 208 | VL | | EIVLTQSPGTLSLSPGERATLSCRASQSVSSTY LAWYQQKPGQAPRLLIYGASSREAGIPDRFSGS GSGTDFTLTISRLEPEDFAVYYCQQTVHSPYTF GGGTKVEIK |
| 209 | VL | | EIVLTQSPGTLSLSPGERATLSCQASQAVSSNY LAWYQQKPGQAPRLLIYGASNRAAGIPDRFSGS GSGTDFTLTISRLEPEDFAVYYCQQAIHSPYTF GGGTKVEIK |
| 210 | VL | | EIVLTQSPGTLSLSPGERATLSCQASQSVSSSY LAWYQQKPGQAPRLLIYGASNRAAGIPDRFSGS GSGTDFTLTISRLEPEDFAVYYCQQVHSPYTF GGGTKVEIK |
| 211 | VL | | EIVLTQSPGTLSLSPGERATLSCKASQAVSSSY LAWYQQKPGQAPRLLIYGASSRQDGIPDRFSGS GSGTDFTLTISRLEPEDFAVYYCQQVHSPYTF GGGTKVEIK |
| 212 | VL | | EIVLTQSPGTLSLSPGERATLSCRASQSVSSSY LAWYQQKPGQAPRLLIYGASSRATGIPDRFSGS GSGTDFTLTISRLEPEDFAVYYCQQHSSYPPTF GGGTKVEIK |
| 213 | VL | | EIVLTQSPGTLSLSPGERATLSCEASQSVSSSY LAWYQQKPGQAPRLLIYGASNRATGIPDRFSGS GSGTDFTLTISRLEPEDFAVYYCQQHSLYPPTF GGGTKVEIK |
| 214 | VL | | EIVLTQSPGTLSLSPGFRATLSCEASQSVSASY LAWYQQKPGQAPRLLIYDASSRASGIPDRFSGS GSGTDFTLTISRLEPEDFAVYYCQQFSSYPPTF GGGTKVEIK |
| 215 | VL | | EIVLTQSPGTLSLSPGERATLSCEASQSVSSAY LAWYQQKPGQAPRLLIYDASTRATGIPDRFSGS GSGTDFTLTISRLEPEDFAVYYCQQVSSYPPTF GGGTKVEIK |
| 216 | VL | | EIVLTQSPGTLSLSPGERAALSCRVSQSVSDAY LAWYQQKPGQAPRLLIYDASSRASGIPDRFSGS GSGTDFTLTISRLEPEDFAVYYCQQVSSYPPTF GGGTKVEIK |
| 217 | VL | | EIVLTQSPGTLSLSPGERATLSCEVSQSVSASY LAWYQQKPGQAPRLLIYGASSRATGIPDRFSGS GSGTDFTLTISRLEPEDFAVYYCQQHSLYPPTF GGGTKVEIK |
| 218 | VL | | EIVLTQSPGTLSLSPGERATLSCRASQSVSSAY LAWYQQKPGQAPRLLIYGASDRANGIPDRFSGS GSGTDFTLTISRLEPEDFAVYYCQQHSLYPPTF GGGTKVEIK |
| 219 | VL | | EIVLTQSPGTLSLSPGERATLSCRASNAVSSSY LAWYQQKPGQAPRLLIYGASDRANGIPDRFSGS GSGTDFTLTISRLEPEDFAVYYCQQHSIYPPTF GGGTKVEIK |
| 220 | VL | | EIVLTQSPGTLSLSPGERATLSCRASNAVSSSY LAWYQQKPGQAPRLLIYGASYRATGIPDRFSGS GSGTDFTLTISRLEPEDFAVYYCQQHSLYPPTF GGGTKVEIK |
| 221 | VL | | DIQMTQSPSTLSASVGDRVTITCRASQSINSWL AWYQQKPGKAPKLLISDASSLESGVPSRFSGSG SGTEFTLTISSLQPDDFATYYCQQYDSHITFGG GTKVEIK |
| 222 | VL | | DIQMTQSPSSVSASVGDRVTITCAASQGISSDL AWYQQKPGKAPKLLIYSASSTQSGVPSRFSGSG SGTDFTLTISSLQPEDFATYYCQQAYLYPITFG GGTKVEIK |
| 223 | VL | | GVQMTQSPSSLSASVGDRVTITCRASQDISTYL NWYQQKPGKAPKLLIYDAFNLETGVPSRFSGSG SGTDFTFTISSLQPEDIATYYCQQLPFLPITFG GGTKVEIK |
| 224 | VL | | DIVMTQSPLSLPVTPGEPASISCRSSQSLLHSN GYNYLDWYLQKPGQSPQLLIYLGSNRASGVPDR FSGSGSGTDFTLKISRVEAEDVGVYYCMQALGG PWTFGGGTKVEIK |
| 225 | VL | | EIVLTQSPGTLSLSPGERATLSCRASQSVSSSY LAWYQQKPGQAPRLLIYGASRRATGIPDRFSGS GSGTDFTLTISRLEPEDFAVYYCQQYVSDPITF GGGTKVEIK |
| 226 | VL | | EIVLTQSPGTLSLSPGERATLSCRASQSVSSSY LAWYQQKPGQAPRLLIYGASRRATGIPDRFSGS GSGTDFTLTISRLEPEDFAVYYCQQVGSSPITF GGGTKVEIK |
| 227 | VL | | DIQMTQSPSSLSASVGDRVTITCRASQSISSYL NWYQQKPGKAPKLLIYAASSLQSGVPSRFSGSG SGTDFTLTISSLQPEDFATYYCQQSHLVPRTFG GGTKVEIK |
| 228 | VL | | EIVMTQSPATLSVSPGERATLSCRASQSVSSNL AWYQQKPGQAPRLLIYGASTRATGIPARFSGSG SGTEFTLTISSLQSEDFAVYYCQQANHHPPFTF GGGTKVEIK |
| 229 | | | |
| 230 | | | |
| 231 | | | |
| 232 | IGG1 | 33343 AAA HC | QLQLQESGPGLVKPSETLSLTCTVSGGSISSSD YYWGWIRQPPGKGLEWIGSIYYSGSTYYNPSLK SRVTISVDTSKNQFSLKLSSVTAADTAVYYCAR GVRRAWPFDYWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGK |
| 233 | IGG1 | 37268 AAA HC | QLQLQESGPGLVKPSETLSLTCTVSGGSISSSS TYWAWIRQPPGKGLEWIGSISSSGSTYYNPSLK SRVTISVDTSKNQFSLKLSSVTAADTAVYYCAR GIARAVPFDYWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGK |

TABLE S-continued

Sequences.

| SEQ ID NO: | Region | Scheme/Clone | Sequence |
|---|---|---|---|
| 234 | IGG1 AAA HC | 37269 | QLQLQESGPGLVKPSETLSLTCTVSGGSISSSS TYWGWIRQSPGKGLEWIGSIHHSGATYYNPSLK SRVTISVDTSKNQFSLKLSSVTAADTAVYYCAR GPKRAVPFDYWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGK |
| 235 | IGG1 AAA HC | 37271 | QLQLQESGPGLVKPSETLSLTCTVSGGSISSSD TYWGWIRQPPGKGLEWIGSIHYSGSTLYNPSLK SRVTISVDTSKNQFSLKLSSVTAADTAVYYCAR GVRRAVPFVDWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGK |
| 236 | IGG1 AAA HC | 37272 | QLQLQESGPGLVKPSETLSLTCTVSGGSISSAD NYWGWIRQPPGKGLEWIGSIHYSGSTYYNPSLK SRVTISVDTSKNQFSLKLSSVTAADTAVYYCAR GVRRAVPFQRWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGK |
| 237 | IGG1 AAA HC | 37277 | QLQLQESGPGLVKPSETLSLTCTVSGGSISSSD TYWGWIRQPPGKGPEWIGSIHYSGSTLYNPSLK SRVTISVDTSKNQFSLKLSSVTAADTAVYYCAR GVRRAVPFDYWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGK |
| 238 | IGG1 AAA HC | 38373 | QLQLQESGPGLVKPSETLSLTCTVSGGSISSSS TYWSWIRQPPGKGLEWIGGIAYSGSTYYNPSLK SRVTISVDTSKNQFSLKLSSVTAADTAVYYCAR GVRRAVPFDYWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGK |
| 239 | IGG1 AAA HC | 38375 | QLQLQESGPGLVKPSETLSLTCTVSGGSISSSS TYWSWIRQPPGKGLEWIGSISYNALTYYNPSLK SRVTISVDTSKNQFSLKLSSVTAADTAVYYCAR GTRRAVPFDYWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGK |
| 240 | IGG1 AAA HC | 38379 | QLQLQESGPGLVKPSETLSLTCTVSGGSISSSS TYWSWIRQPPGKGLEWIGGIAYSGSTYYNPSLK SRVTISVDTSKNQFSLKLSSVTAADTAVYYCAR GVRRAVPFADWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGK |
| 241 | IGG1 AAA HC | 38381 | QLQLQESGPGLVKPSETLSLTCTVSGGSVSSSS TYWSWIRQPPGKGLEWIGGIAYSGSTYYNPSLK SRVTISVDTSKNQFSLKLSSVTAADTAVYYCAR GVRRAVPFDYWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGK |
| 242 | IGG1 AAA HC | 38383 | QLQLQESGPGLVKPSETLSLTCTVSGGSISSSS TYWSWIRQPPGKGLEWIGGIAYSGSTYYNPSLK SRVTISVDTSKNQFSLKLSSVTAADTAVYYCAR GTRRAVPFDYWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT |
| 243 | IGG1 AAA HC | 38386 | QLQLQESCPGLVKPSETLSLTCTVSGGSISSSD TYWGWIRQPPGKGLEWIGSIHYSGSTLYNPSLK SRVTISVDTSKNQFSLKLSSVTAADTAVYYCAR GIRRAVPFDYWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK |

TABLE S-continued

Sequences.

| SEQ ID NO: | Region | Scheme/Clone | Sequence |
|---|---|---|---|
| | | | NQVSLTCLVKGFYPSDIAVEWESNGQPENNYKTTPPVLDSDGSFFLYSKLTVDKSRWQQGNVFSCSVMHEALHNHYTQKSLSLSPGK |
| 244 | IGG1 AAA HC | 37273 | QLQLQESGPGLVKPSETLSLTCTVSGGSISSSDTYWGWIRQPPGKGLEWIGSIHYSGSTLYNPSLKSRVTISVDTSKNQFSLKLSSVTAADTAVYYCARGQFRAVPFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 245 | IGG1 AAA HC | 33361 | QVQLQESGPGLVKPSETLSLTCAVSGYSISSGYYWGWIRQPPGKGLEWIGSIYHSGSTYYNPSLKSRVTISVDTSKNQFSLKLSSVTAADTAVYYCARGGTHTYSRGPMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 246 | IGG1 AAA HC | 35624 | QLQLQESGPRLVKPSETLSLTCAVSGYSISSGYYWGWIRQPPCKGLEWIGSIYHSGSTYYNPSLKSRVTISVDTSKNQFSLKLSSVTAADTAVYYCARGGTHTYSRGPPDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 247 | IGG1 AAA HC | 38410 | LVQLQESGPGLVKPSETLSLTCAVSGYSILSGYYWFWIRQPPGKGLEWIGGIYHSASTAYNPSLKSRVTISVDTSKNQFSLKLSSVTAADTAVYYCARGGTPIYSRGPLDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 248 | IGG1 AAA HC | 38418 | QVQLQESGPGLVKPSETLSLTCAVSGYSISSGHYWIWIRQPPGKGLEWIGGIYHSGSTYYNPSLKSRVTISVDTSKDQFSLKLSSVTAADTAVYYCARGGQTYSRGPLDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 249 | IGG1 AAA HC | 38420 | QVQLQESGPGLVKPPETLSLTCAVSGYSISSGHYWIWIRQPPGKGLEWIGGIYHSGSTYYNPSLKSRVTISVDTSKNQFSLKLSSVTAADTAVYYCARGGGATYSRGPLDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 250 | IGG1 AAA HC | 38421 | QVQLQESGPGLVKPSETLSLTCAVSGYSILSGYYWFWIRQPPGKGLEWIGGIYHSGSTYYNPSLKSRVTISVDTSKNQFSLKLSSVTAADTAVYYCARGGTHTYSRGPLDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 251 | IGG1 AAA HC | 38422 | QVQLQESGPGLVKPSETLSLTCAVSGYSISSGFYWTWIRQPPGKGLEWIGAIYHSGSTVYNPSLKSRVTISVDTSKNQFSLKLSSVTAADTAVYYCARGGTHTYSRGPLDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDCVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 252 | IGG1 AAA HC | 38424 | QVQLQESGPGLVKPSETLSLTCAVSGYSISSGYYWLWIRQPPGKGLEWIGGIYHSASTAYNPSLKSRVTISVDTSKNQFSLKLSSVTAADTAVYYCARGGTVKYSRGPLDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 253 | IGG1 AAA HC | 38425 | QVQLQESGPGLVKPSETLSLTCAVSGYSISSGHYWTWIRQPPGKGLEWIGAIYHSGSTVYNPSLKSRVTISVDTSKNQFSLKLSSVTAADTAVYYCARGGQTYSRGPLDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPR |

TABLE S-continued

Sequences.

| SEQ ID NO: | Region | Scheme/Clone | Sequence |
|---|---|---|---|
| | | | EEQYNSTYRVVSVLTVLHQDWLNGKEYKCKVSN KALPAPIEKTISKAKGQPREPQVYTLPPSREEM TKNQVSLTCLVKGFYPSDIAVEWESNGQPENNY KTTPPVLDSDGSFFLYSKLTVDKSRWQQGNVFS CSVMHEALHNHYTQKSLSLSPGK |
| 254 | IGG1 AAA HC | 38426 | QVQLQESGPGIVKPSETLSLTCAVSGYSILSGY YWFWIRQPPGKGLEWIGGIYHSGSTAYNPSLKS RVTISVDTSKNQFSLKLSSVTAADTAVYYCARG GEVTYSRGPLDVWGQGTTVTVSSASTKGPSVFP LAPSSKSTSGGTAALGCLVKDYFPEPVTVSWNS GALTSGVHTFPAVLQSSGLYSLSSVVTVPSSSL GTQTYICNVNHKPSNTKVDKKVEPKSCDKTHTC PPCPAPEAAGAPSVFLFPPKPKDTLMISRTPEV TCVVVDVSHEDPEVKFNWYVDGVEVHNAKTKPR EEQYNSTYRVVSVLTVLHQDWLNGKEYKCKVSN KALPAPIEKTISKAKGQPREPQVYTLPPSREEM TKNQVSLTCLVKGFYPSDIAVEWESNGQPENNY KTTPPVLDSDGSFFLYSKLTVDKSRWQQGNVFS CSVMHEALHNHYTQKSLSLSPGK |
| 255 | IGG1 AAA HC | 37323 | EVQLLESGGGLVQPGGSLRLSCAASGFTFDNYA MHWVRQAPGKGLEWVSAISARAGITYYADSVKG RFTISRDNSKNTLYLQMNSLRAEDTAVYYCARR IGYSYGTAPPFDVWGQGTTVTVSSASTKGPSVF PLAPSSKSTSGGTAALGCLVKDYFPEPVTVSWN SGALTSGVHTFPAVLQSSGLYSLSSVVTVPSSS LGTQTYICNVNHKPSNTKVDKKVEPKSCDKTHT CPPCPAPEAAGAPSVFLFPPKPKDTLMISRTPE VTCVVVDVSHEDPEVKFNWYVDGVEVHNAKTKP REEQYNSTYRVVSVLTVLHQDWLNGKEYKCKVS NKALPAPIEKTISKAKGQPREPQVYTLPPSREE MTKNQVSLTCLVKGFYPSDIAVEWESNGQPENN YKTTPPVLDSDGSFFLYSKLTVDKSRWQQGNVF SCSVMHEALHNHYTQKSLSLSPGK |
| 256 | IGG1 AAA HC | 38389 | QVQLVESGGGLVQPGGSLRLSCAASGFTFSDYY MSWIRQAPGKGLEWVSYIASSGSVIYYADSVKG RFTISRDNAKNSLYLQMNSLRAEDTAVYYCARH GTPRAFDIWGQGTTVTVSSASTKGPSVFPLAPS SKSTSGGTAALGCLVKDYFPEPVTVSWNSGALT SGVHTFPAVLQSSGLYSLSSVVTVPSSSLGTQT YICNVNHKPSNTKVDKKVEPKSCDKTHTCPPCP APEAAGAPSVFLFPPKPKDTLMISRTPEVTCVV VDVSHEDPEVKFNWYVDGVEVHNAKTKPREEQY NSTYRVVSVLTVLHQDWLNGKEYKCKVSNKALP APIEKTISKAKGQPREPQVYTLPPSREEMTKNQ VSLTCLVKGFYPSDIAVEWESNGQPENNYKTTP PVLDSDGSFFLYSKLTVDKSRWQQGNVFSCSVM HEALHNHYTQKSLSLSPGK |
| 257 | IGG1 AAA HC | 38358 | EVQLLESGGGLVQPGGSLRLSCAASGFTFSSSA MAWVRQAPGKGLEWVSTISGSGITTWYADSVKG RFTISRDNSKNTLYLQMNSLRAEDTAVYYCAKG SRHLNAFNRWGQGTTVTVSSASTKGPSVFPLAP SSKSTSGGTAALGCLVKDYFPEPVTVSWNSGAL TSGVHTFPAVLQSSGLYSLSSVVTVPSSSLGTQ TYICNVNHKPSNTKVDKKVEPKSCDKTHTCPPC PAPEAAGAPSVFLFPPKPKDTLMISRTPEVTCV VVDVSHEDPENKFNWYVDGVEVHNAKTKPREEQ YNSTYRVVSVLTVLHQDWLNGKEYKCKVSNKAL PAPIEKTISKAKGQPREPQVYTLPPSREEMTKN QVSLTCLVKGFYPSDIAVEWESNGQPENNYKTT PPVLDSDGSFFLYSKLTVDKSRWQQGNVFSCSV MHEALHNHYTQKSLSLSPGK |
| 258 | IGG1 AAA HC | 33303 | QVQLQESHPGLVKPSGTLSLTCAVSGGSISSSN WWSWVRQPPGKGLEWIGEIYHSGSTNYNPSLKS RVTISVDKSKNQFSLKLSSVTAADTAVYYCARG VYHYDPYGMDVWGQGTTVTVSSASTKGPSVFPL APSSKSTSGGTAALGCLVKDYFPEPVTVSWNSG ALTSGVHTFPAVLQSSGLYSLSSVVTVPSSSLG TQTYICNVNHKPSNTKVDKKVEPKSCDKTHTCP PCPAPEAAGAPSVFLFPPKPKDTLMISRTPEVT CVVVDVSHEDPEVKFNWYVDGVEVHNAKTKPRE EQYNSTYRVVSVLTVLHQDWLNGKEYKCKVSNK ALPAPIEKTISKAKGQPREPQVYTLPPSREEMT KNQVSLTCLVKGFYPSDIAVEWESNGQPENNYK TTPPVLDSDGSFFLYSKLTVDKSRWQQGNVFSC SVMMEALHNHYTQKSLSLSPGK |
| 259 | IGG1 AAA HC | 33342 | QLQLQESGPGLVKPSETLSLTCTVSGGSISSSS YYWGWIRQPPGKGLEWIGSISYGSTYYNPSLK SRVTISVDTSKNQFSLKLSSVTAADTAVYYCAR TELGKMHFDYWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPEAAGAPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGK |
| 260 | IGG1 AAA HC | 33299 | QLQLQESGPGLVKPSETLSLTCTVSGGSISSSD YYWGWIRQPPGKGLEWIGSIYYGSTYYNPSLK SRVTISVDTSKNQFSLKLSSVTAADTAVYYCAR GSPRYMQDWGQGTLVTVSSASTKGPSVFPLAPS SKSTSGGTAALGCLVKDYFPEPVTVSWNSGALT SGVHTFPAVLQSSGLYSLSSVVTVPSSSLGTQT YICNVNHKPSNTKVDKKVEPKSCDKTHTCPPCP APEAAGAPSVFLFPPKPKDTLMISRTPEVTCVV VDVSHEDPEVKFNWYVDGVEVHNAKTKPREEQY NSTYRVVSVLTVLHQDWLNGKEYKCKVSNKALP APIEKTISKAKGQPREPQVYTLPPSREEMTKNQ VSLTCLVKGFYPSDIAVEWESNGQPENNYKTTP PVLDSDGSFFLYSKLTVDKSRWQQGNVFSCSVM HEALHNHYTQKSLSLSPGK |
| 261 | IGG1 AAA HC | 33351 | QVQLVESGGGLVKPGGSLRLSCAASGFTFSDYY MSWIRQAPGKGLEWVSYISSSGSTIYYADSVKG RFTISRDNAKNSLYLQMNSLRAEDTAVYYCARH SSLGTHNWFDPWGQGTLVTVSSASTKGPSVFPL APSSKSTSGGTAALGCLVKDYFPEPVTVSWNSG ALTSGVHTFPAVLQSSGLYSLSSVVTVPSSSLG TQTYICNVNHKPSNTKVDKKVEPKSCDKTHTCP PCPAPEAAGAPSVFLFPPKPKDTLMISRTPEVT CVVVDVSHEDPEVKFNWYVDGVEVHNAKTKPRE EQYNSTYRVVSVLTVLHQDWLNGKEYKCKVSNK ALPAPIEKTISKAKGQPREPQVYTLPPSREEMT KNQVSLTCLVKGFYPSDIAVEWESNGQPENNYK TTPPVLDSDGSFFLYSKLTVDKSRWQQGNVFSC SVMHEALHNHYTQKSLSLSPGK |
| 262 | IGG1 AAA HC | 33357 | QVQLQESGPGLVKPSETLSLTCAVSGYSISSGY YWGWIRQPPGKGLEWIGSIYHSGSTYYNPSLKS RVTISVDTSKNQFSLKLSSVTAADTAVYYCARE GALSYSWLAAFDIWGQGTMVTVSSASTKGPSVF PLAPSSKSTSGGTAALGCLVKDYFPEPVTVSWN SGALTSGVHTFPAVLQSSGLYSLSSVVTVPSSS LGTQTYICNVNHKPSNTKVDKKVEPKSCDKTHT CPPCPAPEAAGAPSVFLFPPKPKDTLMISRTPE VTCVVVDVSHEDPEVKFNWYVDGVEVHNAKTKP REEQYNSTYRVVSVLTVLHQDWLNGKEYKCKVS NKALPAPIEKTISKAKGQPREPQVYTLPPSREE MTKNQVSLTCLVKGFYPSDIAVEWESNGQPENN YKTTPPVLDSDGSFFLYSKLTVDKSRWQQGNVF SCSVMHEALHNHYTQKSLSLSPGK |
| 263 | | | |
| 264 | | | |
| 265 | | | |

TABLE S-continued

Sequences.

| SEQ ID NO: | Region | Scheme/Clone | Sequence |
|---|---|---|---|
| 266 | IGG4 HC | 33343 | QLQLQESGPGLVKPSETLSLTCTVSGGSISSSD YYWGWIRQPPGKGLEWIGSIYYSGSTYYNPSLK SRVTISVDTSKNQFSLKLSSVTAADTAVYYCAR GVRRAVPFDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 267 | IGG4 HC | 37268 | QLQLQESGPGLVKPSETLSLTCTVSGGSISSSS TYWAWIRQPPGKGLEWIGSISSSGSTYYNPSLK SRVTISVDTSKNQFSLKLSSVTAADTAVYYCAR GIARAVPFDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 268 | IGG4 HC | 37269 | QLQLQESGPGLVKPSETLSLTCTVSGGSISSSS TYWGWIRQSPGKGLEWIGSIHHSGATYYNPSLK SRVTISVDTSKNQFSLKLSSVTAADTAVYYCAR GPKRAVPFDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 269 | IGG4 HC | 37271 | QLQLQESGPGLVKPSETLSLTCTVSGGSISSSD TYWGWIRQPPGRGLEWIGSIHYSGSTLYNPSLK SRVTISVDTSKNQFSLKLSSVTAADTAVYYCAR GVRRAVPFVDWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWTVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQRGNVFSCSVMH EALHNHYTQKSLSLSPGK |
| 270 | IGG4 HC | 37272 | QLQLQESGPGLVKPSETLSLTCTVSGGSISSAD NYWGWIRQPPGKGLEWIGSIHYSGSTYYNPSLK SRVTISVDTSKNQFSLKLSSVTAADTAVYYCAR GVRRAVPFQRWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 271 | IGG4 HC | 37277 | QLQLQESGPGLVKPSETLSLTCTVSGGSISSSD TYWGWIRQPPGKGPEWIGSIHYSGSTLYNPSLK SRVTISVDTSKNQFSLKLSSVTAADTAVYYCAR GVRRAVPFDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKOQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 272 | IGG4 HC | 38373 | QLQLQESGPGLVKPSETLSLTCTVSGGSISSSS TYWSWIRQPPGKGLEWIGGIAYSGSTYYNPSLK SRVTISVDTSKNQFSLKLSSVTAADTAVYYCAR GVRRAVPFDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 273 | IGG4 HC | 38375 | QLQLQESGPGLVKPSETLSLTCTVSGGSISSSS TYWSWIRQPPGKGLEWIGSISYNALTYYNPSLK SRVTISVDTSKNQFSLKLSSVTAADTAVYYCAR GTRRAVPFDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 274 | IGG4 HC | 38379 | QLQLQESGPGLVKPSETLSLTCTVSGGSISSSS TYWSWIRQPPGKGLEWIGGIAYSGSTYYNPSLK SRVTISVDTSKNQFSLKLSSVTAADTAVYYCAR GVRRAVPFADWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 275 | IGG4 HC | 38381 | QLQLQESGPGLVKPSETLSLTCTVSGGSVSSSS TYWSWIRQPPGKGLEWIGGIAYSGSTYYNPSLK SRVTISVDTSKNQFSLKLSSVTAADTAVYYCAR GVRRAVPFDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVDLFPPKPKDTLMISRTPEVTCVVV DVSQEDPWCQFNWYVDGVWVHNAKTKPREEQFN STYRVVSVLTVLHQDWLNGKEYKCKVSNKGLPS SIEKTISKAKGQPREPQVYTLPPSQEEMTKNQV |

TABLE S-continued

Sequences.

| SEQ ID NO: | Region | Scheme/Clone | Sequence |
|---|---|---|---|
| | | | SLTCLVKGFYPSDIAVEWESNGQPENNYKTTPP VLDSDGSFFLYSRLTVDKSRWQEGNVFSCSVMH EALHNHYTQKSLSLSPGK |
| 276 | IGG4 HC | 38383 | QLQLQESGPGLVKPSETLSLTCTVSGGSISSSS TYWSWIRQPPGRGLEWIGGIAYSGSTYYNPSLK SRVTISVDTSKNQFSLKLSSVTAADTAVYYCAR GTRRAVPFDYWGQGTLVTSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 277 | IGG4 HC | 38386 | QLQLQRSGPGLVKPSETLSLTCTVSGGSISSSD TYWGWIRQPPGKGLEWIGSIHYSGSTLYNPSLK SRVTISVDTSKNQFSLKLSSVTAADTAVYYCAR GIRRAVPFDYWGQGTLVTSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 278 | IGG4 HC | 37273 | QLQLQESGPGLVKPSETLSLTCTVSGGSISSSD TYWGWIRQPPGKGLEWIGSIHYSGSTLYNPSLK SRVTISVDTSKNQFSLKLSSVTAADTAVYYCAR GQFRAVPFDYWGQGTLVTSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 279 | IGG4 HC | 33361 | QVQLQESGPGLVKPSETLSLTCAVSGYSISSGY YWGWIRQPPGKGLEWIGSIYHSGSTYYNPSLKS RVTISVDTSKNQFSLKLSSVTAADTAVYYCARG GTHTYSRGPMDVWGQGTTVTSSASTKGPSVFP LAPCSRSTSESTAALGCLVKDYFPEPVTVSWNS GALTSGVHTFPAVLQSSGLYSLSSVVTVPSSSL GTKTYTCNVDHKPSNTKVDKRVESKYGPPCPPC PAPEFLGGPSVFLFPPKPKDTLMISRTPEVTCV VVDVSQEDPEVQFNWYVDGVEVHNAKTKPREEQ FNSTYRVVSVLTVLHQDWLNGKEYKCKVSNKGL PSSIEKTISKAKGQPREPQVYTLPPSQEEMTKN QVSLTCLVKGFYPSDIAVEWESNGQPENNYKTT PPVLDSDGSFFLYSRLTVDKSRWQEGNVFSCSV MHEALHNHYTQKSLSLSPGK |
| 280 | IGG4 HC | 35624 | QLQLQESGPRLVKPSETLSLTCAVSGYSISSGY YWGWIRQPPGKGLEWIGSIYHSGSTYYNPSLKS RVTISVDTSKNQFSLKLSSVTAADTAVYYCARG GTHTYSRGPFDVWGQGTTVTSSASTKGPSVFP LAPCSRSTSESTAALGCLVKDYFPEPVTVSWNS GALTSGVHTFPAVLQSSGLYSLSSVVTVPSSSL GTKTYTCNVDHKPSNTKVDKRVESKYGPPCPPC PAPEFLGGPSVFLFPPKPKDTLMISRTPEVTCV VVDVSQEDPEVQFNWYVDGVEVHNAKTKPREEQ FNSTYRVVSVLTVLHQDWLNGKEYKCKVSNKGL PSSIEKTISKAKGQPREPQVYTLPPSQEEMTKN QVSLTCLVKGFYPSDIAVEWESNGQPENNYKTT PPVLDSDGSFFLYSRLTVDKSRWQEGNVFSCSV MHEALHNHYTQKSLSLSPGK |
| 281 | IGG4 HC | 38410 | LVQLQESGPGLVKPSETLSLTCAVSGYSILSGY YWFWIRQPPGKGLEWIGGIYHSASTAYNPSLKS RVTISVDTSKNQFSLKLSSVTAADTAVYYCARG GTPIYSRGPLDVWGQGTTVTSSASTKGPSVFP LAPCSRSTSESTAALGCLVKDYFPEPVTVSWNS GALTSGVHTFPAVLQSSGLYSLSSVVTVPSSSL GTKTYTCNVDHKPSNTKVDKRVESKYGPPCPPC PAPEFLGGPSVFLFPPKPKDTLMISRTPEVTCV VVDVSQEDPEVQFNWYVDGVEVHNAKTKPREEQ FNSTYRVVSVLTVLHQDWLNGKEYKCKVSNKGL PSSIEKTISKAKGQPREPQVYTLPPSQEEMTKN QVSLTCLVKGFYPSDIAVEWESNGQPENNYKTT PPVLDSDGSFFLYSRLTVDKSRWQEGNVFSCSV MHEALHNHYTQKSLSLSPGK |
| 282 | IGG4 HC | 38418 | QVQLQESGPGLVKPSETLSLTCAVSGYSISSGH YWIWIRQPPCKGLEWIGGIYHSGSTYYNPSLKS RVTISVDTSKDQFSLKLSSVTAADTAVYYCARG GGQTYSRGPLDVWGQGTTVTSSASTKGPSVFP LAPCSRSTSESTAALGCLVKDYFPEPVTVSWNS GALTSGVHTFPAVLQSSGLYSLSSVVTVPSSSL GTKTYTCNVDHKPSNTKVDKRVESKYGPPCPPC PAPEFLGGPSVFLFPPKPKDTLMISRTPEVTCV VVDVSQEDPEVQFNWTVDGVEVHNAKTKPREEQ FNSTYRVVSVLTVLHQDWLNGKEYKCKVSNKGL PSSIEKTISKAKGQPREPQVYTLPPSQEEMTKN QVSLTCLVKGFYPSDIAVEWESNGQPENNYKTT PPVLDSDGSFFLYSRLTVDKSRWQEGNVFSCSV MHEALHNHYTQKSLSLSPGK |
| 283 | IGG4 HC | 38420 | QVQLQESGPGLVKPPETLSLTCAVSGYSISSGH YWIWIRQPPGKGLEWIGGIYHSGSTYYNPSLKS RVTISVDTSKNQFSLKLSSVTAADTAVYYCARG GGATYSRGPLDVWGQGTTVTSSASTKGPSVFP LAPCSRSTSESTAALGCLVKDYFPFPVTVSWNS GALTSGVHTFPAVLQSSGLYSLSSVVTVPSSSL GTKTYTCNVDHKPSNTKVDKRVESKYGPPCPPC PAPEFLGGPSVFLFPPKPKDTLMISRTPEVTCV VVDVSQEDPEVQFNWYVDGVEVHNAKTKPREEQ FNSTYRVVSVLTVLHQDWLNGKEYKCKVSNKGL PSSIEKTISKAKGQPREPQVYTLPPSQEEMTKN QVSLTCLVKGFYPSDIAVEWESNGQPENNYKTT PPVLDSDGSFFLYSRLTVDKSRWQEGNVFSCSV MHEALHNHYTQKSLSLSPGK |
| 284 | IGG4 HC | 38421 | QVQLQESGPGLVKPSETLSLTCAVSGYSILSGY YWFWIRQPPGKGLEWIGGIYHSGSTYYNPSLKS RVTISVDTSKNQFSLKLSSVTAADTAVYYCARG GTHTYSRGPLDVWGQGTTVTSSASTKGPSVFP LAPCSRSTSESTAALGCLVKDYFPEPVTVSWNS GALTSGVHTFPAVLQSSGLYSLSSVVTVPSSSL GTKTYTCNVDHKPSNTKVDKRVESKYGPPCPPC PAPEFLGGPSVFLFPPKPKDTLMISRTPEVTCV VVDVSQEDPEVQFNWYVDGVEVHNAKTKPREEQ FNSTYRVVSVLTVLHQDWLNGKEYKCKVSNKGL PSSIEKTISKAKGQPREPQVYTLPPSQEEMTKN QVSLTCLVKGFYPSDIAVEWESNGQPENNYKTT PPVLDSDGSFFLYSRLTVDKSRWQEGNVFSCSV MHEALHNHYTQKSLSLSPGK |
| 285 | IGG4 HC | 38422 | QVQLQESGPGLVKPSETLSLTCAVSGYSISSGF YWTWIRQPPGKGLEWIGAIYHSGSTYYNPSLKS RVTISVDTSKNQFSLKLSSVTAADTAVYYCARG GTHTYSRGPLDVWGQGTTVTSSASTKGPSVFP LAPCSRSTSESTAALGCLVKDYFPEPVTVSWNS GALTSGVHTFPAVLQSSGLYSLSSVVTVPSSSL GTKTYTCNVDHKPSNTKVDKRVESKYGPPCPPC PAPEFLGGPSVFLFPPKPKDTLMISRTPEVTCV VVDVSQEDPEVQFNWYVDGVEVHNAKTKPREEQ |

TABLE S-continued

Sequences

| SEQ ID NO: | Region | Scheme/Clone | Sequence |
|---|---|---|---|
| | | | FNSTYRVVSVLTVLHQDWLNGKEYKCKVSNKGL PSSIEKTISKAKGQPREPQVYTLPPSQEEMTKN QVSLTCLVKGFYPSDIAVEWESNGQPENNYKTT PPVLDSDGSFFLYSRLTVDKSRWQEGNVFSCSV MHEALHNHYTQKSLSLSPGK |
| 286 | IGG4 HC | 38424 | QVQLQESGPGLVKPSETLSLTCAVSGYSISSGY YWLWIRQPPGKGLEWIGGIYHSASTAYNPSLKS RVTISVDTSKNQFSLKLSSVTAADTAVYYCARG GTVKYSRGPLDVWGQGTTVTVSSASTKGPSVFP LAPCSRSTSESTAALGCLVKDYFPEPVTVSWNS GALTSGVHTFPAVLQSSGLYSLSSVVTVPSSSL GTKTYTCNVDHKPSNTKVDKRVESKYGPPCPPC PAPEFLGGPSVFLFPPKPKDTLMISRTPEVTCV VVDVSQEDPEVQFNWYVDGVEVHNAKTKPREEQ FNSTYRVVSVLTVLHQDWLNGKEYKCKVSNKGL PSSIEKTISKAKGQPREPQVYTLPPSQEEMTKN QVSLTCLVKGFYPSDIAVEWESNSQPENNYKTT PPVLDSDGSFFLYSRLTVDKSRWQEGNVFSCSV MHEALHNHYTQKSLSLSPGK |
| 287 | IGG4 HC | 38425 | QVQLQESGPGLVKPSETLSLTCAVSGYSISSGH YWTWIRQPPGKGLEWIGAIYHSGSTVYNPSLKS RVTISVDTSKNQFSLKLSSVTAADTAVYYCARG GQVTYSRGPLDVWGQGTTVTVSSASTKGPSVFP LAPCSRSTSESTAALGCLVKDYFPEPVTVSWNS GALTSGIHTFPAVLQSSGLYSLSSVVTVPSSSL GTKTYTCNVDHKPSNTKVDKRVESKYGPPCPPC PAPEFLGGPSVFLFPPKPKDTLMISRTPEVTCV VVDVSQEDPEVQFNWYVDGVEVHNAKTKPREEQ FNSTYRVVSVLTVLHQDWLNGKEYKCKVSNKGL PSSIEKTISKAKGQPREPQVYTLPPSQEEMTKN QVSLTCLVKGFYPSDIAVEWESNGQPENNYKTT PPVLDSDGSFFLYSRLTVDKSRWQEGNVFSCSV MHEALHNHYTQKSLSLSPGK |
| 288 | IGG4 HC | 38426 | QVQLQESGPGLVKPSETLSLTCAVSGYSILSGY YWFWIRQPPGKGLEWIGGIYHSGSTAYNPSLKS RVTISVDTSKNQFSLKLSSVTAADTAVYYCARG GEVTSRGPLDVWGQGTTVTVSSASTKGPSVFP LAPCSRSTSFSTAALGCLVKDYFPEPVTVSWNS GALTSGVHTFPAVLQSSGLYSLSSVVTVPSSSL GTKTYTCNVDHKPSNTKVDKRVESKYGPPCPPC PAPEFLGGPSVFLFPPKPKDTLMISRTPEVTCV VVDVSQEDPEVQFNWYVDGVEVHNAKTKPREEQ FNSTYRVVSVLTVLHQDWLNGKEYKCKVSNKGL PSSIEKTISKAKGQPREPQVYTLPPSQEEMTKN QVSLTCLVKGFYPSDIAVEWESNGQPENNYKTT PPVLDSDGSFFLYSRLTVDKSRWQEGNVFSCSV MHEALHNHYTQKSLSLSPGK |
| 289 | IGG4 HC | 37323 | EVQLLESGGGLVQPGGSLRLSCAASGFTFDNYA MHWVRQAPGKCLEWVSAISARAGITYYADSVKG RFTISRDNSKNTLYLQMNSLRAEDTAVYYCARR IGYSYGTAPPFDVWGQGTTVTVSSASTKGPSVF PLAPCSRSTSESTAALGCLVKDYFPEPVTVSWN SGALTSGVHTFPAVLQSSGLYSLSSVVTVPSSS LGTKTYTCNVDHKPSNTKVDKRVESKYGPPCPP CPAPEFLGGPSVFLPPPKPKDTLMISRTPEVTC VVVDVSQEDPEVQFNWYVDGVEVHNAKTKPREE QFNSTYRVVSVLTVLHQDWLNGKEYKCKVSNKG LPSSIEKTISKAKGQPREPQVYTLPPSQEEMTK NQVSLTCLVKGFYPSDIAVEWESNGQPENNYKT TPPVLDSDGSFFLYSRLTVDKSRWQEGNVFSCS VMHEALHNHYTQKSLSLSPGK |
| 290 | IGG4 HC | 38389 | QVQLVESGGGLVQPGGSLRLSCAASGFTFSDYY MSWIRQAPGKGLEWVSYIASSGSVIYYADSVKG RFTISRDNAKNSLYLQMNSLRAEDTAVYYCARH GTPRAFDIWGQGTTVTVSSASTKGPSVFPLAPC SRSTSESTAALGCLVKDYFPEPVTVSWNSGALT SGVHTFPAVLQSSGLYSLSSVVTVPSSSLGTKT YTCNVDHKPSNTKVDKRVESKYGPPCPPCPAPE FLGGPSVFLFPPKPKDTLMISRTPEVTCVVVDV SQEDPEVQFNWYVDGVEVHNAKTKPREEQFNST YRVVSVLTVLHQDWLNGKEYKCKVSNKGLPSSI EKTISKAKGQPREPQVYTLPPSQEEMTKNQVSL TCLVKGFYPSDIAVEWESNGQPENNYKTTPPVL DSDGSFFLYSRLTVDKSRWQESNVFSCSVMHEA LHNHYTQKSLSLSPGK |
| 291 | IGG4 HC | 38358 | EVQLLESGGGLVQPGGSLRLSCAASGFTFSSSA MAWVRQAPGKGLEWVSTISGSCITTWYADSVKG RFTISRDNSKNTLYLQMNSLRAEDTAVYYCAKG SRHLNAFNRWGQGTTVTVSSASTKGPSVFPLAP CSRSTSESTAALGCLVKDYFPEPVTVSWNSGAL TSGVHTFPAVLQSSGLYSLSSVVTVPSSSLGTK TYTCNVDHKPSNTKVDKRVESKYGPPCPPCPAP EFLGGPSVFLFPPKPKDTLMISRTPEVTCVVVD VSQEDPEVQFNWYVDGVEVHHAKTKPREEQFNS TYRVVSVLTVLHQDWLNGKEYKCKVSNKGLPSS IEKTISKAKGQPREPQVYTLPPSQEEMTKNQVS LTCLVKGFYPSDIAVEWESNGQPENNYKTTPPV LDSDGSFFLYSRLTVDKSRWQEGNVFSCSVMHE ALHNHYTQKSLSLSPGK |
| 292 | IGG4 HC | 33303 | QVQLQESGPGLVKPSGTLSLTCAVSGGSISSSN WWSWVRQPPGKGLEWIGEIYHSGSTNYNPSLKS RVTISVDKSKNQFSLKLSSVTAADTAVYYCARG VYHYDPYGMDVWGQGTTVTVSSASTKGPSVFPL APCSRSTSESTAALOCLVKDFPEPVTVSWNSGA LTSGVHTFPAVLQSSGLYSLSSVVTVPSSSLG TKTYTCNVDHKPSNTKVDKRVESKYGPPCPPCP APEFLGGPSVFLFPPKPKDTLMISRTPEVTCVV VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTTP PVLDSDGSFFLYSRLTVDKSRWQEGNVFSCSVM HEALHNHYTQKSLSLSPGK |
| 293 | IGG4 HC | 33342 | QLQLQESGPGLVKPSETLSLTCTVSGGSISSSS YYWGWIRQPPGKGLEWIGSISYSGSTYYNPSLK SRVTISVDTSKNQFSLKLSSVTAADTAVYYCAR TELGKMHFDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSPGK |
| 294 | IGG4 HC | 33329 | QLQLQESGPGLVKPSETLSLTCTVSGGSISSSD YYWGWIRQPPGKGLEWIGSIYYSGSTYYNPSLK SRVTISVDTSKNQFSLKLSSVTAADTAVYYCAR GSPRYMQDWGQGTLVTVSSASTKGPSVFPLAPC SRSTSESTAALGCLVKDYFPEPVTVSWNSGALT SGVHTFPAVLQSSGLYSLSSVVTVPSSSLGTKT YTCNVDHKPSNTKVDKRVESKYGPPCPPCPAPE FLGGPSVFLFPPKPKDTLMISRTPEVTCVVVDV SQEDPEVQFNWYVDGVEVHNAKTKPREEQFNST YRVVSVLTVLHQDWLNGKEYKCKVSNKGLPSSI EKTISKAKGQPREPQVYTLPPSQEEMTKNQVSL TCLVKGFYPSDIAVEWESNGQPENNYKTTPPVL DSDGSFFLYSRLTVDKSRWQEGNVFSCSVMHEA LHNHYTQKSLSLSPGK |
| 295 | IGG4 HC | 33351 | QVQLVESGGGLVKPGGSLRLSCAASGFTFSDYY MSWIRQAPGKGLEWVSYISSSGSTIYYADSVKG RFTISRDNAKNSLYLQMNSLRAEDTAVYYCARH SSLGTHNWFDPWGQGTLVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP |

TABLE S-continued

Sequences.

| SEQ ID NO: | Region | Scheme/Clone | Sequence |
|---|---|---|---|
| | | | APEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSPGK |
| 296 | IGG4 HC | 33357 | QVQLQESGPGLVKPSETLSLTCAVSGYSISSGYYWGWIRQPPGKGLEWIGSIYHSGSTYYNPSLKSRVTISVDTSKNQFSLKLSSVTAADTAVYYCAREGALSYSWLAAFDIWGQGTMVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSPGK |
| 297 | | | |
| 298 | | | |
| 299 | | | |
| 300 | LC | 33343 | EIVLTQSPGTLSLSPGERATLSCRASQSVSSSYLAWYQQKPGQAPRLLIYGASSRATGIPDRFSGSGSGTDFTLTISRLEPEDFAVYYCQQAVHSPYTFGGGTKVEIKRTVAAPSVFIFPPSDEQLKSGTASVVCLLKNFYPREAKVQWKVDNALQSGNSQESVTEQDSKDSTYSLSSTLTLSKADYEKHKVYACEVTHQGLSSPVTKSFNRGEC |
| 301 | LC | 37268 | EIVLTQSPGTLSLSPGERATLSCRASQSVSSSYLAWYQQKPGQAPRLLIYGASSRATGIPDRFSGSGSGTDFTLTISRLEPEDFAVYYCQQAVHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKEKVYACEVTHQGLSSPVTKSFNRCEC |
| 302 | LC | 37269 | EIVLTQSPGTLSLSPGERATLSCRASQSVSSSYLAWYQQKPGQAPRLLIYGASSRATGIPDRFSGSGSGTDFTLTISRLEPEDFAVYYCQQAVHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 303 | LC | 37271 | EIVLTQSPGTLSLSPGERATLSCRASQSVSSSYLAWYQQKPGQAPRLLIYGASSRATGIPDRFSGSGSGTDFTLTISRLEPEDFAVYYCQQAVHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 304 | LC | 37272 | EIVLTQSPGTLSLSPGERATLSCRASQSVSSSYLAWYQQKPGQAPRLLIYGASSRATGIPDRFSGSGSGTDFTLTISRLEPEDFAVYYCQQAVHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 305 | LC | 37277 | EIVLTQSPGTLSLSPGFRATLSCGASQSVSSDYLAWYQQKPGQAPRLLIYGAYSLATGIPDRFSGSGSGTDFTLTISRLEPEDFAVYYCWAVHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 306 | LC | 38373 | EIVLTQSPGTLSLSPGERATLSCQASQAVSSNYLAWYQQKPGQAPRLLIYGASSRATGIPDRFSGSGSGTDFTLTISRLEPEDFAVYYCQQVVHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 307 | LC | 38375 | EIVLTQSPGTLSLSPGERATLSCGASQSVSSAFLAWYQQKPGQAPRLLIYGASARATGIPDRFSGSGSGTDFTLTISRLEPEDFAVYYCQQVVHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 308 | LC | 38379 | EIVLTQSPGTLSLSPGERATLSCRASQSVSSTYLAWYQQKPGQAPRLLIYGASSREAGIPDRFSGSGSGTDFTLTISRLEPEDFAVYYCQQTVHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 309 | LC | 38381 | EIVLTQSPGTLSLSPGERATLSCQASQAVSSNYLAWYQQKPGQAPRLLIYGASNRAAGIPDRFSGSGSGTDFTLTISRLEPEDFAVYYCQQAIHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 310 | LC | 38383 | EIVLTQSPGTLSLSPGERATLSCQASQSVSSSYLAWYQQKPGQAPRLLIYGASNRAAGIPDRFSGSGSGTDFTLTISRLEPEDFAVYYCQQVVHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 311 | LC | 38386 | EIVLTQSPGTLSLSPGERATLSCKASQAVSSSYLAWYQQKPGQAPRLLIYGASSRQDGIPDRFSGSGSGTDFTLTISRLEPEDFAVYYGQQVVHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 312 | LC | 37273 | EIVLTQSPGTLSLSPGERATLSCRASQSVSSSYLAWYQQKPGQAPRLLIYGASSRATGIPDRFSGSGSGTDFTLTISRLEPEDFAVYYCQQAVHSPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 313 | LC | 33361 | EIVLTQSPGTLSLSPGERATLSCRASQSVSSSYLAWYQQKPGQAPRLLIYGASSRATGIPDRFSGSGSGTDFTLTISRLEPEDFAVYYCQQHSSYPPTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 314 | LC | 35624 | EIVLTQSPGTLSLSPGERATLSCRASQSVSSSYLAWYQQKPGQAPRLLIYGASSRATGIPDRFSGSGSGTDFTLTISPLEPEDFAVYYCQQHSSYPPTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE S-continued

Sequences.

| SEQ ID NO: | Region | Scheme/Clone | Sequence |
|---|---|---|---|
| 315 | LC | 38410 | EIVLTQSPGTLSLSPGERATLSCEASQSVSSSY LAWYQQKPGQAPRLLIYGASNPATGIPDRFSGS GSGTDFTLTISRLEPEDFAVYYCQQHSLYPPTF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 316 | LC | 38418 | EIVLTQSPGTLSLSPGERATLSCEASQSVSASY LAWYQQKPGQAPRLLIYDASSRASGIPDRFSGS GSGTDFTLTISRLEPEDFAVYYCQQFSSYPPTF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 317 | LC | 38420 | EIVLTQSPGTLSLSPGERATLSCEASQSVSSAY LAWYQQKPGQAPRLLIYDASTRATGIPDRFSGS GSGTDFTLTISRLEPEDFAVYYCQQVSSYPPTF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 318 | LC | 38421 | EIVLTQSPGTLSLSPGERAALSCRVSQSVSDAY LAWYQQKPGQAPRLLIYDASSRASGIPDRFSGS GSGTDFTLTISRLEPEDFAVYYCQQVSSYPPTF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 319 | LC | 38422 | EIVLTQSPGTLSLSPGERATLSCEVSQSVSASY LAWYQQKPGQAPRLLIYGASSRATGIPDRFSGS GSGTDFTLTISRLEPEDFAVYYCQQHSLYPPTF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 320 | LC | 38424 | EIVLTQSPGTLSLSPGERATLSCRASQSVSSAY LAWYQQKPGQAPRLLIYGASDRANGIPDRFSGS GSGTDFTLTISRLEPEDFAVYYCQQHSLYPPTF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 321 | LC | 38425 | EIVLTQSPGTLSLSPGERATLSCRASNAVSSSY LAWYQQKPGQAPRLLIYGASDRANGIPDRFSGS GSGTDFTLTISRLEPEDFAVYYCQQHSIYPPTF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 322 | LC | 38426 | EIVLTQSPGTLSLSPGERATLSCRASNAVSSSY LAWYQQKPGQAPRLLIYGASYRATGIPDRFSGS GSGTDFTLTISRLEPEDFAVYYCQQHSLYPPTF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 323 | LC | 37323 | DIQMTQSPSTLSASVGDRVTITCRASQSINSWL AWYQQKPGKAPKLLISDASSLESGVPSRFSGSG SGTEFTLTISSLQPDDFATYYCQQYDSHITFGG GTKVEIKRTVAAPSVFIFPPSDEQLKSGTASVV CLLNNFYPREAKVQWKVDNALQSGNSQESVTEQ DSKDSTYSLSSTLTLSKADYEKHKVYACEVTHQ GLSSPVTKSFNRGEC |
| 324 | LC | 38389 | DIQMTQSPSSVSASVGDRVTITCAASQGISSDL AWYQQKPGKAPKLLIYSASSTQSGVPSRFSGSG SGTDFTLTISSLQPEDFATYYCQQAYLYPITFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 325 | LC | 38358 | GVQMTQSPSSLSASVGDRVTITCRASQDISTYL NWYQQKPGKAPKLLIYDAFNLETGVPSRFSGSG SGTDFTFTISSLQPEDIATYYCQQLPFLPITFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 326 | LC | 33303 | DIVMTQSPLSLPVTPGEPASISCRSSQSLLHSN GYNYLDWYLQKPGQSPQLLIYLGSNRASGVPDR FSGSGSGTDFTLKISRVEAEDVGVYYCMQALGG PWTFGGSTKVEIKRTVAAPSVFIFPPSDEQLKS GTASVVCLLNNFYPREAKVQWKVDNALQSGNSQ ESVTEQDSKDSTYSLSSTLTLSKADYEKHKVYA CEVTHQGLSSPVTKSFNRGEC |
| 327 | LC | 33342 | EIVLTQSPGTLSLSPGERATLSCRASQSVSSSY LAWYQQKPGQAPRLLIYGASRRATGIPDRFSGS GSGTDFTLTISRLEPEDFAVYYCQQYVSDPITF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 328 | LC | 33299 | EIVLTQSPGTLSLSPGERATLSCRASQSVSSSY LAWYQQKPGQAPRLLIYGASRRATGIPDRFSGS GSGTDFTLTISRLEPEDFAVYYCQQVGSSPITF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 329 | LC | 33351 | DIQMTQSPSSLSASVGDRVTITCRASQSISSYL NWYQQKPGKAPKLLIYAASSLQSGVPSRFSGSG SGTDFTLTISSLQPEDFATYYCQQSHLVPRTFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACFVTH QGLSSPVTKSFNRGEC |
| 330 | LC | 33357 | EIVMTQSPATLSVSPGERATLSCRASQSVSSNL AWYQQKPGQAPRLLIYGASTRATGIPARFSGSG SGTEFTLTISSLQSEDFAVYYCQQNHHPPFTF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 331 | | | |
| 332 | | | |
| 333 | | | |
| 334 | Fc for IGG1 | | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPEAAGAPSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSREEMTKNQVSLTCLVKGFYPSDIAVEW ESNGQPENNYKTTPPVLDSDGSFFLYSKLTVDK SRWQQGNVFSCSVMHEALHNHYTQKSLSLSPGK |

| SEQ ID NO: | Region | Scheme/ Clone | Sequence |
|---|---|---|---|
| 335 | Fc region for IGG4 | | ASTKGPSVFPLAPCSRSTSESTAALGCLVKDYF PEPVTVSWNSGALTSGVHTFPAVLQSSGLYSLS SVVTVPSSSLGTKTYTCNVDHKPSNTKVDKRVE SKYGPPCPPCPAPEFLGGPSVFLFPPKPKDTLM ISRTPEVTCVVVDVSQEDPEVQFNWYVDGVEVH NAKTKPREEQFNSTYRVVSVLTVLHQDWLNGKE YKCKVSNKGLPSSIEKTISKAKGQPREPQVYTL PPSQEEMTKNQVSLTCLVKGFYPSDIAVEWESN GQPENNYKTTPPVLDSDGSFFLYSRLTVDKSRW QEGNVFSCSVMHEALHNHYTQKSLSLSPGK |
| 336 | Kappa region for LC | | RTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVT KSFNRGEC |
| 337 | | hHLA-G1 | MVVMAPRTLFLLLSGALTLTETWAGSHSMRYFS AAVSRPGRGEPRFIAMGYVDDTQFVRFDSDSAC PRMEPRAPWVEQEGPEYWEEETRNTKAHAQTDR MNLQTLRGYYNQSEASSHTLQWMIGCDLGSDGR LLRGYEQYAYDGKDYLALNEDLRSWTAADTAAQ ISKRKCEAANVAEQRRAYLEGTCVEWLHRYLEN GKEMLQRADPPKTHVTHHPVFDYEATLRCWALG FYPAEIILTWQRDGEDQTQDVELVETRPAGDGT FQKWAAVVVPSGEEQRYTCHVQHEGLPEPLMLR WKQSSLPTIPIMGIVAGLVVLAAVVTGAAVAAV LWRKKSSD |
| 338 | | hHLA-G5 | MVVMAPRTLFLLLSGALTLTETWAGSHSMRYFS AAVSRPGRGEPRFIAMGYVDDTQFVRFDSDSAC PRMEPRAPWVEQEGPEYWEEETRNTKAHAQTDR MNLQTLRGYYNQSEASSHTLQWMIGCDLGSDGR LLRGYEQYAYDGKDYLALNEDLRSWTAADTAAQ ISKRKCEAANVAEQRRAYLEGTCVEWLHRYLEN GKEMLQRADPPKTHVTHHPVFDYEATLRCWALG FYPAEIILTWQRDGEDQTQDVELVETRPAGDGT FQKWAAVVVPSGEEQRYTCHVQHEGLPEPLMLR WSKEGDGGIMSVRESRSLSEDL |
| 339 | | Cyno HLA-AG | MAVMAPRTLLLVLSGVLALTQPRAGSHSMRYFY TAVSRPGRGQPRFIAVGYVDDTQFVRFDSDAES PRMEPRAPWVEQEGPEYWDRETQNMKTATQTYQ ANLRTLLRYYNQSEAGSHTFQKMYGCDLGPDGR LLRGYEQFAYDGRDYIILNEDLRSWTAADMAAQ NTQRKWEAAGAAEQHRTYLEGECLEWLRRYLEN GKETLQRADPPKTNVTHHPVSDYEATLRCWALG FYPAEITLTWQRDGEEQTEDTELVETRPTGDGT FQKWAAVVVPSGEEQRYTCHVQHEGLPKPLTLR WEPSSQSTILIVGIIAGLVLLGTVVTGAVVAAV MWRRKS |
| 340 | | Rhesus HLA-AG | MAVMAPRTLLLVLSGVLALTQTRAGSHSMRYFY TSMSRPGRGQPRFIAVGYVDDTQFVRFDSDAES PRMEPRAPWVEQEGPEYWDRETQNMKTATQTYR ENLRTLLRYYNQSEAGSHTIQKMYGCDLHPFGR LLRGYEQFAYDGRDYIALNEDLRSWTAADMAAQ FTQRKWEAAGAAEQHRTYLEGECLEWLRRYLES GKETLQRADPPKTNVTHHPVSDYEATLRCWALG FYPAEITLTWQRDGEEQTEDTETVETRPTGDGT FQKWAAVVVPSGEEQRYTCHVQHEGLPEPLTLR WEPSSQSTILIVGIIAGLVLLGTVVTGAVVAAV MWRRKSSDR |
| 341 | | hHLA-G ECD with signal peptide | MVVMAPRTLFLLLSGALTLTETWAGSHSMRYFS AAVSRPGRGEPRFIAMGYVDDTQFVRFDSDSAC PRMEPRAPWVEQEGPEYWEEETRNTKAHAQTDR MNLQTLRGYYNQSEASSHTLQWMIGCDLGSDGR LLRGYEQYAYDGKDYLALNEDLRSWTAADTAAQ ISKRKCEAANVAEQRRAYLEGTCVEWLHRYLEN GKEMLQRADPPKTHVTHHPVFDYEATLRCWALG FYPAEIILTWQRDGEDQTQDVELVETRPAGDGT FQKWAAVVVPSGEEQRYTCHVQHEGLPEPLMLR W |
| 342 | | hHLA-G ECD without signal peptide | GSHSMRYFSPAVSRPGRGEPRFIAMGYVDDTQF VRFDSDSACPRMEPRAPWVEQEGPEYWEEETRN TKAHAQTDRMNLQTLRGYYNQSEASSHTLQWMI GCDLGSDGRLLRGYEQYAYDGKDYLALNEDLRS WTAADTAAQISKRKCEAANVAEQRRAYLEGTCV EWLHRYLENGKEMLQRADPPKTHVTHHPVFDYE ATLRCWALGFYPAEIILTWQRDGEDQTQDVELV ETRPAGDGTFQKWAAVVVPSGEEQRYTCHVQHE GLPEPLMLRW |

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

What is claimed is:

1. An antibody that specifically binds to human HLA-G (hHLA-G), comprising a heavy chain variable region ($V_H$) and a light chain variable region (VL), wherein
   a) the $V_H$ comprises:
      i) a $V_H$-complementarity determining region (CDR) 1 comprising the amino acid sequence set forth in SEQ ID NO: 7; a VHCDR2 comprising the amino acid sequence set forth in SEQ ID NO: 44; and a VHCDR3 comprising the amino acid sequence set forth in SEQ ID NO: 93, wherein the CDRs are according to Chothia; or
      ii) a VHCDR1 comprising the amino acid sequence set forth in SEQ ID NO: 25; a VHCDR2 comprising the amino acid sequence set forth in SEQ ID NO: 65; and a VHCDR3 comprising the amino acid sequence set forth in SEQ ID NO: 93, wherein the CDRs are according to Kabat; and
   b) the VL comprises:
      i) a VLCDR1 comprising the amino acid sequence set forth in SEQ ID NO: 118; a VLCDR2 comprising the amino acid sequence set forth in SEQ ID NO: 138; and a VLCDR3 comprising the amino acid sequence set forth in SEQ ID NO: 155, wherein the CDRs are according to Chothia and Kabat.

2. The antibody of claim 1, comprising a $V_H$ sequence that is at least 85% identical to the amino acid sequence set forth in SEQ ID NO: 192 and a VL sequence that is at least 85% identical to the amino acid sequence set forth in SEQ ID NO: 220.

3. The antibody of claim 1, comprising a $V_H$ sequence that is at least 95% identical to the amino acid sequence set forth in SEQ ID NO: 192 and a VL sequence that is at least 95% identical to the amino acid sequence of SEQ ID NO: 220.

4. The antibody of claim 1, wherein the antibody comprises a heavy chain of SEQ ID NO: 254 and a light chain of SEQ ID NO: 322.

5. The antibody of claim 1, wherein the antibody comprises a heavy chain of SEQ ID NO: 288 and a light chain of SEQ ID NO: 322.

6. The antibody of claim 1, wherein the antibody is a monoclonal antibody.

7. A pharmaceutical composition comprising the antibody of claim 1 and a pharmaceutically acceptable carrier or excipient.

8. The pharmaceutical composition of claim 7, further comprising an effective amount of at least one of the following:
   a) an anti-ILT2 antibody;
   b) an anti-ILT4 antibody;
   c) an anti-KIR2DL4 antibody;
   d) an anti-HLA-E antibody;
   e) an anti-NKG2A antibody;
   f) an anti-HLA-F antibody
   g) an anti-PD-L1 antibody;
   h) an anti-PD-1 antibody;
   i) an anti-CD38 antibody;
   j) an anti-CD39 antibody;
   k) an anti-CD73 antibody;

l) an anti-A2A receptor antibody;
m) an anti-A2B receptor antibody;
n) an anti-A2A/A2B dual receptor antibody or a combination thereof;
o) an anti-CD47 antibody;
p) an anti-CTLA-4 antibody;
q) an anti-TIM-3 antibody;
r) an anti-TIGIT antibody;
s) an anti-VISTA antibody;
t) an anti-CD94 antibody;
u) a small molecule inhibitor;
v) an oncolytic virus;
w) a chemotherapy; and/or
x) ADCC capable therapies using effector competent antibodies selected from the group consisting of anti-CD19, anti-CD20, anti-EGFR, anti-Her2, anti-SLAMF7, anti-CD52, anti-BCMA, anti-GD2, and anti-CCR4.

9. The pharmaceutical composition of claim 8, further comprising one or both of
   a) an antibody to an immune inhibitory receptor or ligand and/or
   b) an antibody to an immune stimulatory receptor or ligand.

10. A kit comprising the antibody of claim 1.

* * * * *

SEQUENCE LISTING

<160> NUMBER OF SEQ ID NOS: 342

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

```
Gly Gly Ser Ile Ser Ser Ser Asp Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Gly Gly Ser Ile Ser Ser Ser Ser Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Gly Gly Ser Ile Ser Ser Ser Asp Thr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Gly Gly Ser Ile Ser Ser Ala Asp Asn
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Gly Gly Ser Val Ser Ser Ser Ser Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Gly Tyr Ser Ile Ser Ser Gly Tyr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Gly Tyr Ser Ile Leu Ser Gly Tyr
```

```
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Gly Tyr Ser Ile Ser Ser Gly His
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Gly Tyr Ser Ile Ser Ser Gly Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Gly Phe Thr Phe Asp Asn Tyr
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Gly Phe Thr Phe Ser Asp Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Gly Phe Thr Phe Ser Ser Ser
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Gly Gly Ser Ile Ser Ser Ser Asn
1               5
```

```
<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Gly Gly Ser Ile Ser Ser Ser Ser Tyr
1               5

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Ser Ser Asp Tyr Tyr Trp Gly
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Ser Ser Ser Thr Tyr Trp Ala
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Ser Ser Ser Thr Tyr Trp Gly
1               5

<210> SEQ ID NO 21
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 21

Ser Ser Asp Thr Tyr Trp Gly
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Ser Ala Asp Asn Tyr Trp Gly
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Ser Ser Ser Thr Tyr Trp Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic

<400> SEQUENCE: 24

Ser Gly Tyr Tyr Trp Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic

<400> SEQUENCE: 25

Ser Gly Tyr Tyr Trp Phe
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Ser Gly His Tyr Trp Ile
1               5

<210> SEQ ID NO 27
<211> LENGTH: 6
<212> TYPE: PRT
<213> ORGANISM: Artificial Sequence
<220> FEATURE:
```

```
<223> OTHER INFORMATION: Synthetic

<400> SEQUENCE: 27

Ser Gly Phe Tyr Trp Thr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Ser Gly Tyr Tyr Trp Leu
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Ser Gly His Tyr Trp Thr
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic

<400> SEQUENCE: 30

Asn Tyr Ala Met His
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic

<400> SEQUENCE: 31

Asp Tyr Tyr Met Ser
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic

<400> SEQUENCE: 32

Ser Ser Ala Met Ala
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic
```

```
<400> SEQUENCE: 33

Ser Ser Asn Trp Trp Ser
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic

<400> SEQUENCE: 34

Ser Ser Ser Tyr Tyr Trp Gly
1               5

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38
<211> LENGTH: 5
<212> TYPE: PRT
<213> ORGANISM: Artificial Sequence
<220> FEATURE:
<223> OTHER INFORMATION: Synthetic

<400> SEQUENCE: 38

Tyr Tyr Ser Gly Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic

<400> SEQUENCE: 39

Ser Ser Ser Gly Ser
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic

<400> SEQUENCE: 40

His His Ser Gly Ala
1               5
```

```
<210> SEQ ID NO 41
<211> LENGTH: 5
<212> TYPE: PRT
<213> ORGANISM: Artificial Sequence
<220> FEATURE:
<223> OTHER INFORMATION: Synthetic

<400> SEQUENCE: 41

His Tyr Ser Gly Ser
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic

<400> SEQUENCE: 42

Ala Tyr Ser Gly Ser
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic

<400> SEQUENCE: 43

Ser Tyr Asn Ala Leu
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic

<400> SEQUENCE: 44

Tyr His Ser Gly Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic

<400> SEQUENCE: 45

Tyr His Ser Ala Ser
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic

<400> SEQUENCE: 46

Ser Ala Arg Ala Gly Ile
1               5
```

```
<210> SEQ ID NO 47
<211> LENGTH: 6
<212> TYPE: PRT
<213> ORGANISM: Artificial Sequence
<220> FEATURE:
<223> OTHER INFORMATION: Synthetic

<400> SEQUENCE: 47

Ala Ser Ser Gly Ser Val
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic

<400> SEQUENCE: 48

Ser Gly Ser Gly Ile Thr
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic

<400> SEQUENCE: 49

Ser Tyr Ser Gly Ser
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic

<400> SEQUENCE: 50

Ser Ser Ser Gly Ser Thr
1               5

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54
<211> LENGTH: 16
<212> TYPE: PRT
<213> ORGANISM: Artificial Sequence
<220> FEATURE:
<223> OTHER INFORMATION: Synthetic
```

<400> SEQUENCE: 54

Ser Ile Tyr Tyr Ser Gly Ser Thr Tyr Tyr Asn Pro Ser Leu Lys Ser
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Synthetic

<400> SEQUENCE: 55

Ser Ile Ser Ser Ser Gly Ser Thr Tyr Tyr Asn Pro Ser Leu Lys Ser
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Synthetic

<400> SEQUENCE: 56

Ser Ile His His Ser Gly Ala Thr Tyr Tyr Asn Pro Ser Leu Lys Ser
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Synthetic

<400> SEQUENCE: 57

Ser Ile His Tyr Ser Gly Ser Thr Leu Tyr Asn Pro Ser Leu Lys Ser
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Synthetic

<400> SEQUENCE: 58

Ser Ile His Tyr Ser Gly Ser Thr Tyr Tyr Asn Pro Ser Leu Lys Ser
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Synthetic

<400> SEQUENCE: 59

Gly Ile Ala Tyr Ser Gly Ser Thr Tyr Tyr Asn Pro Ser Leu Lys Ser
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Synthetic

```
<400> SEQUENCE: 60

Ser Ile Ser Tyr Asn Ala Leu Thr Tyr Tyr Asn Pro Ser Leu Lys Ser
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Synthetic

<400> SEQUENCE: 61

Ser Ile Tyr His Ser Gly Ser Thr Tyr Tyr Asn Pro Ser Leu Lys Ser
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic

<400> SEQUENCE: 62

Gly Ile Tyr His Ser Ala Ser Thr Ala Tyr Asn Pro Ser Leu Lys Ser
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Synthetic

<400> SEQUENCE: 63

Gly Ile Tyr His Ser Gly Ser Thr Tyr Tyr Asn Pro Ser Leu Lys Ser
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Synthetic

<400> SEQUENCE: 64

Ala Ile Tyr His Ser Gly Ser Thr Val Tyr Asn Pro Ser Leu Lys Ser
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Synthetic

<400> SEQUENCE: 65

Gly Ile Tyr His Ser Gly Ser Thr Ala Tyr Asn Pro Ser Leu Lys Ser
1               5                   10                  15

<210> SEQ ID NO 66
<211> LENGTH: 17
<212> TYPE: PRT
<213> ORGANISM: Artificial Sequence
<220> FEATURE:
<223> OTHER INFORMATION: Synthetic

<400> SEQUENCE: 66
```

```
Ala Ile Ser Ala Arg Ala Gly Ile Thr Tyr Tyr Ala Asp Ser Val Lys
1               5                   10                  15

Gly

<210> SEQ ID NO 67
<211> LENGTH: 17
<212> TYPE: PRT
<213> ORGANISM: Artificial Sequence
<220> FEATURE:
<223> OTHER INFORMATION: Synthetic

<400> SEQUENCE: 67

Tyr Ile Ala Ser Ser Gly Ser Val Ile Tyr Tyr Ala Asp Ser Val Lys
1               5                   10                  15

Gly

<210> SEQ ID NO 68
<211> LENGTH: 17
<212> TYPE: PRT
<213> ORGANISM: Artificial Sequence
<220> FEATURE:
<223> OTHER INFORMATION: Synthetic

<400> SEQUENCE: 68

Thr Ile Ser Gly Ser Gly Ile Thr Thr Trp Tyr Ala Asp Ser Val Lys
1               5                   10                  15

Gly

<210> SEQ ID NO 69
<211> LENGTH: 16
<212> TYPE: PRT
<213> ORGANISM: Artificial Sequence
<220> FEATURE:
<223> OTHER INFORMATION: Synthetic

<400> SEQUENCE: 69

Glu Ile Tyr His Ser Gly Ser Thr Asn Tyr Asn Pro Ser Leu Lys Ser
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Synthetic

<400> SEQUENCE: 70

Ser Ile Ser Tyr Ser Gly Ser Thr Tyr Tyr Asn Pro Ser Leu Lys Ser
1               5                   10                  15

<210> SEQ ID NO 71
<211> LENGTH: 17
<212> TYPE: PRT
<213> ORGANISM: Artificial Sequence
<220> FEATURE:
<223> OTHER INFORMATION: Synthetic

<400> SEQUENCE: 71

Tyr Ile Ser Ser Ser Gly Ser Thr Ile Tyr Tyr Ala Asp Ser Val Lys
1               5                   10                  15

Gly

<210> SEQ ID NO 72
```

```
<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76
<211> LENGTH: 10
<212> TYPE: PRT
<213> ORGANISM: Artificial Sequence
<220> FEATURE:
<223> OTHER INFORMATION: Synthetic

<400> SEQUENCE: 76

Gly Val Arg Arg Ala Val Pro Phe Asp Tyr
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic

<400> SEQUENCE: 77

Gly Ile Ala Arg Ala Val Pro Phe Asp Tyr
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthetic

<400> SEQUENCE: 78

Gly Pro Lys Arg Ala Val Pro Phe Asp Tyr
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Synthetic

<400> SEQUENCE: 79

Gly Val Arg Arg Ala Val Pro Phe Val Asp
1               5                   10
```

```
<210> SEQ ID NO 80
<211> LENGTH: 10
<212> TYPE: PRT
<213> ORGANISM: Artificial Sequence
<220> FEATURE:
<223> OTHER INFORMATION: Synthetic

<400> SEQUENCE: 80

Gly Val Arg Arg Ala Val Pro Phe Gln Arg
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic

<400> SEQUENCE: 81

Gly Thr Arg Arg Ala Val Pro Phe Asp Tyr
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic

<400> SEQUENCE: 82

Gly Val Arg Arg Ala Val Pro Phe Ala Asp
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic

<400> SEQUENCE: 83

Gly Ile Arg Arg Ala Val Pro Phe Asp Tyr
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic

<400> SEQUENCE: 84

Gly Gln Phe Arg Ala Val Pro Phe Asp Tyr
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Synthetic

<400> SEQUENCE: 85

Gly Gly Thr His Thr Tyr Ser Arg Gly Pro Met Asp Val
1               5                   10

<210> SEQ ID NO 86
```

```
<211> LENGTH: 13
<212> TYPE: PRT
<213> ORGANISM: Artificial Sequence
<220> FEATURE:
<223> OTHER INFORMATION: Synthetic

<400> SEQUENCE: 86

Gly Gly Thr His Thr Tyr Ser Arg Gly Pro Phe Asp Val
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Synthetic

<400> SEQUENCE: 87

Gly Gly Thr Pro Ile Tyr Ser Arg Gly Pro Leu Asp Val
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Synthetic

<400> SEQUENCE: 88

Gly Gly Gly Gln Thr Tyr Ser Arg Gly Pro Leu Asp Val
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic

<400> SEQUENCE: 89

Gly Gly Gly Ala Thr Tyr Ser Arg Gly Pro Leu Asp Val
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Synthetic

<400> SEQUENCE: 90

Gly Gly Thr His Thr Tyr Ser Arg Gly Pro Leu Asp Val
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Synthetic

<400> SEQUENCE: 91

Gly Gly Thr Val Lys Tyr Ser Arg Gly Pro Leu Asp Val
1               5                   10

<210> SEQ ID NO 92
<211> LENGTH: 13
```

```
<212> TYPE: PRT
<213> ORGANISM: Artificial Sequence
<220> FEATURE:
<223> OTHER INFORMATION: Synthetic

<400> SEQUENCE: 92

Gly Gly Gln Val Thr Tyr Ser Arg Gly Pro Leu Asp Val
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Synthetic

<400> SEQUENCE: 93

Gly Gly Glu Val Thr Tyr Ser Arg Gly Pro Leu Asp Val
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Synthetic

<400> SEQUENCE: 94

Arg Ile Gly Tyr Ser Tyr Gly Thr Ala Pro Pro Phe Asp Val
1               5                   10

<210> SEQ ID NO 95
<211> LENGTH: 9
<212> TYPE: PRT
<213> ORGANISM: Artificial Sequence
<220> FEATURE:
<223> OTHER INFORMATION: Synthetic

<400> SEQUENCE: 95

His Gly Thr Pro Arg Ala Phe Asp Ile
1               5

<210> SEQ ID NO 96
<211> LENGTH: 10
<212> TYPE: PRT
<213> ORGANISM: Artificial Sequence
<220> FEATURE:
<223> OTHER INFORMATION: Synthetic

<400> SEQUENCE: 96

Gly Ser Arg His Leu Asn Ala Phe Asn Arg
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic

<400> SEQUENCE: 97

Gly Val Tyr His Tyr Asp Pro Tyr Gly Met Asp Val
1               5                   10

<210> SEQ ID NO 98
<211> LENGTH: 10
<212> TYPE: PRT
```

```
<213> ORGANISM: Artificial Sequence
<220> FEATURE:
<223> OTHER INFORMATION: Synthetic

<400> SEQUENCE: 98

Thr Glu Leu Gly Lys Met His Phe Asp Tyr
1               5                   10

<210> SEQ ID NO 99
<211> LENGTH: 8
<212> TYPE: PRT
<213> ORGANISM: Artificial Sequence
<220> FEATURE:
<223> OTHER INFORMATION: Synthetic

<400> SEQUENCE: 99

Gly Ser Pro Arg Tyr Met Gln Asp
1               5

<210> SEQ ID NO 100
<211> LENGTH: 12
<212> TYPE: PRT
<213> ORGANISM: Artificial Sequence
<220> FEATURE:
<223> OTHER INFORMATION: Synthetic

<400> SEQUENCE: 100

His Ser Ser Leu Gly Thr His Asn Trp Phe Asp Pro
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthetic

<400> SEQUENCE: 101

Glu Gly Ala Leu Ser Tyr Ser Trp Leu Ala Ala Phe Asp Ile
1               5                   10

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105
<211> LENGTH: 12
<212> TYPE: PRT
<213> ORGANISM: Artificial Sequence
<220> FEATURE:
<223> OTHER INFORMATION: Synthetic

<400> SEQUENCE: 105
```

```
Arg Ala Ser Gln Ser Val Ser Ser Tyr Leu Ala
1               5                   10
```

<210> SEQ ID NO 106
<211> LENGTH: 12
<212> TYPE: PRT
<213> ORGANISM: Artificial Sequence
<220> FEATURE:
<223> OTHER INFORMATION: Synthetic

<400> SEQUENCE: 106

```
Gly Ala Ser Gln Ser Val Ser Ser Asp Tyr Leu Ala
1               5                   10
```

<210> SEQ ID NO 107
<211> LENGTH: 12
<212> TYPE: PRT
<213> ORGANISM: Artificial Sequence
<220> FEATURE:
<223> OTHER INFORMATION: Synthetic

<400> SEQUENCE: 107

```
Gln Ala Ser Gln Ala Val Ser Ser Asn Tyr Leu Ala
1               5                   10
```

<210> SEQ ID NO 108
<211> LENGTH: 12
<212> TYPE: PRT
<213> ORGANISM: Artificial Sequence
<220> FEATURE:
<223> OTHER INFORMATION: Synthetic

<400> SEQUENCE: 108

```
Gly Ala Ser Gln Ser Val Ser Ser Ala Phe Leu Ala
1               5                   10
```

<210> SEQ ID NO 109
<211> LENGTH: 12
<212> TYPE: PRT
<213> ORGANISM: Artificial Sequence
<220> FEATURE:
<223> OTHER INFORMATION: Synthetic

<400> SEQUENCE: 109

```
Arg Ala Ser Gln Ser Val Ser Ser Thr Tyr Leu Ala
1               5                   10
```

<210> SEQ ID NO 110
<211> LENGTH: 12
<212> TYPE: PRT
<213> ORGANISM: Artificial Sequence
<220> FEATURE:
<223> OTHER INFORMATION: Synthetic

<400> SEQUENCE: 110

```
Gln Ala Ser Gln Ser Val Ser Ser Ser Tyr Leu Ala
1               5                   10
```

<210> SEQ ID NO 111
<211> LENGTH: 12
<212> TYPE: PRT
<213> ORGANISM: Artificial Sequence
<220> FEATURE:
<223> OTHER INFORMATION: Synthetic

<400> SEQUENCE: 111

```
Lys Ala Ser Gln Ala Val Ser Ser Ser Tyr Leu Ala
```

```
1               5                  10
```

<210> SEQ ID NO 112
<211> LENGTH: 12
<212> TYPE: PRT
<213> ORGANISM: Artificial Sequence
<220> FEATURE:
<223> OTHER INFORMATION: Synthetic

<400> SEQUENCE: 112

```
Glu Ala Ser Gln Ser Val Ser Ser Ser Tyr Leu Ala
1               5                  10
```

<210> SEQ ID NO 113
<211> LENGTH: 12
<212> TYPE: PRT
<213> ORGANISM: Artificial Sequence
<220> FEATURE:
<223> OTHER INFORMATION: Synthetic

<400> SEQUENCE: 113

```
Glu Ala Ser Gln Ser Val Ser Ala Ser Tyr Leu Ala
1               5                  10
```

<210> SEQ ID NO 114
<211> LENGTH: 12
<212> TYPE: PRT
<213> ORGANISM: Artificial Sequence
<220> FEATURE:
<223> OTHER INFORMATION: Synthetic

<400> SEQUENCE: 114

```
Glu Ala Ser Gln Ser Val Ser Ser Ala Tyr Leu Ala
1               5                  10
```

<210> SEQ ID NO 115
<211> LENGTH: 12
<212> TYPE: PRT
<213> ORGANISM: Artificial Sequence
<220> FEATURE:
<223> OTHER INFORMATION: Synthetic

<400> SEQUENCE: 115

```
Arg Val Ser Gln Ser Val Ser Asp Ala Tyr Leu Ala
1               5                  10
```

<210> SEQ ID NO 116
<211> LENGTH: 12
<212> TYPE: PRT
<213> ORGANISM: Artificial Sequence
<220> FEATURE:
<223> OTHER INFORMATION: Synthetic

<400> SEQUENCE: 116

```
Glu Val Ser Gln Ser Val Ser Ala Ser Tyr Leu Ala
1               5                  10
```

<210> SEQ ID NO 117
<211> LENGTH: 12
<212> TYPE: PRT
<213> ORGANISM: Artificial Sequence
<220> FEATURE:
<223> OTHER INFORMATION: Synthetic

<400> SEQUENCE: 117

```
Arg Ala Ser Gln Ser Val Ser Ser Ala Tyr Leu Ala
1               5                  10
```

<210> SEQ ID NO 118
<211> LENGTH: 12
<212> TYPE: PRT
<213> ORGANISM: Artificial Sequence
<220> FEATURE:
<223> OTHER INFORMATION: Synthetic

<400> SEQUENCE: 118

Arg Ala Ser Asn Ala Val Ser Ser Ser Tyr Leu Ala
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic

<400> SEQUENCE: 119

Arg Ala Ser Gln Ser Ile Asn Ser Trp Leu Ala
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Synthetic

<400> SEQUENCE: 120

Ala Ala Ser Gln Gly Ile Ser Ser Asp Leu Ala
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Synthetic

<400> SEQUENCE: 121

Arg Ala Ser Gln Asp Ile Ser Thr Tyr Leu Asn
1               5                   10

<210> SEQ ID NO 122
<211> LENGTH: 16
<212> TYPE: PRT
<213> ORGANISM: Artificial Sequence
<220> FEATURE:
<223> OTHER INFORMATION: Synthetic

<400> SEQUENCE: 122

Arg Ser Ser Gln Ser Leu Leu His Ser Asn Gly Tyr Asn Tyr Leu Asp
1               5                   10                  15

<210> SEQ ID NO 123
<211> LENGTH: 11
<212> TYPE: PRT
<213> ORGANISM: Artificial Sequence
<220> FEATURE:
<223> OTHER INFORMATION: Synthetic

<400> SEQUENCE: 123

Arg Ala Ser Gln Ser Ile Ser Ser Tyr Leu Asn
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Synthetic

<400> SEQUENCE: 124

Arg Ala Ser Gln Ser Val Ser Ser Asn Leu Ala
1               5                   10

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128
<211> LENGTH: 7
<212> TYPE: PRT
<213> ORGANISM: Artificial Sequence
<220> FEATURE:
<223> OTHER INFORMATION: Synthetic

<400> SEQUENCE: 128

Gly Ala Ser Ser Arg Ala Thr
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic

<400> SEQUENCE: 129

Gly Ala Tyr Ser Leu Ala Thr
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic

<400> SEQUENCE: 130

Gly Ala Ser Ala Arg Ala Thr
1               5

<210> SEQ ID NO 131
<211> LENGTH: 7
<212> TYPE: PRT
<213> ORGANISM: Artificial Sequence
<220> FEATURE:

<223> OTHER INFORMATION: Synthetic

<400> SEQUENCE: 131

Gly Ala Ser Ser Arg Glu Ala
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic

<400> SEQUENCE: 132

Gly Ala Ser Asn Arg Ala Ala
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic

<400> SEQUENCE: 133

Gly Ala Ser Ser Arg Gln Asp
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Gly Ala Ser Asn Arg Ala Thr
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic

<400> SEQUENCE: 135

Asp Ala Ser Ser Arg Ala Ser
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic

<400> SEQUENCE: 136

Asp Ala Ser Thr Arg Ala Thr
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic

```
<400> SEQUENCE: 137

Gly Ala Ser Asp Arg Ala Asn
1               5

<210> SEQ ID NO 138
<211> LENGTH: 7
<212> TYPE: PRT
<213> ORGANISM: Artificial Sequence
<220> FEATURE:
<223> OTHER INFORMATION: Synthetic

<400> SEQUENCE: 138

Gly Ala Ser Tyr Arg Ala Thr
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic

<400> SEQUENCE: 139

Asp Ala Ser Ser Leu Glu Ser
1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic

<400> SEQUENCE: 140

Ser Ala Ser Ser Thr Gln Ser
1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic

<400> SEQUENCE: 141

Asp Ala Phe Asn Leu Glu Thr
1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic

<400> SEQUENCE: 142

Leu Gly Ser Asn Arg Ala Ser
1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic
```

```
<400> SEQUENCE: 143

Gly Ala Ser Arg Arg Ala Thr
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic

<400> SEQUENCE: 144

Ala Ala Ser Ser Leu Gln Ser
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic

<400> SEQUENCE: 145

Gly Ala Ser Thr Arg Ala Thr
1               5

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149
<211> LENGTH: 9
<212> TYPE: PRT
<213> ORGANISM: Artificial Sequence
<220> FEATURE:
<223> OTHER INFORMATION: Synthetic

<400> SEQUENCE: 149

Gln Gln Ala Val His Ser Pro Tyr Thr
1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic

<400> SEQUENCE: 150

Gln Trp Ala Val His Ser Pro Tyr Thr
1               5
```

```
<210> SEQ ID NO 151
<211> LENGTH: 9
<212> TYPE: PRT
<213> ORGANISM: Artificial Sequence
<220> FEATURE:
<223> OTHER INFORMATION: Synthetic

<400> SEQUENCE: 151

Gln Gln Val Val His Ser Pro Tyr Thr
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic

<400> SEQUENCE: 152

Gln Gln Thr Val His Ser Pro Tyr Thr
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic

<400> SEQUENCE: 153

Gln Gln Ala Ile His Ser Pro Tyr Thr
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic

<400> SEQUENCE: 154

Gln Gln His Ser Ser Tyr Pro Pro Thr
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic

<400> SEQUENCE: 155

Gln Gln His Ser Leu Tyr Pro Pro Thr
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic

<400> SEQUENCE: 156

Gln Gln Phe Ser Ser Tyr Pro Pro Thr
1               5

<210> SEQ ID NO 157
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 157

Gln Gln Val Ser Ser Tyr Pro Pro Thr
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic

<400> SEQUENCE: 158

Gln Gln His Ser Ile Tyr Pro Pro Thr
1               5

<210> SEQ ID NO 159
<211> LENGTH: 8
<212> TYPE: PRT
<213> ORGANISM: Artificial Sequence
<220> FEATURE:
<223> OTHER INFORMATION: Synthetic

<400> SEQUENCE: 159

Gln Gln Tyr Asp Ser His Ile Thr
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Ala Tyr Leu Tyr Pro Ile Thr
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic

<400> SEQUENCE: 161

Gln Gln Leu Pro Phe Leu Pro Ile Thr
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic

<400> SEQUENCE: 162

Met Gln Ala Leu Gly Gly Pro Trp Thr
1               5

<210> SEQ ID NO 163
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 163

Gln Gln Tyr Val Ser Asp Pro Ile Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic

<400> SEQUENCE: 164

Gln Gln Val Gly Ser Ser Pro Ile Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic

<400> SEQUENCE: 165

Gln Gln Ser His Leu Val Pro Arg Thr
1               5

<210> SEQ ID NO 166
<211> LENGTH: 10
<212> TYPE: PRT
<213> ORGANISM: Artificial Sequence
<220> FEATURE:
<223> OTHER INFORMATION: Synthetic

<400> SEQUENCE: 166

Gln Gln Ala Asn His His Pro Pro Phe Thr
1               5                   10

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170
<211> LENGTH: 120
<212> TYPE: PRT
<213> ORGANISM: Artificial Sequence
<220> FEATURE:
<223> OTHER INFORMATION: Synthetic

<400> SEQUENCE: 170
```

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Val Arg Arg Ala Val Pro Phe Asp Tyr Trp Gly Gln
            100                 105                 110

Gly Thr Leu Val Thr Val Ser Ser
        115                 120

<210> SEQ ID NO 171
<211> LENGTH: 120
<212> TYPE: PRT
<213> ORGANISM: Artificial Sequence
<220> FEATURE:
<223> OTHER INFORMATION: Synthetic

<400> SEQUENCE: 171

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Ala Trp Ile Arg Gln Pro Pro Gly Lys Gly Leu Glu
        35                  40                  45

Trp Ile Gly Ser Ile Ser Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Ile Ala Arg Ala Val Pro Phe Asp Tyr Trp Gly Gln
            100                 105                 110

Gly Thr Leu Val Thr Val Ser Ser
        115                 120

<210> SEQ ID NO 172
<211> LENGTH: 120
<212> TYPE: PRT
<213> ORGANISM: Artificial Sequence
<220> FEATURE:
<223> OTHER INFORMATION: Synthetic

<400> SEQUENCE: 172

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Gly Trp Ile Arg Gln Ser Pro Gly Lys Gly Leu Glu
        35                  40                  45

Trp Ile Gly Ser Ile His His Ser Gly Ala Thr Tyr Tyr Asn Pro Ser
```

```
                50                   55                   60
Leu Lys Ser Arg Val Thr Ile Ser Val Asp Thr Ser Lys Asn Gln Phe
 65                   70                   75                   80

Ser Leu Lys Leu Ser Ser Val Thr Ala Ala Asp Thr Ala Val Tyr Tyr
                 85                   90                   95

Cys Ala Arg Gly Pro Lys Arg Ala Val Pro Phe Asp Tyr Trp Gly Gln
                100                  105                  110

Gly Thr Leu Val Thr Val Ser Ser
            115                  120

<210> SEQ ID NO 173
<211> LENGTH: 120
<212> TYPE: PRT
<213> ORGANISM: Artificial Sequence
<220> FEATURE:
<223> OTHER INFORMATION: Synthetic

<400> SEQUENCE: 173

Gln Leu Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Ser Ser
                 20                  25                  30

Asp Thr Tyr Trp Gly Trp Ile Arg Gln Pro Pro Gly Lys Gly Leu Glu
             35                  40                  45

Trp Ile Gly Ser Ile His Tyr Ser Gly Ser Thr Leu Tyr Asn Pro Ser
         50                  55                  60

Leu Lys Ser Arg Val Thr Ile Ser Val Asp Thr Ser Lys Asn Gln Phe
 65                  70                  75                   80

Ser Leu Lys Leu Ser Ser Val Thr Ala Ala Asp Thr Ala Val Tyr Tyr
                 85                  90                  95

Cys Ala Arg Gly Val Arg Arg Ala Val Pro Phe Val Asp Trp Gly Gln
                100                  105                 110

Gly Thr Leu Val Thr Val Ser Ser
            115                  120

<210> SEQ ID NO 174
<211> LENGTH: 120
<212> TYPE: PRT
<213> ORGANISM: Artificial Sequence
<220> FEATURE:
<223> OTHER INFORMATION: Synthetic

<400> SEQUENCE: 174

Gln Leu Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Ser Ala
                 20                  25                  30

Asp Asn Tyr Trp Gly Trp Ile Arg Gln Pro Pro Gly Lys Gly Leu Glu
             35                  40                  45

Trp Ile Gly Ser Ile His Tyr Ser Gly Ser Thr Tyr Tyr Asn Pro Ser
         50                  55                  60

Leu Lys Ser Arg Val Thr Ile Ser Val Asp Thr Ser Lys Asn Gln Phe
 65                  70                  75                   80

Ser Leu Lys Leu Ser Ser Val Thr Ala Ala Asp Thr Ala Val Tyr Tyr
                 85                  90                  95

Cys Ala Arg Gly Val Arg Arg Ala Val Pro Phe Gln Arg Trp Gly Gln
                100                  105                 110
```

```
Gly Thr Leu Val Thr Val Ser Ser
        115                 120
```

<210> SEQ ID NO 175
<211> LENGTH: 120
<212> TYPE: PRT
<213> ORGANISM: Artificial Sequence
<220> FEATURE:
<223> OTHER INFORMATION: Synthetic

<400> SEQUENCE: 175

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Thr Tyr Trp Gly Trp Ile Arg Gln Pro Pro Gly Lys Gly Pro Glu
        35                  40                  45

Trp Ile Gly Ser Ile His Tyr Ser Gly Ser Thr Leu Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Arg Arg Ala Val Pro Phe Asp Tyr Trp Gly Gln
            100                 105                 110

Gly Thr Leu Val Thr Val Ser Ser
        115                 120
```

<210> SEQ ID NO 176
<211> LENGTH: 120
<212> TYPE: PRT
<213> ORGANISM: Artificial Sequence
<220> FEATURE:
<223> OTHER INFORMATION: Synthetic

<400> SEQUENCE: 176

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Ser Trp Ile Arg Gln Pro Pro Gly Lys Gly Leu Glu
        35                  40                  45

Trp Ile Gly Gly Ile Ala Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Arg Arg Ala Val Pro Phe Asp Tyr Trp Gly Gln
            100                 105                 110

Gly Thr Leu Val Thr Val Ser Ser
        115                 120
```

<210> SEQ ID NO 177
<211> LENGTH: 120
<212> TYPE: PRT
<213> ORGANISM: Artificial Sequence
<220> FEATURE:
<223> OTHER INFORMATION: Synthetic

<400> SEQUENCE: 177

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Ser Trp Ile Arg Gln Pro Pro Gly Lys Gly Leu Glu
        35                  40                  45

Trp Ile Gly Ser Ile Ser Tyr Asn Ala Leu Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Thr Arg Arg Ala Val Pro Phe Asp Tyr Trp Gly Gln
            100                 105                 110

Gly Thr Leu Val Thr Val Ser Ser
        115                 120
```

<210> SEQ ID NO 178
<211> LENGTH: 120
<212> TYPE: PRT
<213> ORGANISM: Artificial Sequence
<220> FEATURE:
<223> OTHER INFORMATION: Synthetic

<400> SEQUENCE: 178

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Ser Trp Ile Arg Gln Pro Pro Gly Lys Gly Leu Glu
        35                  40                  45

Trp Ile Gly Gly Ile Ala Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Arg Arg Ala Val Pro Phe Ala Asp Trp Gly Gln
            100                 105                 110

Gly Thr Leu Val Thr Val Ser Ser
        115                 120
```

<210> SEQ ID NO 179
<211> LENGTH: 120
<212> TYPE: PRT
<213> ORGANISM: Artificial Sequence
<220> FEATURE:
<223> OTHER INFORMATION: Synthetic

<400> SEQUENCE: 179

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Ser
            20                  25                  30

Ser Thr Tyr Trp Ser Trp Ile Arg Gln Pro Pro Gly Lys Gly Leu Glu
        35                  40                  45
```

```
Trp Ile Gly Gly Ile Ala Tyr Ser Gly Ser Thr Tyr Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Val Arg Arg Ala Val Pro Phe Asp Tyr Trp Gly Gln
            100                 105                 110

Gly Thr Leu Val Thr Val Ser Ser
            115                 120
```

<210> SEQ ID NO 180
<211> LENGTH: 120
<212> TYPE: PRT
<213> ORGANISM: Artificial Sequence
<220> FEATURE:
<223> OTHER INFORMATION: Synthetic

<400> SEQUENCE: 180

```
Gln Leu Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Ser
                 20                  25                  30

Ser Thr Tyr Trp Ser Trp Ile Arg Gln Pro Pro Gly Lys Gly Leu Glu
             35                  40                  45

Trp Ile Gly Gly Ile Ala Tyr Ser Gly Ser Thr Tyr Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Thr Arg Arg Ala Val Pro Phe Asp Tyr Trp Gly Gln
            100                 105                 110

Gly Thr Leu Val Thr Val Ser Ser
            115                 120
```

<210> SEQ ID NO 181
<211> LENGTH: 120
<212> TYPE: PRT
<213> ORGANISM: Artificial Sequence
<220> FEATURE:
<223> OTHER INFORMATION: Synthetic

<400> SEQUENCE: 181

```
Gln Leu Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Ser
                 20                  25                  30

Asp Thr Tyr Trp Gly Trp Ile Arg Gln Pro Pro Gly Lys Gly Leu Glu
             35                  40                  45

Trp Ile Gly Ser Ile His Tyr Ser Gly Ser Thr Leu Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Ile Arg Arg Ala Val Pro Phe Asp Tyr Trp Gly Gln
            100                 105                 110
```

```
Gly Thr Leu Val Thr Val Ser Ser
        115                 120

<210> SEQ ID NO 182
<211> LENGTH: 120
<212> TYPE: PRT
<213> ORGANISM: Artificial Sequence
<220> FEATURE:
<223> OTHER INFORMATION: Synthetic

<400> SEQUENCE: 182

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Thr Tyr Trp Gly Trp Ile Arg Gln Pro Pro Gly Lys Gly Leu Glu
        35                  40                  45

Trp Ile Gly Ser Ile His Tyr Ser Gly Ser Thr Leu Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gln Phe Arg Ala Val Pro Phe Asp Tyr Trp Gly Gln
            100                 105                 110

Gly Thr Leu Val Thr Val Ser Ser
        115                 120

<210> SEQ ID NO 183
<211> LENGTH: 122
<212> TYPE: PRT
<213> ORGANISM: Artificial Sequence
<220> FEATURE:
<223> OTHER INFORMATION: Synthetic

<400> SEQUENCE: 183

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Thr His Thr Tyr Ser Arg Gly Pro Met Asp Val Trp
            100                 105                 110

Gly Gln Gly Thr Thr Val Thr Val Ser Ser
        115                 120

<210> SEQ ID NO 184
<211> LENGTH: 122
<212> TYPE: PRT
<213> ORGANISM: Artificial Sequence
<220> FEATURE:
<223> OTHER INFORMATION: Synthetic
```

<400> SEQUENCE: 184

Gln Leu Gln Leu Gln Glu Ser Gly Pro Arg Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Gly Thr His Thr Tyr Ser Arg Gly Pro Phe Asp Val Trp
        100                 105                 110

Gly Gln Gly Thr Thr Val Thr Val Ser Ser
        115                 120

<210> SEQ ID NO 185
<211> LENGTH: 122
<212> TYPE: PRT
<213> ORGANISM: Artificial Sequence
<220> FEATURE:
<223> OTHER INFORMATION: Synthetic

<400> SEQUENCE: 185

Leu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Leu Ser Gly
            20                  25                  30

Tyr Tyr Trp Phe Trp Ile Arg Gln Pro Pro Gly Lys Gly Leu Glu Trp
        35                  40                  45

Ile Gly Gly Ile Tyr His Ser Ala Ser Thr Ala Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Gly Thr Pro Ile Tyr Ser Arg Gly Pro Leu Asp Val Trp
        100                 105                 110

Gly Gln Gly Thr Thr Val Thr Val Ser Ser
        115                 120

<210> SEQ ID NO 186
<211> LENGTH: 122
<212> TYPE: PRT
<213> ORGANISM: Artificial Sequence
<220> FEATURE:
<223> OTHER INFORMATION: Synthetic

<400> SEQUENCE: 186

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

His Tyr Trp Ile Trp Ile Arg Gln Pro Pro Gly Lys Gly Leu Glu Trp
        35                  40                  45

Ile Gly Gly Ile Tyr His Ser Gly Ser Thr Tyr Tyr Asn Pro Ser Leu
             50                  55                  60

Lys Ser Arg Val Thr Ile Ser Val Asp Thr Ser Lys Asp Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Gly Gln Thr Tyr Ser Arg Gly Pro Leu Asp Val Trp
                100                 105                 110

Gly Gln Gly Thr Thr Val Thr Val Ser Ser
            115                 120

<210> SEQ ID NO 187
<211> LENGTH: 122
<212> TYPE: PRT
<213> ORGANISM: Artificial Sequence
<220> FEATURE:
<223> OTHER INFORMATION: Synthetic

<400> SEQUENCE: 187

Gln Val Gln Leu Gln Glu Ser Gly Pro Gly Leu Val Lys Pro Pro Glu
 1                5                  10                  15

Thr Leu Ser Leu Thr Cys Ala Val Ser Gly Tyr Ser Ile Ser Ser Gly
                 20                  25                  30

His Tyr Trp Ile Trp Ile Arg Gln Pro Pro Gly Lys Gly Leu Glu Trp
             35                  40                  45

Ile Gly Gly Ile Tyr His Ser Gly Ser Thr Tyr Tyr Asn Pro Ser Leu
             50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Gly Ala Thr Tyr Ser Arg Gly Pro Leu Asp Val Trp
                100                 105                 110

Gly Gln Gly Thr Thr Val Thr Val Ser Ser
            115                 120

<210> SEQ ID NO 188
<211> LENGTH: 122
<212> TYPE: PRT
<213> ORGANISM: Artificial Sequence
<220> FEATURE:
<223> OTHER INFORMATION: Synthetic

<400> SEQUENCE: 188

Gln Val Gln Leu Gln Glu Ser Gly Pro Gly Leu Val Lys Pro Ser Glu
 1                5                  10                  15

Thr Leu Ser Leu Thr Cys Ala Val Ser Gly Tyr Ser Ile Leu Ser Gly
                 20                  25                  30

Tyr Tyr Trp Phe Trp Ile Arg Gln Pro Pro Gly Lys Gly Leu Glu Trp
             35                  40                  45

Ile Gly Gly Ile Tyr His Ser Gly Ser Thr Tyr Tyr Asn Pro Ser Leu
             50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Thr His Thr Tyr Ser Arg Gly Pro Leu Asp Val Trp

```
                    100                 105                 110
Gly Gln Gly Thr Thr Val Thr Val Ser Ser
        115                 120

<210> SEQ ID NO 189
<211> LENGTH: 122
<212> TYPE: PRT
<213> ORGANISM: Artificial Sequence
<220> FEATURE:
<223> OTHER INFORMATION: Synthetic

<400> SEQUENCE: 189

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Phe Tyr Trp Thr Trp Ile Arg Gln Pro Pro Gly Lys Gly Leu Glu Trp
        35                  40                  45

Ile Gly Ala Ile Tyr His Ser Gly Ser Thr Val Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Thr His Thr Tyr Ser Arg Gly Pro Leu Asp Val Trp
            100                 105                 110

Gly Gln Gly Thr Thr Val Thr Val Ser Ser
        115                 120

<210> SEQ ID NO 190
<211> LENGTH: 122
<212> TYPE: PRT
<213> ORGANISM: Artificial Sequence
<220> FEATURE:
<223> OTHER INFORMATION: Synthetic

<400> SEQUENCE: 190

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Leu Trp Ile Arg Gln Pro Pro Gly Lys Gly Leu Glu Trp
        35                  40                  45

Ile Gly Gly Ile Tyr His Ser Ala Ser Thr Ala Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Thr Val Lys Tyr Ser Arg Gly Pro Leu Asp Val Trp
            100                 105                 110

Gly Gln Gly Thr Thr Val Thr Val Ser Ser
        115                 120

<210> SEQ ID NO 191
<211> LENGTH: 122
<212> TYPE: PRT
<213> ORGANISM: Artificial Sequence
<220> FEATURE:
```

<223> OTHER INFORMATION: Synthetic

<400> SEQUENCE: 191

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

His Tyr Trp Thr Trp Ile Arg Gln Pro Pro Gly Lys Gly Leu Glu Trp
        35                  40                  45

Ile Gly Ala Ile Tyr His Ser Gly Ser Thr Val Tyr Asn Pro Ser Leu
    50                  55                  60

Lys Ser Arg Val Thr Ile Ser Val Asp Thr Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gln Val Thr Tyr Ser Arg Gly Pro Leu Asp Val Trp
            100                 105                 110

Gly Gln Gly Thr Thr Val Thr Val Ser Ser
        115                 120
```

<210> SEQ ID NO 192
<211> LENGTH: 122
<212> TYPE: PRT
<213> ORGANISM: Artificial Sequence
<220> FEATURE:
<223> OTHER INFORMATION: Synthetic

<400> SEQUENCE: 192

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Leu Ser Gly
            20                  25                  30

Tyr Tyr Trp Phe Trp Ile Arg Gln Pro Pro Gly Lys Gly Leu Glu Trp
        35                  40                  45

Ile Gly Gly Ile Tyr His Ser Gly Ser Thr Ala Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Glu Val Thr Tyr Ser Arg Gly Pro Leu Asp Val Trp
            100                 105                 110

Gly Gln Gly Thr Thr Val Thr Val Ser Ser
        115                 120
```

<210> SEQ ID NO 193
<211> LENGTH: 123
<212> TYPE: PRT
<213> ORGANISM: Artificial Sequence
<220> FEATURE:
<223> OTHER INFORMATION: Synthetic

<400> SEQUENCE: 193

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn Tyr
            20                  25                  30

Ala Met His Trp Val Arg Gln Ala Pro Gly Lys Gly Leu Glu Trp Val
```

```
            35                  40                  45
Ser Ala Ile Ser Ala Arg Ala Gly Ile Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Arg Ile Gly Tyr Ser Tyr Gly Thr Ala Pro Pro Phe Asp Val
                100                 105                 110
Trp Gly Gln Gly Thr Thr Val Thr Val Ser Ser
            115                 120
```

<210> SEQ ID NO 194
<211> LENGTH: 118
<212> TYPE: PRT
<213> ORGANISM: Artificial Sequence
<220> FEATURE:
<223> OTHER INFORMATION: Synthetic

<400> SEQUENCE: 194

```
Gln Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Asp Tyr
             20                  25                  30
Tyr Met Ser Trp Ile Arg Gln Ala Pro Gly Lys Gly Leu Glu Trp Val
         35                  40                  45
Ser Tyr Ile Ala Ser Ser Gly Ser Val Ile Tyr Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg His Gly Thr Pro Arg Ala Phe Asp Ile Trp Gly Gln Gly Thr
                100                 105                 110
Thr Val Thr Val Ser Ser
            115
```

<210> SEQ ID NO 195
<211> LENGTH: 119
<212> TYPE: PRT
<213> ORGANISM: Artificial Sequence
<220> FEATURE:
<223> OTHER INFORMATION: Synthetic

<400> SEQUENCE: 195

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Ser
             20                  25                  30
Ala Met Ala Trp Val Arg Gln Ala Pro Gly Lys Gly Leu Glu Trp Val
         35                  40                  45
Ser Thr Ile Ser Gly Ser Gly Ile Thr Thr Trp Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
```

```
Ala Lys Gly Ser Arg His Leu Asn Ala Phe Asn Arg Trp Gly Gln Gly
                100                 105                 110

Thr Thr Val Thr Val Ser Ser
            115
```

<210> SEQ ID NO 196
<211> LENGTH: 121
<212> TYPE: PRT
<213> ORGANISM: Artificial Sequence
<220> FEATURE:
<223> OTHER INFORMATION: Synthetic

<400> SEQUENCE: 196

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Val Tyr His Tyr Asp Pro Tyr Gly Met Asp Val Trp Gly
            100                 105                 110

Gln Gly Thr Thr Val Thr Val Ser Ser
            115                 120
```

<210> SEQ ID NO 197
<211> LENGTH: 120
<212> TYPE: PRT
<213> ORGANISM: Artificial Sequence
<220> FEATURE:
<223> OTHER INFORMATION: Synthetic

<400> SEQUENCE: 197

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Glu Leu Gly Lys Met His Phe Asp Tyr Trp Gly Gln
            100                 105                 110

Gly Thr Leu Val Thr Val Ser Ser
            115                 120
```

<210> SEQ ID NO 198
<211> LENGTH: 118
<212> TYPE: PRT
<213> ORGANISM: Artificial Sequence
<220> FEATURE:
<223> OTHER INFORMATION: Synthetic

<400> SEQUENCE: 198

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Pro Arg Tyr Met Gln Asp Trp Gly Gln Gly Thr
            100                 105                 110

Leu Val Thr Val Ser Ser
        115

<210> SEQ ID NO 199
<211> LENGTH: 121
<212> TYPE: PRT
<213> ORGANISM: Artificial Sequence
<220> FEATURE:
<223> OTHER INFORMATION: Synthetic

<400> SEQUENCE: 199

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Ser Leu Gly His Asn Trp Phe Asp Pro Trp Gly
            100                 105                 110

Gln Gly Thr Leu Val Thr Val Ser Ser
        115                 120

<210> SEQ ID NO 200
<211> LENGTH: 123
<212> TYPE: PRT
<213> ORGANISM: Artificial Sequence
<220> FEATURE:
<223> OTHER INFORMATION: Synthetic

<400> SEQUENCE: 200

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

```
Tyr Tyr Trp Gly Trp Ile Arg Gln Pro Pro Gly Lys Gly Leu Glu Trp
             35                  40                  45

Ile Gly Ser Ile Tyr His Ser Gly Ser Thr Tyr Tyr Asn Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Glu Gly Ala Leu Ser Tyr Ser Trp Leu Ala Ala Phe Asp Ile
                100                 105                 110

Trp Gly Gln Gly Thr Met Val Thr Val Ser Ser
            115                 120

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204
<211> LENGTH: 108
<212> TYPE: PRT
<213> ORGANISM: Artificial Sequence
<220> FEATURE:
<223> OTHER INFORMATION: Synthetic

<400> SEQUENCE: 204

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Ala Val His Ser Pro
                 85                  90                  95

Tyr Thr Phe Gly Gly Gly Thr Lys Val Glu Ile Lys
            100                 105

<210> SEQ ID NO 205
<211> LENGTH: 108
<212> TYPE: PRT
<213> ORGANISM: Artificial Sequence
<220> FEATURE:
<223> OTHER INFORMATION: Synthetic

<400> SEQUENCE: 205
```

Glu Ile Val Leu Thr Gln Ser Pro Gly Thr Leu Ser Leu Ser Pro Gly
1               5                   10                  15

Glu Arg Ala Thr Leu Ser Cys Gly Ala Ser Gln Ser Val Ser Ser Asp
            20                  25                  30

Tyr Leu Ala Trp Tyr Gln Gln Lys Pro Gly Gln Ala Pro Arg Leu Leu
        35                  40                  45

Ile Tyr Gly Ala Tyr Ser Leu Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Trp Ala Val His Ser Pro
                85                  90                  95

Tyr Thr Phe Gly Gly Gly Thr Lys Val Glu Ile Lys
            100                 105

<210> SEQ ID NO 206
<211> LENGTH: 108
<212> TYPE: PRT
<213> ORGANISM: Artificial Sequence
<220> FEATURE:
<223> OTHER INFORMATION: Synthetic

<400> SEQUENCE: 206

Glu Ile Val Leu Thr Gln Ser Pro Gly Thr Leu Ser Leu Ser Pro Gly
1               5                   10                  15

Glu Arg Ala Thr Leu Ser Cys Gln Ala Ser Gln Ala Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Val His Ser Pro
                85                  90                  95

Tyr Thr Phe Gly Gly Gly Thr Lys Val Glu Ile Lys
            100                 105

<210> SEQ ID NO 207
<211> LENGTH: 108
<212> TYPE: PRT
<213> ORGANISM: Artificial Sequence
<220> FEATURE:
<223> OTHER INFORMATION: Synthetic

<400> SEQUENCE: 207

Glu Ile Val Leu Thr Gln Ser Pro Gly Thr Leu Ser Leu Ser Pro Gly
1               5                   10                  15

Glu Arg Ala Thr Leu Ser Cys Gly Ala Ser Gln Ser Val Ser Ser Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ala Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Val His Ser Pro

```
                85                  90                  95

Tyr Thr Phe Gly Gly Gly Thr Lys Val Glu Ile Lys
            100                 105

<210> SEQ ID NO 208
<211> LENGTH: 108
<212> TYPE: PRT
<213> ORGANISM: Artificial Sequence
<220> FEATURE:
<223> OTHER INFORMATION: Synthetic

<400> SEQUENCE: 208

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Glu Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Val His Ser Pro
                85                  90                  95

Tyr Thr Phe Gly Gly Gly Thr Lys Val Glu Ile Lys
            100                 105

<210> SEQ ID NO 209
<211> LENGTH: 108
<212> TYPE: PRT
<213> ORGANISM: Artificial Sequence
<220> FEATURE:
<223> OTHER INFORMATION: Synthetic

<400> SEQUENCE: 209

Glu Ile Val Leu Thr Gln Ser Pro Gly Thr Leu Ser Leu Ser Pro Gly
1               5                   10                  15

Glu Arg Ala Thr Leu Ser Cys Gln Ala Ser Gln Ala Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ile His Ser Pro
                85                  90                  95

Tyr Thr Phe Gly Gly Gly Thr Lys Val Glu Ile Lys
            100                 105

<210> SEQ ID NO 210
<211> LENGTH: 108
<212> TYPE: PRT
<213> ORGANISM: Artificial Sequence
<220> FEATURE:
<223> OTHER INFORMATION: Synthetic

<400> SEQUENCE: 210

Glu Ile Val Leu Thr Gln Ser Pro Gly Thr Leu Ser Leu Ser Pro Gly
1               5                   10                  15
```

Glu Arg Ala Thr Leu Ser Cys Gln Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Val His Ser Pro
                85                  90                  95

Tyr Thr Phe Gly Gly Gly Thr Lys Val Glu Ile Lys
            100                 105

<210> SEQ ID NO 211
<211> LENGTH: 108
<212> TYPE: PRT
<213> ORGANISM: Artificial Sequence
<220> FEATURE:
<223> OTHER INFORMATION: Synthetic

<400> SEQUENCE: 211

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Ala Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Gln Asp Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Val His Ser Pro
                85                  90                  95

Tyr Thr Phe Gly Gly Gly Thr Lys Val Glu Ile Lys
            100                 105

<210> SEQ ID NO 212
<211> LENGTH: 108
<212> TYPE: PRT
<213> ORGANISM: Artificial Sequence
<220> FEATURE:
<223> OTHER INFORMATION: Synthetic

<400> SEQUENCE: 212

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Ser Ser Tyr Pro
                85                  90                  95

Pro Thr Phe Gly Gly Gly Thr Lys Val Glu Ile Lys

<210> SEQ ID NO 213
<211> LENGTH: 108
<212> TYPE: PRT
<213> ORGANISM: Artificial Sequence
<220> FEATURE:
<223> OTHER INFORMATION: Synthetic

<400> SEQUENCE: 213

Glu Ile Val Leu Thr Gln Ser Pro Gly Thr Leu Ser Leu Ser Pro Gly
1               5                   10                  15

Glu Arg Ala Thr Leu Ser Cys Glu Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Ser Leu Tyr Pro
                85                  90                  95

Pro Thr Phe Gly Gly Gly Thr Lys Val Glu Ile Lys
            100                 105

<210> SEQ ID NO 214
<211> LENGTH: 108
<212> TYPE: PRT
<213> ORGANISM: Artificial Sequence
<220> FEATURE:
<223> OTHER INFORMATION: Synthetic

<400> SEQUENCE: 214

Glu Ile Val Leu Thr Gln Ser Pro Gly Thr Leu Ser Leu Ser Pro Gly
1               5                   10                  15

Glu Arg Ala Thr Leu Ser Cys Glu Ala Ser Gln Ser Val Ser Ala Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Ser Ser Tyr Pro
                85                  90                  95

Pro Thr Phe Gly Gly Gly Thr Lys Val Glu Ile Lys
            100                 105

<210> SEQ ID NO 215
<211> LENGTH: 108
<212> TYPE: PRT
<213> ORGANISM: Artificial Sequence
<220> FEATURE:
<223> OTHER INFORMATION: Synthetic

<400> SEQUENCE: 215

Glu Ile Val Leu Thr Gln Ser Pro Gly Thr Leu Ser Leu Ser Pro Gly
1               5                   10                  15

Glu Arg Ala Thr Leu Ser Cys Glu Ala Ser Gln Ser Val Ser Ser Ala
            20                  25                  30

```
Tyr Leu Ala Trp Tyr Gln Gln Lys Pro Gly Gln Ala Pro Arg Leu Leu
            35                  40                  45

Ile Tyr Asp Ala Ser Thr Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Val Ser Ser Tyr Pro
                 85                  90                  95

Pro Thr Phe Gly Gly Gly Thr Lys Val Glu Ile Lys
            100                 105

<210> SEQ ID NO 216
<211> LENGTH: 108
<212> TYPE: PRT
<213> ORGANISM: Artificial Sequence
<220> FEATURE:
<223> OTHER INFORMATION: Synthetic

<400> SEQUENCE: 216

Glu Ile Val Leu Thr Gln Ser Pro Gly Thr Leu Ser Leu Ser Pro Gly
 1               5                  10                  15

Glu Arg Ala Ala Leu Ser Cys Arg Val Ser Gln Ser Val Ser Asp Ala
             20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Ser Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Val Ser Ser Tyr Pro
                 85                  90                  95

Pro Thr Phe Gly Gly Gly Thr Lys Val Glu Ile Lys
            100                 105

<210> SEQ ID NO 217
<211> LENGTH: 108
<212> TYPE: PRT
<213> ORGANISM: Artificial Sequence
<220> FEATURE:
<223> OTHER INFORMATION: Synthetic

<400> SEQUENCE: 217

Glu Ile Val Leu Thr Gln Ser Pro Gly Thr Leu Ser Leu Ser Pro Gly
 1               5                  10                  15

Glu Arg Ala Thr Leu Ser Cys Glu Val Ser Gln Ser Val Ser Ala Ser
             20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln His Ser Leu Tyr Pro
                 85                  90                  95

Pro Thr Phe Gly Gly Gly Thr Lys Val Glu Ile Lys
            100                 105
```

-continued

```
<210> SEQ ID NO 218
<211> LENGTH: 108
<212> TYPE: PRT
<213> ORGANISM: Artificial Sequence
<220> FEATURE:
<223> OTHER INFORMATION: Synthetic

<400> SEQUENCE: 218

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ala
            20                  25                  30

Tyr Leu Ala Trp Tyr Gln Gln Lys Pro Gly Gln Ala Pro Arg Leu Leu
        35                  40                  45

Ile Tyr Gly Ala Ser Asp Arg Ala Asn Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Ser Leu Tyr Pro
                85                  90                  95

Pro Thr Phe Gly Gly Gly Thr Lys Val Glu Ile Lys
            100                 105

<210> SEQ ID NO 219
<211> LENGTH: 108
<212> TYPE: PRT
<213> ORGANISM: Artificial Sequence
<220> FEATURE:
<223> OTHER INFORMATION: Synthetic

<400> SEQUENCE: 219

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Asn Ala Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asp Arg Ala Asn Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Ser Ile Tyr Pro
                85                  90                  95

Pro Thr Phe Gly Gly Gly Thr Lys Val Glu Ile Lys
            100                 105

<210> SEQ ID NO 220
<211> LENGTH: 108
<212> TYPE: PRT
<213> ORGANISM: Artificial Sequence
<220> FEATURE:
<223> OTHER INFORMATION: Synthetic

<400> SEQUENCE: 220

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Asn Ala Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Tyr Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln His Ser Leu Tyr Pro
                 85                  90                  95

Pro Thr Phe Gly Gly Gly Thr Lys Val Glu Ile Lys
            100                 105
```

<210> SEQ ID NO 221
<211> LENGTH: 106
<212> TYPE: PRT
<213> ORGANISM: Artificial Sequence
<220> FEATURE:
<223> OTHER INFORMATION: Synthetic

<400> SEQUENCE: 221

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Asn Ser Trp
             20                  25                  30

Leu Ala Trp Tyr Gln Gln Lys Pro Gly Lys Ala Pro Lys Leu Leu Ile
         35                  40                  45

Ser Asp Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Ser His Ile Thr
                 85                  90                  95

Phe Gly Gly Gly Thr Lys Val Glu Ile Lys
            100                 105
```

<210> SEQ ID NO 222
<211> LENGTH: 107
<212> TYPE: PRT
<213> ORGANISM: Artificial Sequence
<220> FEATURE:
<223> OTHER INFORMATION: Synthetic

<400> SEQUENCE: 222

```
Asp Ile Gln Met Thr Gln Ser Pro Ser Val Ser Ala Ser Val Gly
 1               5                  10                  15

Asp Arg Val Thr Ile Thr Cys Ala Ala Ser Gln Gly Ile Ser Ser Asp
             20                  25                  30

Leu Ala Trp Tyr Gln Gln Lys Pro Gly Lys Ala Pro Lys Leu Leu Ile
         35                  40                  45

Tyr Ser Ala Ser Ser Thr Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Tyr Leu Tyr Pro Ile
                 85                  90                  95

Thr Phe Gly Gly Gly Thr Lys Val Glu Ile Lys
            100                 105
```

<210> SEQ ID NO 223
<211> LENGTH: 107
<212> TYPE: PRT

<213> ORGANISM: Artificial Sequence
<220> FEATURE:
<223> OTHER INFORMATION: Synthetic

<400> SEQUENCE: 223

Gly Val Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Tyr
            20                  25                  30

Leu Asn Trp Tyr Gln Gln Lys Pro Gly Lys Ala Pro Lys Leu Leu Ile
        35                  40                  45

Tyr Asp Ala Phe Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Pro Phe Leu Pro Ile
                85                  90                  95

Thr Phe Gly Gly Gly Thr Lys Val Glu Ile Lys
            100                 105

<210> SEQ ID NO 224
<211> LENGTH: 112
<212> TYPE: PRT
<213> ORGANISM: Artificial Sequence
<220> FEATURE:
<223> OTHER INFORMATION: Synthetic

<400> SEQUENCE: 224

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gly Gly Pro Trp Thr Phe Gly Gly Gly Thr Lys Val Glu Ile Lys
            100                 105                 110

<210> SEQ ID NO 225
<211> LENGTH: 108
<212> TYPE: PRT
<213> ORGANISM: Artificial Sequence
<220> FEATURE:
<223> OTHER INFORMATION: Synthetic

<400> SEQUENCE: 225

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Val Ser Asp Pro
                85                  90                  95

Ile Thr Phe Gly Gly Gly Thr Lys Val Glu Ile Lys
            100                 105

<210> SEQ ID NO 226
<211> LENGTH: 108
<212> TYPE: PRT
<213> ORGANISM: Artificial Sequence
<220> FEATURE:
<223> OTHER INFORMATION: Synthetic

<400> SEQUENCE: 226

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Arg Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Gly Ser Ser Pro
                85                  90                  95

Ile Thr Phe Gly Gly Gly Thr Lys Val Glu Ile Lys
            100                 105

<210> SEQ ID NO 227
<211> LENGTH: 107
<212> TYPE: PRT
<213> ORGANISM: Artificial Sequence
<220> FEATURE:
<223> OTHER INFORMATION: Synthetic

<400> SEQUENCE: 227

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Leu Val Pro Arg
                85                  90                  95

Thr Phe Gly Gly Gly Thr Lys Val Glu Ile Lys
            100                 105

<210> SEQ ID NO 228
<211> LENGTH: 108
<212> TYPE: PRT
<213> ORGANISM: Artificial Sequence
<220> FEATURE:
<223> OTHER INFORMATION: Synthetic

<400> SEQUENCE: 228

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ala Asn His His Pro Pro
                85                  90                  95

Phe Thr Phe Gly Gly Gly Thr Lys Val Glu Ile Lys
            100                 105

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232
<211> LENGTH: 450
<212> TYPE: PRT
<213> ORGANISM: Artificial Sequence
<220> FEATURE:
<223> OTHER INFORMATION: Synthetic

<400> SEQUENCE: 232

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Arg Arg Ala Val Pro Phe Asp Tyr Trp Gly Gln
            100                 105                 110

Gly Thr Leu Val Thr Val Ser Ser Ala Ser Thr Lys Gly Pro Ser Val
        115                 120                 125

```
Phe Pro Leu Ala Pro Ser Ser Lys Ser Thr Ser Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 233
<211> LENGTH: 450
<212> TYPE: PRT
<213> ORGANISM: Artificial Sequence
<220> FEATURE:
<223> OTHER INFORMATION: Synthetic

<400> SEQUENCE: 233

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30
```

-continued

```
Ser Thr Tyr Trp Ala Trp Ile Arg Gln Pro Pro Gly Lys Gly Leu Glu
         35                  40                  45
Trp Ile Gly Ser Ile Ser Ser Gly Ser Thr Tyr Tyr Asn Pro Ser
 50                  55                  60
Leu Lys Ser Arg Val Thr Ile Ser Val Asp Thr Ser Lys Asn Gln Phe
 65                  70                  75                  80
Ser Leu Lys Leu Ser Ser Val Thr Ala Ala Asp Thr Ala Val Tyr Tyr
                 85                  90                  95
Cys Ala Arg Gly Ile Ala Arg Ala Val Pro Phe Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Ala Ala Gly Ala
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys
```

450

<210> SEQ ID NO 234
<211> LENGTH: 450
<212> TYPE: PRT
<213> ORGANISM: Artificial Sequence
<220> FEATURE:
<223> OTHER INFORMATION: Synthetic

<400> SEQUENCE: 234

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Gly Trp Ile Arg Gln Ser Pro Gly Lys Gly Leu Glu
        35                  40                  45

Trp Ile Gly Ser Ile His His Ser Gly Ala Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Pro Lys Arg Ala Val Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
                355                 360                 365
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 235
<211> LENGTH: 450
<212> TYPE: PRT
<213> ORGANISM: Artificial Sequence
<220> FEATURE:
<223> OTHER INFORMATION: Synthetic

<400> SEQUENCE: 235

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Thr Tyr Trp Gly Trp Ile Arg Gln Pro Pro Gly Lys Gly Leu Glu
        35                  40                  45

Trp Ile Gly Ser Ile His Tyr Ser Gly Ser Thr Leu Tyr Asn Pro Ser
    50                  55                  60

Leu Lys Ser Arg Val Thr Ile Ser Val Asp Thr Ser Lys Asn Gln Phe
65              70                  75                  80

Ser Leu Lys Leu Ser Ser Val Thr Ala Ala Asp Thr Ala Val Tyr Tyr
            85                  90                  95

Cys Ala Arg Gly Val Arg Arg Ala Val Pro Phe Val Asp Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
```

```
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 236
<211> LENGTH: 450
<212> TYPE: PRT
<213> ORGANISM: Artificial Sequence
<220> FEATURE:
<223> OTHER INFORMATION: Synthetic

<400> SEQUENCE: 236

Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Ala
            20                  25                  30
Asp Asn Tyr Trp Gly Trp Ile Arg Gln Pro Pro Gly Lys Gly Leu Glu
        35                  40                  45
Trp Ile Gly Ser Ile His Tyr Ser Gly Ser Thr Tyr Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Gly Val Arg Arg Ala Val Pro Phe Gln Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
```

```
                165                 170                 175
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 237
<211> LENGTH: 450
<212> TYPE: PRT
<213> ORGANISM: Artificial Sequence
<220> FEATURE:
<223> OTHER INFORMATION: Synthetic

<400> SEQUENCE: 237

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser
            20                  25                  30

Asp Thr Tyr Trp Gly Trp Ile Arg Gln Pro Pro Gly Lys Gly Pro Glu
        35                  40                  45

Trp Ile Gly Ser Ile His Tyr Ser Gly Ser Thr Leu Tyr Asn Pro Ser
    50                  55                  60

Leu Lys Ser Arg Val Thr Ile Ser Val Asp Thr Ser Lys Asn Gln Phe
```

```
                65                  70                  75                  80
Ser Leu Lys Leu Ser Ser Val Thr Ala Ala Asp Thr Ala Val Tyr Tyr
                    85                  90                  95

Cys Ala Arg Gly Val Arg Arg Ala Val Pro Phe Asp Tyr Trp Gly Gln
                100                 105                 110

Gly Thr Leu Val Thr Val Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 238
<211> LENGTH: 450
<212> TYPE: PRT
<213> ORGANISM: Artificial Sequence
```

<220> FEATURE:
<223> OTHER INFORMATION: Synthetic

<400> SEQUENCE: 238

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Ser Trp Ile Arg Gln Pro Pro Gly Lys Gly Leu Glu
        35                  40                  45

Trp Ile Gly Gly Ile Ala Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Arg Arg Ala Val Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 239
<211> LENGTH: 450
<212> TYPE: PRT
<213> ORGANISM: Artificial Sequence
<220> FEATURE:
<223> OTHER INFORMATION: Synthetic

<400> SEQUENCE: 239

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Ser Trp Ile Arg Gln Pro Pro Gly Lys Gly Leu Glu
            35                  40                  45

Trp Ile Gly Ser Ile Ser Tyr Asn Ala Leu Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Thr Arg Arg Ala Val Pro Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 240
<211> LENGTH: 450
<212> TYPE: PRT
<213> ORGANISM: Artificial Sequence
<220> FEATURE:
<223> OTHER INFORMATION: Synthetic

<400> SEQUENCE: 240

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Ser Trp Ile Arg Gln Pro Pro Gly Lys Gly Leu Glu
        35                  40                  45

Trp Ile Gly Gly Ile Ala Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Arg Arg Ala Val Pro Phe Ala Asp Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 241
<211> LENGTH: 450
<212> TYPE: PRT
<213> ORGANISM: Artificial Sequence
<220> FEATURE:
<223> OTHER INFORMATION: Synthetic

<400> SEQUENCE: 241

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Ser
            20                  25                  30

Ser Thr Tyr Trp Ser Trp Ile Arg Gln Pro Pro Gly Lys Gly Leu Glu
        35                  40                  45

Trp Ile Gly Gly Ile Ala Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Arg Arg Ala Val Pro Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 242
<211> LENGTH: 450
<212> TYPE: PRT
<213> ORGANISM: Artificial Sequence
<220> FEATURE:
<223> OTHER INFORMATION: Synthetic

<400> SEQUENCE: 242

Gln Leu Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Ser Ser Ser
             20                  25                  30

Ser Thr Tyr Trp Ser Trp Ile Arg Gln Pro Pro Gly Lys Gly Leu Glu
             35                  40                  45

Trp Ile Gly Gly Ile Ala Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Thr Arg Arg Ala Val Pro Phe Asp Tyr Trp Gly Gln
             100                 105                 110

Gly Thr Leu Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
                 180                 185                 190

Ser Ser Ser Leu Gly Thr Gln Thr Tyr Ile Cys Asn Val Asn His Lys
                 195                 200                 205

Pro Ser Asn Thr Lys Val Asp Lys Lys Val Glu Pro Lys Ser Cys Asp
     210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
             245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
             275                 280                 285

Asn Ala Lys Thr Lys Pro Arg Glu Glu Gln Tyr Asn Ser Thr Tyr Arg
     290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
             325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
             355                 360                 365

Thr Cys Leu Val Lys Gly Phe Tyr Pro Ser Asp Ile Ala Val Glu Trp
             370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430
```

```
Glu Ala Leu His Asn His Tyr Thr Gln Lys Ser Leu Ser Leu Ser Pro
            435                 440                 445
Gly Lys
    450

<210> SEQ ID NO 243
<211> LENGTH: 450
<212> TYPE: PRT
<213> ORGANISM: Artificial Sequence
<220> FEATURE:
<223> OTHER INFORMATION: Synthetic

<400> SEQUENCE: 243

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Thr Tyr Trp Gly Trp Ile Arg Gln Pro Pro Gly Lys Gly Leu Glu
        35                  40                  45

Trp Ile Gly Ser Ile His Tyr Ser Gly Ser Thr Leu Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ile Arg Arg Ala Val Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 244
<211> LENGTH: 450
<212> TYPE: PRT
<213> ORGANISM: Artificial Sequence
<220> FEATURE:
<223> OTHER INFORMATION: Synthetic

<400> SEQUENCE: 244

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Thr Tyr Trp Gly Trp Ile Arg Gln Pro Pro Gly Lys Gly Leu Glu
        35                  40                  45

Trp Ile Gly Ser Ile His Tyr Ser Gly Ser Thr Leu Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gln Phe Arg Ala Val Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 245
<211> LENGTH: 452
<212> TYPE: PRT
<213> ORGANISM: Artificial Sequence
<220> FEATURE:
<223> OTHER INFORMATION: Synthetic

<400> SEQUENCE: 245

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Thr His Thr Tyr Ser Arg Gly Pro Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140
```

```
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 246
<211> LENGTH: 452
<212> TYPE: PRT
<213> ORGANISM: Artificial Sequence
<220> FEATURE:
<223> OTHER INFORMATION: Synthetic

<400> SEQUENCE: 246

Gln Leu Gln Leu Gln Glu Ser Gly Pro Arg Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45
```

```
Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Thr His Thr Tyr Ser Arg Gly Pro Phe Asp Val Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450
```

```
<210> SEQ ID NO 247
<211> LENGTH: 452
<212> TYPE: PRT
<213> ORGANISM: Artificial Sequence
<220> FEATURE:
<223> OTHER INFORMATION: Synthetic

<400> SEQUENCE: 247

Leu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Leu Ser Gly
            20                  25                  30

Tyr Tyr Trp Phe Trp Ile Arg Gln Pro Pro Gly Lys Gly Leu Glu Trp
        35                  40                  45

Ile Gly Gly Ile Tyr His Ser Ala Ser Thr Ala Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Thr Pro Ile Tyr Ser Arg Gly Pro Leu Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
```

```
            370                 375                 380
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
            435                 440                 445

Ser Pro Gly Lys
    450

<210> SEQ ID NO 248
<211> LENGTH: 452
<212> TYPE: PRT
<213> ORGANISM: Artificial Sequence
<220> FEATURE:
<223> OTHER INFORMATION: Synthetic

<400> SEQUENCE: 248

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

His Tyr Trp Ile Trp Ile Arg Gln Pro Pro Gly Lys Gly Leu Glu Trp
        35                  40                  45

Ile Gly Gly Ile Tyr His Ser Gly Ser Thr Tyr Tyr Asn Pro Ser Leu
    50                  55                  60

Lys Ser Arg Val Thr Ile Ser Val Asp Thr Ser Lys Asp Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Gln Thr Tyr Ser Arg Gly Pro Leu Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
```

-continued

```
                275                 280                 285
Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 249
<211> LENGTH: 452
<212> TYPE: PRT
<213> ORGANISM: Artificial Sequence
<220> FEATURE:
<223> OTHER INFORMATION: Synthetic

<400> SEQUENCE: 249

Gln Val Gln Leu Gln Glu Ser Gly Pro Gly Leu Val Lys Pro Pro Glu
1               5                   10                  15

Thr Leu Ser Leu Thr Cys Ala Val Ser Gly Tyr Ser Ile Ser Ser Gly
            20                  25                  30

His Tyr Trp Ile Trp Ile Arg Gln Pro Pro Gly Lys Gly Leu Glu Trp
        35                  40                  45

Ile Gly Gly Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ala Thr Tyr Ser Arg Gly Pro Leu Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
```

```
            180                 185                 190
Val Pro Ser Ser Leu Gly Thr Gln Thr Tyr Ile Cys Asn Val Asn
        195                 200                 205
His Lys Pro Ser Asn Thr Lys Val Asp Lys Val Glu Pro Lys Ser
    210                 215                 220
Cys Asp Lys Thr His Thr Cys Pro Pro Cys Pro Ala Pro Glu Ala Ala
225                 230                 235                 240
Gly Ala Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 250
<211> LENGTH: 452
<212> TYPE: PRT
<213> ORGANISM: Artificial Sequence
<220> FEATURE:
<223> OTHER INFORMATION: Synthetic

<400> SEQUENCE: 250

Gln Val Gln Leu Gln Glu Ser Gly Pro Gly Leu Val Lys Pro Ser Glu
1               5                   10                  15
Thr Leu Ser Leu Thr Cys Ala Val Ser Gly Tyr Ser Ile Leu Ser Gly
            20                  25                  30
Tyr Tyr Trp Phe Trp Ile Arg Gln Pro Pro Gly Lys Gly Leu Glu Trp
        35                  40                  45
Ile Gly Gly Ile Tyr His Ser Gly Ser Thr Tyr Tyr Asn Pro Ser Leu
    50                  55                  60
Lys Ser Arg Val Thr Ile Ser Val Asp Thr Ser Lys Asn Gln Phe Ser
65                  70                  75                  80
Leu Lys Leu Ser Ser Val Thr Ala Ala Asp Thr Ala Val Tyr Tyr Cys
```

```
            85                  90                  95
Ala Arg Gly Gly Thr His Thr Tyr Ser Arg Gly Pro Leu Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 251
<211> LENGTH: 452
<212> TYPE: PRT
<213> ORGANISM: Artificial Sequence
<220> FEATURE:
<223> OTHER INFORMATION: Synthetic
```

<400> SEQUENCE: 251

```
Gln Val Gln Leu Gln Glu Ser Gly Pro Gly Leu Val Lys Pro Ser Glu
 1               5                  10                  15
Thr Leu Ser Leu Thr Cys Ala Val Ser Gly Tyr Ser Ile Ser Ser Gly
            20                  25                  30
Phe Tyr Trp Thr Trp Ile Arg Gln Pro Pro Gly Lys Gly Leu Glu Trp
        35                  40                  45
Ile Gly Ala Ile Tyr His Ser Gly Ser Thr Val Tyr Asn Pro Ser Leu
    50                  55                  60
Lys Ser Arg Val Thr Ile Ser Val Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Gly Gly Thr His Thr Tyr Ser Arg Gly Pro Leu Asp Val Trp
            100                 105                 110
Gly Gln Gly Thr Thr Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Ala Ala
225                 230                 235                 240
Gly Ala Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
```

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 252
<211> LENGTH: 452
<212> TYPE: PRT
<213> ORGANISM: Artificial Sequence
<220> FEATURE:
<223> OTHER INFORMATION: Synthetic

<400> SEQUENCE: 252

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Leu Trp Ile Arg Gln Pro Pro Gly Lys Gly Leu Glu Trp
            35                  40                  45

Ile Gly Gly Ile Tyr His Ser Ala Ser Thr Ala Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Gly Thr Val Lys Tyr Ser Arg Gly Pro Leu Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
        210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320
```

```
Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 253
<211> LENGTH: 452
<212> TYPE: PRT
<213> ORGANISM: Artificial Sequence
<220> FEATURE:
<223> OTHER INFORMATION: Synthetic

<400> SEQUENCE: 253

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

His Tyr Trp Thr Trp Ile Arg Gln Pro Pro Gly Lys Gly Leu Glu Trp
        35                  40                  45

Ile Gly Ala Ile Tyr His Ser Gly Ser Thr Val Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gln Val Thr Tyr Ser Arg Gly Pro Leu Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220
```

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 254
<211> LENGTH: 452
<212> TYPE: PRT
<213> ORGANISM: Artificial Sequence
<220> FEATURE:
<223> OTHER INFORMATION: Synthetic

<400> SEQUENCE: 254

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Leu Ser Gly
            20                  25                  30

Tyr Tyr Trp Phe Trp Ile Arg Gln Pro Pro Gly Lys Gly Leu Glu Trp
        35                  40                  45

Ile Gly Gly Ile Tyr His Ser Gly Ser Thr Ala Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Glu Val Thr Tyr Ser Arg Gly Pro Leu Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 255
<211> LENGTH: 453
<212> TYPE: PRT
<213> ORGANISM: Artificial Sequence
<220> FEATURE:
<223> OTHER INFORMATION: Synthetic

<400> SEQUENCE: 255

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn Tyr
            20                  25                  30

```
Ala Met His Trp Val Arg Gln Ala Pro Gly Lys Gly Leu Glu Trp Val
         35                  40                  45

Ser Ala Ile Ser Ala Arg Ala Gly Ile Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Ile Gly Tyr Ser Tyr Gly Thr Ala Pro Pro Phe Asp Val
                100                 105                 110

Trp Gly Gln Gly Thr Thr Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Ala
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445
```

Leu Ser Pro Gly Lys
            450

<210> SEQ ID NO 256
<211> LENGTH: 448
<212> TYPE: PRT
<213> ORGANISM: Artificial Sequence
<220> FEATURE:
<223> OTHER INFORMATION: Synthetic

<400> SEQUENCE: 256

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ala Ser Ser Gly Ser Val Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Thr Pro Arg Ala Phe Asp Ile Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 257
<211> LENGTH: 449
<212> TYPE: PRT
<213> ORGANISM: Artificial Sequence
<220> FEATURE:
<223> OTHER INFORMATION: Synthetic

<400> SEQUENCE: 257

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ala Trp Val Arg Gln Ala Pro Gly Lys Gly Leu Glu Trp Val
        35                  40                  45

Ser Thr Ile Ser Gly Ser Gly Ile Thr Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Arg His Leu Asn Ala Phe Asn Arg Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 258
<211> LENGTH: 451
<212> TYPE: PRT
<213> ORGANISM: Artificial Sequence
<220> FEATURE:
<223> OTHER INFORMATION: Synthetic

<400> SEQUENCE: 258

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Val Tyr His Tyr Asp Pro Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

```
              180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Val Glu Pro Lys Ser Cys
        210                 215                 220
Asp Lys Thr His Thr Cys Pro Pro Cys Pro Ala Pro Glu Ala Ala Gly
225                 230                 235                 240
Ala Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 259
<211> LENGTH: 450
<212> TYPE: PRT
<213> ORGANISM: Artificial Sequence
<220> FEATURE:
<223> OTHER INFORMATION: Synthetic

<400> SEQUENCE: 259

Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Ser
                20                  25                  30
Ser Tyr Tyr Trp Gly Trp Ile Arg Gln Pro Pro Gly Lys Gly Leu Glu
            35                  40                  45
Trp Ile Gly Ser Ile Ser Tyr Ser Gly Ser Thr Tyr Tyr Asn Pro Ser
        50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
```

```
                        85                  90                  95
Cys Ala Arg Thr Glu Leu Gly Lys Met His Phe Asp Tyr Trp Gly Gln
                    100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Ala Ala Gly Ala
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
450

<210> SEQ ID NO 260
<211> LENGTH: 448
<212> TYPE: PRT
<213> ORGANISM: Artificial Sequence
<220> FEATURE:
<223> OTHER INFORMATION: Synthetic
```

```
<400> SEQUENCE: 260

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Pro Arg Tyr Met Gln Asp Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445
```

<210> SEQ ID NO 261
<211> LENGTH: 451
<212> TYPE: PRT
<213> ORGANISM: Artificial Sequence
<220> FEATURE:
<223> OTHER INFORMATION: Synthetic

<400> SEQUENCE: 261

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Ser Leu Gly Thr His Asn Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

```
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 262
<211> LENGTH: 453
<212> TYPE: PRT
<213> ORGANISM: Artificial Sequence
<220> FEATURE:
<223> OTHER INFORMATION: Synthetic

<400> SEQUENCE: 262

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
            35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65              70                  75                  80

Leu Lys Leu Ser Ser Val Thr Ala Ala Asp Thr Ala Val Tyr Tyr Cys
            85                  90                  95

Ala Arg Glu Gly Ala Leu Ser Tyr Ser Trp Leu Ala Ala Phe Asp Ile
            100                 105                 110

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Ala
225                 230                 235                 240
```

Ala Gly Ala Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266
<211> LENGTH: 447
<212> TYPE: PRT
<213> ORGANISM: Artificial Sequence
<220> FEATURE:
<223> OTHER INFORMATION: Synthetic

<400> SEQUENCE: 266

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

```
Asp Tyr Tyr Trp Gly Trp Ile Arg Gln Pro Pro Gly Lys Gly Leu Glu
         35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Val Arg Arg Ala Val Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

```
<210> SEQ ID NO 267
<211> LENGTH: 447
<212> TYPE: PRT
<213> ORGANISM: Artificial Sequence
<220> FEATURE:
<223> OTHER INFORMATION: Synthetic

<400> SEQUENCE: 267

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Ala Trp Ile Arg Gln Pro Pro Gly Lys Gly Leu Glu
        35                  40                  45

Trp Ile Gly Ser Ile Ser Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ile Ala Arg Ala Val Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445
```

<210> SEQ ID NO 268
<211> LENGTH: 447
<212> TYPE: PRT
<213> ORGANISM: Artificial Sequence
<220> FEATURE:
<223> OTHER INFORMATION: Synthetic

<400> SEQUENCE: 268

```
Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Ser
            20                  25                  30
Ser Thr Tyr Trp Gly Trp Ile Arg Gln Ser Pro Gly Lys Gly Leu Glu
        35                  40                  45
Trp Ile Gly Ser Ile His His Ser Gly Ala Thr Tyr Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
            85                  90                  95
Cys Ala Arg Gly Pro Lys Arg Ala Val Pro Phe Asp Tyr Trp Gly Gln
        100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
```

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
                435                 440                 445

<210> SEQ ID NO 269
<211> LENGTH: 447
<212> TYPE: PRT
<213> ORGANISM: Artificial Sequence
<220> FEATURE:
<223> OTHER INFORMATION: Synthetic

<400> SEQUENCE: 269

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Asp Thr Tyr Trp Gly Trp Ile Arg Gln Pro Pro Gly Lys Gly Leu Glu
            35                  40                  45

Trp Ile Gly Ser Ile His Tyr Ser Gly Ser Thr Leu Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Arg Arg Ala Val Pro Phe Val Asp Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

```
Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 270
<211> LENGTH: 447
<212> TYPE: PRT
<213> ORGANISM: Artificial Sequence
<220> FEATURE:
<223> OTHER INFORMATION: Synthetic

<400> SEQUENCE: 270

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ala
            20                  25                  30

Asp Asn Tyr Trp Gly Trp Ile Arg Gln Pro Pro Gly Lys Gly Leu Glu
        35                  40                  45

Trp Ile Gly Ser Ile His Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Arg Arg Ala Val Pro Phe Gln Arg Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 271
<211> LENGTH: 447
<212> TYPE: PRT
<213> ORGANISM: Artificial Sequence
<220> FEATURE:
<223> OTHER INFORMATION: Synthetic

<400> SEQUENCE: 271

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Asp Thr Tyr Trp Gly Trp Ile Arg Gln Pro Pro Gly Lys Gly Pro Glu
            35                  40                  45
```

Trp Ile Gly Ser Ile His Tyr Ser Gly Ser Thr Leu Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Val Arg Arg Ala Val Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 272
<211> LENGTH: 447
<212> TYPE: PRT

<213> ORGANISM: Artificial Sequence
<220> FEATURE:
<223> OTHER INFORMATION: Synthetic

<400> SEQUENCE: 272

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Ser Trp Ile Arg Gln Pro Pro Gly Lys Gly Leu Glu
        35                  40                  45

Trp Ile Gly Gly Ile Ala Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Val Arg Arg Ala Val Pro Phe Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
    195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
```

```
              385                 390                 395                 400
Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445
```

<210> SEQ ID NO 273
<211> LENGTH: 447
<212> TYPE: PRT
<213> ORGANISM: Artificial Sequence
<220> FEATURE:
<223> OTHER INFORMATION: Synthetic

<400> SEQUENCE: 273

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Thr Tyr Trp Ser Trp Ile Arg Gln Pro Pro Gly Lys Gly Leu Glu
            35                  40                  45

Trp Ile Gly Ser Ile Ser Tyr Asn Ala Leu Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Thr Arg Arg Ala Val Pro Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
```

| | | | | | | 305 | | | | 310 | | | | 315 | | | | 320 |

Cys Lys Val Ser Asn Lys Gly Leu Pro Ser Ser Ile Glu Lys Thr Ile
                325                330                335

Ser Lys Ala Lys Gly Gln Pro Arg Glu Pro Gln Val Tyr Thr Leu Pro
            340                345                350

Pro Ser Gln Glu Glu Met Thr Lys Asn Gln Val Ser Leu Thr Cys Leu
            355                360                365

Val Lys Gly Phe Tyr Pro Ser Asp Ile Ala Val Glu Trp Glu Ser Asn
      370                375                380

Gly Gln Pro Glu Asn Asn Tyr Lys Thr Thr Pro Pro Val Leu Asp Ser
385                  390                395              400

Asp Gly Ser Phe Phe Leu Tyr Ser Arg Leu Thr Val Asp Lys Ser Arg
                405              410              415

Trp Gln Glu Gly Asn Val Phe Ser Cys Ser Val Met His Glu Ala Leu
            420              425              430

His Asn His Tyr Thr Gln Lys Ser Leu Ser Leu Ser Pro Gly Lys
            435              440              445

<210> SEQ ID NO 274
<211> LENGTH: 447
<212> TYPE: PRT
<213> ORGANISM: Artificial Sequence
<220> FEATURE:
<223> OTHER INFORMATION: Synthetic

<400> SEQUENCE: 274

Gln Leu Gln Leu Gln Glu Ser Gly Pro Gly Leu Val Lys Pro Ser Glu
1                  5                  10                15

Thr Leu Ser Leu Thr Cys Thr Val Ser Gly Gly Ser Ile Ser Ser Ser
            20                25                30

Ser Thr Tyr Trp Ser Trp Ile Arg Gln Pro Pro Gly Lys Gly Leu Glu
         35                40                45

Trp Ile Gly Gly Ile Ala Tyr Ser Gly Ser Thr Tyr Tyr Asn Pro Ser
50                  55                60

Leu Lys Ser Arg Val Thr Ile Ser Val Asp Thr Ser Lys Asn Gln Phe
65                  70                75              80

Ser Leu Lys Leu Ser Ser Val Thr Ala Ala Asp Thr Ala Val Tyr Tyr
            85                90                95

Cys Ala Arg Gly Val Arg Arg Ala Val Pro Phe Ala Asp Trp Gly Gln
              100                105              110

Gly Thr Leu Val Thr Val Ser Ser Ala Ser Thr Lys Gly Pro Ser Val
            115                120                125

Phe Pro Leu Ala Pro Cys Ser Arg Ser Thr Ser Glu Ser Thr Ala Ala
      130                135                140

Leu Gly Cys Leu Val Lys Asp Tyr Phe Pro Glu Pro Val Thr Val Ser
145                  150                155              160

Trp Asn Ser Gly Ala Leu Thr Ser Gly Val His Thr Phe Pro Ala Val
              165                170              175

Leu Gln Ser Ser Gly Leu Tyr Ser Leu Ser Ser Val Val Thr Val Pro
            180                185              190

Ser Ser Ser Leu Gly Thr Lys Thr Tyr Thr Cys Asn Val Asp His Lys
         195                200                205

Pro Ser Asn Thr Lys Val Asp Lys Arg Val Glu Ser Lys Tyr Gly Pro
      210                215                220

Pro Cys Pro Pro Cys Pro Ala Pro Glu Phe Leu Gly Gly Pro Ser Val

```
                    225                 230                 235                 240
        Phe Leu Phe Pro Pro Lys Pro Lys Asp Thr Leu Met Ile Ser Arg Thr
                        245                 250                 255

Pro Glu Val Thr Cys Val Val Val Asp Val Ser Gln Glu Asp Pro Glu
                        260                 265                 270

Val Gln Phe Asn Trp Tyr Val Asp Gly Val Glu Val His Asn Ala Lys
                        275                 280                 285

Thr Lys Pro Arg Glu Glu Gln Phe Asn Ser Thr Tyr Arg Val Val Ser
                        290                 295                 300

Val Leu Thr Val Leu His Gln Asp Trp Leu Asn Gly Lys Glu Tyr Lys
        305                 310                 315                 320

Cys Lys Val Ser Asn Lys Gly Leu Pro Ser Ser Ile Glu Lys Thr Ile
                        325                 330                 335

Ser Lys Ala Lys Gly Gln Pro Arg Glu Pro Gln Val Tyr Thr Leu Pro
                        340                 345                 350

Pro Ser Gln Glu Glu Met Thr Lys Asn Gln Val Ser Leu Thr Cys Leu
                        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Arg Leu Thr Val Asp Lys Ser Arg
                        405                 410                 415

Trp Gln Glu Gly Asn Val Phe Ser Cys Ser Val Met His Glu Ala Leu
                        420                 425                 430

His Asn His Tyr Thr Gln Lys Ser Leu Ser Leu Ser Pro Gly Lys
                        435                 440                 445

<210> SEQ ID NO 275
<211> LENGTH: 447
<212> TYPE: PRT
<213> ORGANISM: Artificial Sequence
<220> FEATURE:
<223> OTHER INFORMATION: Synthetic

<400> SEQUENCE: 275

Gln Leu Gln Leu Gln Glu Ser Gly Pro Gly Leu Val Lys Pro Ser Glu
        1               5                   10                  15

Thr Leu Ser Leu Thr Cys Thr Val Ser Gly Gly Ser Val Ser Ser Ser
                        20                  25                  30

Ser Thr Tyr Trp Ser Trp Ile Arg Gln Pro Pro Gly Lys Gly Leu Glu
                        35                  40                  45

Trp Ile Gly Gly Ile Ala Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
        65                  70                  75                  80

Ser Leu Lys Leu Ser Ser Val Thr Ala Ala Asp Thr Ala Val Tyr Tyr
                        85                  90                  95

Cys Ala Arg Gly Val Arg Arg Ala Val Pro Phe Asp Tyr Trp Gly Gln
                        100                 105                 110

Gly Thr Leu Val Thr Val Ser Ser Ala Ser Thr Lys Gly Pro Ser Val
                        115                 120                 125

Phe Pro Leu Ala Pro Cys Ser Arg Ser Thr Ser Glu Ser Thr Ala Ala
                        130                 135                 140

Leu Gly Cys Leu Val Lys Asp Tyr Phe Pro Glu Pro Val Thr Val Ser
```

```
145                 150                 155                 160
Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 276
<211> LENGTH: 447
<212> TYPE: PRT
<213> ORGANISM: Artificial Sequence
<220> FEATURE:
<223> OTHER INFORMATION: Synthetic

<400> SEQUENCE: 276

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Thr Tyr Trp Ser Trp Ile Arg Gln Pro Pro Gly Lys Gly Leu Glu
            35                  40                  45

Trp Ile Gly Gly Ile Ala Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
```

65                  70                  75                  80
Ser Leu Lys Leu Ser Ser Val Thr Ala Ala Asp Thr Ala Val Tyr Tyr
                    85                  90                  95

Cys Ala Arg Gly Thr Arg Arg Ala Val Pro Phe Asp Tyr Trp Gly Gln
                100                 105                 110

Gly Thr Leu Val Thr Val Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 277
<211> LENGTH: 447
<212> TYPE: PRT
<213> ORGANISM: Artificial Sequence
<220> FEATURE:
<223> OTHER INFORMATION: Synthetic

<400> SEQUENCE: 277

```
Gln Leu Gln Leu Gln Glu Ser Gly Pro Gly Leu Val Lys Pro Ser Glu
1               5                   10                  15
Thr Leu Ser Leu Thr Cys Thr Val Ser Gly Ser Ile Ser Ser Ser
            20                  25                  30
Asp Thr Tyr Trp Gly Trp Ile Arg Gln Pro Pro Gly Lys Gly Leu Glu
                35                  40                  45
Trp Ile Gly Ser Ile His Tyr Ser Gly Ser Thr Leu Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Gly Ile Arg Arg Ala Val Pro Phe Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
```

-continued

```
Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 278
<211> LENGTH: 447
<212> TYPE: PRT
<213> ORGANISM: Artificial Sequence
<220> FEATURE:
<223> OTHER INFORMATION: Synthetic

<400> SEQUENCE: 278

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser
            20                  25                  30

Asp Thr Tyr Trp Gly Trp Ile Arg Gln Pro Pro Gly Lys Gly Leu Glu
            35                  40                  45

Trp Ile Gly Ser Ile His Tyr Ser Gly Ser Thr Leu Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gln Phe Arg Ala Val Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335
```

-continued

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 279
<211> LENGTH: 449
<212> TYPE: PRT
<213> ORGANISM: Artificial Sequence
<220> FEATURE:
<223> OTHER INFORMATION: Synthetic

<400> SEQUENCE: 279

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Thr His Thr Tyr Ser Arg Gly Pro Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

```
Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 280
<211> LENGTH: 449
<212> TYPE: PRT
<213> ORGANISM: Artificial Sequence
<220> FEATURE:
<223> OTHER INFORMATION: Synthetic

<400> SEQUENCE: 280

Gln Leu Gln Leu Gln Glu Ser Gly Pro Arg Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Thr His Thr Tyr Ser Arg Gly Pro Phe Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160
```

-continued

```
Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 281
<211> LENGTH: 449
<212> TYPE: PRT
<213> ORGANISM: Artificial Sequence
<220> FEATURE:
<223> OTHER INFORMATION: Synthetic

<400> SEQUENCE: 281

```
Leu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Leu Ser Gly
            20                  25                  30

Tyr Tyr Trp Phe Trp Ile Arg Gln Pro Pro Gly Lys Gly Leu Glu Trp
        35                  40                  45

Ile Gly Gly Ile Tyr His Ser Ala Ser Thr Ala Tyr Asn Pro Ser Leu
    50                  55                  60

Lys Ser Arg Val Thr Ile Ser Val Asp Thr Ser Lys Asn Gln Phe Ser
```

```
                65                  70                  75                  80
Leu Lys Leu Ser Ser Val Thr Ala Ala Asp Thr Ala Val Tyr Tyr Cys
                    85                  90                  95
Ala Arg Gly Gly Thr Pro Ile Tyr Ser Arg Gly Pro Leu Asp Val Trp
                100                 105                 110
Gly Gln Gly Thr Thr Val Thr Val Ser Ser Ala Ser Thr Lys Gly Pro
                115                 120                 125
Ser Val Phe Pro Leu Ala Pro Cys Ser Arg Ser Thr Ser Glu Ser Thr
            130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Lys Thr Tyr Thr Cys Asn Val Asp
            195                 200                 205
His Lys Pro Ser Asn Thr Lys Val Asp Lys Arg Val Glu Ser Lys Tyr
        210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
                260                 265                 270
Pro Glu Val Gln Phe Asn Trp Tyr Val Asp Gly Val Glu Val His Asn
            275                 280                 285
Ala Lys Thr Lys Pro Arg Glu Glu Gln Phe Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 282
<211> LENGTH: 449
<212> TYPE: PRT
<213> ORGANISM: Artificial Sequence
<220> FEATURE:
```

<223> OTHER INFORMATION: Synthetic

<400> SEQUENCE: 282

```
Gln Val Gln Leu Gln Glu Ser Gly Pro Gly Leu Val Lys Pro Ser Glu
1               5                   10                  15
Thr Leu Ser Leu Thr Cys Ala Val Ser Gly Tyr Ser Ile Ser Ser Gly
            20                  25                  30
His Tyr Trp Ile Trp Ile Arg Gln Pro Pro Gly Lys Gly Leu Glu Trp
        35                  40                  45
Ile Gly Gly Ile Tyr His Ser Gly Ser Thr Tyr Tyr Asn Pro Ser Leu
    50                  55                  60
Lys Ser Arg Val Thr Ile Ser Val Asp Thr Ser Lys Asp Gln Phe Ser
65                  70                  75                  80
Leu Lys Leu Ser Ser Val Thr Ala Ala Asp Thr Ala Val Tyr Tyr Cys
                85                  90                  95
Ala Arg Gly Gly Gly Gln Thr Tyr Ser Arg Gly Pro Leu Asp Val Trp
            100                 105                 110
Gly Gln Gly Thr Thr Val Thr Val Ser Ser Ala Ser Thr Lys Gly Pro
        115                 120                 125
Ser Val Phe Pro Leu Ala Pro Cys Ser Arg Ser Thr Ser Glu Ser Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Lys Thr Tyr Thr Cys Asn Val Asp
        195                 200                 205
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 283
<211> LENGTH: 449
<212> TYPE: PRT
<213> ORGANISM: Artificial Sequence
<220> FEATURE:
<223> OTHER INFORMATION: Synthetic

<400> SEQUENCE: 283

Gln Val Gln Leu Gln Glu Ser Gly Pro Gly Leu Val Lys Pro Pro Glu
1               5                   10                  15

Thr Leu Ser Leu Thr Cys Ala Val Ser Gly Tyr Ser Ile Ser Ser Gly
            20                  25                  30

His Tyr Trp Ile Trp Ile Arg Gln Pro Pro Gly Lys Gly Leu Glu Trp
        35                  40                  45

Ile Gly Gly Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ala Thr Tyr Ser Arg Gly Pro Leu Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 284
<211> LENGTH: 449
<212> TYPE: PRT
<213> ORGANISM: Artificial Sequence
<220> FEATURE:
<223> OTHER INFORMATION: Synthetic

<400> SEQUENCE: 284

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Leu Ser Gly
            20                  25                  30

Tyr Tyr Trp Phe Trp Ile Arg Gln Pro Pro Gly Lys Gly Leu Glu Trp
        35                  40                  45

Ile Gly Gly Ile Tyr His Ser Gly Ser Thr Tyr Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Gly Thr His Thr Tyr Ser Arg Gly Pro Leu Asp Val Trp
        100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

```
Gly Pro Pro Cys Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 285
<211> LENGTH: 449
<212> TYPE: PRT
<213> ORGANISM: Artificial Sequence
<220> FEATURE:
<223> OTHER INFORMATION: Synthetic

<400> SEQUENCE: 285

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Phe Tyr Trp Thr Trp Ile Arg Gln Pro Pro Gly Lys Gly Leu Glu Trp
            35                  40                  45

Ile Gly Ala Ile Tyr His Ser Gly Ser Thr Val Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Gly Thr His Thr Tyr Ser Arg Gly Pro Leu Asp Val Trp
            100                 105                 110

Gly Gln Gly Thr Thr Val Thr Val Ser Ser Ala Ser Thr Lys Gly Pro
            115                 120                 125
```

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 286
<211> LENGTH: 449
<212> TYPE: PRT
<213> ORGANISM: Artificial Sequence
<220> FEATURE:
<223> OTHER INFORMATION: Synthetic

<400> SEQUENCE: 286

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Leu Trp Ile Arg Gln Pro Pro Gly Lys Gly Leu Glu Trp

```
             35                  40                  45
Ile Gly Gly Ile Tyr His Ser Ala Ser Thr Ala Tyr Asn Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Thr Val Lys Tyr Ser Arg Gly Pro Leu Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
            210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 287
<211> LENGTH: 449
<212> TYPE: PRT
<213> ORGANISM: Artificial Sequence
<220> FEATURE:
<223> OTHER INFORMATION: Synthetic

<400> SEQUENCE: 287

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

His Tyr Trp Thr Trp Ile Arg Gln Pro Pro Gly Lys Gly Leu Glu Trp
        35                  40                  45

Ile Gly Ala Ile Tyr His Ser Gly Ser Thr Val Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gln Val Thr Tyr Ser Arg Gly Pro Leu Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 288
<211> LENGTH: 449
<212> TYPE: PRT
<213> ORGANISM: Artificial Sequence
<220> FEATURE:
<223> OTHER INFORMATION: Synthetic

<400> SEQUENCE: 288

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Leu Ser Gly
            20                  25                  30

Tyr Tyr Trp Phe Trp Ile Arg Gln Pro Pro Gly Lys Gly Leu Glu Trp
        35                  40                  45

Ile Gly Gly Ile Tyr His Ser Gly Ser Thr Ala Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Glu Val Thr Tyr Ser Arg Gly Pro Leu Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
```

```
                275                 280                 285
Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 289
<211> LENGTH: 450
<212> TYPE: PRT
<213> ORGANISM: Artificial Sequence
<220> FEATURE:
<223> OTHER INFORMATION: Synthetic

<400> SEQUENCE: 289

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn Tyr
            20                  25                  30

Ala Met His Trp Val Arg Gln Ala Pro Gly Lys Gly Leu Glu Trp Val
        35                  40                  45

Ser Ala Ile Ser Ala Arg Ala Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ile Gly Tyr Ser Tyr Gly Thr Ala Pro Pro Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Leu Gly Thr Lys Thr Tyr Thr Cys Asn Val
        195                 200                 205
Asp His Lys Pro Ser Asn Thr Lys Val Asp Lys Arg Val Glu Ser Lys
210                 215                 220
Tyr Gly Pro Pro Cys Pro Pro Cys Pro Ala Pro Glu Phe Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
                260                 265                 270
Asp Pro Glu Val Gln Phe Asn Trp Tyr Val Asp Gly Val Glu Val His
                275                 280                 285
Asn Ala Lys Thr Lys Pro Arg Glu Glu Gln Phe Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Gln Glu Glu Met Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
    450

<210> SEQ ID NO 290
<211> LENGTH: 445
<212> TYPE: PRT
<213> ORGANISM: Artificial Sequence
<220> FEATURE:
<223> OTHER INFORMATION: Synthetic

<400> SEQUENCE: 290

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
                20                  25                  30
Tyr Met Ser Trp Ile Arg Gln Ala Pro Gly Lys Gly Leu Glu Trp Val
                35                  40                  45
Ser Tyr Ile Ala Ser Ser Gly Ser Val Ile Tyr Tyr Ala Asp Ser Val
                50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
```

```
Ala Arg His Gly Thr Pro Arg Ala Phe Asp Ile Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 291
<211> LENGTH: 446
<212> TYPE: PRT
<213> ORGANISM: Artificial Sequence
<220> FEATURE:
<223> OTHER INFORMATION: Synthetic

<400> SEQUENCE: 291

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser
            20                  25                  30

Ala Met Ala Trp Val Arg Gln Ala Pro Gly Lys Gly Leu Glu Trp Val
            35                  40                  45

Ser Thr Ile Ser Gly Ser Gly Ile Thr Thr Trp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ser Arg His Leu Asn Ala Phe Asn Arg Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430
```

Asn His Tyr Thr Gln Lys Ser Leu Ser Leu Ser Pro Gly Lys
         435                 440                 445

<210> SEQ ID NO 292
<211> LENGTH: 448
<212> TYPE: PRT
<213> ORGANISM: Artificial Sequence
<220> FEATURE:
<223> OTHER INFORMATION: Synthetic

<400> SEQUENCE: 292

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Val Tyr His Tyr Asp Pro Tyr Gly Met Asp Val Trp Gly
            100                 105                 110

Gln Gly Thr Thr Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

<210> SEQ ID NO 293
<211> LENGTH: 447
<212> TYPE: PRT
<213> ORGANISM: Artificial Sequence
<220> FEATURE:
<223> OTHER INFORMATION: Synthetic

<400> SEQUENCE: 293

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Glu Leu Gly Lys Met His Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270
```

```
Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 294
<211> LENGTH: 445
<212> TYPE: PRT
<213> ORGANISM: Artificial Sequence
<220> FEATURE:
<223> OTHER INFORMATION: Synthetic

<400> SEQUENCE: 294

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Ser
            20                  25                  30

Asp Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Pro Arg Tyr Met Gln Asp Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 295
<211> LENGTH: 448
<212> TYPE: PRT
<213> ORGANISM: Artificial Sequence
<220> FEATURE:
<223> OTHER INFORMATION: Synthetic

<400> SEQUENCE: 295

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg His Ser Ser Leu Gly Thr His Asn Trp Phe Asp Pro Trp Gly
            100                 105                 110

```
Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 296
<211> LENGTH: 450
<212> TYPE: PRT
<213> ORGANISM: Artificial Sequence
<220> FEATURE:
<223> OTHER INFORMATION: Synthetic

<400> SEQUENCE: 296

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30
```

```
Tyr Tyr Trp Gly Trp Ile Arg Gln Pro Pro Gly Lys Gly Leu Glu Trp
         35                  40                  45

Ile Gly Ser Ile Tyr His Ser Gly Ser Thr Tyr Tyr Asn Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Glu Gly Ala Leu Ser Tyr Ser Trp Leu Ala Ala Phe Asp Ile
            100                 105                 110

Trp Gly Gln Gly Thr Met Val Thr Val Ser Ser Ala Ser Thr Lys Gly
            115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
```

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 215
<212> TYPE: PRT
<213> ORGANISM: Artificial Sequence
<220> FEATURE:
<223> OTHER INFORMATION: Synthetic

<400> SEQUENCE: 300

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Val His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 301
<211> LENGTH: 215
<212> TYPE: PRT

<213> ORGANISM: Artificial Sequence
<220> FEATURE:
<223> OTHER INFORMATION: Synthetic

<400> SEQUENCE: 301

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Val His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 302
<211> LENGTH: 215
<212> TYPE: PRT
<213> ORGANISM: Artificial Sequence
<220> FEATURE:
<223> OTHER INFORMATION: Synthetic

<400> SEQUENCE: 302

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Val His Ser Pro
                85                  90                  95

Tyr Thr Phe Gly Gly Gly Thr Lys Val Glu Ile Lys Arg Thr Val Ala
            100                 105                 110
```

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215

<210> SEQ ID NO 303
<211> LENGTH: 215
<212> TYPE: PRT
<213> ORGANISM: Artificial Sequence
<220> FEATURE:
<223> OTHER INFORMATION: Synthetic

<400> SEQUENCE: 303

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Val His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215

<210> SEQ ID NO 304
<211> LENGTH: 215
<212> TYPE: PRT
<213> ORGANISM: Artificial Sequence
<220> FEATURE:

<223> OTHER INFORMATION: Synthetic

<400> SEQUENCE: 304

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Val His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 305
<211> LENGTH: 215
<212> TYPE: PRT
<213> ORGANISM: Artificial Sequence
<220> FEATURE:
<223> OTHER INFORMATION: Synthetic

<400> SEQUENCE: 305

Glu Ile Val Leu Thr Gln Ser Pro Gly Thr Leu Ser Leu Ser Pro Gly
1               5                   10                  15

Glu Arg Ala Thr Leu Ser Cys Gly Ala Ser Gln Ser Val Ser Ser Asp
            20                  25                  30

Tyr Leu Ala Trp Tyr Gln Gln Lys Pro Gly Gln Ala Pro Arg Leu Leu
        35                  40                  45

Ile Tyr Gly Ala Tyr Ser Leu Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Trp Ala Val His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 306
<211> LENGTH: 215
<212> TYPE: PRT
<213> ORGANISM: Artificial Sequence
<220> FEATURE:
<223> OTHER INFORMATION: Synthetic

<400> SEQUENCE: 306

Glu Ile Val Leu Thr Gln Ser Pro Gly Thr Leu Ser Leu Ser Pro Gly
1               5                   10                  15

Glu Arg Ala Thr Leu Ser Cys Gln Ala Ser Gln Ala Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Val His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 307
<211> LENGTH: 215
<212> TYPE: PRT
<213> ORGANISM: Artificial Sequence
<220> FEATURE:
<223> OTHER INFORMATION: Synthetic

```
<400> SEQUENCE: 307

Glu Ile Val Leu Thr Gln Ser Pro Gly Thr Leu Ser Leu Ser Pro Gly
1               5                   10                  15

Glu Arg Ala Thr Leu Ser Cys Gly Ala Ser Gln Ser Val Ser Ser Ala
            20                  25                  30

Phe Leu Ala Trp Tyr Gln Lys Pro Gly Gln Ala Pro Arg Leu Leu
        35                  40                  45

Ile Tyr Gly Ala Ser Ala Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Val His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 308
<211> LENGTH: 215
<212> TYPE: PRT
<213> ORGANISM: Artificial Sequence
<220> FEATURE:
<223> OTHER INFORMATION: Synthetic

<400> SEQUENCE: 308

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Glu Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Val His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
```

```
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 309
<211> LENGTH: 215
<212> TYPE: PRT
<213> ORGANISM: Artificial Sequence
<220> FEATURE:
<223> OTHER INFORMATION: Synthetic

<400> SEQUENCE: 309

Glu Ile Val Leu Thr Gln Ser Pro Gly Thr Leu Ser Leu Ser Pro Gly
1               5                   10                  15

Glu Arg Ala Thr Leu Ser Cys Gln Ala Ser Gln Ala Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ile His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 310
<211> LENGTH: 215
<212> TYPE: PRT
<213> ORGANISM: Artificial Sequence
<220> FEATURE:
<223> OTHER INFORMATION: Synthetic

<400> SEQUENCE: 310
```

Glu Ile Val Leu Thr Gln Ser Pro Gly Thr Leu Ser Leu Ser Pro Gly
1               5                   10                  15

Glu Arg Ala Thr Leu Ser Cys Gln Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Ala Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Val His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215

<210> SEQ ID NO 311
<211> LENGTH: 215
<212> TYPE: PRT
<213> ORGANISM: Artificial Sequence
<220> FEATURE:
<223> OTHER INFORMATION: Synthetic

<400> SEQUENCE: 311

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Ala Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Gln Asp Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Val His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 312
<211> LENGTH: 215
<212> TYPE: PRT
<213> ORGANISM: Artificial Sequence
<220> FEATURE:
<223> OTHER INFORMATION: Synthetic

<400> SEQUENCE: 312

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Val His Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 313
<211> LENGTH: 215
<212> TYPE: PRT
<213> ORGANISM: Artificial Sequence
<220> FEATURE:
<223> OTHER INFORMATION: Synthetic

<400> SEQUENCE: 313

Glu Ile Val Leu Thr Gln Ser Pro Gly Thr Leu Ser Leu Ser Pro Gly
1               5                   10                  15
```

-continued

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Ser Ser Tyr Pro
                85                  90                  95

Pro Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
            210                 215

<210> SEQ ID NO 314
<211> LENGTH: 215
<212> TYPE: PRT
<213> ORGANISM: Artificial Sequence
<220> FEATURE:
<223> OTHER INFORMATION: Synthetic

<400> SEQUENCE: 314

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Ser Ser Tyr Pro
                85                  90                  95

Pro Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

```
Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 315
<211> LENGTH: 215
<212> TYPE: PRT
<213> ORGANISM: Artificial Sequence
<220> FEATURE:
<223> OTHER INFORMATION: Synthetic

<400> SEQUENCE: 315

Glu Ile Val Leu Thr Gln Ser Pro Gly Thr Leu Ser Leu Ser Pro Gly
1               5                   10                  15

Glu Arg Ala Thr Leu Ser Cys Glu Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Ser Leu Tyr Pro
                85                  90                  95

Pro Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 316
<211> LENGTH: 215
<212> TYPE: PRT
<213> ORGANISM: Artificial Sequence
<220> FEATURE:
<223> OTHER INFORMATION: Synthetic

<400> SEQUENCE: 316

Glu Ile Val Leu Thr Gln Ser Pro Gly Thr Leu Ser Leu Ser Pro Gly
1               5                   10                  15

Glu Arg Ala Thr Leu Ser Cys Glu Ala Ser Gln Ser Val Ser Ala Ser
```

```
            20                  25                  30
Tyr Leu Ala Trp Tyr Gln Gln Lys Pro Gly Gln Ala Pro Arg Leu Leu
            35                  40                  45
Ile Tyr Asp Ala Ser Ser Arg Ala Ser Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Phe Ser Ser Tyr Pro
                85                  90                  95
Pro Thr Phe Gly Gly Gly Thr Lys Val Glu Ile Lys Arg Thr Val Ala
                100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 317
<211> LENGTH: 215
<212> TYPE: PRT
<213> ORGANISM: Artificial Sequence
<220> FEATURE:
<223> OTHER INFORMATION: Synthetic

<400> SEQUENCE: 317

Glu Ile Val Leu Thr Gln Ser Pro Gly Thr Leu Ser Leu Ser Pro Gly
1               5                   10                  15
Glu Arg Ala Thr Leu Ser Cys Glu Ala Ser Gln Ser Val Ser Ser Ala
            20                  25                  30
Tyr Leu Ala Trp Tyr Gln Gln Lys Pro Gly Gln Ala Pro Arg Leu Leu
        35                  40                  45
Ile Tyr Asp Ala Ser Thr Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Val Ser Ser Tyr Pro
                85                  90                  95
Pro Thr Phe Gly Gly Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
```

165                 170                 175
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 318
<211> LENGTH: 215
<212> TYPE: PRT
<213> ORGANISM: Artificial Sequence
<220> FEATURE:
<223> OTHER INFORMATION: Synthetic

<400> SEQUENCE: 318

Glu Ile Val Leu Thr Gln Ser Pro Gly Thr Leu Ser Leu Ser Pro Gly
1               5                   10                  15

Glu Arg Ala Ala Leu Ser Cys Arg Val Ser Gln Ser Val Ser Asp Ala
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Ser Ser Tyr Pro
                85                  90                  95

Pro Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 319
<211> LENGTH: 215
<212> TYPE: PRT
<213> ORGANISM: Artificial Sequence
<220> FEATURE:
<223> OTHER INFORMATION: Synthetic

<400> SEQUENCE: 319

Glu Ile Val Leu Thr Gln Ser Pro Gly Thr Leu Ser Leu Ser Pro Gly
1               5                   10                  15

Glu Arg Ala Thr Leu Ser Cys Val Ser Gln Ser Val Ser Ala Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln His Ser Leu Tyr Pro
                 85                  90                  95

Pro Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 320
<211> LENGTH: 215
<212> TYPE: PRT
<213> ORGANISM: Artificial Sequence
<220> FEATURE:
<223> OTHER INFORMATION: Synthetic

<400> SEQUENCE: 320

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ala
            20                  25                  30

Tyr Leu Ala Trp Tyr Gln Gln Lys Pro Gly Gln Ala Pro Arg Leu Leu
            35                  40                  45

Ile Tyr Gly Ala Ser Asp Arg Ala Asn Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln His Ser Leu Tyr Pro
                 85                  90                  95

Pro Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 321
<211> LENGTH: 215
<212> TYPE: PRT
<213> ORGANISM: Artificial Sequence
<220> FEATURE:
<223> OTHER INFORMATION: Synthetic

<400> SEQUENCE: 321

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Asn Ala Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asp Arg Ala Asn Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Ser Ile Tyr Pro
                85                  90                  95

Pro Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 322
<211> LENGTH: 215
<212> TYPE: PRT
<213> ORGANISM: Artificial Sequence
<220> FEATURE:
<223> OTHER INFORMATION: Synthetic

<400> SEQUENCE: 322

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Asn Ala Val Ser Ser Ser
            20                  25                  30

Tyr Leu Ala Trp Tyr Gln Gln Lys Pro Gly Gln Ala Pro Arg Leu Leu
        35                  40                  45

```
Ile Tyr Gly Ala Ser Tyr Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln His Ser Leu Tyr Pro
                 85                  90                  95

Pro Thr Phe Gly Gly Gly Thr Lys Val Glu Ile Lys Arg Thr Val Ala
             100                 105                 110

Ala Pro Ser Val Phe Ile Phe Pro Pro Ser Asp Glu Gln Leu Lys Ser
         115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 323
<211> LENGTH: 213
<212> TYPE: PRT
<213> ORGANISM: Artificial Sequence
<220> FEATURE:
<223> OTHER INFORMATION: Synthetic

<400> SEQUENCE: 323

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Asn Ser Trp
             20                  25                  30

Leu Ala Trp Tyr Gln Gln Lys Pro Gly Lys Ala Pro Lys Leu Leu Ile
         35                  40                  45

Ser Asp Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Ser His Ile Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
         115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

```
Cys Glu Val Thr His Gln Gly Leu Ser Ser Pro Val Thr Lys Ser Phe
        195                 200                 205
Asn Arg Gly Glu Cys
    210
```

<210> SEQ ID NO 324
<211> LENGTH: 214
<212> TYPE: PRT
<213> ORGANISM: Artificial Sequence
<220> FEATURE:
<223> OTHER INFORMATION: Synthetic

<400> SEQUENCE: 324

```
Asp Ile Gln Met Thr Gln Ser Pro Ser Ser Val Ser Ala Ser Val Gly
1               5                   10                  15
Asp Arg Val Thr Ile Thr Cys Ala Ala Ser Gln Gly Ile Ser Ser Asp
            20                  25                  30
Leu Ala Trp Tyr Gln Gln Lys Pro Gly Lys Ala Pro Lys Leu Leu Ile
        35                  40                  45
Tyr Ser Ala Ser Ser Thr Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Tyr Leu Tyr Pro Ile
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 325
<211> LENGTH: 214
<212> TYPE: PRT
<213> ORGANISM: Artificial Sequence
<220> FEATURE:
<223> OTHER INFORMATION: Synthetic

<400> SEQUENCE: 325

```
Gly Val Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Thr Tyr
            20                  25                  30
Leu Asn Trp Tyr Gln Gln Lys Pro Gly Lys Ala Pro Lys Leu Leu Ile
        35                  40                  45
Tyr Asp Ala Phe Asn Leu Glu Thr Gly Val Pro Ser Arg Phe Ser Gly
```

```
            50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Leu Pro Phe Leu Pro Ile
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 326
<211> LENGTH: 219
<212> TYPE: PRT
<213> ORGANISM: Artificial Sequence
<220> FEATURE:
<223> OTHER INFORMATION: Synthetic

<400> SEQUENCE: 326

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gly Gly Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
                195                 200                 205
Pro Val Thr Lys Ser Phe Asn Arg Gly Glu Cys
    210                 215

<210> SEQ ID NO 327
<211> LENGTH: 215
<212> TYPE: PRT
<213> ORGANISM: Artificial Sequence
<220> FEATURE:
<223> OTHER INFORMATION: Synthetic

<400> SEQUENCE: 327

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Val Ser Asp Pro
                85                  90                  95

Ile Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 328
<211> LENGTH: 215
<212> TYPE: PRT
<213> ORGANISM: Artificial Sequence
<220> FEATURE:
<223> OTHER INFORMATION: Synthetic

<400> SEQUENCE: 328

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Val Gly Ser Ser Pro
                 85                  90                  95

Ile Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 329
<211> LENGTH: 214
<212> TYPE: PRT
<213> ORGANISM: Artificial Sequence
<220> FEATURE:
<223> OTHER INFORMATION: Synthetic

<400> SEQUENCE: 329

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser His Leu Val Pro Arg
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 330
<211> LENGTH: 215
<212> TYPE: PRT
<213> ORGANISM: Artificial Sequence
<220> FEATURE:
<223> OTHER INFORMATION: Synthetic

<400> SEQUENCE: 330

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ala Asn His His Pro Pro
                85                  90                  95

Phe Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334
<211> LENGTH: 330
```

```
<212> TYPE: PRT
<213> ORGANISM: Artificial Sequence
<220> FEATURE:
<223> OTHER INFORMATION: Synthetic

<400> SEQUENCE: 334
```

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Lys | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Ala | Ala | Gly | Ala | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| | 130 | | | | | 135 | | | | | 140 | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | 195 | | | | | 200 | | | | | 205 | | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Glu | Glu |
| 225 | | | | | 230 | | | | | 235 | | | | | 240 |
| Met | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | 275 | | | | | 280 | | | | | 285 | | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys | | | | | | |
| | | | | 325 | | | | | 330 | | | | | | |

```
<210> SEQ ID NO 335
<211> LENGTH: 327
<212> TYPE: PRT
<213> ORGANISM: Artificial Sequence
<220> FEATURE:
<223> OTHER INFORMATION: Synthetic

<400> SEQUENCE: 335
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 336
<211> LENGTH: 107
<212> TYPE: PRT
<213> ORGANISM: Artificial Sequence
<220> FEATURE:
<223> OTHER INFORMATION: Synthetic

<400> SEQUENCE: 336

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 337
<211> LENGTH: 338
<212> TYPE: PRT
<213> ORGANISM: Artificial Sequence
<220> FEATURE:
<223> OTHER INFORMATION: Synthetic

<400> SEQUENCE: 337

Met Val Val Met Ala Pro Arg Thr Leu Phe Leu Leu Leu Ser Gly Ala
 1               5                  10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
                35                  40                  45

Met Gly Tyr Val Asp Asp Thr Gln Phe Val Arg Phe Asp Ser Asp Ser
 50                  55                  60

Ala Cys Pro Arg Met Glu Pro Arg Ala Pro Trp Val Glu Gln Glu Gly
 65                  70                  75                  80

Pro Glu Tyr Trp Glu Glu Thr Arg Asn Thr Lys Ala His Ala Gln
                 85                  90                  95

Thr Asp Arg Met Asn Leu Gln Thr Leu Arg Gly Tyr Tyr Asn Gln Ser
                100                 105                 110

Glu Ala Ser Ser His Thr Leu Gln Trp Met Ile Gly Cys Asp Leu Gly
                115                 120                 125

Ser Asp Gly Arg Leu Leu Arg Gly Tyr Glu Gln Tyr Ala Tyr Asp Gly
                130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
                180                 185                 190

His Arg Tyr Leu Glu Asn Gly Lys Glu Met Leu Gln Arg Ala Asp Pro
                195                 200                 205

Pro Lys Thr His Val Thr His His Pro Val Phe Asp Tyr Glu Ala Thr
                210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
                260                 265                 270

Val Pro Ser Gly Glu Glu Gln Arg Tyr Thr Cys His Val Gln His Glu
                275                 280                 285
```

```
Gly Leu Pro Glu Pro Leu Met Leu Arg Trp Lys Gln Ser Ser Leu Pro
    290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp

<210> SEQ ID NO 338
<211> LENGTH: 319
<212> TYPE: PRT
<213> ORGANISM: Artificial Sequence
<220> FEATURE:
<223> OTHER INFORMATION: Synthetic

<400> SEQUENCE: 338

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Ser Lys Glu Gly Asp Gly
    290                 295                 300
```

```
Gly Ile Met Ser Val Arg Glu Ser Arg Ser Leu Ser Glu Asp Leu
305                 310                 315
```

<210> SEQ ID NO 339
<211> LENGTH: 336
<212> TYPE: PRT
<213> ORGANISM: Artificial Sequence
<220> FEATURE:
<223> OTHER INFORMATION: Synthetic

<400> SEQUENCE: 339

```
Met Ala Val Met Ala Pro Arg Thr Leu Leu Leu Val Leu Ser Gly Val
1               5                   10                  15

Leu Ala Leu Thr Gln Pro Arg Ala Gly Ser His Ser Met Arg Tyr Phe
                20                  25                  30

Tyr Thr Ala Val Ser Arg Pro Gly Arg Gly Gln Pro Arg Phe Ile Ala
            35                  40                  45

Val Gly Tyr Val Asp Asp Thr Gln Phe Val Arg Phe Asp Ser Asp Ala
        50                  55                  60

Glu Ser Pro Arg Met Glu Pro Arg Ala Pro Trp Val Glu Gln Glu Gly
65                  70                  75                  80

Pro Glu Tyr Trp Asp Arg Glu Thr Gln Asn Met Lys Thr Ala Thr Gln
                85                  90                  95

Thr Tyr Gln Ala Asn Leu Arg Thr Leu Leu Arg Tyr Tyr Asn Gln Ser
            100                 105                 110

Glu Ala Gly Ser His Thr Phe Gln Lys Met Tyr Gly Cys Asp Leu Gly
        115                 120                 125

Pro Asp Gly Arg Leu Leu Arg Gly Tyr Glu Gln Phe Ala Tyr Asp Gly
130                 135                 140

Arg Asp Tyr Ile Ile Leu Asn Glu Asp Leu Arg Ser Trp Thr Ala Ala
145                 150                 155                 160

Asp Met Ala Ala Gln Asn Thr Gln Arg Lys Trp Glu Ala Ala Gly Ala
                165                 170                 175

Ala Glu Gln His Arg Thr Tyr Leu Glu Gly Glu Cys Leu Glu Trp Leu
            180                 185                 190

Arg Arg Tyr Leu Glu Asn Gly Lys Glu Thr Leu Gln Arg Ala Asp Pro
        195                 200                 205

Pro Lys Thr Asn Val Thr His His Pro Val Ser Asp Tyr Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Glu Gln Thr Glu Asp Thr Glu Leu Val Glu
                245                 250                 255

Thr Arg Pro Thr Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
290                 295                 300

Thr Ile Leu Ile Val Gly Ile Ile Ala Gly Leu Val Leu Leu Gly Thr
305                 310                 315                 320

Val Val Thr Gly Ala Val Val Ala Ala Val Met Trp Arg Arg Lys Ser
                325                 330                 335
```

<210> SEQ ID NO 340
<211> LENGTH: 331

<212> TYPE: PRT
<213> ORGANISM: Artificial Sequence
<220> FEATURE:
<223> OTHER INFORMATION: Synthetic

<400> SEQUENCE: 340

```
Leu Leu Leu Val Leu Ser Gly Val Leu Ala Leu Thr Gln Thr Arg Ala
1               5                   10                  15
Gly Ser His Ser Met Arg Tyr Phe Tyr Thr Ser Met Ser Arg Pro Gly
            20                  25                  30
Arg Gly Gln Pro Arg Phe Ile Ala Val Gly Tyr Val Asp Asp Thr Gln
        35                  40                  45
Phe Val Arg Phe Asp Ser Asp Ala Glu Ser Pro Arg Met Glu Pro Arg
    50                  55                  60
Ala Pro Trp Val Glu Gln Glu Gly Pro Glu Tyr Trp Asp Arg Glu Thr
65                  70                  75                  80
Gln Asn Met Lys Thr Ala Thr Gln Thr Tyr Arg Glu Asn Leu Arg Thr
                85                  90                  95
Leu Leu Arg Tyr Tyr Asn Gln Ser Glu Ala Gly Ser His Thr Ile Gln
            100                 105                 110
Lys Met Tyr Gly Cys Asp Leu Gly Pro Asp Gly Arg Leu Leu Arg Gly
        115                 120                 125
Tyr Glu Gln Phe Ala Tyr Asp Gly Arg Asp Tyr Ile Ala Leu Asn Glu
    130                 135                 140
Asp Leu Arg Ser Trp Thr Ala Ala Asp Met Ala Ala Gln Phe Thr Gln
145                 150                 155                 160
Arg Lys Trp Glu Ala Ala Gly Ala Ala Glu Gln His Arg Thr Tyr Leu
                165                 170                 175
Glu Gly Glu Cys Leu Glu Trp Leu Arg Arg Tyr Leu Glu Asn Gly Lys
            180                 185                 190
Glu Thr Leu Gln Arg Ala Asp Pro Pro Lys Thr Asn Val Thr His His
        195                 200                 205
Pro Val Ser Asp Tyr Glu Ala Thr Leu Arg Cys Trp Ala Leu Gly Phe
    210                 215                 220
Tyr Pro Ala Glu Ile Thr Leu Thr Trp Gln Arg Asp Gly Glu Glu Gln
225                 230                 235                 240
Thr Glu Asp Thr Glu Leu Val Glu Thr Arg Pro Thr Gly Asp Gly Thr
                245                 250                 255
Phe Gln Lys Trp Ala Ala Val Val Pro Ser Gly Glu Glu Gln Arg
            260                 265                 270
Tyr Thr Cys His Val Gln His Glu Gly Leu Pro Glu Pro Leu Thr Leu
    275                 280                 285
Arg Trp Glu Pro Ser Ser Gln Ser Thr Ile Leu Ile Val Gly Ile Ile
290                 295                 300
Ala Gly Leu Val Leu Leu Gly Thr Val Thr Gly Ala Val Val Ala
305                 310                 315                 320
Ala Val Met Trp Arg Arg Lys Ser Ser Asp Arg
                325                 330
```

<210> SEQ ID NO 341
<211> LENGTH: 298
<212> TYPE: PRT
<213> ORGANISM: Artificial Sequence
<220> FEATURE:
<223> OTHER INFORMATION: Synthetic

<400> SEQUENCE: 341

```
Met Val Val Met Ala Pro Arg Thr Leu Phe Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
50                  55                  60

Ala Cys Pro Arg Met Glu Pro Arg Ala Pro Trp Val Glu Gln Glu Gly
65              70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp
290                 295

<210> SEQ ID NO 342
<211> LENGTH: 274
<212> TYPE: PRT
<213> ORGANISM: Artificial Sequence
<220> FEATURE:
<223> OTHER INFORMATION: Synthetic

<400> SEQUENCE: 342

Gly Ser His Ser Met Arg Tyr Phe Ser Ala Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ser Ala Cys Pro Arg Met Glu Pro Arg
        35                  40                  45

Ala Pro Trp Val Glu Gln Glu Gly Pro Glu Tyr Trp Glu Glu Glu Thr
50                  55                  60
```

-continued

```
Arg Asn Thr Lys Ala His Ala Gln Thr Asp Arg Met Asn Leu Gln Thr
 65              70                  75                  80

Leu Arg Gly Tyr Tyr Asn Gln Ser Glu Ala Ser Ser His Thr Leu Gln
             85                  90                  95

Trp Met Ile Gly Cys Asp Leu Gly Ser Asp Gly Arg Leu Leu Arg Gly
            100                 105                 110

Tyr Glu Gln Tyr Ala Tyr Asp Gly Lys Asp Tyr Leu Ala Leu Asn Glu
        115                 120                 125

Asp Leu Arg Ser Trp Thr Ala Ala Asp Thr Ala Ala Gln Ile Ser Lys
    130                 135                 140

Arg Lys Cys Glu Ala Ala Asn Val Ala Glu Gln Arg Arg Ala Tyr Leu
145                 150                 155                 160

Glu Gly Thr Cys Val Glu Trp Leu His Arg Tyr Leu Glu Asn Gly Lys
                165                 170                 175

Glu Met Leu Gln Arg Ala Asp Pro Pro Lys Thr His Val Thr His His
            180                 185                 190

Pro Val Phe Asp Tyr Glu Ala Thr Leu Arg Cys Trp Ala Leu Gly Phe
        195                 200                 205

Tyr Pro Ala Glu Ile Ile Leu Thr Trp Gln Arg Asp Gly Glu Asp Gln
    210                 215                 220

Thr Gln Asp Val Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Met Leu
                260                 265                 270

Arg Trp
```